(12) United States Patent
Meldrum et al.

(10) Patent No.: US 11,492,347 B2
(45) Date of Patent: *Nov. 8, 2022

(54) FUSED THIOPHENE DERIVATIVES AND THEIR USES

(71) Applicant: ENYO PHARMA, Lyons (FR)

(72) Inventors: Eric Meldrum, Riehen (CH); Benoît De Chassey, Lyons (FR); Peter Machin, London (GB); Roberta Lanaro, Cambridge (GB); Calum MacLeod, Harlow (GB); Karine Fabienne Malagu, Cambridge (GB); Nicolas Proisy, Harlow (GB); David Robert Vesey, Harlow Essex (GB); Paul Colin Michael Winship, Cambridge (GB); Mark Chambers, Saffron Walden Essex (GB)

(73) Assignee: ENYO PHARMA, Lyons (FR)

( * ) Notice: Subject to any disclaimer, the term of this patent is extended or adjusted under 35 U.S.C. 154(b) by 0 days.

This patent is subject to a terminal disclaimer.

(21) Appl. No.: 16/967,746

(22) PCT Filed: Feb. 8, 2019

(86) PCT No.: PCT/EP2019/053074
§ 371 (c)(1),
(2) Date: Aug. 6, 2020

(87) PCT Pub. No.: WO2019/154950
PCT Pub. Date: Aug. 15, 2019

(65) Prior Publication Data
US 2020/0361924 A1    Nov. 19, 2020

(30) Foreign Application Priority Data
Feb. 8, 2018   (EP) .................................. 18305133

(51) Int. Cl.
| | | |
|---|---|---|
| *C07D 333/66* | (2006.01) |
| *C07D 409/12* | (2006.01) |
| *C07D 409/14* | (2006.01) |
| *C07D 491/107* | (2006.01) |
| *A61P 25/28* | (2006.01) |
| *A61P 29/00* | (2006.01) |
| *C07D 413/14* | (2006.01) |
| *A61P 31/14* | (2006.01) |
| *A61P 31/16* | (2006.01) |
| *A61P 35/00* | (2006.01) |
| *C07D 333/68* | (2006.01) |
| *C07D 401/12* | (2006.01) |
| *C07D 403/12* | (2006.01) |
| *C07D 413/12* | (2006.01) |
| *C07D 495/04* | (2006.01) |

(52) U.S. Cl.
CPC ............ *C07D 413/14* (2013.01); *A61P 25/28* (2018.01); *A61P 29/00* (2018.01); *A61P 31/14* (2018.01); *A61P 31/16* (2018.01); *A61P 35/00* (2018.01); *C07D 333/66* (2013.01); *C07D 333/68* (2013.01); *C07D 401/12* (2013.01); *C07D 403/12* (2013.01); *C07D 409/12* (2013.01); *C07D 409/14* (2013.01); *C07D 413/12* (2013.01); *C07D 491/107* (2013.01); *C07D 495/04* (2013.01)

(58) Field of Classification Search
CPC .. C07D 333/66; C07D 409/12; C07D 409/14; C07D 491/107; A61P 31/12; A61P 31/14; A61P 31/16; A61P 35/00; A61P 25/28; A61P 29/00
See application file for complete search history.

(56) References Cited

U.S. PATENT DOCUMENTS

| | | |
|---|---|---|
| 2019/0352275 A1 | 11/2019 | Meldrum et al. |
| 2020/0369655 A1 | 11/2020 | Meldrum et al. |
| 2020/0369682 A1 | 11/2020 | Meldrum et al. |
| 2021/0038566 A1 | 2/2021 | Meldrum et al. |
| 2021/0040059 A1 | 2/2021 | Meldrum et al. |

FOREIGN PATENT DOCUMENTS

| | | |
|---|---|---|
| JP | 2014-169257 | 9/2014 |
| WO | WO 2006/044826 | 4/2006 |
| WO | WO 2009/026172 | 2/2009 |
| WO | WO 2010/088414 | 8/2010 |
| WO | WO 2019/154949 | 8/2019 |
| WO | WO 2019/154953 | 8/2019 |
| WO | WO 2019/154956 | 8/2019 |

OTHER PUBLICATIONS

Chemical Abstracts Registry No. 946407-75-6, indexed in the Registry file on STN CAS Online Sep. 7, 2007. (Year: 2007).*
A machine generated English translation of JP 2014/169257 A (Hirata et al.), 2014. (Year: 2014).*

(Continued)

*Primary Examiner* — Laura L Stockton
(74) *Attorney, Agent, or Firm* — Saliwanchik, Lloyd & Eisenschenk

(57) ABSTRACT

The present invention relates to a new class of fused thiophene derivatives and their uses for treating diseases such as infection, cancer, metabolic diseases, cardiovascular diseases, iron storage disorders and inflammatory disorders.

12 Claims, No Drawings
Specification includes a Sequence Listing.

(56) References Cited

OTHER PUBLICATIONS

Massari, S. et al. "Structural Investigation of Cycloheptathiophene-3-carboxamide Derivatives Targeting Influenza Virus Polymerase Assembly" *J. Med. Chem.*, 2013, pp. 10118-10131, vol. 56, No. 24.
Pinkerton, A. B. et al. "Synthesis and SAR of thiophene containing kinesin spindle protein (KSP) inhibitors" *Bioorganic & Medicinal Chemistry Letters*, 2007, pp. 3562-3569, vol. 17, No. 13.
Bai, F. et al. "The Fe—S cluster-containing NEET proteins mitoNEET and NAF-1 as chemotherapeutic targets in breast cancer" *PNAS*, Mar. 24, 2015, pp. 3698-3703, vol. 112, No. 12.
Database Registry [Online] Chemical Abstracts Service, Accession No. 2128688-81-1, Sep. 19, 2017, XP-002780167, p. 1.
Written Opinion in International Application No. PCT/EP2019/053074, dated May 7, 2019, pp. 1-9.

* cited by examiner

SEQUENCE LISTING

<160> NUMBER OF SEQ ID NOS: 4

<210> SEQ ID NO 1
<211> LENGTH: 35
<212> TYPE: DNA
<213> ORGANISM: artificial
<220> FEATURE:
<223> OTHER INFORMATION: NFKB-NLUC-F

<400> SEQUENCE: 1
ggctctatgg gtcgacggcc taactggccg gtacc                                35

<210> SEQ ID NO 2
<211> LENGTH: 37
<212> TYPE: DNA
<213> ORGANISM: artificial
<220> FEATURE:
<223> OTHER INFORMATION: NFKB-NLUC-R

<400> SEQUENCE: 2

```
agcttagtac tgtcgacgat cagcggaaga gcgccca                               37

<210> SEQ ID NO 3
<211> LENGTH: 25
<212> TYPE: DNA
<213> ORGANISM: artificial
<220> FEATURE:
<223> OTHER INFORMATION: AAVS1-T2A-1

<400> SEQUENCE: 3
caccgggggc cactagggac aggat                                            25

<210> SEQ ID NO 4
<211> LENGTH: 25
<212> TYPE: DNA
<213> ORGANISM: artificial
<220> FEATURE:
<223> OTHER INFORMATION: AAVS1-T2A-2

<400> SEQUENCE: 4
aaacatcctg tccctagtgg ccccc                                            25
```

FUSED THIOPHENE DERIVATIVES AND THEIR USES

CROSS-REFERENCE TO RELATED APPLICATION

This application is the U.S. national stage application of International Patent Application No. PCT/EP2019/053074, filed Feb. 8, 2019.

The Sequence Listing for this application is labeled "Seq-List.txt" which was created on Jul. 6, 2020 and is 1 KB. The entire content of the sequence listing is incorporated herein by reference in its entirety.

FIELD OF THE INVENTION

The present invention relates to the field of medicine, in particular fused thiophene derivatives and their uses for treating diseases such as infection, cancer, metabolic diseases, cardiovascular diseases, iron storage disorders and inflammatory disorders.

BACKGROUND OF THE INVENTION

Viruses are small infectious agents that replicates only inside living cells of other organisms. They can infect all types of life forms, from animals and plants to microorganisms, including bacteria and archaea. Among them, more than 400 species of virus are known to be responsible of diseases in humans, many of them leading to serious pathologies and eventually death. In particular, HIV was classified at the sixth leading cause of death worldwide in 2012 with 1.5 millions of deaths per year (WHO, Fact sheet No 310, 2014). Seasonal influenza viruses are responsible of flu that affects approximately 20% of the world population and causes 250,000 to 500,000 deaths per year (WHO, Fact sheet No 211, 2014). Among other examples, Hepatitis B and C are responsible altogether for about 1.4 million of death each year and human Papillomaviruses are responsible of cervix cancer, the second most common women cancer worldwide, leading to 270,000 death in 2012 (WHO, Fact sheets, 2016).

Because viruses use vital metabolic pathways within host cells to replicate, they are difficult to eliminate without using drugs that cause toxic effects to host cells in general. The most effective medical approaches to viral diseases are vaccinations to provide immunity to infection, and antiviral drugs that selectively interfere with viral replication. Vaccines are very effective on stable viruses for a preventive use. However, vaccines are of limited use in treating a patient who has already been infected. They are also difficult to successfully deploy against rapidly mutating viruses, such as influenza (the vaccine for which is updated every year) and HIV. Antiviral drugs may be particularly useful in these cases.

Antiviral drugs are a class of medication used specifically for treating viral infections. Antiviral drugs do not destroy their target pathogens, instead they inhibit their development. Antiviral drugs may target any stage of the viral life cycle: attachment to a host cell, release of viral genes and possibly enzymes into the host cell, replication of viral components using host-cell machinery, assembly of viral components into complete viral particles, and release of viral particles to infect new host cells. The most common antiviral drugs are nucleoside analogues that block viruses' replication. Most antiviral drugs are used for specific viral infections, while broad-spectrum antiviral drugs are effective against a wide range of viruses.

Soon after the development of antiviral drugs, resistance appeared. Antiviral drug resistance can be defined as a decreased susceptibility to a drug through either a minimally effective, or completely ineffective, treatment response to prevent associated illnesses from a particular virus. Antiviral drug resistance remains a major obstacle to antiviral therapy as it has developed to almost all specific and effective antiviral drugs. For example, there are two main groups of antiviral drugs available for treatment and prophylaxis of influenza: M2 inhibitors (amantadine and rimantadine) and neuraminidase inhibitors (oseltamivir and zanamivir). Despite the effectiveness of these drugs in reducing influenza-related morbidity and mortality, the emergence of drug resistance poses a critical limitation on their application and have raised an urgent need for developing new anti-influenza drugs against resistant forms.

Thus, there is nowadays a strong need for the development of new antiviral drugs, and in particular broad-spectrum antiviral drugs. The present invention seeks to meet these and other needs.

SUMMARY OF THE INVENTION

The present invention relates to a compound of formula (I):

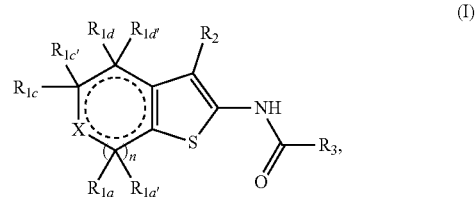

wherein:
X represents:
  a —CR$_{1b}$R$_{1b'}$ unit,
n is 0, 1, or 2;
R$_{1a}$, R$_{1a'}$, R$_{1b}$, R$_{1b'}$, R$_{1c}$, R$_{1c'}$, R$_{1d}$, and R$_{1d'}$ represent independently:
  a hydrogen,
  a halogen,
  a (C$_1$-C$_6$)alkyl, optionally substituted by at least one halogen, preferably optionally substituted by at least one fluorine,
  a (C$_1$-C$_6$)alkyloxy,
  a cyano,
  an aryl optionally substituted by at least one radical selected in the group consisting of:
    a halogen,
    a (C$_1$-C$_6$)alkyl optionally substituted by at least one halogen, preferably optionally substituted by at least one fluorine,
    a hydroxy, and
    a (C$_1$-C$_6$)alkyloxy; or
  R$_{1a}$ and R$_{1a'}$, R$_{1b}$ and R$_{1b'}$, R$_{1c}$ and R$_{1c'}$, and R$_{1d}$ and R$_{1d'}$ form together a cycloalkyl, preferably a cyclopropyl; or
  R$_{1a}$ or R$_{1a'}$ and R$_{1d}$ or R$_{1d'}$ form together a bridged carbocyclyl;
and wherein at least two groups chosen among R$_{1a}$, R$_{1a'}$, R$_{1b}$, R$_{1b'}$, R$_{1c}$, R$_{1c'}$, R$_{1d}$, and R$_{1d'}$ are not a hydrogen;
R$_2$ represents —COOH;

3

$R_3$ represents:
  a 5-10 membered ring, saturated or unsaturated selected in the group consisting of:
    an aryl optionally fused to a dioxole,
    a heteroaryl,
    a cycloalkyl,
    a heterocycloalkyl, and
    a 5-10 membered bridged carbocyclyl or heterocyclyl, said 5-10 membered ring is optionally substituted by at least one radical selected in the group consisting of:
      a halogen,
      a $(C_1-C_6)$alkyl optionally substituted by at least one halogen, preferably optionally substituted by at least one fluorine, or a $(C_1-C_6)$alkyloxy,
      a —NH—$(C_1-C_6)$alkyl or a —N—$((C_1-C_6)$alkyl$)_2$, optionally substituted by a heterocycloalkyl or a $(C_1-C_6)$alkyloxy,
      a —NH-heterocycloalkyl, a —NH-cycloalkyl, a —N$((C_1-C_6)$alkyl$)$-heterocycloalkyl or a —N$((C_1-C_6)$alkyl$)$-cycloalkyl, optionally substituted by a $(C_1-C_6)$alkyloxy or a —CO—$R_4$ with $R_4$ being a hydrogen or a $(C_1-C_6)$alkyl,
      a hydroxy, a —CO—$R_4$ or a —CO$_2R_4$ with $R_4$ being a hydrogen or a $(C_1-C_6)$alkyl,
      a $(C_1-C_6)$alkyloxy optionally substituted by at least one radical selected in the group consisting of a halogen, preferably a fluorine, a hydroxy, a $(C_1-C_6)$alkyloxy, a —$NR_5R_6$ with $R_5$ and $R_6$ are independently a hydrogen or a $(C_1-C_6)$alkyl, a —$NHCOR_7$, a —$NHCO_2R_7$, with $R_7$ being a $(C_1-C_6)$alkyl, a —$CO_2R_4$ with $R_4$ being a hydrogen or a $(C_1-C_6)$alkyl, and a heterocycle,
      a —$NHCOR_7$ or —$NHCO_2R_7$ with $R_7$ being a $(C_1-C_6)$alkyl, and
      a heterocycloalkyl, a heterocycloalkyloxy or a spiroheterocycloalkyl, optionally substituted by a $(C_1-C_6)$alkyloxy, a hydroxy, a halogen or a $(C_1-C_6)$alkyl optionally substituted by a $(C_1-C_6)$alkyloxy; and the stereoisomers, and the pharmaceutical salts thereof; and with the proviso that the compound of formula (I) is not 2-[(4-Chlorobenzoylamino]-6,6-dimethyl-5,7-dihydro-4H-benzothiophene-3-carboxylic acid.

The present invention also relates to a compound for use for treating a disease selected from the group consisting of an infection, preferably a viral or a bacterial infection, a cancer, a metabolic disease, a cardiovascular disease, an inflammatory disorder, and iron storage disease/disorder, wherein the compound has the formula (I):

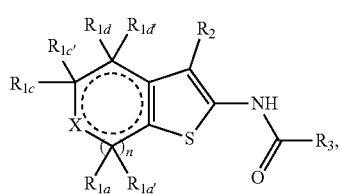

(I)

4 wherein:
  X represents:
    a —$CR_{1b}R_{1b'}$ unit;
  n is 0, 1, or 2;
  $R_{1a}$, $R_{1a'}$, $R_{1b}$, $R_{1b'}$, $R_{1c}$, $R_{1c'}$, $R_{1d}$, and $R_{1d'}$ represent independently:
    a hydrogen,
    a halogen,
    a $(C_1-C_6)$alkyl, optionally substituted by at least one halogen, preferably optionally substituted by at least one fluorine,
    a $(C_1-C_6)$alkyloxy,
    a cyano,
    an aryl optionally substituted by at least one radical selected in the group consisting of:
      a halogen,
      a $(C_1-C_6)$alkyl optionally substituted by at least one halogen, preferably optionally substituted by at least one fluorine,
      a hydroxy, and
      a $(C_1-C_6)$alkyloxy,
    $R_{1a}$ and $R_{1a'}$, $R_{1b}$ and $R_{1b'}$, $R_{1c}$ and $R_{1c'}$, and $R_{1d'}$ and $R_{1d'}$ form together a cycloalkyl, preferably a cyclopropyl; or
    $R_{1a}$ or $R_{1a'}$, and $R_{1d'}$ or $R_{1d'}$ form together a bridged carbocyclyl;
  and wherein at least two groups chosen among $R_{1a}$, $R_{1a'}$, $R_{1b}$, $R_{1b'}$, $R_{1c}$, $R_{1c'}$, $R_{1d}$, and $R_{1d'}$ are not a hydrogen;
  $R_2$ represents —COOH;
  $R_3$ represents:
    a 5-10 membered ring, saturated or unsaturated selected in the group consisting of:
      an aryl optionally fused to a dioxole,
      a heteroaryl,
      a cycloalkyl,
      a heterocycloalkyl, and
      a 5-10 membered bridged carbocyclyl or heterocyclyl,
      said 5-10 membered ring is optionally substituted by at least one radical selected in the group consisting of:
        a halogen,
        a $(C_1-C_6)$alkyl optionally substituted by at least one halogen, preferably optionally substituted by at least one fluorine, or a $(C_1-C_6)$alkyloxy,
        a —NH—$(C_1-C_6)$alkyl or a —N—$((C_1-C_6)$alkyl$)_2$, optionally substituted by a heterocycloalkyl or a $(C_1-C_6)$alkyloxy,
        a —NH-heterocycloalkyl, a —NH-cycloalkyl, a —N$((C_1-C_6)$alkyl$)$-heterocycloalkyl or a —N$((C_1-C_6)$alkyl$)$-cycloalkyl, optionally substituted by a $(C_1-C_6)$alkyloxy or a —CO—$R_4$ with $R_4$ being a hydrogen or a $(C_1-C_6)$alkyl,
        a hydroxy, a —CO—$R_4$ or a —CO$_2R_4$ with $R_4$ being a hydrogen or a $(C_1-C_6)$alkyl,
        a $(C_1-C_6)$alkyloxy optionally substituted by at least one radical selected in the group consisting of a halogen, preferably a fluorine, a hydroxy, a $(C_1-C_6)$alkyloxy, a —$NR_5R_6$ with $R_5$ and $R_6$ are independently a hydrogen or a $(C_1-C_6)$alkyl, a —$NHCOR_7$, a —$NHCO_2R_7$, with $R_7$ being a $(C_1-C_6)$alkyl, a —$CO_2R_4$ with $R_4$ being a hydrogen or a $(C_1-C_6)$alkyl, and a heterocycle,
        a —$NHCOR_7$ or —$NHCO_2R_7$ with $R_7$ being a $(C_1-C_6)$alkyl, and
        a heterocycloalkyl, a heterocycloalkyloxy or a spiroheterocycloalkyl, optionally substituted by a ($C_1$-$C_6$)alkyloxy, a hydroxy, a halogen or a ($C_1$-$C_6$)alkyl optionally substituted by a ($C_1$-$C_6$)alkyloxy, and the stereoisomers, and the pharmaceutical salts thereof.

In a particular embodiment, $R_{1a}$, $R_{1a'}$, $R_{1b}$, $R_{1b'}$, $R_{1c}$, $R_{1c'}$, $R_{1d}$, and $R_{1d'}$ represent independently a hydrogen, a ($C_1$-$C_6$)alkyl, preferably a ($C_1$-$C_3$)alkyl, optionally substituted by at least one halogen, preferably optionally substituted by at least one fluorine, or a halogen, preferably a fluorine; $R_{1a}$ or $R_{1a'}$ and $R_{1d}$ or $R_{1d'}$ form together a bridged carbocyclyl; and/or $R_{1a}$ and $R_{1a'}$, $R_{1b}$ and $R_{1b'}$, $R_{1c}$ and $R_{1c'}$, or $R_{1d}$ and $R_{1d'}$ forms together a cyclopropyl.

Preferably, $R_{1a}$=$R_{1a'}$, $R_{1b}$=$R_{1b'}$, $R_{1c}$=$R_{1c'}$, and $R_{1d}$=$R_{1d'}$.

In one particular embodiment, two groups chosen among $R_{1a}$, $R_{1a'}$, $R_{1b}$, $R_{1b'}$, $R_{1c}$, $R_{1c'}$, $R_{1d}$, and $R_{1d'}$ represent a methyl, the others are a hydrogen.

In a second particular embodiment, at least three groups, preferably four groups, chosen among $R_{1a}$, $R_{1a'}$, $R_{1b}$, $R_{1b'}$, $R_{1c}$, $R_{1c'}$, $R_{1d}$, and $R_{1d'}$ represent a methyl, the others are a hydrogen.

In a third particular embodiment, $R_{1b}$ and $R_{1b'}$ form together a cycloalkyl, preferably a cyclopropyl, and $R_{1a}$, $R_{1a'}$, $R_{1c}$, $R_{1c'}$, $R_{1d}$, and $R_{1d'}$ are a hydrogen.

Particularly, $R_3$ represents a phenyl, a pyridinyl, a pyridazinyl, a pyrimidinyl, a pyrazinyl, an imidazolyl, or a pyrazolyl, preferably a phenyl, optionally substituted by at least one radical as defined herein.

In an embodiment, $R_3$ represents a phenyl optionally substituted by at least one radical selected in the group consisting of:
- a halogen, preferably a fluorine or a bromine;
- a ($C_1$-$C_6$)alkyl optionally substituted by at least one halogen, preferably optionally substituted by at least one fluorine,
- a —NH—($C_1$-$C_6$)alkyl or a —N—(($C_1$-$C_6$)alkyl)$_2$, optionally substituted by a ($C_1$-$C_6$)alkyloxy, a heterocycloalkyl selected in the group consisting of a tetrahydropyranyl, a tetrahydrofuranyl, an oxetanyl, a piperidinyl, and an azetidinyl, or a cycloalkyl, preferably a cyclobutyl or a cyclohexyl, said cycloalkyl and heterocycloalkyl are optionally substituted by a ($C_1$-$C_6$) alkyloxy or a —CO—$R_4$ with $R_4$ being a hydrogen or a ($C_1$-$C_6$)alkyl,
- a —NH-heterocycloalkyl, a —NH-cycloalkyl, a —N(($C_1$-$C_6$)alkyl)-heterocycloalkyl, or a —N(($C_1$-$C_6$)alkyl)-cycloalkyl, preferably a —NH-tetrahydropyranyl, a —N(CH$_3$)-tetrahydropyranyl, a —NH-tetrahydrofuranyl, a NH-piperidinyl, a —NH-azetidinyl, a —NH-oxetanyl, a-NH-cyclohexyl, or a —N(CH$_3$)-cyclobutyl, said —NH-heterocycloalkyl, —NH-cycloalkyl, —N(($C_1$-$C_6$)alkyl)-heterocycloalkyl, or —N(($C_1$-$C_6$)alkyl)-cycloalkyl being optionally substituted by a ($C_1$-$C_6$)alkyloxy or a —CO—$R_4$ with $R_4$ being a hydrogen or a ($C_1$-$C_6$)alkyl,
- a ($C_1$-$C_6$)alkyloxy optionally substituted by at least one radical selected in the group consisting of a halogen, preferably a fluorine, a ($C_1$-$C_6$)alkyloxy, and a heterocycle, preferably a tetrahydropyranyl, or an oxatenyl, and
- a heterocycloalkyl, preferably a morpholinyl, a piperidinyl, a piperazinyl, a tetrahydropyranyl, and an azetidinyl, or a spiroheterocycloalkyl, preferably a piperidinyl spiro-connected with an oxetanyl, said heterocycloalkyl and spiroheterocyclolakyl are optionally substituted by a ($C_1$-$C_6$)alkyloxy, a hydroxy, a halogen or a ($C_1$-$C_6$)alkyl optionally substituted by a ($C_1$-$C_6$)alkyloxy, and
- a heterocycloalkyloxy, preferably a tetrahydropyranyloxy.

In a further embodiment, $R_3$ represents a pyridinyl, a pyridazinyl, a pyrimidinyl, a pyrazolyl, an imidazolyl, or a pyrazinyl, preferably a pyridinyl, a pyridazinyl, a pyrimidinyl, and a pyrazolyl, optionally substituted by at least one radical selected in the group consisting of:
- a ($C_1$-$C_6$)alkyl optionally substituted by at least one halogen, preferably a fluorine, or by a heterocycloalkyl, preferably a tetrahydropyranyl,
- a ($C_1$-$C_6$)alkyloxy optionally substituted by at least one radical selected in the group consisting of a halogen, preferably a fluorine,
- a heterocycloalkyl, preferably a morpholinyl, and
- a heterocycloalkyloxy, preferably a tetrahydropyranyloxy.

In a preferred embodiment, the compound or the compound for use of formula (I) is selected from the group consisting of compounds of the table A.

Another object of the invention is a new compound of formula (I) as defined above for use as a medicine. A further object of the invention is a pharmaceutical composition comprising a new compound as defined above, and an acceptable pharmaceutical excipient. In another further particular embodiment, the present invention relates to a new compound of the present invention for use in the treatment of aging or a neurodegenerative disease or disorder.

In a particular embodiment, the viral infection is an infection by a virus selected from the group consisting of Alphaviridae, Flaviviridae, Hepadnaviridae, Herpesviridae, Orthomyxoviridae, Papovaviridae, Paramyxoviridae, Picornaviridae, Polyomaviridae, Reoviridae, Retroviridae, Rhabdoviridae, and Tobamoviruses.

In a further particular embodiment, the bacterial infection is an infection by a bacterium selected from the group consisting of *Helicobacter pylori*, *Burkholderia cepacia*, *Pseudomonas aeruginosa*, *Pseudomonas fluorescens*, *Pseudomonas acidovorans*, *Pseudomonas alcaligenes*, *Pseudomonas putida*, *Stenotrophomonas maltophilia*, *Aeromonas hydrophilia*, *Escherichia coli*, *Citrobacter freundii*, *Salmonella typhimurium*, *Salmonella typhi*, *Salmonella paratyphi*, *Salmonella enteritidis*, *Shigella dysenteriae*, *Shigella flexneri*, *Shigella sonnei*, *Enterobacter cloacae*, *Enterobacter aerogenes*, *Klebsiella pneumoniae*, *Klebsiella oxytoca*, *Serratia marcescens*, *Francisella tularensis*, *Morganella morganii*, *Proteus mirabilis*, *Proteus vulgaris*, *Providencia alcalifaciens*, *Providencia rettgeri*, *Providencia stuartii*, *Acinetobacter baumannii*, *Acinetobacter calcoaceticus*, *Acinetobacter haemolyticus*, *Yersinia enterocolitica*, *Yersinia pestis*, *Yersinia pseudotuberculosis*, *Yersinia intermedia*, *Bordetella parapertussis*, *Bordetella bronchiseptica*, *Haemophilus parainfluenzae*, *Haemophilus haemolyticus*, *Haemophilus parahaemolyticus*, *Haemophilus ducreyi*, *Pasteurella multocida*, *Pasteurella haemolytica*, *Branhamella catarrhalis*, *Campylobacter fetus*, *Campylobacter jejuni*, *Campylobacter coli*, *Borrelia burgdorferi*, *Vibrio cholerae*, *Vibrio parahaemolyticus*, *Listeria monocytogenes*, *Neisseria gonorrhoeae*, *Neisseria meningitidis*, *Kingella denitrificans*, *Kingella indologenes*, *Kingella kingae*, *Kingella oralis*, *Legionella pneumophila*, *Moraxella bovis*, *Moraxella catarrhalis*, *Moraxella lacunata*, *Gardnerella vaginalis*, *Bacteroides fragilis*, *Bacteroides distasonis*, *Bacteroides vulgatus*, *Bacteroides ovalus*, *Bacteroides thetaiotaomicron*, *Bacteroides uniformis*, *Bacteroides eggerthii*, *Bacteroides splanchnicus*, *Clostridium difficile*, *Clostridium tetani*, *Mycobacterium species*, *Corynebacterium ulcerans*, *Strep-* tococcus agalactiae, Gardnerella vaginitis, Streptococcus pyogenes, Enterococcus faecalis, Enterococcus faecium, Fusobacterium nucleatum, Porphyromonas gingivalis, Vibrio vulnificus, Clostridium botulinum, Corynebacterium diptheriae, Staphylococcus aureus, Staphylococcus epidermidis, Staphylococcus saprophyticus, Staphylococcus intermedius, Staphylococcus hyicus, Staphylococcus haemolyticus, Staphylococcus hominis, and Staphylococcus saccharolyticus.

In a further particular embodiment, the cancer is selected from the group consisting of a breast cancer, a lung cancer, in particular NSCLC, a melanoma, a colorectal cancer, an astrocytoma cancer, a liver cancer, leukemia, in particular acute myeloid leukemia, a gastric cancer, a head and neck cancer, a cervical cancer, a pancreatic cancer, and an ovarian cancer.

In a further particular embodiment, the metabolic disease is selected from the group consisting of Diabetes mellitus, in particular Diabetes mellitus from NEET proteins, insulin resistance, insulin deficiency, hepatic steatosis, nonalcoholic fatty liver disease, Nonalcoholic steatohepatitis (NASH), glucose intolerance, obesity, lipodystrophy, coronary heart disease, diabetic retinopathy, diabetic neuropathy, diabetic nephropathy, hypoglycemia, hyperglycemia, beta cell dysfunction or hyperinsulinaemia, Wolfram syndrome, in particular Wolfram syndrome from NEET proteins, Polycystic ovary syndrome, pyruvate dehydrogenase deficiency, Albright hereditary osteodystrophy, cystinosis, fructose intolerance, Walker-Warburg syndrome, hypobetalipoproteinemia, Alström syndrome, and cirrhosis.

In a further particular embodiment, the cardiovascular disease is selected in the group consisting of myocardial injury, Ischemia, Ischemia reperfusion injury and hypertension.

In an additional particular embodiment, the inflammatory disease or disorder is selected from the group consisting of Crohn disease, inflammatory bowel disease, asthma, chronic obtrusive pulmonary disease (COPD), systemic lupus erythematosus, cystic fibrosis, psoriasis, infectious arthritis, and multiple sclerosis.

In a further particular embodiment, the iron storage disorder or disease is selected from the group consisting of Ferroportin Deficiency, Hereditary Hemochromatosis, including Hereditary Hemochromatosis due to HFE mutations and Hereditary Hemochromatosis due to transferrin receptor 2 mutations, Juvenile Hemochromatosis, including Juvenile Hemochromatosis due to hepcidin mutations and Juvenile Hemochromatosis due to hemojuvelin mutations, Iron Overload, including African Iron Overload, Iron Overload secondary to atransferrinemia and Iron Overload secondary to aceruloplasminemia, Thalassemia, Myelodysplastic Syndromes, Congenital Dyserythropoietic Anemias, Sickle Cell Disease and other Hemoglobinopathies, Red Cell Enzyme Deficiencies and Multiple Blood Transfusions.

DETAILED DESCRIPTION OF THE INVENTION

Definitions

According to the present invention, the terms below have the following meanings:

The terms mentioned herein with prefixes such as for example $C_1$-$C_3$, $C_1$-$C_6$ or $C_2$-$C_6$ can also be used with lower numbers of carbon atoms such as $C_1$-$C_2$, $C_1$-$C_5$, or $C_2$-$C_5$. If, for example, the term $C_1$-$C_3$ is used, it means that the corresponding hydrocarbon chain may comprise from 1 to 3 carbon atoms, especially 1, 2 or 3 carbon atoms. If, for example, the term $C_1$-$C_6$ is used, it means that the corresponding hydrocarbon chain may comprise from 1 to 6 carbon atoms, especially 1, 2, 3, 4, 5 or 6 carbon atoms. If, for example, the term $C_2$-$C_6$ is used, it means that the corresponding hydrocarbon chain may comprise from 2 to 6 carbon atoms, especially 2, 3, 4, 5 or 6 carbon atoms.

The term "alkyl" refers to a saturated, linear or branched aliphatic group. The term "($C_1$-$C_3$)alkyl" more specifically means methyl, ethyl, propyl, or isopropyl. The term "($C_1$-$C_6$)alkyl" more specifically means methyl, ethyl, propyl, isopropyl, butyl, isobutyl, tert-butyl, pentyl or hexyl. In a preferred embodiment, the "alkyl" is a methyl, an ethyl, a propyl, an isopropyl, or a tert-butyl, more preferably a methyl.

The term "alkenyl" refers to an unsaturated, linear or branched aliphatic group comprising at least one carbon-carbon double bound. The term "($C_2$-$C_6$)alkenyl" more specifically means ethenyl, propenyl, isopropenyl, butenyl, isobutenyl, pentenyl, or hexenyl.

The term "alkoxy" or "alkyloxy" corresponds to the alkyl group as above defined bonded to the molecule by an —O— (ether) bond. ($C_1$-$C_3$)alkoxy includes methoxy, ethoxy, propyloxy, and isopropyloxy. ($C_1$-$C_6$)alkoxy includes methoxy, ethoxy, propyloxy, isopropyloxy, butyloxy, isobutyloxy, tert-butyloxy, pentyloxy and hexyloxy. In a preferred embodiment, the "alkoxy" or "alkyloxy" is a methoxy.

The term "cycloalkyl" corresponds to a saturated or unsaturated mono-, bi- or tri-cyclic alkyl group comprising between 3 and 20 atoms of carbons. It also includes fused, bridged, or spiro-connected cycloalkyl groups. The term "cycloalkyl" includes for instance cyclopropyl, cyclobutyl, cyclopentyl, and cyclohexyl. The term "cycloalkyl" may also refer to a 5-10 membered bridged carbocyclyl such as bicyclo[2,2,1]heptanyl, bicyclo[2,2,2]octanyl, or adamantyl, preferably bicyclo[2,2,2]octanyl. In a preferred embodiment, the "cycloalkyl" is a cyclopropyl, cyclobutyl, cyclopentyl or a cyclohexyl.

The term "heterocycloalkyl" corresponds to a saturated or unsaturated cycloalkyl group as above defined further comprising at least one heteroatom such as nitrogen, oxygen, or sulphur atom. It also includes fused, bridged, or spiro-connected heterocycloalkyl groups. Representative heterocycloalkyl groups include, but are not limited to 3-dioxolane, benzo [1,3] dioxolyl, azetidinyl, oxetanyl, pyrazolinyl, pyranyl, thiomorpholinyl, pyrazolidinyl, piperidyl, piperazinyl, 1,4-dioxanyl, imidazolinyl, pyrrolinyl, pyrrolidinyl, piperidinyl, imidazolidinyl, morpholinyl, 1,4-dithianyl, pyrrolidinyl, oxozolinyl, oxazolidinyl, isoxazolinyl, isoxazolidinyl, thiazolinyl, thiazolidinyl, isothiazolinyl, isothiazolidinyl, dihydropyranyl, tetrahydro-2H-pyranyl, tetrahydrofuranyl, and tetrahydrothiophenyl. The term "heterocycloalkyl" may also refer to a 5-10 membered bridged heterocyclyl such as 7-oxabicyclo[2,2,1]heptanyl. In a particular embodiment, it may also refer to spiro-connected heterocycloalkyl groups or spiroheterocycloalkyl groups such as for instance oxetanyl spiro-connected with azetidinyl or piperidinyl. In a preferred embodiment, the heterocycloalkyl group is azetidinyl, oxetanyl, pyranyl, tetrahydrofuranyl, morpholinyl, piperidinyl, piperazinyl, and oxetanyl spiro-connected with azetidinyl or piperidinyl.

The term "aryl" corresponds to a mono- or bi-cyclic aromatic hydrocarbons having from 6 to 12 carbon atoms. For instance, the term "aryl" includes phenyl, biphenyl, or naphthyl. In a preferred embodiment, the aryl is a phenyl.

The term "heteroaryl" as used herein corresponds to an aromatic, mono- or poly-cyclic group comprising between 5 and 14 atoms and comprising at least one heteroatom such as nitrogen, oxygen or sulphur atom. Examples of such mono- and poly-cyclic heteroaryl group may be: pyridinyl, thiazolyl, thiophenyl, furanyl, pyrrolyl, pyrazolyl, imidazolyl, triazolyl, tetrazolyl, benzofuranyl, thianaphthalenyl, indolyl, indolinyl, quinolinyl, isoquinolinyl, benzimidazolyl, tetrahydroquinolinyl, tetrahydroisoquinolinyl, triazinyl, thianthrenyl, isobenzofuranyl, chromenyl, xanthenyl, phenoxanthinyl, isothiazolyl, isoxazolyl, pyrazinyl, pyridazinyl, indolizinyl, isoindolyl, indazolyl, purinyl, quinolizinyl, phtalazinyl, naphthyridinyl, quinoxalinyl, quinazolinyl, cinnolinyl, pteridinyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, indolinyl, isoindolinyl, oxazolidinyl, benzotriazolyl, benzoisoxazolyl, oxindolyl, benzoxazolinyl, benzothienyl, benzothiazolyl, isatinyl, dihydropyridyl, pyrimidinyl, s-triazinyl, oxazolyl, or thiofuranyl. In a preferred embodiment, the heteroaryl group is a pyridinyl, furanyl, pyrazolyl, pyrazinyl, pyrimidinyl, pyridazinyl, and isoxazolyl.

The terms "fused arylheterocycloalkyl" and "fused arylcycloalkyl" correspond to a bicyclic group in which an aryl as above defined is bounded to the heterocycloalkyl or the cycloalkyl as above defined by at least two carbons. In other terms, the aryl shares a carbon bond with the heterocycloalkyl or the cycloalkyl. A fused arylheterocycloalkyl is for instance a benzodioxole (phenyl fused to a dioxole) or an isobenzofurane. A fused arylcycloalkyl is for instance an indane.

The term "halogen" corresponds to a fluorine, chlorine, bromine, or iodine atom, preferably a fluorine, chlorine or bromine.

The expression "substituted by at least" means that the radical is substituted by one or several groups of the list.

The "stereoisomers" are isomeric compounds that have the same molecular formula and sequence of bonded atoms, but differ in the 3D-dimensional orientations of their atoms in space.

The stereoisomers include enantiomers, diastereoisomers, Cis-trans and E-Z isomers, conformers, and anomers. In a preferred embodiment of the invention, the stereoisomers include diastereoisomers and enantiomers. The enantiomers compounds may be prepared from the racemate compound using any purification method known by a skilled person, such as LC/MS and chiral HPLC analysis methods and chiral SFC purification methods.

The "pharmaceutically salts" include inorganic as well as organic acids salts. Representative examples of suitable inorganic acids include hydrochloric, hydrobromic, hydroiodic, phosphoric, and the like. Representative examples of suitable organic acids include formic, acetic, trichloroacetic, trifluoroacetic, propionic, benzoic, cinnamic, citric, fumaric, maleic, methanesulfonic and the like. Further examples of pharmaceutically inorganic or organic acid addition salts include the pharmaceutically salts listed in J. Pharm. Sci. 1977, 66, 2, and in Handbook of Pharmaceutical Salts: Properties, Selection, and Use edited by P. Heinrich Stahl and Camille G. Wermuth 2002. In a preferred embodiment, the salt is selected from the group consisting of maleate, chlorhydrate, bromhydrate, and methanesulfonate. The "pharmaceutically salts" also include inorganic as well as organic base salts. Representative examples of suitable inorganic bases include sodium or potassium salt, an alkaline earth metal salt, such as a calcium or magnesium salt, or an ammonium salt. Representative examples of suitable salts with an organic base includes for instance a salt with methylamine, dimethylamine, trimethylamine, piperidine, morpholine or tris-(2-hydroxyethyl)amine. In a preferred embodiment, the salt is selected from the group consisting of sodium and potassium salt.

As used herein, the terms "treatment", "treat" or "treating" refer to any act intended to ameliorate the health status of patients such as therapy, prevention, prophylaxis and retardation of a disease, in particular an infection, preferably a viral infection. In certain embodiments, such terms refer to the amelioration or eradication of the disease, or symptoms associated with it. In other embodiments, this term refers to minimizing the spread or worsening of the disease, resulting from the administration of one or more therapeutic agents to a subject with such a disease.

As used herein, the terms "subject", "individual" or "patient" are interchangeable and refer to an animal, preferably to a mammal, even more preferably to a human, including adult, child, newborn and human at the prenatal stage. However, the term "subject" can also refer to non-human animals, in particular mammals such as dogs, cats, horses, cows, pigs, sheep and non-human primates, among others.

The terms "quantity," "amount," and "dose" are used interchangeably herein and may refer to an absolute quantification of a molecule.

As used herein, the terms "active principle", "active ingredient" and "active pharmaceutical ingredient" are equivalent and refers to a component of a pharmaceutical composition having a therapeutic effect.

As used herein, the term "therapeutic effect" refers to an effect induced by an active ingredient, or a pharmaceutical composition according to the invention, capable to prevent or to delay the appearance or development of a disease or disorder, or to cure or to attenuate the effects of a disease or disorder.

As used herein, the term "effective amount" refers to a quantity of an active ingredient or of a pharmaceutical composition which prevents, removes or reduces the deleterious effects of the disease, particularly infectious disease. It is obvious that the quantity to be administered can be adapted by the man skilled in the art according to the subject to be treated, to the nature of the disease, etc. In particular, doses and regimen of administration may be function of the nature, of the stage and of the severity of the disease to be treated, as well as of the weight, the age and the global health of the subject to be treated, as well as of the judgment of the doctor.

As used herein, the term "excipient or pharmaceutically acceptable carrier" refers to any ingredient except active ingredients that is present in a pharmaceutical composition. Its addition may be aimed to confer a particular consistency or other physical or gustative properties to the final product. An excipient or pharmaceutically acceptable carrier must be devoid of any interaction, in particular chemical, with the actives ingredients.

The term "modulator", as used herein, refers to a molecule, a chemical or a substance targeting, added, applied or active to another, to modulate a reaction or to prevent an unwanted change. As used herein, the term "modulator" refers to any molecule or compound having an effect on Fe—S cluster binding by the NEET protein. The "modulator" as used herein may be either a stabiliser or a destabiliser. The term "stabiliser" as used herein refers to any compound, chemical, or substance able to stabilize the Fe—S cluster binding the NEET protein. Particularly, a stabiliser reduces the off-rate of iron (Fe) or slows the release of bound Fe—S.

In a preferred embodiment, a compound of the invention as disclosed herein may be a "stabiliser" when it is able to increase the time needed to reach 50% Fe—S cluster bound loss by more than 25%. The term "destabiliser" as used herein refers to any compound, chemical, or substance able to destabilize the Fe—S cluster binding the NEET protein. Particularly, a destabiliser enhances the off-rate of iron (Fe). In a preferred embodiment, a compound of the invention as disclosed herein may be a "destabiliser" when it is able to decrease the time needed to reach 50% Fe—S cluster bound loss by more than 25%. The effect of the modulator can be determined by the protocol detailed in Example B3.

Compounds

The present invention provides new compounds of therapeutic interest.

According to the invention, a compound has the following formula (I):

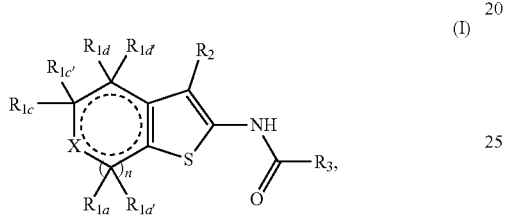

wherein:
X represents:
a —$CR_{1b}R_{1b'}$ unit,
n is 0, 1, or 2;
$R_{1a}$, $R_{1a'}$, $R_{1b}$, $R_{1b'}$, $R_{1c}$, $R_{1c'}$, $R_{1d}$, and $R_{1d'}$ represent independently:
a hydrogen,
a halogen,
a ($C_1$-$C_6$)alkyl, optionally substituted by at least one halogen, preferably optionally substituted by at least one fluorine,
a ($C_1$-$C_6$)alkyloxy,
a cyano,
an aryl optionally substituted by at least one radical selected in the group consisting of:
a halogen,
a ($C_1$-$C_6$)alkyl optionally substituted by at least one halogen, preferably optionally substituted by at least one fluorine,
a hydroxy, and
a ($C_1$-$C_6$)alkyloxy; or
$R_{1a}$ and $R_{1a'}$, $R_{1b}$ and $R_{1b'}$, $R_{1c}$ and $R_{1c'}$, and $R_{1d}$ and $R_{1d'}$ form together a cycloalkyl, preferably a cyclopropyl; or
$R_{1a}$ or $R_{1a'}$ and $R_{1d}$ or $R_{1d'}$ form together a bridged carbocyclyl;
and wherein at least two groups chosen among $R_{1a}$, $R_{1a'}$, $R_{1b}$, $R_{1b'}$, $R_{1c}$, $R_{1c'}$, $R_{1d}$, and $R_{1d'}$ are not a hydrogen;
$R_2$ represents —COOH;
$R_3$ represents:
a 5-10 membered ring, saturated or unsaturated selected in the group consisting of:
an aryl optionally fused to a dioxole,
a heteroaryl,
a cycloalkyl,
a heterocycloalkyl, and
a 5-10 membered bridged carbocyclyl or heterocyclyl, said 5-10 membered ring is optionally substituted by at least one radical selected in the group consisting of:
a halogen,
a ($C_1$-$C_6$)alkyl optionally substituted by at least one halogen, preferably optionally substituted by at least one fluorine, or a ($C_1$-$C_6$)alkyloxy,
a —NH—($C_1$-$C_6$)alkyl or a —N—(($C_1$-$C_6$)alkyl)$_2$, optionally substituted by a heterocycloalkyl or a ($C_1$-$C_6$)alkyloxy,
a —NH-heterocycloalkyl, a —NH-cycloalkyl, a —N(($C_1$-$C_6$)alkyl)-heterocycloalkyl or a —N(($C_1$-$C_6$)alkyl)-cycloalkyl, optionally substituted by a ($C_1$-$C_6$)alkyloxy or a —CO—$R_4$ with $R_4$ being a hydrogen or a ($C_1$-$C_6$)alkyl,
a hydroxy, a —CO—$R_4$ or a —$CO_2R_4$ with $R_4$ being a hydrogen or a ($C_1$-$C_6$)alkyl,
a ($C_1$-$C_6$)alkyloxy optionally substituted by at least one radical selected in the group consisting of a halogen, preferably a fluorine, a hydroxy, a ($C_1$-$C_6$)alkyloxy, a —$NR_5R_6$ with $R_5$ and $R_6$ are independently a hydrogen or a ($C_1$-$C_6$)alkyl, a —$NHCOR_7$, a —$NHCO_2R_7$, with $R_7$ being a ($C_1$-$C_6$)alkyl, a —$CO_2R_4$ with $R_4$ being a hydrogen or a ($C_1$-$C_6$)alkyl, and a heterocycle,
a —$NHCOR_7$ or —$NHCO_2R_7$ with $R_7$ being a ($C_1$-$C_6$)alkyl, and
a heterocycloalkyl, a heterocycloalkyloxy or a spiroheterocycloalkyl, optionally substituted by a ($C_1$-$C_6$)alkyloxy, a hydroxy, a halogen or a ($C_1$-$C_6$)alkyl optionally substituted by a ($C_1$-$C_6$)alkyloxy; and
the stereoisomers, and the pharmaceutical salts thereof; and with the proviso that the compound of formula (I) is not 2-[(4-Chlorobenzoylamino]-6,6-dimethyl-5,7-dihydro-4H-benzothiophene-3-carboxylic acid.

The compound -[(4-Chlorobenzoylamino]-6,6-dimethyl-5,7-dihydro-4H-benzothiophene-3-carboxylic acid has the following formula:

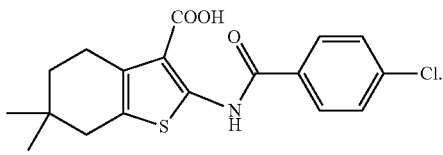 [SMILES: CC1(C)CCc2c(sc(NC(=O)c3ccc(Cl)cc3)c2C(=O)O)C1]

As illustrated by examples, the inventors have demonstrated an antiviral effect for the compounds of formula (I). Accordingly, the compounds can be useful as an antiviral drug, i.e., for treating a viral infection. The compounds can also be useful for treating a bacterial infection, cancer, a metabolic disease, a cardiovascular disease, iron storage disorder or an inflammatory disorder. Accordingly, the present invention relates to a compound for use according to the present invention, said compound having the formula (I):

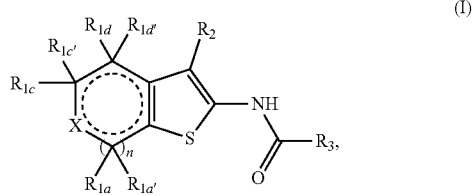

wherein:

X represents:
   a —$CR_{1b}R_{1b'}$ unit, n is 0, 1, or 2;

$R_{1a}$, $R_{1a'}$, $R_{1b}$, $R_{1b'}$, $R_{1c}$, $R_{1c'}$, $R_{1d}$, and $R_{1d'}$ represent independently:
   a hydrogen,
   a halogen,
   a ($C_1$-$C_6$)alkyl, optionally substituted by at least one halogen, preferably optionally substituted by at least one fluorine,
   a ($C_1$-$C_6$)alkyloxy,
   a cyano,
   an aryl optionally substituted by at least one radical selected in the group consisting of:
      a halogen,
      a ($C_1$-$C_6$)alkyl optionally substituted by at least one halogen, preferably optionally substituted by at least one fluorine,
      a hydroxy,
      a ($C_1$-$C_6$)alkyloxy,
   $R_{1a}$ and $R_{1a'}$, $R_{1b}$ and $R_{1b'}$, $R_{1c}$ and $R_{1c'}$, and $R_{1d'}$ and $R_{1d'}$ form together a cycloalkyl, preferably a cyclopropyl; or
   $R_{1a}$ or $R_{1a'}$ and $R_{1d'}$ or $R_{1d'}$ form together a bridged carbocyclyl;

and wherein at least two groups chosen among $R_{1a}$, $R_{1a'}$, $R_{1b}$, $R_{1b'}$, $R_{1c}$, $R_{1c'}$, $R_{1d}$, and $R_{1d'}$ are not a hydrogen;

$R_2$ represents —COOH;

$R_3$ represents:
   a 5-10 membered ring, saturated or unsaturated selected in the group consisting of:
      an aryl optionally fused to a dioxole,
      a heteroaryl,
      a cycloalkyl,
      a heterocycloalkyl, and
      a 5-10 membered bridged carbocyclyl or heterocyclyl, said 5-10 membered ring is optionally substituted by at least one radical selected in the group consisting of:
         a halogen,
         a ($C_1$-$C_6$)alkyl optionally substituted by at least one halogen, preferably optionally substituted by at least one fluorine, or a ($C_1$-$C_6$)alkyloxy,
         a —NH—($C_1$-$C_6$)alkyl or a —N—(($C_1$-$C_6$)alkyl)$_2$, optionally substituted by a heterocycloalkyl or a ($C_1$-$C_6$)alkyloxy,
         a —NH-heterocycloalkyl, a —NH-cycloalkyl, a —N(($C_1$-$C_6$)alkyl)-heterocycloalkyl or a —N(($C_1$-$C_6$)alkyl)-cycloalkyl, optionally substituted by a ($C_1$-$C_6$)alkyloxy or a —CO—$R_4$ with $R_4$ being a hydrogen or a ($C_1$-$C_6$)alkyl,
         a hydroxy, a —CO—$R_4$ or a —$CO_2R_4$ with $R_4$ being a hydrogen or a ($C_1$-$C_6$)alkyl,
         a ($C_1$-$C_6$)alkyloxy optionally substituted by at least one radical selected in the group consisting of a halogen, preferably a fluorine, a hydroxy, a ($C_1$-$C_6$)alkyloxy, a —$NR_5R_6$ with $R_5$ and $R_6$ are independently a hydrogen or a ($C_1$-$C_6$)alkyl, a —$NHCOR_7$, a —$NHCO_2R_7$, with $R_7$ being a ($C_1$-$C_6$)alkyl, a —$CO_2R_4$ with $R_4$ being a hydrogen or a ($C_1$-$C_6$)alkyl, and a heterocycle,
         a —$NHCOR_7$ or —$NHCO_2R_7$ with $R_7$ being a ($C_1$-$C_6$)alkyl, and
         a heterocycloalkyl, a heterocycloalkyloxy or a spiroheterocycloalkyl, optionally substituted by a ($C_1$-$C_6$)alkyloxy, a hydroxy, a halogen or a ($C_1$-$C_6$)alkyl optionally substituted by a ($C_1$-$C_6$)alkyloxy, and the stereoisomers, and the pharmaceutical salts thereof.

According to the invention, at least two groups chosen among $R_{1a}$, $R_{1a'}$, $R_{1b}$, $R_{1b'}$, $R_{1c}$, $R_{1c'}$, $R_{1d}$, and $R_{1d'}$ are not a hydrogen. This excludes the compounds of formula (I) in which all $R_{1a}$, $R_{1a'}$, $R_{1b}$, $R_{1b'}$, $R_{1c}$, $R_{1c'}$, $R_{1d}$, and $R_{1d'}$ are a hydrogen or in which only one of $R_{1a}$, $R_{1a'}$, $R_{1b}$, $R_{1b'}$, $R_{1c}$, $R_{1c'}$, $R_{1d}$, and $R_{1d'}$ is a group as defined herein and the others are a hydrogen. Thus, in a particular aspect, at least two, three or four groups chosen among $R_{1a}$, $R_{1a'}$, $R_{1b}$, $R_{1b'}$, $R_{1c}$, $R_{1c'}$, $R_{1d}$, $R_{1d'}$ are not a hydrogen.

Preferably, $R_{1a}$, $R_{1a'}$, $R_{1b}$, $R_{1b'}$, $R_{1c}$, $R_{1c'}$, $R_{1d}$, and $R_{1d'}$ represent independently a hydrogen or a ($C_1$-$C_6$)alkyl, preferably a ($C_1$-$C_3$)alkyl, still more particularly a methyl, optionally substituted by at least one halogen, preferably optionally substituted by at least one fluorine (e.g., trifluoromethyl).

More preferably, the compound of Formula (I) has $R_{1a}$=$R_{1a'}$, $R_{1b}$=$R_{1b'}$, $R_{1c}$=$R_{1c'}$, and $R_{1d}$=$R_{1d'}$.

In a particular embodiment, two groups chosen among $R_{1a}$, $R_{1a'}$, $R_{1b}$, $R_{1b'}$, $R_{1c}$, $R_{1c'}$, $R_{1d}$, and $R_{1d}$ represent independently a hydrogen or a ($C_1$-$C_6$)alkyl, preferably a ($C_1$-$C_3$)alkyl, still more particularly a methyl, optionally substituted by at least one halogen, preferably optionally substituted by at least one fluorine. Preferably, two groups chosen among $R_{1a}$, $R_{1a'}$, $R_{1b}$, $R_{1b'}$, $R_{1c}$, $R_{1c'}$, $R_{1d}$, and $R_{1d'}$ represent a methyl and the others are a hydrogen. In a preferred embodiment when n is 1 or 2, preferably when n is 1, $R_{1b}$ and Rib-represent a methyl and $R_{1a}$, $R_{1a'}$, $R_{1c}$, $R_{1c'}$, $R_{1d}$, and $R_{1d}$ represent a hydrogen. In a further preferred embodiment when n is 1 or 2, preferably when n is 1, $R_{1c}$ and $R_{1c'}$ represent a methyl and $R_{1a}$, $R_{1a'}$, $R_{1b}$, $R_{1b'}$, $R_{1d}$, and $R_{1d'}$ represent a hydrogen.

In a further preferred embodiment when n is 1 or 2, preferably when n is 1, $R_{1d}$ and $R_{1d'}$ represent a methyl and $R_{1a}$, $R_{1a'}$, $R_{1b}$, $R_{1b'}$, $R_{1c}$, and $R_{1c'}$ represent a hydrogen. In a further preferred embodiment when n is 0, $R_{1d}$ and $R_{1d'}$ represent a methyl and $R_{1b}$, $R_{1b'}$, $R_{1c}$, and $R_{1c'}$ represent a hydrogen.

In a further particular embodiment, at least three groups, preferably three or four groups, chosen among $R_{1a}$, $R_{1a'}$, $R_{1b}$, $R_{1b'}$, $R_{1c}$, $R_{1c'}$, $R_{1d}$, and $R_{1d'}$ represent independently a hydrogen or a ($C_1$-$C_6$)alkyl, preferably a ($C_1$-$C_3$)alkyl, optionally substituted by at least one halogen, preferably optionally substituted by at least one fluorine.

In a preferred embodiment, three groups chosen among $R_{1a}$, $R_{1a'}$, $R_{1b}$, $R_{1b'}$, $R_{1c}$, $R_{1c'}$, $R_{1d}$, and $R_{1d'}$ represent independently a hydrogen or a ($C_1$-$C_6$)alkyl, preferably a ($C_1$-$C_3$)alkyl, optionally substituted by at least one halogen, preferably optionally substituted by at least one fluorine. Preferably three groups chosen among $R_{1a}$, $R_{1a'}$, $R_{1b}$, $R_{1b'}$, $R_{1c}$, $R_{1c'}$, $R_{1d}$, and $R_{1d'}$ represent a methyl and the others are a hydrogen. In a preferred embodiment when n is 1 or 2, preferably when n is 1, $R_{1b}$ and $R_{1b'}$ represent a methyl, $R_{1a}$, $R_{1a'}$, $R_{1c}$, and $R_{1c'}$ represent a hydrogen and one of $R_{1d}$ and $R_{1d'}$ represent a methyl, the other represent a hydrogen. In a preferred embodiment when n is 0, $R_{1b}$ and $R_{1b'}$ represent a methyl, $R_{1c}$, and $R_{1c'}$ represent a hydrogen and one of $R_{1d}$, and $R_{1d'}$ represent a methyl, the other represent a hydrogen.

In a further preferred embodiment, four groups chosen among $R_{1a}$, $R_{1a'}$, $R_{1b}$, $R_{1b'}$, $R_{1c}$, $R_{1c'}$, $R_{1d}$, and $R_{1d'}$ represent independently a hydrogen or a ($C_1$-$C_6$)alkyl, preferably a ($C_1$-$C_3$)alkyl, optionally substituted by at least one halogen, preferably optionally substituted by at least one fluorine. Preferably four groups chosen among $R_{1a}$, $R_{1a'}$, $R_{1b}$, $R_{1b'}$, $R_{1c}$, $R_{1c'}$, $R_{1d}$, and $R_{1d'}$ represent a methyl and the others are a hydrogen. In a preferred embodiment when n is 1 or 2, preferably when n is 1, $R_{1a}$, $R_{1a'}$, $R_{1c}$ and $R_{1c'}$ represent a methyl, and $R_{1b}$, $R_{1b'}$, $R_{1d}$, and $R_{1d'}$ represent a hydrogen.

In a further particular embodiment, $R_{1b}$ and $R_{1b'}$ form together a cyclopropyl, and $R_{1a}$, $R_{1a'}$, $R_{1c}$, $R_{1c'}$, $R_{1d}$, and $R_{1d'}$ are a hydrogen. In a preferred embodiment when n is 1, $R_{1b}$ and $R_{1b'}$ form together a cyclopropyl and $R_{1a}$, $R_{1a'}$, $R_{1c}$, $R_{1c'}$, $R_{1d}$, and $R_{1d'}$ are a hydrogen.

In a further particular embodiment when n is 1, $R_{1a}$ or $R_{1a'}$ and $R_{1d}$ or $R_{1d'}$ form together a bridged carbocyclyl, and $R_{1b}$, $R_{1b'}$, $R_{1c}$, and $R_{1c'}$, are preferably a hydrogen. In a further particular embodiment of the invention, $R_{1a}$, $R_{1a'}$, $R_{1b}$, $R_{1b'}$, $R_{1c}$, $R_{1c'}$, $R_{1d}$, and $R_{1d'}$ represent independently a hydrogen, a halogen, preferably a fluorine, or an optionally substituted aryl and at least two groups chosen among $R_{1a}$, $R_{1a'}$, $R_{1b}$, $R_{1b'}$, $R_{1c}$, $R_{1c'}$, $R_{1d}$, and $R_{1d'}$ are not a hydrogen. The aryl, preferably a phenyl, can be substituted by at least one radical selected in the group consisting of a halogen, a $(C_1-C_6)$alkyl optionally substituted by at least one halogen, preferably optionally substituted by at least one fluorine, a hydroxy, and a $(C_1-C_6)$alkyloxy. In a preferred embodiment, one of $R_{1b}$ and $R_{1b'}$ is a phenyl and the other is cyano and $R_{1a}$, $R_{1a'}$, $R_{1c}$, $R_{1c'}$, $R_{1d}$, and $R_{1d'}$ are a hydrogen. In a further preferred embodiment, $R_{1b}$ and $R_{1b'}$ represent a fluorine and $R_{1a}$, $R_{1a'}$, $R_{1c}$, $R_{1c'}$, $R_{1d}$, and $R_{1d'}$ are a hydrogen.

According to the invention, $R_2$ represents —COOH.

It is also described herein compounds of formula (I) as described above in any particular embodiment in which $R_2$ represents:
- a —$CO_2R_4$ with $R_4$ being a $(C_1-C_6)$alkyl; or
- a 5-10 membered ring, saturated or unsaturated selected in the group consisting of an aryl, a heteroaryl, a cycloalkyl, and a heterocycloalkyl, said 5-10 membered ring is optionally substituted by a hydroxy, a halogen, or a $(C_1-C_6)$alkyl optionally substituted by at least one halogen, preferably optionally substituted by at least one fluorine, and n, $R_{1a}$, $R_{1a'}$, $R_{1c}$, $R_{1c'}$, $R_{1d}$, $R_{1d'}$ and $R_3$ are such as defined herein.

In one embodiment, the 5-10 membered ring is selected so as to be an (bio)isostere of a carboxyl group.

In a preferred embodiment, $R_2$ represents a heteroaryl, preferably a tetrazolyl, an aryl optionally substituted by a hydroxy, preferably a phenyl substituted by a hydroxy, or a —$CO_2R_4$ with $R_4$ being a hydrogen or a $(C_1-C_6)$alkyl, preferably an ethyl. In a more preferred embodiment, $R_2$ represents a —$CO_2R_4$ with $R_4$ being a hydrogen, i.e. —COOH.

According to the present invention, the compounds and the compounds for use are of formula (I) have $R_3$ which represents:
- a 5-10 membered ring, saturated or unsaturated selected in the group consisting of:
  - an aryl optionally fused to a dioxole,
  - a heteroaryl,
  - a cycloalkyl,
  - a heterocycloalkyl, and
  - a 5-10 membered bridged carbocyclyl or heterocyclyl,
  said 5-10 membered ring is optionally substituted by at least one radical selected in the group consisting of:
    - a halogen,
    - a $(C_1-C_6)$alkyl optionally substituted by at least one halogen, preferably optionally substituted by at least one fluorine, or a $(C_1-C_6)$alkyloxy,
    - a —NH—$(C_1-C_6)$alkyl or a —N—$((C_1-C_6)$alkyl$)_2$, optionally substituted by a heterocycloalkyl or a $(C_1-C_6)$alkyloxy,
    - a —NH-heterocycloalkyl, a —NH-cycloalkyl, a —N$((C_1-C_6)$alkyl$)$-heterocycloalkyl or a —N$((C_1-C_6)$alkyl$)$-cycloalkyl, optionally substituted by a $(C_1-C_6)$alkyloxy or a —CO—$R_4$ with $R_4$ being a hydrogen or a $(C_1-C_6)$alkyl,
    - a hydroxy, a —CO—$R_4$ or a —$CO_2R_4$ with $R_4$ being a hydrogen or a $(C_1-C_6)$alkyl,
    - a $(C_1-C_6)$alkyloxy optionally substituted by at least one radical selected in the group consisting of a halogen, preferably a fluorine, a hydroxy, a $(C_1-C_6)$alkyloxy, a —$NR_5R_6$ with $R_5$ and $R_6$ are independently a hydrogen or a $(C_1-C_6)$alkyl, a —NH-$COR_7$, a —$NHCO_2R_7$, with $R_7$ being a $(C_1-C_6)$alkyl, a —$CO_2R_4$ with $R_4$ being a hydrogen or a $(C_1-C_6)$alkyl, and a heterocycle,
    - a —$NHCOR_7$ or —$NHCO_2R_7$ with $R_7$ being a $(C_1-C_6)$alkyl, and
    - a heterocycloalkyl, a heterocycloalkyloxy or a spiroheterocycloalkyl, optionally substituted by a $(C_1-C_6)$alkyloxy, a hydroxy, a halogen or a $(C_1-C_6)$alkyl optionally substituted by a $(C_1-C_6)$alkyloxy, and n, $R_{1a}$, $R_{1a'}$, $R_{1c}$, $R_{1c'}$, $R_{1d}$, $R_{1d'}$ and $R_2$ are such as defined herein.

In a particular embodiment, $R_3$ represents a phenyl, a pyridinyl, a pyridazinyl, a pyrimidinyl, a pyrazinyl, an imidazolyl, or a pyrazolyl, preferably a phenyl, optionally substituted by at least one radical as above defined.

In a preferred embodiment, $R_3$ represents a phenyl optionally substituted by at least one radical selected in the group consisting of:
- a halogen, preferably a fluorine or a bromine;
- a $(C_1-C_6)$alkyl optionally substituted by at least one halogen, preferably optionally substituted by at least one fluorine,
- a —NH—$(C_1-C_6)$alkyl, a —N—$((C_1-C_6)$alkyl$)_2$, optionally substituted by a $(C_1-C_6)$alkyloxy, a heterocycloalkyl selected in the group consisting of a tetrahydropyranyl, a tetrahydrofuranyl, an oxetanyl, a piperidinyl, and an azetidinyl, or a cycloalkyl, preferably a cyclobutyl or a cyclohexyl, said cycloalkyl and heterocycloalkyl are optionally substituted by a $(C_1-C_6)$alkyloxy or a —CO—$R_4$ with $R_4$ being a hydrogen or a $(C_1-C_6)$alkyl,
- a —NH-heterocycloalkyl, a —NH-cycloalkyl, a —N$((C_1-C_6)$alkyl$)$-heterocycloalkyl, or a —N$((C_1-C_6)$alkyl$)$-cycloalkyl, preferably a —NH-tetrahydropyranyl, a —N$(CH_3)$-tetrahydropyranyl, a —NH-tetrahydrofuranyl, a NH-piperidinyl, a —NH-azetidinyl, a —NH-oxetanyl, a-NH-cyclohexyl, or a —N$(CH_3)$-cyclobutyl, said —NH-heterocycloalkyl, —NH-cycloalkyl, —N$((C_1-C_6)$alkyl$)$-heterocycloalkyl, or —N$((C_1-C_6)$alkyl$)$-cycloalkyl are optionally substituted by a $(C_1-C_6)$alkyloxy or a —CO—$R_4$ with $R_4$ being a hydrogen or a $(C_1-C_6)$alkyl,
- a $(C_1-C_6)$alkyloxy optionally substituted by at least one radical selected in the group consisting of a halogen, preferably a fluorine, a $(C_1-C_6)$alkyloxy, and a heterocycle, preferably a tetrahydropyranyl, or an oxetanyl,
- a heterocycloalkyl, preferably a morpholinyl, a piperidinyl, a piperazinyl, a tetrahydropyranyl, and an azetidinyl, or a spiroheterocycloalkyl, preferably a piperidinyl spiro-connected with an oxetanyl, said heterocycloalkyl and spiroheterocyclolakyl are optionally substituted by a $(C_1-C_6)$alkyloxy, a hydroxy, a halogen or a $(C_1-C_6)$alkyl optionally substituted by a $(C_1-C_6)$alkyloxy, and a heterocycloalkyloxy, preferably a tetrahydropyranyloxy.

In a preferred embodiment, $R_3$ is a phenyl, i.e. an unsubstituted phenyl.

In a further preferred embodiment, $R_3$ is a phenyl substituted by at least one radical selected in the group consisting of a halogen, preferably a chlorine, a fluorine, or a bromine, a methyl, a trifluoromethyl, a hydroxy, a methoxy, a difluoromethoxy, a trifluoromethoxy, an ethoxy substituted by a methoxy ($—O—(CH_2)_2—OCH_3$) or by a hydroxy ($—O—(CH_2)_2—OH$), and a $—NHCOR_7$ with $R_7$ being a methyl.

In a further preferred embodiment, $R_3$ is a phenyl substituted by a heterocycle, preferably an azetidinyl, an oxatenyl, a morpholinyl, a piperidinyl, a piperazinyl, a tetrahydropyranyl, or an azetidinyl or a piperidinyl spiro-connected with an oxetanyl, said heterocycle being optionally substituted by a methoxy, an ethoxy, a hydroxy, a methyl optionally substituted by a methoxy, a halogen, preferably a fluorine.

In a further preferred embodiment, $R_3$ is a phenyl substituted by a $—NH—(C_1-C_6)$alkyl or a $—N—((C_1-C_6)$alkyl$)_2$, optionally substituted by a heterocycloalkyl or a $(C_1-C_6)$alkyloxy, preferably a $—NH—CH_2$-azetidinyl, a $—NH—CH_2$-oxatenyl, a $—NH—(CH_2)_2—OCH_3$, a $—NH—(CH_2)_3—OCH_3$, a $—NH—CH_2$-tetrahydropyranyl, a $—N(CH_3)—CH_2$-tetrahydropyranyl, and a $—N(CH_3)—(CH_2)_2—OCH_3$.

In a further preferred embodiment, $R_3$ is a phenyl substituted by a $—NH$-heterocycloalkyl, a $—NH$-cycloalkyl, a $—N((C_1-C_6)$alkyl)-cycloalkyl, or a $—N((C_1-C_6)$alkyl)-heterocycloalkyl, optionally substituted by a $(C_1-C_6)$alkyloxy or a $—CO—R_4$ with $R_4$ being a hydrogen or a $(C_1-C_6)$alkyl, preferably a $—NH—$ tetrahydropyranyl, a $—NH$-tetrahydrofuranyl, a $—NH$-oxetanyl, a $—NH$-piperidinyl optionally substituted by a $—CO—CH_3$, a $—NH$-azetidinyl optionally substituted by a $—CO—CH_3$, a $—N(CH_3)$-azetidinyl optionally substituted by a $—CO—CH3$, a $—N(CH_3)$-tetrahydropyranyl, and a $—NH$-cyclohexyl.

In a further preferred embodiment, $R_3$ is a phenyl substituted by a $(C_1-C_6)$alkyloxy, preferably a methoxy, an ethoxy, a propoxy, a butoxy or a pentoxy substituted by a radical selected in the group consisting of a $—NHCO_2R_7$, with $R_7$ being a methyl, a $—NR_5R_6$ with $R_5$ and $R_6$ are a hydrogen, a $—CO_2R_4$ with $R_4$ being a methyl, and a heterocycle, preferably a tetrahydropyranyl or a oxetanyl.

In a further preferred embodiment, $R_3$ is a phenyl substituted by a heterocycloalkyloxy, preferably a tetrahydropyranyloxy.

In a more preferred embodiment, $R_3$ is a radical selected in the group consisting of:

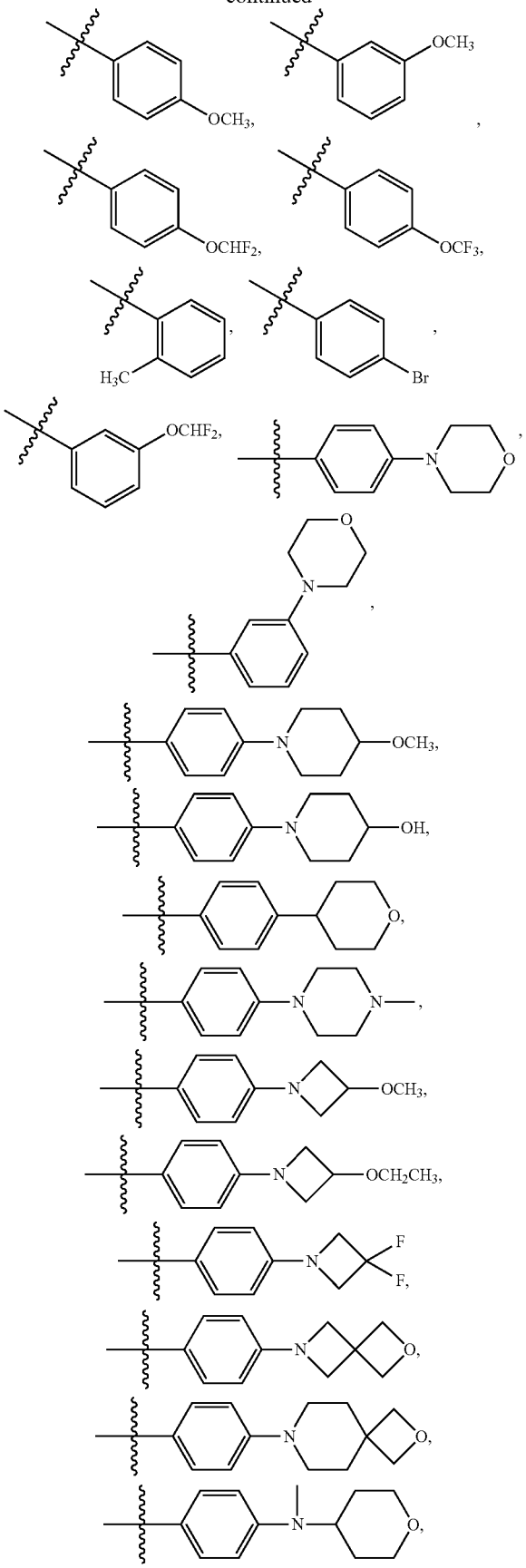

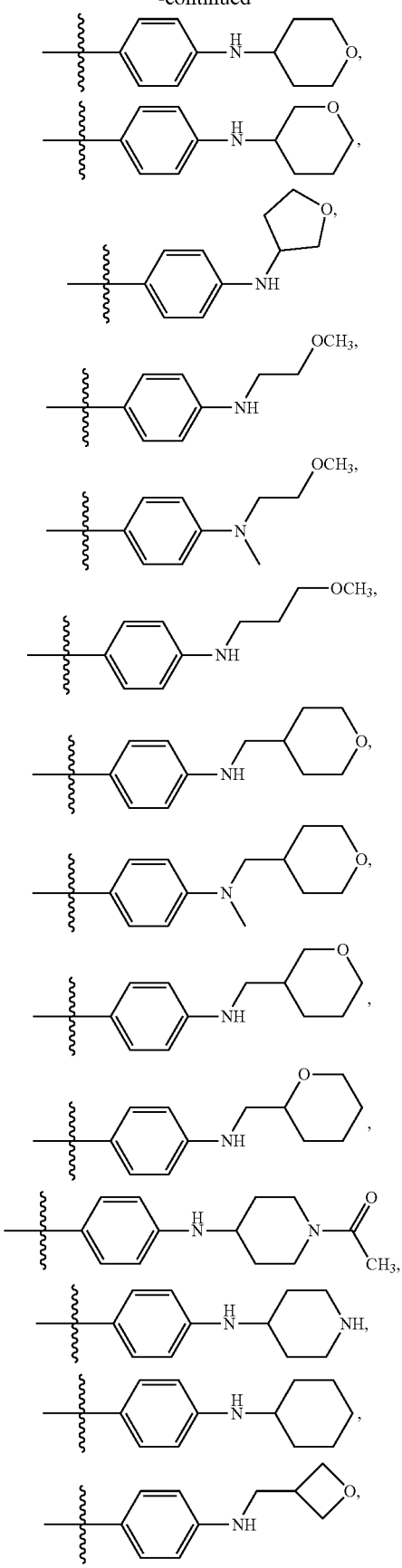
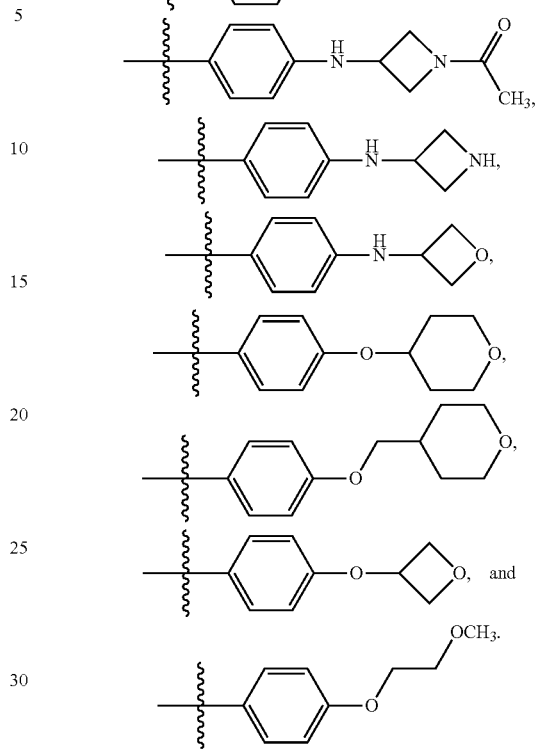

In a further particular embodiment, $R_3$ is an aryl fused to a dioxole, preferably a benzo[1,3]dioxole optionally substituted by at least one fluorine.

In a further particular embodiment, $R_3$ is a heteroaryl, a pyridinyl, a pyridazinyl, a pyrimidinyl, a pyrazolyl, an imidazolyl, or a pyrazinyl, preferably a pyridinyl, a pyridazinyl, a pyrimidinyl, and a pyrazolyl, said heteroaryl being optionally substituted by at least one radical as above defined.

In a preferred embodiment, $R_3$ represents a pyridinyl, a pyridazinyl, a pyrimidinyl, a pyrazolyl, an imidazolyl, or a pyrazinyl, preferably a pyridinyl, a pyridazinyl, a pyrimidinyl, and a pyrazolyl optionally substituted by at least one radical selected in the group consisting of:
- a $(C_1-C_6)$alkyl optionally substituted by at least one halogen, preferably a fluorine, or by a heterocycloalkyl, preferably a tetrahydropyranyl,
- a $(C_1-C_6)$alkyloxy optionally substituted by at least one radical selected in the group consisting of a halogen, preferably a fluorine,
- a heterocycloalkyl, preferably a morpholinyl, and
- a heterocycloalkyloxy, preferably a tetrahydropyranyloxy.

In a further preferred embodiment, $R_3$ represents a pyridinyl, a pyridazinyl, a pyrimidinyl, and a pyrazolyl unsubstituted.

In a further preferred embodiment, $R_3$ represents a pyridinyl, a pyridazinyl, a pyrimidinyl, and a pyrazolyl substituted by at least one radical selected in the group consisting of a $(C_1-C_6)$alkyl, preferably a methyl, a $(C_1-C_6)$alkyloxy, preferably a methoxy, a $(C_1-C_6)$alkyl substituted by a $(C_1-C_6)$alkyloxy, preferably a —$(CH_2)_2$—$OCH_3$, a tetrahydropyranyl, and a —$CH_2$-tetrahydropyranyl.

In a more preferred embodiment, R₃ is a radical selected in the group consisting of:
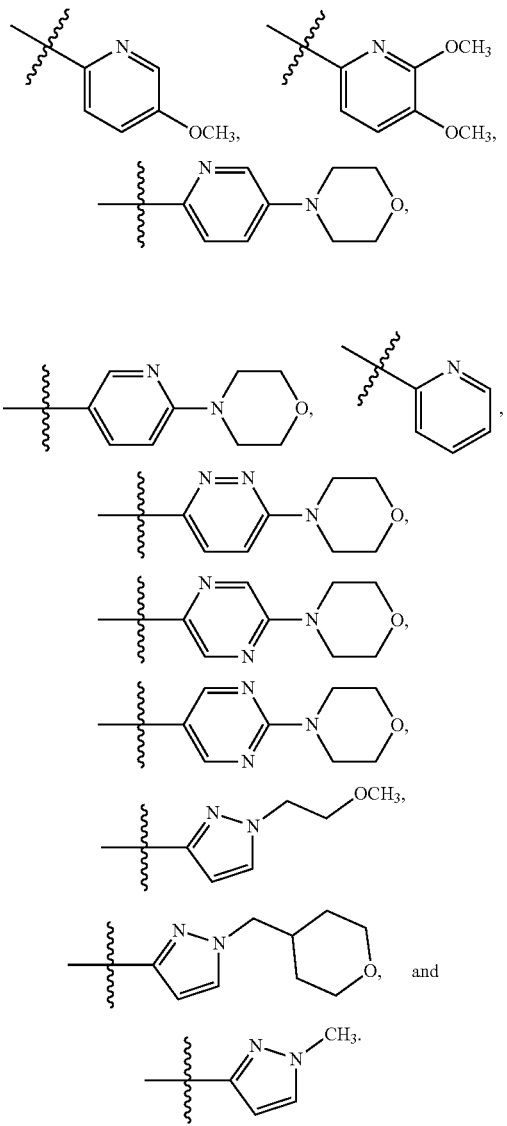
In a more preferred embodiment, a compound and a compound for use of formula (I) according to the present invention is selected in the group consisting of compounds of the table A below:
TABLE A
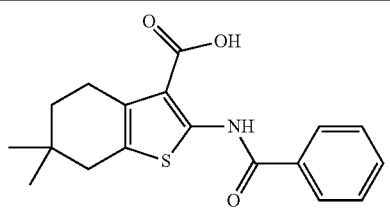
Compound #15
TABLE A-continued
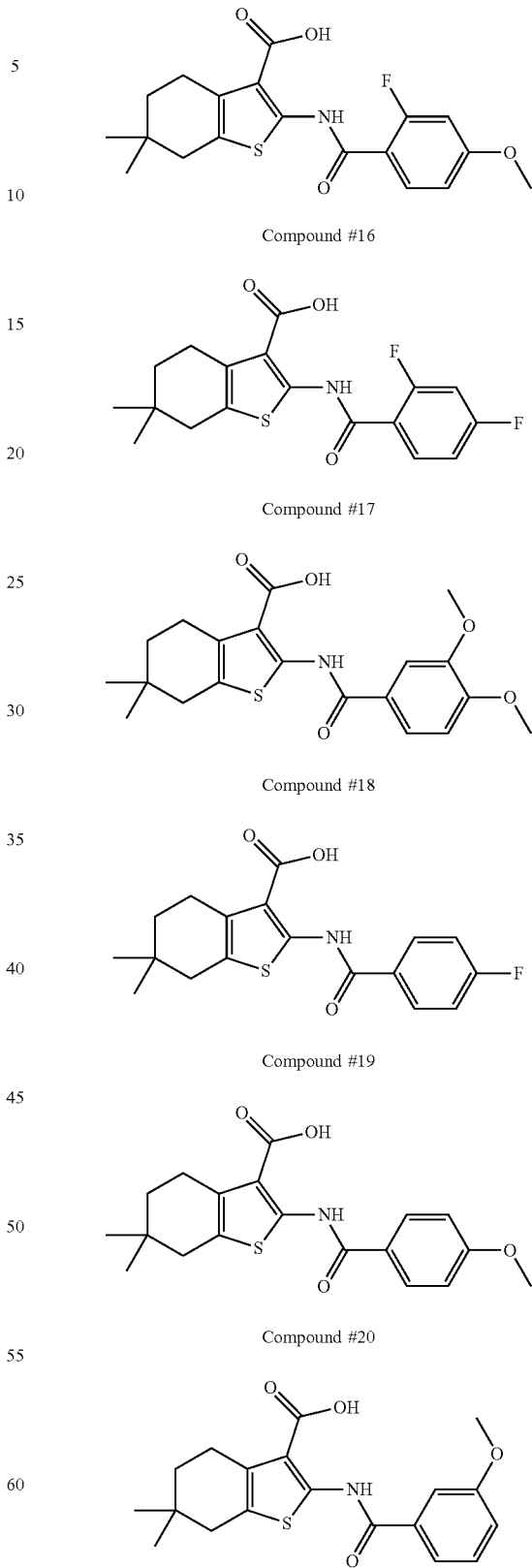
Compound #16
Compound #17
Compound #18
Compound #19
Compound #20
Compound #21

TABLE A-continued
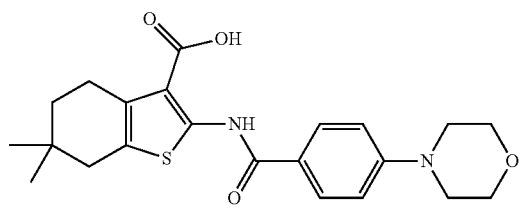 [SMILES: CC1(C)CCc2c(sc(NC(=O)c3ccc(N4CCOCC4)cc3)c2C(=O)O)C1]
Compound #22
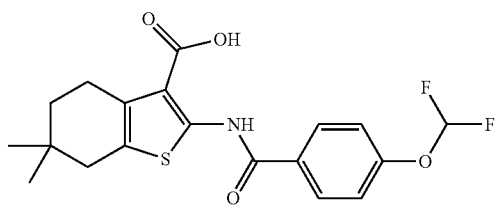
Compound #23
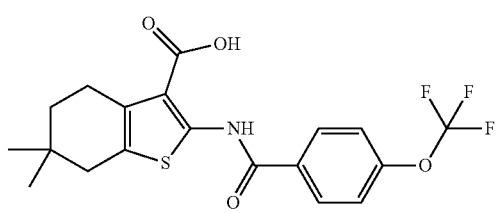 [SMILES: CC1(C)CCc2c(sc(NC(=O)c3ccc(OC(F)(F)F)cc3)c2C(=O)O)C1]
Compound #24
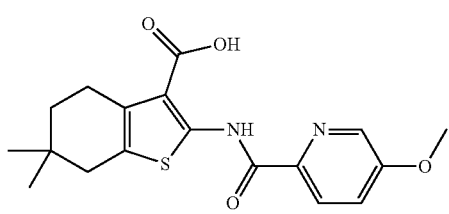
Compound #25
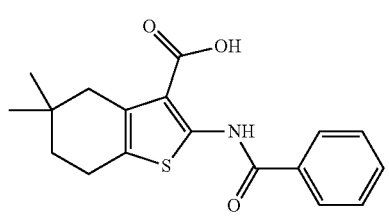 [SMILES: CC1(C)CCc2sc(NC(=O)c3ccccc3)c(C(=O)O)c2C1]
Compound #26
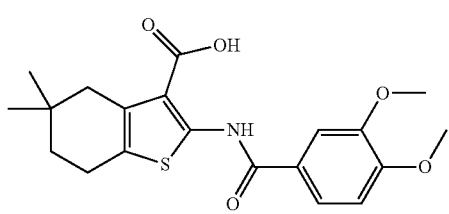
Compound #27
TABLE A-continued
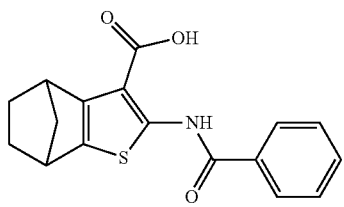 [SMILES: O=C(Nc1sc2c(c1C(=O)O)C1CCC2C1)c1ccccc1]
Compound #28
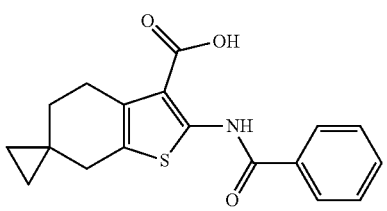 [SMILES: O=C(Nc1sc2c(c1C(=O)O)CCC1(CC1)C2)c1ccccc1]
Compound #29
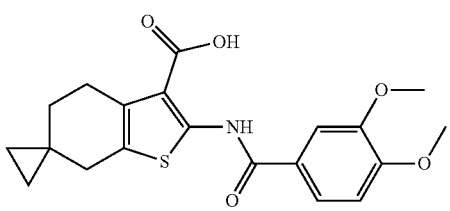 [SMILES: COc1ccc(C(=O)Nc2sc3c(c2C(=O)O)CCC2(CC2)C3)cc1OC]
Compound #30
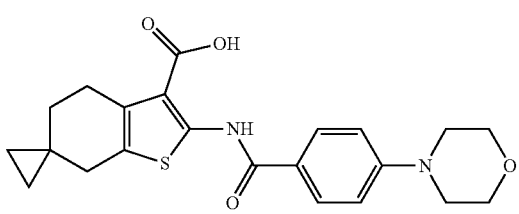 [SMILES: O=C(Nc1sc2c(c1C(=O)O)CCC1(CC1)C2)c1ccc(N2CCOCC2)cc1]
Compound #31
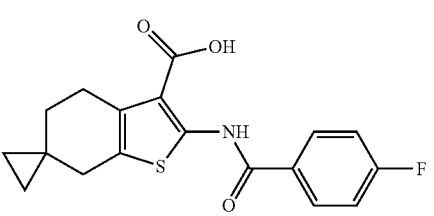 [SMILES: O=C(Nc1sc2c(c1C(=O)O)CCC1(CC1)C2)c1ccc(F)cc1]
Compound #32
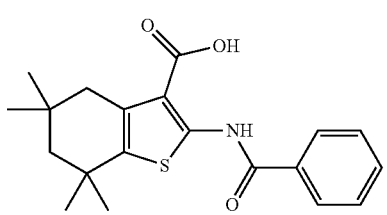 [SMILES: CC1(C)Cc2c(sc(NC(=O)c3ccccc3)c2C(=O)O)C(C)(C)C1]
Compound #33

TABLE A-continued
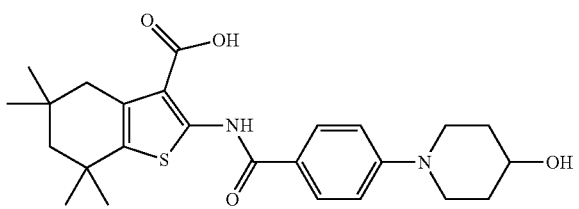 [SMILES: CC1(C)Cc2c(sc(NC(=O)c3ccc(N4CCC(O)CC4)cc3)c2C(=O)O)C(C)(C)C1]
Compound #34
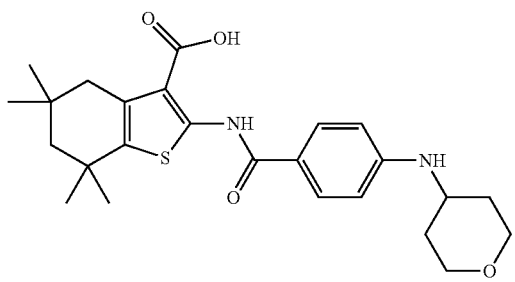 [SMILES: CC1(C)Cc2c(sc(NC(=O)c3ccc(NC4CCOCC4)cc3)c2C(=O)O)C(C)(C)C1]
Compound #35
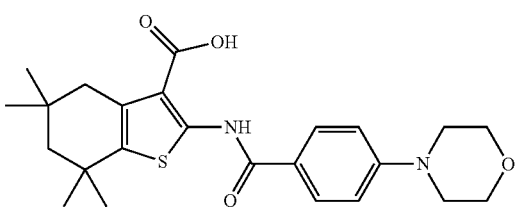 [SMILES: CC1(C)Cc2c(sc(NC(=O)c3ccc(N4CCOCC4)cc3)c2C(=O)O)C(C)(C)C1]
Compound #36
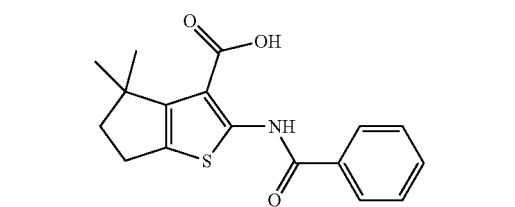 [SMILES: CC1(C)CCc2sc(NC(=O)c3ccccc3)c(C(=O)O)c21]
Compound #37
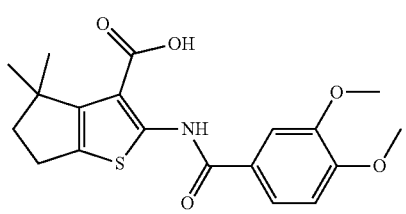
Compound #38
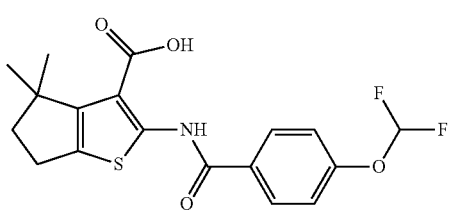 [SMILES: CC1(C)CCc2sc(NC(=O)c3ccc(OC(F)F)cc3)c(C(=O)O)c21]
Compound #39
TABLE A-continued
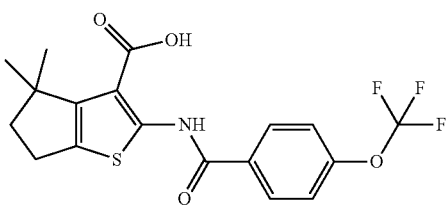 [SMILES: CC1(C)CCc2sc(NC(=O)c3ccc(OC(F)(F)F)cc3)c(C(=O)O)c21]
Compound #40
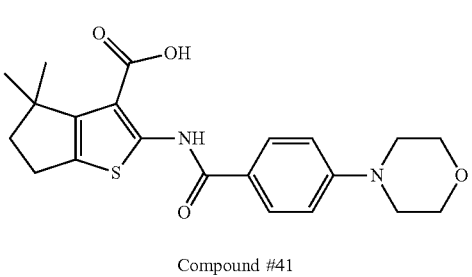
Compound #41
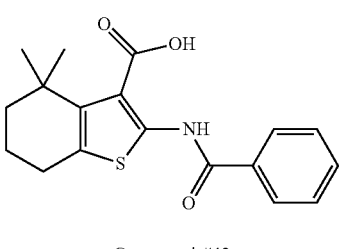
Compound #42
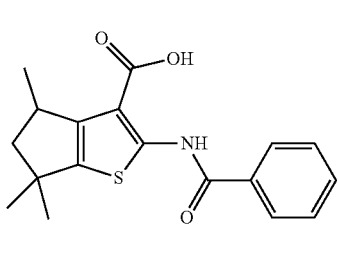 [SMILES: CC1CC(C)(C)c2sc(NC(=O)c3ccccc3)c(C(=O)O)c21]
Compound #43
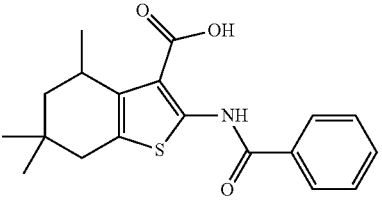 [SMILES: CC1CC(C)(C)Cc2sc(NC(=O)c3ccccc3)c(C(=O)O)c21]
Compound #44
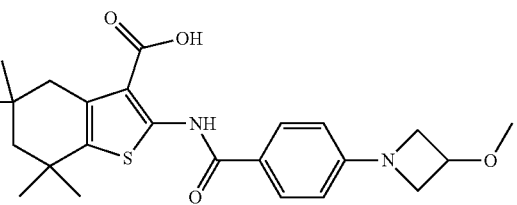
Compound #58

TABLE A-continued
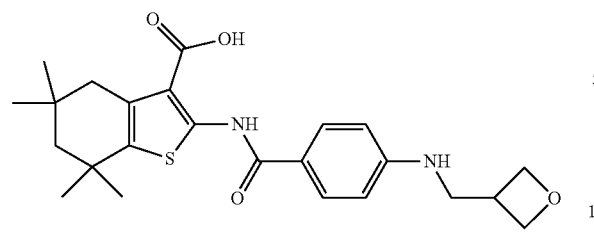
Compound #59
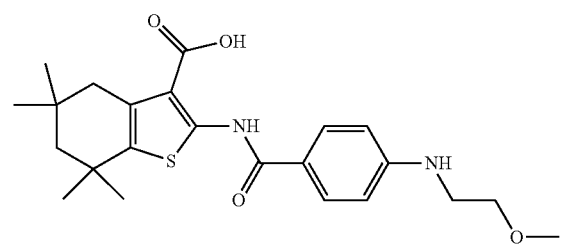
Compound #60
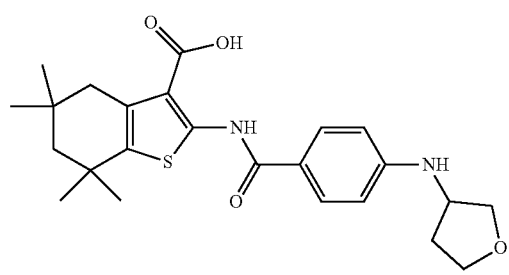 [SMILES: CC1(C)Cc2c(sc(NC(=O)c3ccc(NC4CCOC4)cc3)c2C(=O)O)C(C)(C)C1]
Compound #61
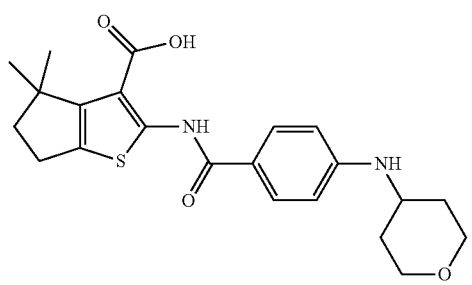 [SMILES: CC1(C)CCc2sc(NC(=O)c3ccc(NC4CCOCC4)cc3)c(C(=O)O)c21]
Compound #62
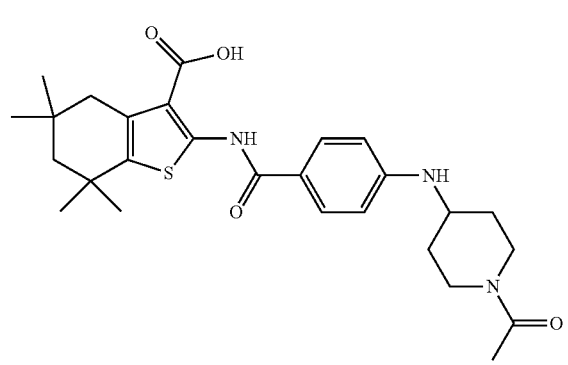 [SMILES: CC(=O)N1CCC(Nc2ccc(C(=O)Nc3sc4c(c3C(=O)O)CC(C)(C)CC4(C)C)cc2)CC1]
Compound #63
TABLE A-continued
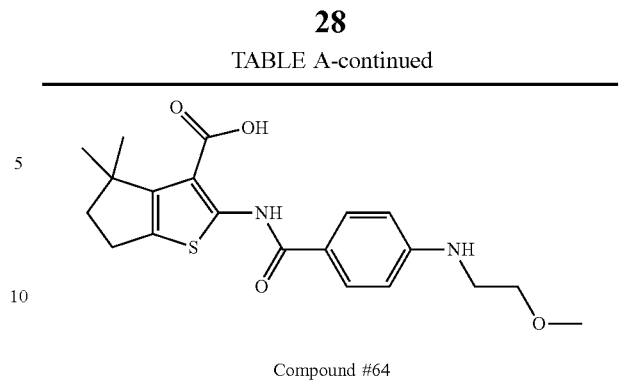
Compound #64
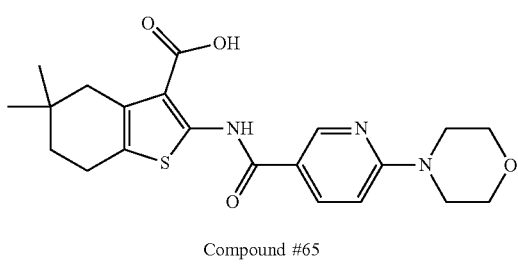
Compound #65
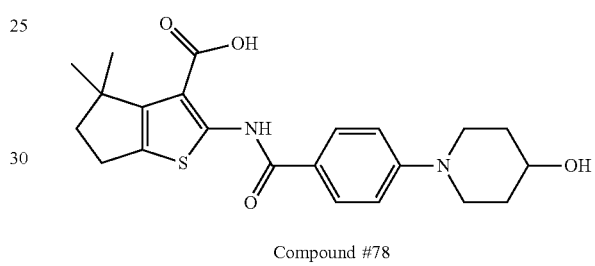
Compound #78
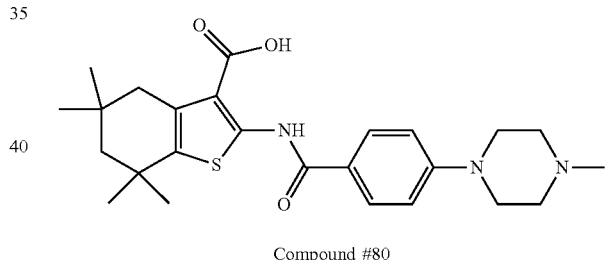
Compound #80
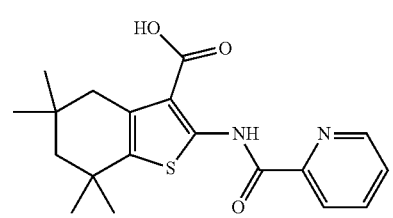 [SMILES: CC1(C)Cc2c(sc(NC(=O)c3ccccn3)c2C(=O)O)C(C)(C)C1]
Compound #90
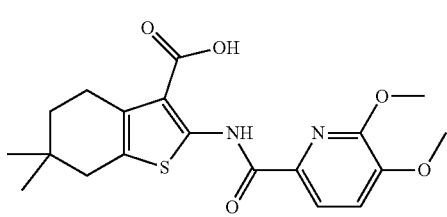
Compound #94

TABLE A-continued
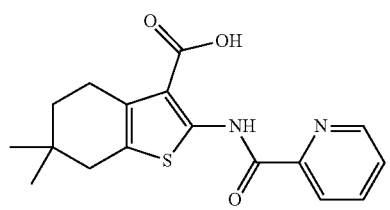
Compound #96
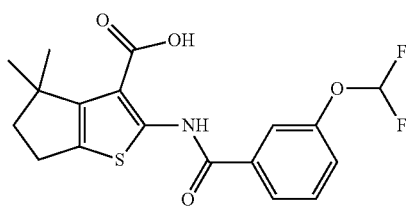 [SMILES: CC1(C)CCc2sc(NC(=O)c3cccc(OC(F)F)c3)c(C(=O)O)c21]
Compound #98
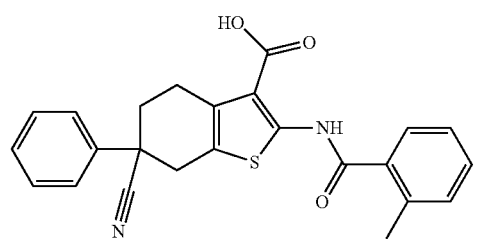 [SMILES: Cc1ccccc1C(=O)Nc1sc2c(c1C(=O)O)CCC(C#N)(c1ccccc1)C2]
Compound #105
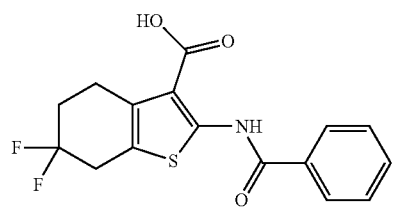 [SMILES: O=C(Nc1sc2c(c1C(=O)O)CCC(F)(F)C2)c1ccccc1]
Compound #117
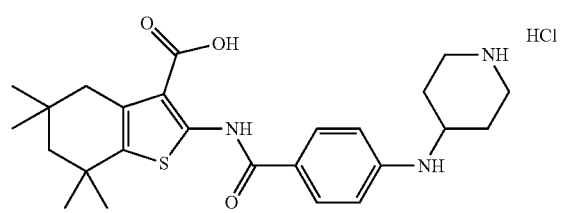 [SMILES: CC1(C)Cc2c(sc(NC(=O)c3ccc(NC4CCNCC4)cc3)c2C(=O)O)C(C)(C)C1 ; Cl]
Compound #131
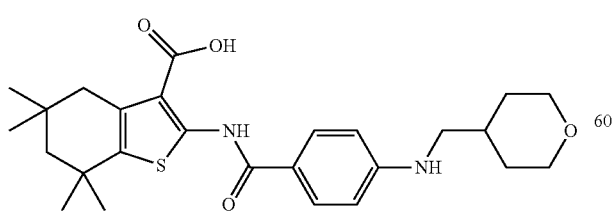
Compound #132
TABLE A-continued
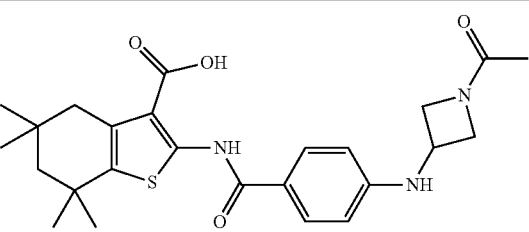 [SMILES: CC(=O)N1CC(Nc2ccc(C(=O)Nc3sc4c(c3C(=O)O)CC(C)(C)CC4(C)C)cc2)C1]
Compound #133
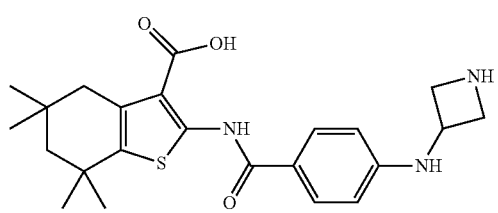 [SMILES: CC1(C)Cc2c(sc(NC(=O)c3ccc(NC4CNC4)cc3)c2C(=O)O)C(C)(C)C1]
Compound #134
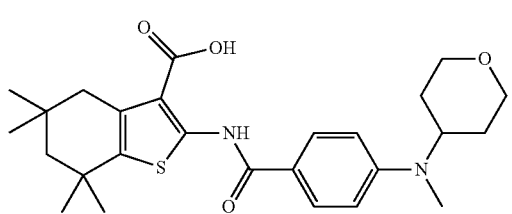 [SMILES: CN(c1ccc(C(=O)Nc2sc3c(c2C(=O)O)CC(C)(C)CC3(C)C)cc1)C1CCOCC1]
Compound #135
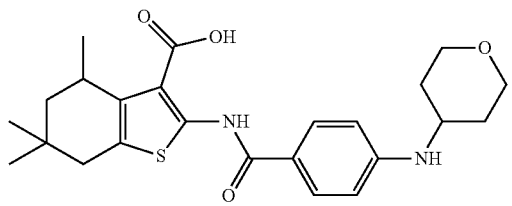 [SMILES: CC1CC(C)(C)Cc2sc(NC(=O)c3ccc(NC4CCOCC4)cc3)c(C(=O)O)c21]
Compound #136
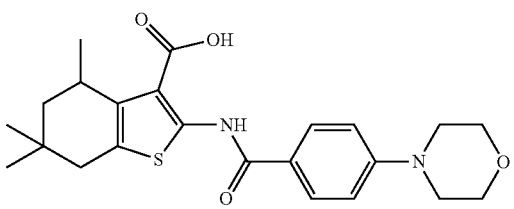 [SMILES: CC1CC(C)(C)Cc2sc(NC(=O)c3ccc(N4CCOCC4)cc3)c(C(=O)O)c21]
Compound #137
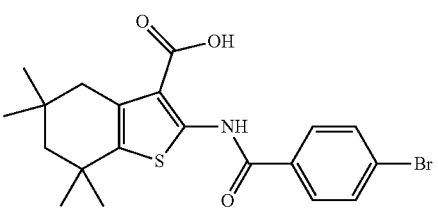 [SMILES: CC1(C)Cc2c(sc(NC(=O)c3ccc(Br)cc3)c2C(=O)O)C(C)(C)C1]
Compound #138

TABLE A-continued
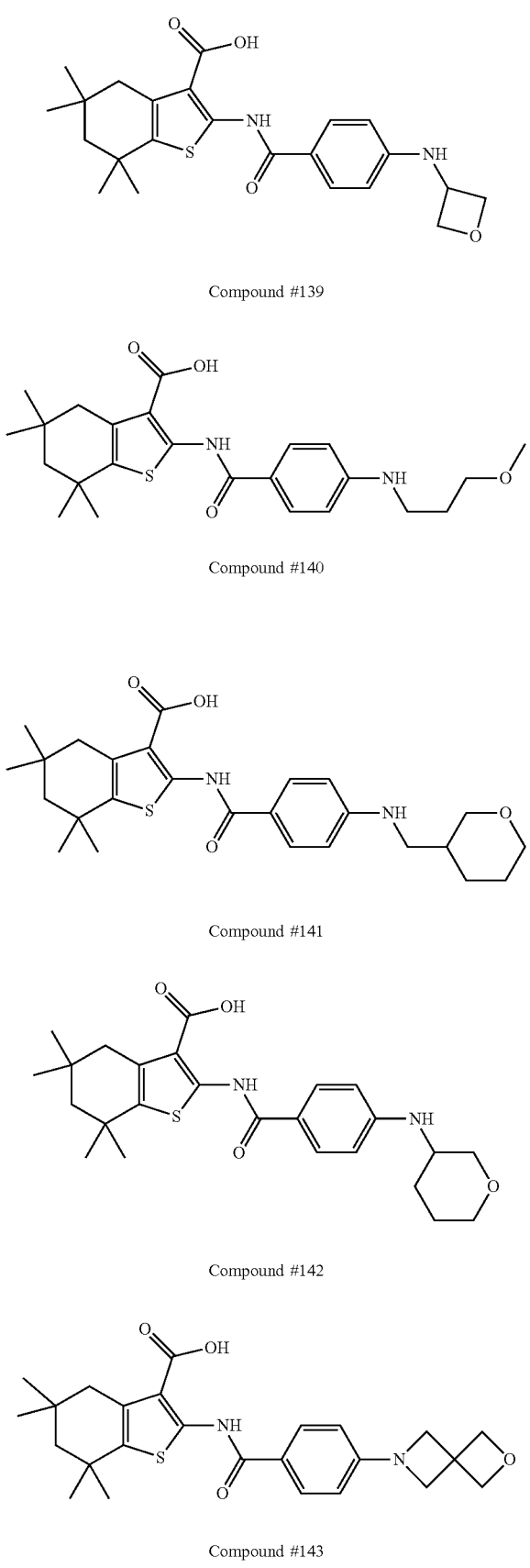
Compound #139
Compound #140
Compound #141
Compound #142
Compound #143
TABLE A-continued
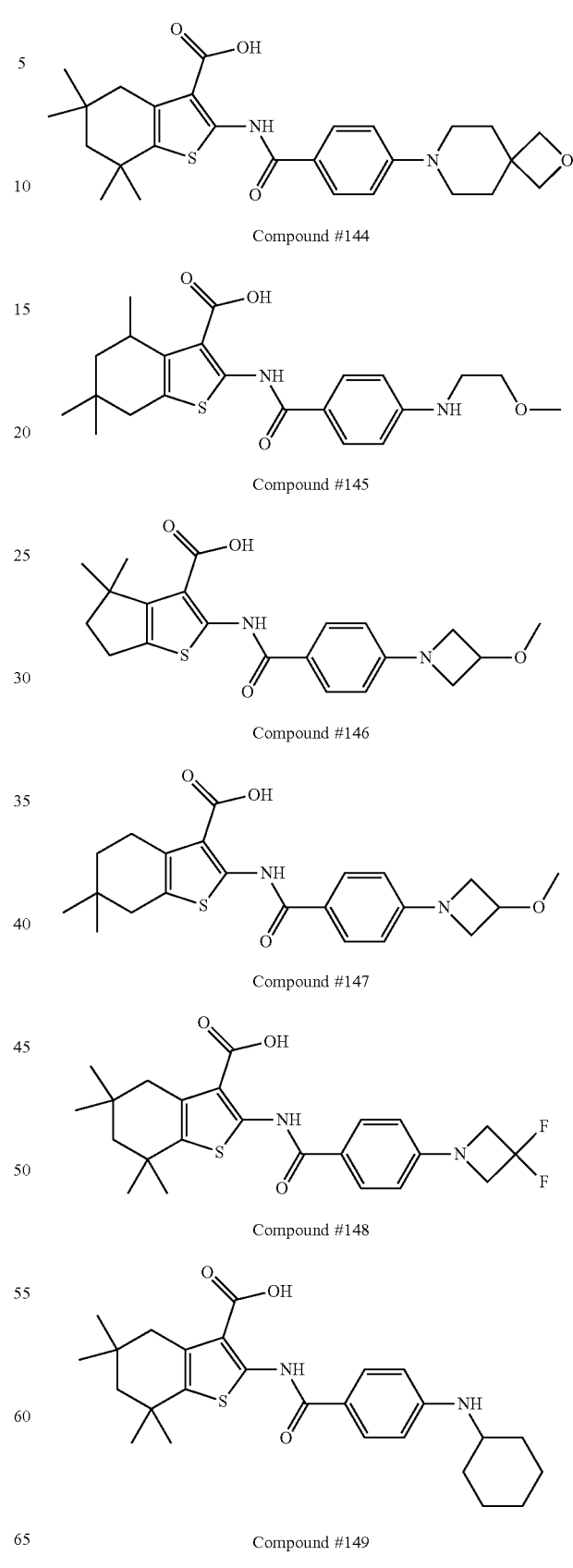
Compound #144
Compound #145
Compound #146
Compound #147
Compound #148
Compound #149

TABLE A-continued
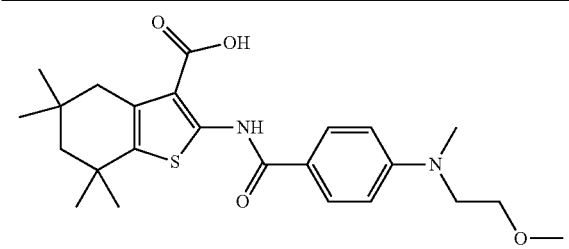
Compound #150
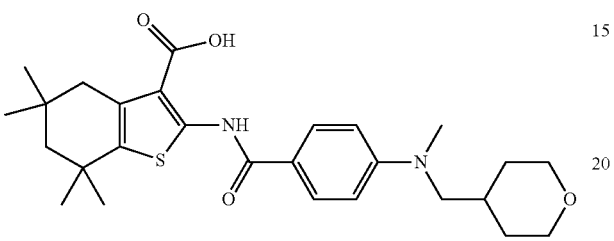
Compound #152
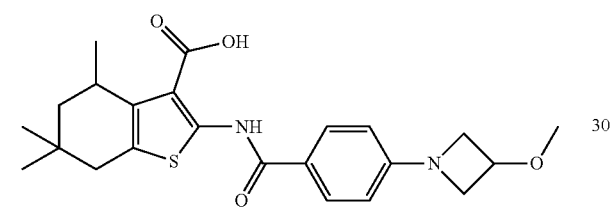
Compound #153
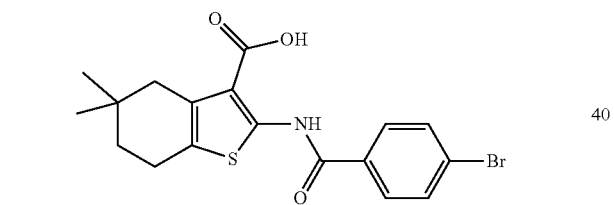
Compound #154
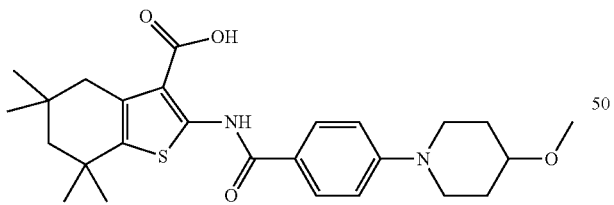
Compound #155
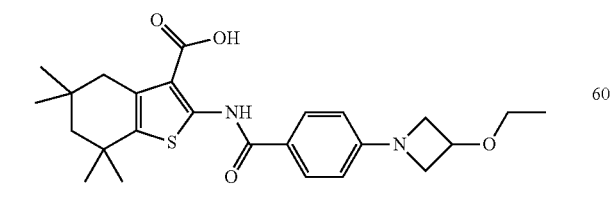
Compound #156
TABLE A-continued
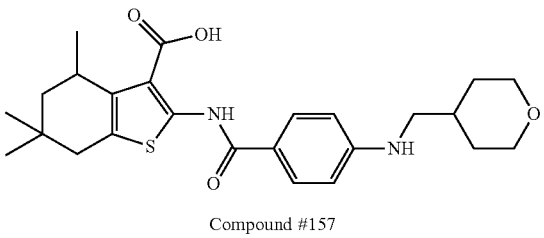
Compound #157
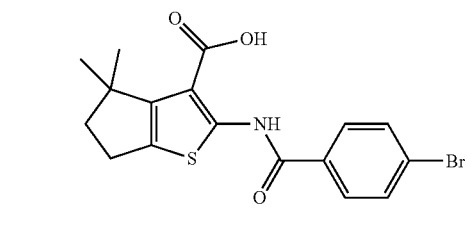 [SMILES: CC1(C)CCc2sc(NC(=O)c3ccc(Br)cc3)c(C(=O)O)c21]
Compound #158
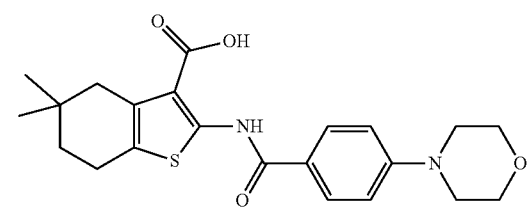 [SMILES: CC1(C)CCc2sc(NC(=O)c3ccc(N4CCOCC4)cc3)c(C(=O)O)c2C1]
Compound #159
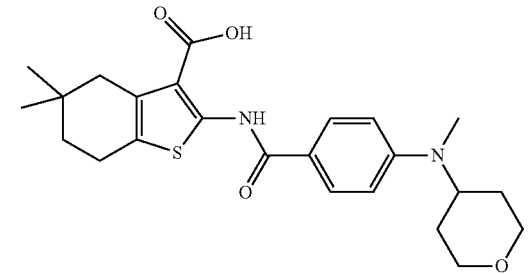 [SMILES: CN(c1ccc(C(=O)Nc2sc3c(c2C(=O)O)CC(C)(C)CC3)cc1)C1CCOCC1]
Compound #160
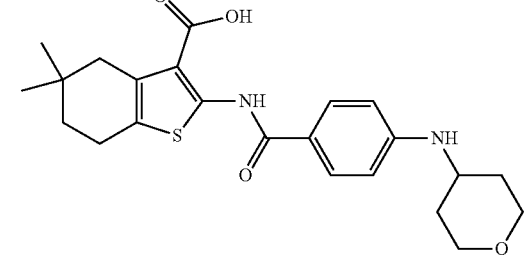
Compound #161
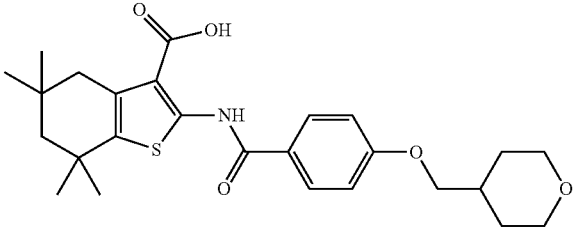 [SMILES: CC1(C)Cc2c(sc(NC(=O)c3ccc(OCC4CCOCC4)cc3)c2C(=O)O)C(C)(C)C1]
Compound #162

TABLE A-continued
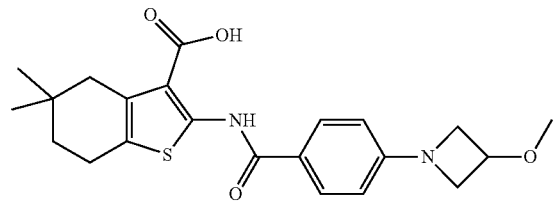
Compound #163
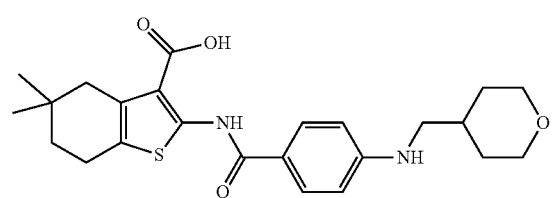 [SMILES: CC1(C)CCc2sc(NC(=O)c3ccc(NCC4CCOCC4)cc3)c(C(=O)O)c2C1]
Compound #164
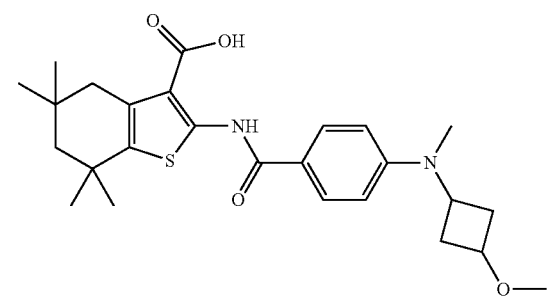
Compound #165
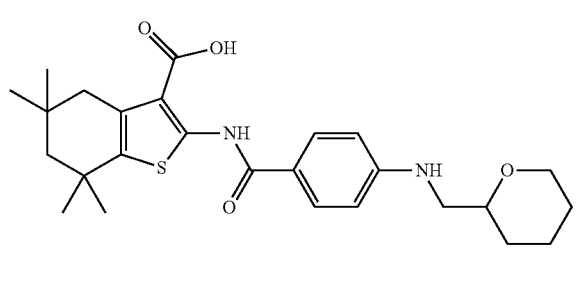 [SMILES: CC1(C)Cc2c(sc(NC(=O)c3ccc(NCC4CCCCO4)cc3)c2C(=O)O)C(C)(C)C1]
Compound #166
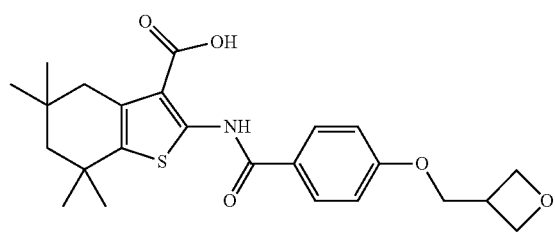 [SMILES: CC1(C)Cc2c(sc(NC(=O)c3ccc(OCC4COC4)cc3)c2C(=O)O)C(C)(C)C1]
Compound #167
TABLE A-continued
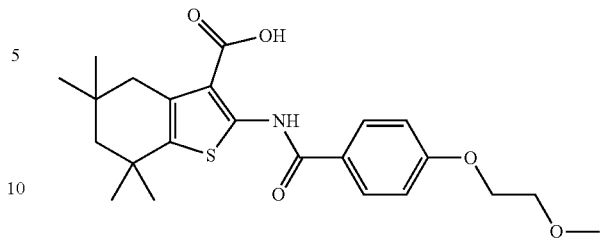
Compound #168
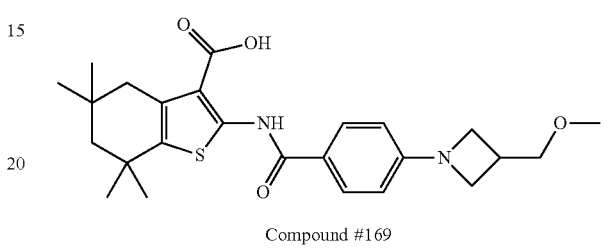
Compound #169
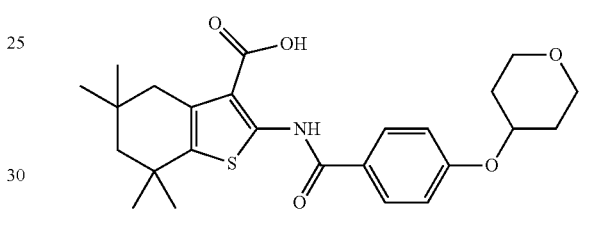
Compound #170
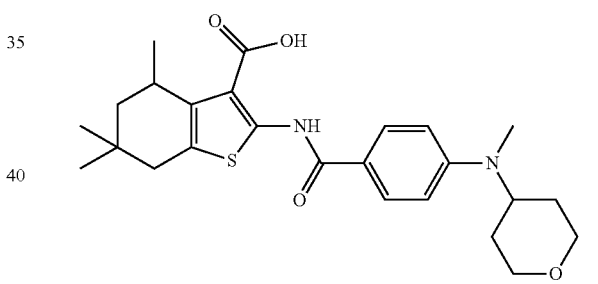
Compound #171
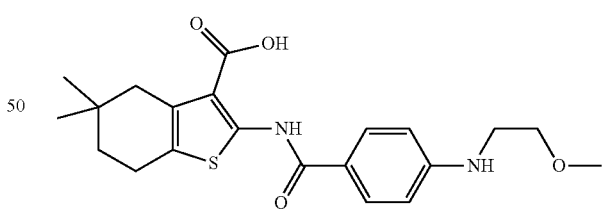
Compound #173
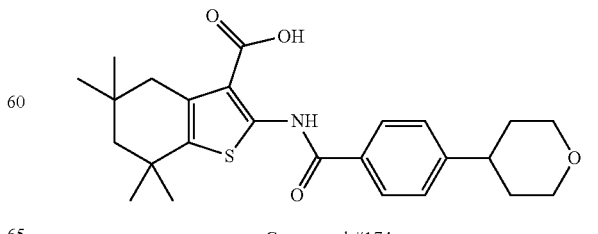
Compound #174

TABLE A-continued
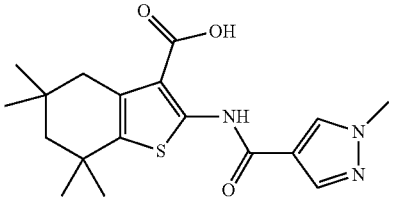
Compound #176
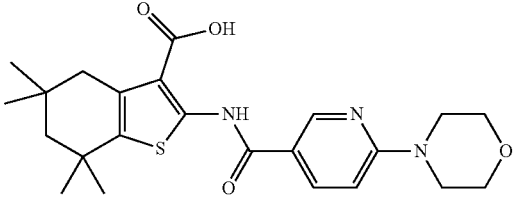 [SMILES: CC1(C)Cc2c(sc(NC(=O)c3ccc(N4CCOCC4)nc3)c2C(=O)O)C(C)(C)C1]
Compound #201
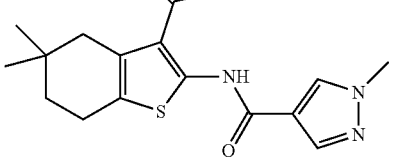
Compound #202
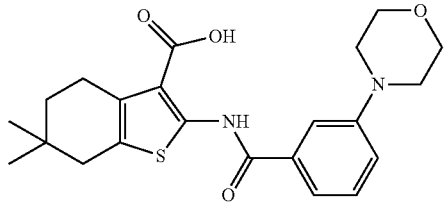 [SMILES: CC1(C)CCc2c(sc(NC(=O)c3cccc(N4CCOCC4)c3)c2C(=O)O)C1]
Compound #203
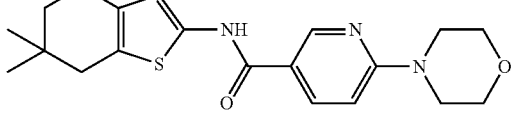
Compound #204
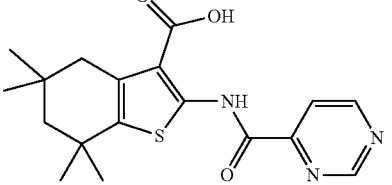
Compound #205
TABLE A-continued
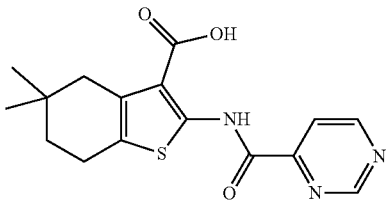 [SMILES: CC1(C)CCc2sc(NC(=O)c3ccncn3)c(C(=O)O)c2C1]
Compound #206
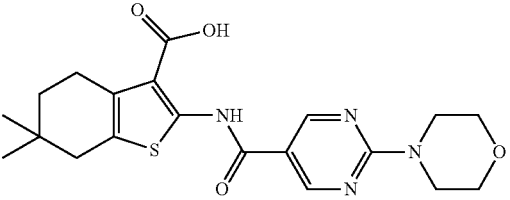
Compound #208
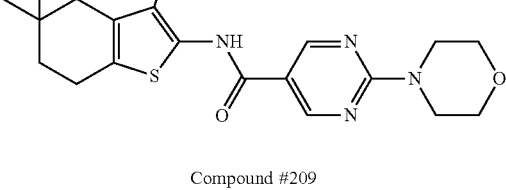
Compound #209
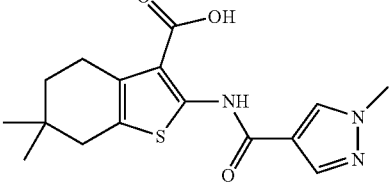
Compound #212
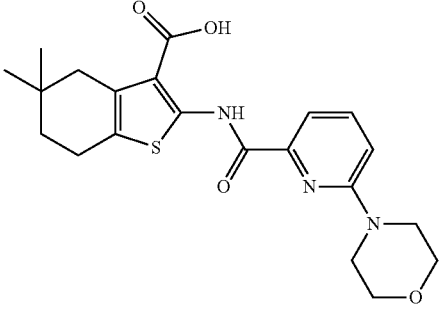 [SMILES: CC1(C)CCc2sc(NC(=O)c3cccc(N4CCOCC4)n3)c(C(=O)O)c2C1]
Compound #213

TABLE A-continued

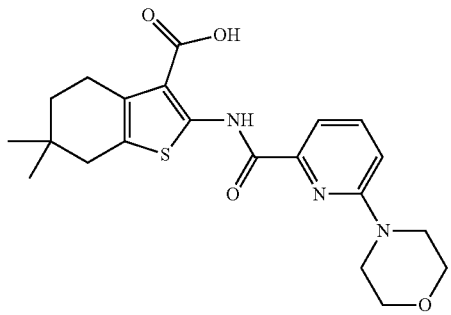 [SMILES: CC1(C)CCc2c(sc(NC(=O)c3cccc(N4CCOCC4)n3)c2C(=O)O)C1]

Compound #219

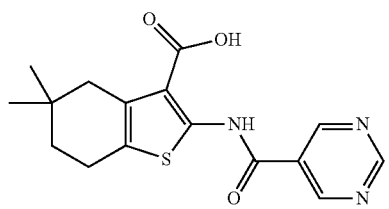 [SMILES: CC1(C)CCc2sc(NC(=O)c3cncnc3)c(C(=O)O)c2C1]

Compound #220

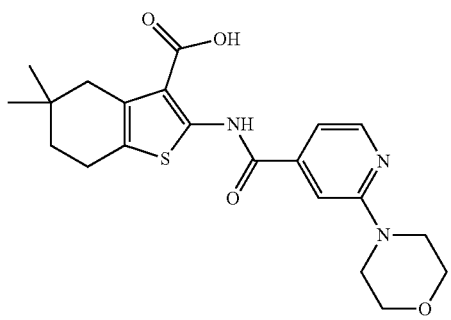 [SMILES: CC1(C)CCc2sc(NC(=O)c3ccnc(N4CCOCC4)c3)c(C(=O)O)c2C1]

Compound #221

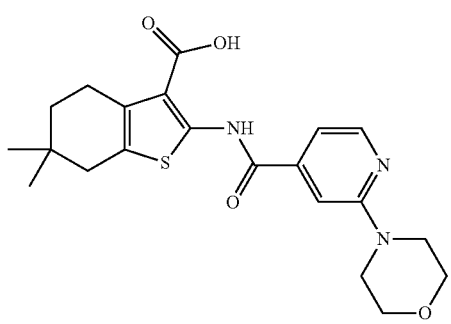 [SMILES: CC1(C)CCc2c(sc(NC(=O)c3ccnc(N4CCOCC4)c3)c2C(=O)O)C1]

Compound #22

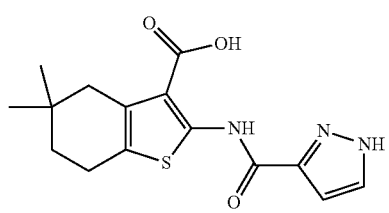 [SMILES: CC1(C)CCc2sc(NC(=O)c3cc[nH]n3)c(C(=O)O)c2C1]

Compound #225

TABLE A-continued

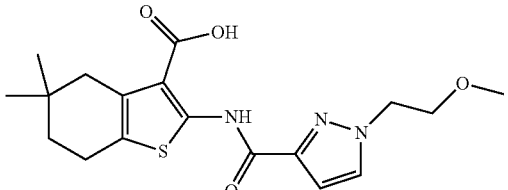

Compound #226

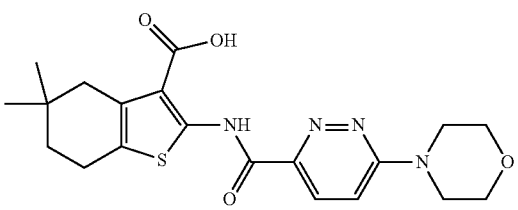

Compound #227

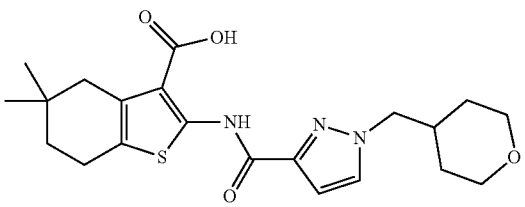 [SMILES: CC1(C)CCc2sc(NC(=O)c3ccn(CC4CCOCC4)n3)c(C(=O)O)c2C1]

Compound #228

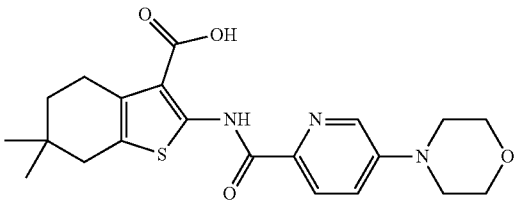 [SMILES: CC1(C)CCc2c(sc(NC(=O)c3ccc(N4CCOCC4)cn3)c2C(=O)O)C1]

Compound #229

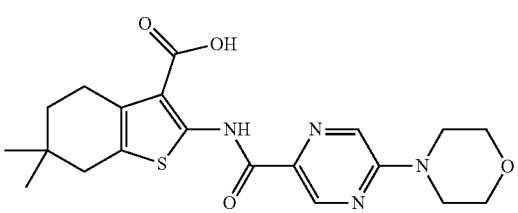 [SMILES: CC1(C)CCc2c(sc(NC(=O)c3cnc(N4CCOCC4)cn3)c2C(=O)O)C1]

Compound #230

Therapeutic Uses of Compounds

The present invention relates to a pharmaceutical or veterinary composition comprising a new compound according to the invention. Preferably, the pharmaceutical composition further comprises a pharmaceutically or veterinary acceptable carrier or excipient. The present invention relates to the use of a new compound according to the invention as a drug. The invention further relates to a method for treating a disease in a subject, wherein a therapeutically effective amount of a new compound according to the invention, is administered to said subject in need thereof. The invention also relates to the use of a new compound according to the invention, for the manufacture of a medicine.

In addition, the present invention relates to a method for treating an infectious disease, preferably a viral disease, in a subject, wherein a therapeutically effective amount of a compound according to the invention, is administered to said subject suffering of an infectious disease, preferably a viral disease. The present invention relates to the use of the compounds according to the invention as an anti-infectious agent, preferably an antiviral agent. The invention also relates to the use of the compounds according to the invention, for the manufacture of a medicine for the treatment of an infectious disease, preferably a viral infection. The invention relates to a compound according to the invention for use in the treatment of an infectious disease, preferably a viral infection.

The present invention further relates to a method for treating a cancer in a subject, wherein a therapeutically effective amount of a compound according to the invention is administered to said subject suffering of a cancer. The present invention relates to the use of the compounds according to the invention as an antitumor agent. The invention also relates to the use of the compounds according to the invention, for the manufacture of a medicine for the treatment of a cancer. The invention relates to a compound according to the invention for use in the treatment of a cancer.

The present invention further relates to a method for treating a metabolic disorder or disease in a subject, wherein a therapeutically effective amount of a compound according to the invention is administered to said subject suffering of a metabolic disorder or disease. The invention also relates to the use of the compounds according to the invention, for the manufacture of a medicine for the treatment of a metabolic disorder or disease. The invention relates to a compound according to the invention for use in the treatment of a metabolic disorder or disease.

The present invention further relates to a method for treating a cardiovascular disease in a subject, wherein a therapeutically effective amount of a compound according to the invention is administered to said subject suffering of a cardiovascular disease. The invention also relates to the use of the compounds according to the invention, for the manufacture of a medicine for the treatment of a cardiovascular disease. The invention relates to a compound according to the invention for use in the treatment of a cardiovascular disease.

The present invention further relates to a method for treating an inflammatory disease or disorder in a subject, wherein a therapeutically effective amount of a compound according to the invention is administered to said subject suffering of an inflammatory disease or disorder. The invention also relates to the use of the compounds according to the invention, for the manufacture of a medicine for the treatment of an inflammatory disease or disorder. The invention relates to a compound according to the invention for use in the treatment of an inflammatory disease or disorder.

The present invention also relates to a phytosanitary composition comprising a compound according to the invention, preferably a new compound according to the invention. It also relates to the use of a compound according to the invention, preferably a new compound according to the invention, as a phytosanitary agent. Thereby, the compound according to the invention. It further relates to a method for treating a plant against infection, especially infection by a virus, comprising contacting the plant with an efficient amount of a compound according to the invention, preferably a new compound according to the invention.

The present invention further relates to a method for treating aging or a neurodegenerative disease or disorder in a subject, wherein a therapeutically effective amount of a new compound according to the invention is administered to said subject suffering of aging or a neurodegenerative disease or disorder. The invention also relates to the use of a new compound according to the invention, for the manufacture of a medicine for the treatment of aging or a neurodegenerative disease or disorder. The invention relates to a new compound according to the invention for use in the treatment of aging or a neurodegenerative disease or disorder.

Antiviral Agents

The present invention relates to the use of a compound according to the invention as an antiviral agent. The present invention also relates to a compound of the present invention for use in the treatment of viral infections, the use of a compound of the present invention for the manufacture of a medicine for the treatment of viral infections, and to a method for treating a viral infection in a subject, comprising administering a therapeutically effective amount of a compound according to the invention to the subject.

The present invention also relates to the use of a compound of the present invention as a research tool, especially for studying viral infections. It further relates to a method for blocking viral infection in a cell, a tissue or a subject.

The viral agent can be a DNA virus or a RNA virus. The viral agent can be selected from the group consisting of Alphaviridae, Flaviviridae, Hepadnaviridae, Herpesviridae, Orthomyxoviridae, Papovaviridae, Paramyxoviridae, Picornaviridae, Polyomaviridae, Reoviridae, Retroviridae, Rhabdoviridae, and Tobamoviruses.

In one embodiment, the Alphaviridae is selected from the group consisting of Barmah Forest virus, Middelburg virus, Ndumu virus, Bebaru virus, Chikungunya virus, Mayaro virus, O'nyong'nyong virus, Ross River virus, Semliki Forest virus, Sindbis virus, Una virus, Eastern equine encephalitis virus, Tonate virus, Venezuelan equine encephalitis virus, Cabassou virus, Everglades virus, Mosso das Pedras virus, Mucambo virus, Parmana virus, Pixuna virus, Rio Negro virus, Trocara virus, Aura virus, Babanki virus, Kyzylagach virus, Ockelbo virus, Whataroa virus, Sleeping disease virus, Samon pancreatic disease virus, Southern elephant seal virus, and Western equine encephalitis virus; preferably selected from the group consisting of Barmah Forest virus, Chikungunya virus, Mayaro virus, O'nyong'nyong virus, Ross River virus, Semliki Forest virus, Sindbis virus, Una virus, Eastern equine encephalitis virus, Tonate virus, Venezuelan equine encephalitis virus and Western equine encephalitis virus.

In one embodiment, the Flaviviridae is selected from the group consisting of dengue virus, Hepatitis C virus, Japanese encephalitis virus, West Nile virus, yellow fever virus, Zika virus, Tick-borne encephalitis virus, Kyasanur forest disease virus, Murray Valley encephalitis virus, and Saint Louis encephalitis virus.

In one embodiment, the Hepadnaviridae is selected from the group consisting of Hepatitis B virus.

In one embodiment, the Herpesviridae is selected from the group consisting of Herpes Simplex virus 1 (HSV-1), Herpes Simplex virus 2 (HSV-2), Varicella zoster virus (VZV), Epstein-Barr virus (EBV), Cytomegalovirus (CMV), Roseolovirus (HHV-6A and 6B), HHV-7 and Kaposi's sarcoma-associated herpesvirus (KSHV).

In one embodiment, the Orthomyxoviridae is selected from the group consisting of Influenza virus A, Influenza virus B, Influenza virus C, Isavirus, Thogotovirus and Quaranjavirus, preferably selected from the group consisting of Influenza virus A and Influenza virus B. In one embodiment, the Influenza virus A is selected from the subtypes consisting of H1N1, H1N2, H2N2, H3N1, H3N2, H3N8, H5N1, H5N2, H5N3, H5N8, H5N9, H7N1, H7N2, H7N3, H7N4, H7N7, H7N9, H9N2, and H10N7.

In one embodiment, the Papovaviridae is selected from the group consisting of Papillomavirus (HPC) and Polyomavirus, especially Simian virus 40, Merkel cell polyomavirus, Trichodysplasia spinulosa polyomavirus, BK polyomavirus, JC polyomavirus and Human polyomavirus 7.

In one embodiment, the Paramyxoviridae is selected from the group consisting of Rubulavirus, Morbillivirus, Pneumovirus, Metapneumovirus, Avulavirus, Ferlavirus, Henipavirus, and Respirovirus. In a particular embodiment, the Paramyxoviridae is the mumps virus, measles virus, human parainfluenza viruses (HPIV), especially HPIV-1, HPIV-2, HPIV-3 or HPIV-4, respiratory syncytial virus (RSV), in particular Human respiratory syncytial virus (HRSV), canine distemper virus, phocine distemper virus, cetacean morbillivirus, Newcastle disease virus, rinderpest virus, Hendra virus and Nipah virus.

In one embodiment, the Picornaviridae is selected from the group consisting of Aphthovirus, Aquamavirus, Avihepatovirus, Cardiovirus, Cosavirus, Dicipivirus, Enterovirus, Erbovirus, Hepatovirus, Kobuvirus, Megrivirus, Parechovirus, Piscevirus, Rhinovirus, Salivirus, Sapelovirus, Senecavirus, Techovirus, and Tremovirus. In a particular embodiment, the Picornaviridae is a Rhinovirus, for instance a Rhinovirus A, Rhinovirus B or Rhinovirus C.

In one embodiment, the Retroviridae is selected from the group consisting of Alpharetrovirus; especially Avian leukosis virus and Rous sarcoma virus; Betaretrovirus, especially Mouse mammary tumour virus; Gammaretrovirus, especially Murine leukemia virus and Feline leukemia virus; Deltaretrovirus, especially Bovine leukemia virus and Human T-lymphotropic virus; Epsilonretrovirus, especially Walleye dermal sarcoma virus; Lentivirus, especially Human immunodeficiency virus 1 and Simian, Feline immunodeficiency viruses; Spumavirus, especially Simian foamy virus.

In one embodiment, the Rhabdoviridae is selected from the group consisting of vesiculovirus, especially vesicular stomatitis virus, lyssavirus, rabies virus, Ephemerovirus, novirhabdovirus, cytorhabdovirus and nucleorhabdovirus.

In one preferred embodiment, the viral agent according to the invention is selected from the group consisting in Herpesviridae such as Varicella zoster virus (VZV), Epstein-Barr (EB) virus, Herpes simplex virus of type 1 (HSV-1), Kaposis sarcoma herpesvirus (KSHV), murine γ-HV68 virus (γ-MHV68), or human cytomegalovirus (HCMV); Hepadnaviridae such as Hepatitis virus B (HBV); Papovaviridae such as Human papillomavirus type 16 (HPV16); Parvoviridae such as Human parvovirus B19; Polyomaviridae such as Simian virus 40; Retroviridae such has Human immunodeficiency virus 1 (HIV-1), or Simian immunodeficiency virus type 1 (SIV 1); Orthomyxoviridae such as Influenza A virus; Flaviviridae such as Dengue virus, or Hepatitis C virus; Picornaviridae such as Poliovirus, Coxsakievirus B3 (CVB3), or Coxsakievirus B4 (CVB4); Reoviridae such as Rotavirus; Alphaviridae such as Sindbis virus; Tobamoviruses such as Tabacco mosaic virus; Rhabdoviridae such as vesicular stomatitis virus. More preferably, the viral agent according to the invention is an influenza virus. Still preferably, the viral agent according to the invention is an influenza virus A or B, even more preferably an influenza virus A.

In another preferred embodiment, the viral agent according to the invention presents an antiviral resistance to classic antiviral drugs. The terms “antiviral resistance”, “antiviral agent resistance” or “antiviral drug resistance”, as used herein, are equivalent and refer to the ability of viruses to resist the effects of an antiviral agent previously used to treat them. Antiviral resistance can be defined by a decreased susceptibility to a drug through either a minimally effective, or completely ineffective, treatment response to prevent associated illnesses from a particular virus.

In one embodiment, the compound of the invention can be used in combination with another antiviral drug, for instance and non-exhaustively, an agent selected from the group consisting of neuraminidase inhibitors, M2 inhibitors, RNA polymerase inhibitors, interferons (immune system modulators interferon alpha-2a and PEGylated interferon alpha-2a (Pegasys) and interferon alpha-2b (ViraferonPeg ou Introna)), antiviral vaccine, antigenic polypeptides or neutralizing antibodies directed to a viral antigenic polypeptide.

Antibacterial Agents

The present invention relates to the use of a compound according to the invention as an antibacterial agent. The present invention also relates to a compound of the present invention for use in the treatment of bacterial infections, the use of a compound of the present invention for the manufacture of a medicine for the treatment of bacterial infections, and to a method for treating a bacterial infection in a subject, comprising administering a therapeutically effective amount of a compound according to the invention to the subject.

The bacterium can be gram-negative and gram-positive bacteria, preferably an infectious bacterium. Such gram-positive bacteria include, but are not limited to, *Pasteurella* species, Staphylococci species, and *Streptococcus* species.

Specific examples of bacteria include but are not limited to, *Helicobacter pylori, Burkholderia cepacia, Pseudomonas aeruginosa, Pseudomonas fluorescens, Pseudomonas acidovorans, Pseudomonas alcaligenes, Pseudomonas putida, Stenotrophomonas maltophilia, Aeromonas hydrophilia, Escherichia coli, Citrobacter freundii, Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Francisella tularensis, Morganella morganii, Proteus mirabilis, Proteus vulgaris, Providencia alcalifaciens, Providencia rettgeri, Providencia stuartii, Acinetobacter baumannii, Acinetobacter calcoaceticus, Acinetobacter haemolyticus, Yersinia enterocolitica, Yersinia pestis, Yersinia pseudotuberculosis, Yersinia intermedia, Bordetella parapertussis, Bordetella bronchiseptica, Haemophilus parainfluenzae, Haemophilus haemolyticus, Haemophilus parahaemolyticus, Haemophilus ducreyi, Pasteurella multocida, Pasteurella haemolytica, Branhamella catarrhalis, Campylobacter fetus, Campylobacter jejuni, Campylobacter coli, Borrelia burgdorferi, Vibrio cholerae, Vibrio parahaemolyticus, Listeria monocytogenes, Neisseria gonorrhoeae, Neisseria meningitidis, Kingella denitrificans, Kingella indologenes, Kingella kingae, Kingella oralis, Legionella pneumophila, Moraxella bovis, Moraxella catarrhalis, Moraxella lacunata, Gardnerella vaginalis, Bacteroides fragilis, Bacteroides distasonis, Bacteroides vulgatus, Bacteroides ovalus, Bacteroides thetaiotaomicron, Bacteroides uniformis, Bacteroides eggerthii, Bacteroides splanchnicus, Clostridium difficile, Clostridium tetani, Mycobacterium species, Corynebacterium ulcerans, Streptococcus agalactiae, Gardnerella vaginitis, Streptococcus pyogenes, Entero-*

*coccus faecalis, Enterococcus faecium, Fusobacterium nucleatum, Porphyromonas gingivalis, Vibrio vulnificus, Clostridium botulinum, Corynebacterium diptheriae, Staphylococcus aureus, Staphylococcus epidermidis, Staphylococcus saprophyticus, Staphylococcus intermedius, Staphylococcus hyicus, Staphylococcus haemolyticus, Staphylococcus hominis,* or *Staphylococcus saccharolyticus.*

In a particular embodiment, the bacterium is a *Mycobacterium*, for instance *Mycobacterium* species is selected from the group consisting of *M. africanum, M. bovis, M. bovis* BCG, *M. canetti, M. caprae, M. microti, M. mungi, M. orygis, M. pinnipedii, M. suricattae, M. tuberculosis, M. avium, M. avium paratuberculosis, M. avium silvaticum, M. avium* "hominissuis", *M. colombiense, M. indicus pranii, M. asiaticum, M. gordonae, M. gastri* and *M. kansasii, M. hiberniae, M. nonchromogenicum, M. terrae, M. triviale, M. ulcerans, M. pseudoshottsii, M. shottsii, M. triplex, M. genavense, M. florentinum, M. lentiflavum, M. palustre, M. kubicae, M. parascrofulaceum, M. heidelbergense, M. interjectum, M. simiae, M. bohemicum, M. botniense, M. branderi, M. celatum, M. chimaera, M. conspicuum, M. cookie, M. doricum, M. farcinogenes, M. haemophilum, M. heckeshornense, M. intracellular, M. lacus, M. leprae, M. lepraemurium, M. lepromatosis, M. liflandii, M. malmoense, M. marinum, M. monacense, M. montefiorense, M. murale, M. nebraskense, M. saskatchewanense, M. scrofulaceum, M. shimoidei, M. szulgai, M. tusciae, M. xenopi, M. yongonense, M. intermedium, M. abscessus, M. chelonae, M. bolletii, M. fortuitum, M. fortuitum* subsp. *Acetamidolyticum, M. boenickei, M. peregrinum, M. porcinum, M. senegalense, M. septicum, M. neworleansense, M. houstonense, M. mucogenicum, M. mageritense, M. brisbanense, M. cosmeticum, M. parafortuitum, M. austroafricanum, M. diernhoferi, M. hodleri, M. neoaurum, M. frederiksbergense, M. aurum, M. vaccae, M. chitae, M. fallax, M. confluentis, M. flavescens, M. madagascariense, M. phlei, M. smegmatis, M. goodie, M. wolinskyi, M. thermoresistibile, M. gadium, M. komossense, M. obuense, M. sphagni, M. agri, M. aichiense, M. alvei, M. arupense, M. brumae, M. canariasense, M. chubuense, M. conceptionense, M. duvalii, M. elephantis, M. gilvum, M. hassiacum, M. holsaticum, M. immunogenum, M. massiliense, M. moriokaense, M. psychrotolerans, M. pyrenivorans, M. vanbaalenii, M. pulveris, M. arosiense, M. aubagnense, M. caprae, M. chlorophenolicum, M. fluoroanthenivorans, M. kumamotonense, M. novocastrense, M. parmense, M. phocaicum, M. poriferae, M. rhodesiae, M. seoulense,* and *M. tokaiense,* preferably *Mycobacterium tuberculosis, Mycobacterium leprae,* or *Mycobacterium ulcerans.*

In another preferred embodiment, the bacterium according to the invention presents a resistance to classic antibacterial drugs. The terms "antibacterial resistance", "antibacterial agent resistance" or "antibacterial drug resistance", as used herein, are equivalent and refer to the ability of bacteria to resist the effects of an antibacterial agent previously used to treat them. Antibacterial resistance can be defined by a decreased susceptibility to a drug through either a minimally effective, or completely ineffective, treatment response to prevent associated illnesses from a particular bacterium.

In one embodiment, the compound of the invention can be used in combination with another antibacterial drug.

NEET Proteins Modulators

Compounds of the present invention are able to modulate NEET proteins. In particular, the compounds can be a NEET protein stabiliser. Alternatively, the compounds can be a NEET protein destabiliser.

The NEET protein family includes three class of proteins encoded by the CISD1, CISD2 and CISD3 genes.

CISD1 gene encodes the protein mitoNEET. It was previously called $C_{10}$orf70 or ZCD1 or MDS029. The gene encoding the protein is described in databases GeneCards GCID GC10P058269; HGNC: 30880; Entrez Gene: 55847; and UniGene: Hs.370102. The protein is described in UniProtKB under: Q9NZ45. Amino acid and nucleotide reference sequences of mitoNEET are disclosed in GenPept and Genbank under NP_060934.1 and NM_018464.4, respectively.

CISD2 gene encodes the protein NAF-1 (nutrient-deprivation autophagy factor-1). It was previously called WFS2 or ZCD2 and is also called Miner1, ERIS (endoplasmic reticulum intermembrane small protein) and mitoNEET related 1. The gene encoding the protein is described in databases GeneCards GCID GC04P102868; HGNC: 24212; Entrez Gene: 493856; and UniGene: Hs.444955. and Hs.745013. The protein is described in UniProtKB under: Q8N5K1. Amino acid and nucleotide reference sequences of NAF-1 are disclosed in GenPept and Genbank under NP_001008389.1 and NM_001008388.4, respectively.

CISD3 gene encodes the protein Miner2. It is also called mitoNEET-Related protein 2 or mitochondrial matrix-localized mitochondrial inner NEET protein (MiNT). The gene encoding the protein is described in databases GeneCards GCID GC17P038730; HGNC: 27578; Entrez Gene: 284106; and UniGene: Hs.713595. The protein is described in UniProtKB under ID P0C7P0. Amino acid and nucleotide reference sequences of Miner2 are disclosed in GenPept and Genbank under NP_001129970.1 and NM_001136498.1, respectively. NEET proteins are important for human health and disease. For instance, they are involved in oncology (Holt et al, 2016, J Cell Sci, 129, 155-165; Bai et al, 2015, Proc Natl Acad Sci USA, 112, 3698-3703; Tamir et al, 2014, Proc Natl Acad Sci USA, 111, 5177-5182; Sohn et al, 2013, Proc Natl Acad Sci USA, 110, 14676-14681; Darash-Yahana et al, 2016, Proc Natl Acad Sci USA, 113, 10890-10895), especially apoptosis and autophagy; in metabolic disorders and diseases (Tamir et al, 2015, Biochim Biophys Acta, 1853, 1294-1315; Takahashi et al, Journal of Pharmacology and experimental therapeutics, 2015, 352, 338-345); cardiovascular diseases (Du et al, 2015, Cell Biol Int, 39, 816-823; Habener et al, 2016, PLoS One, 11, e0156054); inflammatory diseases and disorders (Taminelli et al, 2008, Biochem Biophys Res Commun, 365, 856-862); iron storage disorders (REF); aging (Chen et al, 2009, Genes Dev, 23, 1183-1194) and neurodegenerative diseases or disorders (He et al, 2016, Sci Rep, 6, 35205). Studies demonstrated a role for mitoNEET and NAF-1 in the regulation of cellular iron, calcium and ROS homeostasis, and a key role for NEET proteins in critical processes, such as cancer cell proliferation and tumor growth, lipid and glucose homeostasis in obesity and diabetes, control of autophagy, longevity in mice, and senescence in plants (Tamir et al, 2015, Biochim Biophys Acta, 1853, 1294-1315). Abnormal regulation of NEET proteins was consequently found to result in multiple health conditions. For instance, missplicing of NAF-1 causes Wolfram syndrome 2. NAF-1 is also functionally linked to the regulation of autophagy in cancer and aging.

Cancers

The compounds of the present invention are able to kill tumor cells. In addition, the compounds of the present invention are also able to modulate NEET proteins (Holt et al, 2016, J Cell Sci, 129, 155-165; Bai et al, 2015, Proc Natl Acad Sci USA, 112, 3698-3703; Tamir et al, 2014, Proc Natl Acad Sci USA, 111, 5177-5182; Sohn et al, 2013, Proc Natl Acad Sci USA, 110, 14676-14681; Darash-Yahana et al, 2016, Proc Natl Acad Sci USA, 113, 10890-10895). NEET proteins are involved in the regulation of apoptosis/autophagy in cancer biology. Accordingly, the present invention relates to the use of a compound of the present invention as an antitumor agent. The present invention also relates to a compound of the present invention for use for treating a cancer, the use of a compound of the present invention for the manufacture of a medicine for treating a cancer, and to a method for treating a cancer in a subject, comprising administering an effective amount of a compound of the present invention to the subject.

In one aspect, the cancer can be a solid tumor or a hematopoietic cancer. For instance, the cancer can be selected from the group consisting of bone cancer, gastrointestinal cancer, liver cancer, pancreatic cancer, gastric cancer, colorectal cancer, esophageal cancer, oro-pharyngeal cancer, laryngeal cancer, salivary gland carcinoma, thyroid cancer, lung cancer, cancer of the head or neck, skin cancer, squamous cell cancer, melanoma, uterine cancer, cervical cancer, endometrial carcinoma, vulvar cancer, ovarian cancer, breast cancer, prostate cancer, cancer of the endocrine system, sarcoma of soft tissue, bladder cancer, kidney cancer, glioblastoma and various types of cancers of the central nervous system, lymphoma and leukemia. In a preferred embodiment, the cancer is a breast cancer, in particular a triple-negative breast cancer, prostate cancer and ovarian cancer. In one particular embodiment, the cancer is a breast cancer.

Optionally, the compound of the present invention used for treating cancer is a modulator of mitoNEET and/or NAF-1. In one aspect, the compound is a modulator of mitoNEET. In another aspect, the compound is a modulator of NAF-1. In a further aspect, the compound is a modulator of mitoNEET and NAF-1.

In this aspect, the compound of the present invention can be combined with radiotherapy, immunotherapy, hormonotherapy, or chemotherapy, all well-known by the person skilled in the field.

Metabolic Disorders and Diseases

NEET proteins are involved in metabolic disorders and diseases (Tamir et al, 2015, Biochim Biophys Acta, 1853, 1294-1315). Accordingly, the present invention further relates to a method for treating a metabolic disorder or disease in a subject, wherein a therapeutically effective amount of a compound according to the invention is administered to said subject suffering of a metabolic disorder or disease. The invention also relates to the use of the compounds according to the invention, for the manufacture of a medicine for the treatment of a metabolic disorder or disease. The invention relates to a compound according to the invention for use in the treatment of a metabolic disorder or disease.

The metabolic disorders and diseases can be selected in the group consisting of diabetes mellitus, insulin resistance, insulin deficiency, hepatic steatosis, nonalcoholic fatty liver disease, Nonalcoholic steatohepatitis (NASH), glucose intolerance, obesity, lipodystrophy, coronary heart disease, diabetic retinopathy, diabetic neuropathy, diabetic nephropathy, hypoglycemia, hyperglycemia, beta cell dysfunction or hyperinsulinaemia, Wolfram syndrome, Polycystic ovary syndrome, pyruvate dehydrogenase deficiency, Albright hereditary osteodystrophy, cystinosis, fructose intolerance, Walker-Warburg syndrome, hypobetalipoproteinemia, Alström syndrome, and cirrhosis.

In one aspect, the metabolic disease or disorder can be selected from the group consisting of diabetes, in particular diabetes type I or diabetes type II, atherosclerosis, obesity, diabetic neuropathies, lysosomal storage diseases, severe insulin resistance, hyperinsulinemia, hyperlipidemia, Rabson-Mendenhall syndrome, leprechaunism, lipoatrophic diabetes, acute and chronic renal insufficiency, end-stage chronic renal failure, glomerulonephritis, interstitial nephritis, pyelonephritis, glomerulosclerosis, and lipoatrophic diabetes, hepatic steatosis, nonalcoholic fatty liver disease, Nonalcoholic steatohepatitis (NASH), glucose intolerance, lipodystrophy, coronary heart disease, diabetic retinopathy, diabetic neuropathy, diabetic nephropathy, hypoglycemia, hyperglycemia, beta cell dysfunction or hyperinsulinaemia, Wolfram syndrome, Polycystic ovary syndrome, pyruvate dehydrogenase deficiency, Albright hereditary osteodystrophy, cystinosis, fructose intolerance, Walker-Warburg syndrome, hypobetalipoproteinemia, Alström syndrome, and cirrhosis.

In another aspect, the metabolic disease or disorder can be selected from the group consisting of activator deficiency/GM2 gangliosidosis, alpha-mannosidosis, aspartylglucoaminuria, cholesteryl ester storage disease, chronic hexosaminidase A deficiency, cystinosis, Danon disease, Fabry disease, Farber disease, fucosidosis, galactosialidosis, Gaucher Disease (Types I, II and III), GM1 Ganliosidosis, including infantile, late infantile/juvenile and adult/chronic), Hunter syndrome (MPS II), Mucolipidosis II, Infantile Free Sialic Acid Storage Disease (ISSD), Juvenile Hexosaminidase A Deficiency, Krabbe disease, Lysosomal acid lipase deficiency, Metachromatic Leukodystrophy, Hurler syndrome, Scheie syndrome, Hurler-Scheie syndrome, Sanfilippo syndrome, Morquio Type A and B, Maroteaux-Lamy, Sly syndrome, mucolipidosis, multiple sulfate deficiency, Niemann-Pick disease, Neuronal ceroid lipofuscinoses, CLN6 disease, Jansky-Bielschowsky disease, pycnodysostosis, Sandhoff disease, Schindler disease, and Tay-Sachs or Wolman disease.

In a preferred embodiment, metabolic disorders and diseases can be selected in the group consisting of diabetes mellitus, insulin resistance, obesity and Wolfram syndrome.

Optionally, the compound of the present invention used for treating metabolic diseases or disorders is a modulator of mitoNEET, NAF-1 and/or MiNT. In particular, it can be a modulator of a combination of NEET proteins, such as mitoNEET and NAF-1, mitoNEET and MiNT, NAF-1 and MiNT or mitoNEET, NAF-1 and MiNT. Alternatively, it can be a modulator of mitoNEET, NAF-1 or MiNT.

The compound of the present invention can be combined with other drugs known for their uses in the treatment of metabolic diseases or disorders.

Cardiovascular Diseases

NEET proteins have been disclosed to be involved in cardiovascular diseases and disorders (Du et al, 2015, Cell Biol Int, 39, 816-823; Habener et al, 2016, PLoS One, 11, e0156054; Tamir et al, 2015, Biochim Biophys Acta, 1853, 1294-1315). Therefore, the present invention further relates to a method for treating a cardiovascular disease in a subject, wherein a therapeutically effective amount of a compound according to the invention is administered to said subject suffering of a cardiovascular disease. The invention also relates to the use of the compounds according to the invention, for the manufacture of a medicine for the treatment of a cardiovascular disease. The invention relates to a compound according to the invention for use in the treatment of a cardiovascular disease.

In one aspect, the cardiovascular disease is selected from the group consisting of myocardial injury, Ischemia, Ischemia reperfusion injury and hypertension. In one embodiment, the cardiovascular disease is myocardial injury.

Optionally, the compound of the present invention used for treating a cardiovascular disease is a modulator of mitoNEET and/or NAF-1. In one aspect, the compound is a modulator of mitoNEET. In another aspect, the compound is a modulator of NAF-1. In a further aspect, the compound is a modulator of mitoNEET and NAF-1.

The compound of the present invention can be combined with other drugs known for their uses in the treatment of cardiovascular diseases or disorders.

Inflammatory Diseases

NEET proteins have been disclosed to be involved in inflammation (Tamir et al, 2015, Biochim Biophys Acta, 1853, 1294-1315).

In one aspect, the inflammatory disease or disorder can be selected from the group consisting of Crohn disease, inflammatory bowel disease, asthma, chronic obtrusive pulmonary disease (COPD), systemic lupus erythematosus, cystic fibrosis, psoriasis, infectious arthritis, and multiple sclerosis.

Optionally, the compound of the present invention used for treating inflammatory diseases or disorders is a modulator of mitoNEET.

In one particular embodiment, the inflammatory disease or disorder is cystic fibrosis (Taminelli et al, 2008, Biochem Biophys Res Commun, 365, 856-862). Optionally, the compound of the present invention used for treating cystic fibrosis is a modulator of mitoNEET.

The compound of the present invention can be combined with other drugs known for their uses in the treatment of inflammatory diseases or disorders.

Iron Storage Disorders

NEET proteins are involved in iron homeostasis. The compounds of the present invention are able to modulate the NEET protein binding to iron, for instance by stabilizing and destabilizing this binding.

Accordingly, the present invention relates to a compound of the present invention for use for treating an iron storage disorder, the use of a compound of the present invention for the manufacture of a medicine for treating an iron storage disorder, and to a method for treating an iron storage disorder in a subject, comprising administering an effective amount of a compound of the present invention to the subject.

The iron storage disorder or disease can be associated to an iron deficiency or to an iron overload.

The iron storage disorders or diseases include, but are not limited thereto, Ferroportin Deficiency, Hereditary Hemochromatosis, including Hereditary Hemochromatosis due to HFE mutations and Hereditary Hemochromatosis due to transferrin receptor 2 mutations, Juvenile Hemochromatosis, including Juvenile Hemochromatosis due to hepcidin mutations and Juvenile Hemochromatosis due to hemojuvelin mutations, Iron Overload, including African Iron Overload, Iron Overload secondary to atransferrinemia and Iron Overload secondary to aceruloplasminemia, Thalassemia, Myelodysplastic Syndromes, Congenital Dyserythropoietic Anemias, Sickle Cell Disease and other Hemoglobinopathies, Red Cell Enzyme Deficiencies and Multiple Blood Transfusions.

Aging and Neurodegenerative Diseases

It is known that NEET proteins are involved in aging (Chen et al, 2009, Genes Dev, 23, 1183-1194) and in neurodegenerative diseases and disorders (He et al, 2016, Sci Rep, 6, 35205). Therefore, a compound of the present invention, in particular a new compound of the present invention, can be used for the treatment of aging or a neurodegenerative disease or disorder. Accordingly, the present invention relates to a method for treating aging or a neurodegenerative disease or disorder in a subject, wherein a therapeutically effective amount of a compound according to the invention, preferably a new one, is administered to said subject suffering of aging or a neurodegenerative disease or disorder. The invention also relates to the use of a compound according to the invention, preferably a new one, for the manufacture of a medicine for the treatment of aging or a neurodegenerative disease or disorder. The invention relates to a compound according to the invention, preferably a new one, for use in the treatment of aging or a neurodegenerative disease or disorder.

In one embodiment, the compound of the present invention used for treating aging or treating or preventing aging damage. Optionally, the compound of the present invention used for treating aging is a modulator of NAF-1.

In another embodiment, the compound of the present invention used for treating a neurodegenerative disease or disorder. The neurodegenerative disease can be selected from the group consisting of Adrenal Leukodystrophy, Alexander's disease, Alper's disease, Alzheimer's disease, Amyotrophic lateral sclerosis, ataxia telangiectasia, Batten disease, bovine spongiform encephalopathy, Canavan disease, cerebral palsy, corticobasal degeneration, Creutzfeldt-Jakob disease, familial fatal insomnia, frontotemporal lobar degeneration, Huntington's disease, HIV-associated dementia, Kennedy's disease, Krabbe's disease, Lewy body dementia, neuroborreliosis, Machado-Joseph disease, multiple system atrophy, multiple sclerosis, narcolepsy, Niemann Pick disease, Parkinson's disease, Pelizaeus-Merzbacher disease, Pick's disease, primary lateral sclerosis, prion diseases, progressive supranuclear palsy, Refsum's disease, Sandhoff disease, Schilder's disease, subacute combined degeneration of spinal cord secondary to pernicious anaemia, Spielmeyer-Vogt-Sjogren-Batten disease, spinocerebellar ataxia, spinal muscular atrophy, Steele-Richardson-Olszewski disease, Tabes dorsalis and toxic encephalopathy. Preferably, the neurodegenerative disease or disorder can be selected from the group consisting of multiple sclerosis, Alzheimer's disease, Parkinson's disease and amyotrophic lateral sclerosis.

The neurodegenerative disease or disorder also includes central nervous system (CNS) injury.

Optionally, the compound of the present invention used for treating a neurodegenerative disease or disorder is a modulator of mitoNEET.

The compound of the present invention can be combined with other drugs known for their uses in the treatment of neurodegenerative diseases or disorders.

Pharmaceutical Composition

The present invention also relates to a pharmaceutical composition comprising a compound of the present invention, preferably a new compound of the present invention. The composition further comprises at least one pharmaceutically acceptable carrier or excipient.

In a particular embodiment, the pharmaceutical composition according to the invention further comprises at least another active ingredient, preferably selected from the group consisting in an antiviral agent, an anti-cancerous agent, an antibiotic, or a molecule aimed to treat metabolic diseases, cardiovascular diseases, inflammatory diseases, aging, muscle diseases, neurodegenerative diseases or iron storage disorders. Preferably, the other active ingredient is an antiviral agent. More preferably, the other active ingredient is an antiviral agent against an influenza virus, preferably an influenza A virus.

In a particular embodiment, the pharmaceutical composition according to the invention further comprises an antiviral agent, for instance and non-exhaustively, an agent selected from the group consisting of neuraminidase inhibitors, M2 inhibitors, RNA polymerase inhibitors, interferons (immune system modulators interferon alpha-2a and PEGylated interferon alpha-2a (Pegasys) and interferon alpha-2b (ViraferonPeg ou Introna)), antiviral vaccine, antigenic polypeptides or neutralizing antibodies directed to a viral antigenic polypeptide.

The invention also concerns the pharmaceutical composition of the invention for use in the treatment of a disease. The invention also relates to the use of a pharmaceutical composition according to the invention for the manufacture of a medicine for treating a disease in a subject. The invention further relates to a method for treating a disease in a subject, wherein a therapeutically effective amount of a pharmaceutical composition according to the invention is administered to said subject suffering from said disease.

The subject according to the invention is an animal, preferably a mammal, even more preferably a human. However, the term "subject" can also refer to non-human animals, in particular mammals such as dogs, cats, horses, cows, pigs, sheep, donkeys, rabbits, ferrets, gerbils, hamsters, chinchillas, rats, mice, guinea pigs and non-human primates, among others, that are in need of treatment.

The human subject according to the invention may be a human at the prenatal stage, a newborn, a child, an infant, an adolescent or an adult.

In a preferred embodiment, the subject has been diagnosed with a disease. Preferably, the subject has been diagnosed with a disease selected from the group consisting in viral infections, bacterial infections, cancers, metabolic diseases or disorders, cardiovascular diseases or disorders, inflammatory diseases or disorders, iron storage disorders, aging and neurodegenerative diseases or disorders. Diagnostic methods of these diseases are well known by the man skilled in the art.

The compound according to the invention or the pharmaceutical composition according to the invention may be administered by any conventional route of administration. In particular, the compound or the pharmaceutical composition of the invention can be administered by a topical, enteral, oral, parenteral, intranasal, intravenous, intra-arterial, intramuscular, intratumoral, subcutaneous or intraocular administration and the like.

In particular, the compound according to the invention or the pharmaceutical composition according to the invention can be formulated for a topical, enteral, oral, parenteral, intranasal, intravenous, intra-arterial, intramuscular, intratumoral, subcutaneous or intraocular administration and the like.

Preferably, the compound according to the invention or the pharmaceutical composition according to the invention is administered by enteral or parenteral route of administration. When administered parenterally, the compound according to the invention or the pharmaceutical composition according to the invention is preferably administered by intravenous route of administration. When administered enterally, the compound according to the invention or the pharmaceutical composition according to the invention is preferably administered by oral route of administration.

The pharmaceutical composition comprising the molecule is formulated in accordance with standard pharmaceutical practice (Lippincott Williams & Wilkins, 2000 and Encyclopedia of Pharmaceutical Technology, eds. J. Swarbrick and J. C. Boylan, 1988-1999, Marcel Dekker, New York) known by a person skilled in the art.

For oral administration, the composition can be formulated into conventional oral dosage forms such as tablets, capsules, powders, granules and liquid preparations such as syrups, elixirs, and concentrated drops. Nontoxic solid carriers or diluents may be used which include, for example, pharmaceutical grades of mannitol, lactose, starch, magnesium stearate, sodium saccharine, talcum, cellulose, glucose, sucrose, magnesium, carbonate, and the like. For compressed tablets, binders, which are agents which impart cohesive qualities to powdered materials, are also necessary. For example, starch, gelatine, sugars such as lactose or dextrose, and natural or synthetic gums can be used as binders. Disintegrants are also necessary in the tablets to facilitate break-up of the tablet. Disintegrants include starches, clays, celluloses, algins, gums and crosslinked polymers. Moreover, lubricants and glidants are also included in the tablets to prevent adhesion to the tablet material to surfaces in the manufacturing process and to improve the flow characteristics of the powder material during manufacture. Colloidal silicon dioxide is most commonly used as a glidant and compounds such as talc or stearic acids are most commonly used as lubricants.

For transdermal administration, the composition can be formulated into ointment, cream or gel form and appropriate penetrants or detergents could be used to facilitate permeation, such as dimethyl sulfoxide, dimethyl acetamide and dimethylformamide.

For transmucosal administration, nasal sprays, rectal or vaginal suppositories can be used. The active compound can be incorporated into any of the known suppository bases by methods known in the art. Examples of such bases include cocoa butter, polyethylene glycols (carbowaxes), polyethylene sorbitan monostearate, and mixtures of these with other compatible materials to modify the melting point or dissolution rate.

Pharmaceutical compositions according to the invention may be formulated to release the active drug substantially immediately upon administration or at any predetermined time or time period after administration.

Preferably, the treatment with the compound according to the invention or the pharmaceutical composition according to the invention start no longer than a month, preferably no longer than a week, after the diagnosis of the disease. In a most preferred embodiment, the treatment starts the day of the diagnosis.

The compound according to the invention or the pharmaceutical composition according to the invention may be administered as a single dose or in multiple doses.

Preferably, the treatment is administered regularly, preferably between every day and every month, more preferably between every day and every two weeks, more preferably between every day and every week, even more preferably the treatment is administered every day. In a particular embodiment, the treatment is administered several times a day, preferably 2 or 3 times a day, even more preferably 3 times a day.

The duration of treatment with the compound according to the invention or the pharmaceutical composition according to the invention is preferably comprised between 1 day and 20 weeks, more preferably between 1 day and 10 weeks, still more preferably between 1 day and 4 weeks, even more preferably between 1 day and 2 weeks. In a particular embodiment, the duration of the treatment is of about 1 week. Alternatively, the treatment may last as long as the disease persists.

The amount of compound according to the invention or of pharmaceutical composition according to the invention to be administered has to be determined by standard procedure well known by those of ordinary skills in the art. Physiological data of the patient (e.g. age, size, and weight) and the routes of administration have to be taken into account to determine the appropriate dosage, so as a therapeutically effective amount will be administered to the patient.

In a preferred embodiment, the total compound dose for each administration of the compound according to the invention or of the pharmaceutical composition according to the invention is comprised between 0.00001 and 1 g, preferably between 0.01 and 10 mg.

The form of the pharmaceutical compositions, the route of administration and the dose of administration of the compound according to the invention, or the pharmaceutical composition according to the invention can be adjusted by the man skilled in the art according to the type and severity of the disease, and to the patient, in particular its age, weight, sex, and general physical condition.

Kit and Use of a Kit

The present invention also relates to the combined use of a compound of the present invention with at least another active ingredient, preferably selected from the group consisting in an antiviral agent, an anti-cancerous agent, an anti-apoptotic agent, an anti-autophagy agent, an autophagy inducing agent, an antibiotic, an antiparasitic agent, an antifungal agent, or a molecule aimed to treat neurodegenerative diseases, inflammatory diseases, autoimmune diseases, liver diseases, aging, muscle diseases, or metabolic diseases for the treatment of a disease selected from the group consisting of cancer, infectious diseases, in particular viral diseases, metabolic diseases or disorders, cardiovascular diseases or disorders, inflammatory diseases, iron storage disorders, aging, and neurodegenerative diseases.

The present invention also relates to a product comprising a compound of the present invention, and another active ingredient, as a combined preparation for simultaneous, separate or sequential use, in particular for use for the treatment of a disease selected from the group consisting of cancer, infectious diseases, in particular viral diseases, metabolic diseases or disorders, cardiovascular diseases or disorders, inflammatory diseases, iron storage disorders, aging, and neurodegenerative diseases. Preferably, the other active ingredient is selected from the group consisting in an antiviral agent, an anti-cancerous agent, an anti-apoptotic agent, an anti-autophagy agent, an autophagy inducing agent, an antibiotic, an antiparasitic agent, an antifungal agent, or a molecule aimed to treat cancer, infectious diseases, in particular viral diseases, metabolic diseases or disorders, cardiovascular diseases or disorders, inflammatory diseases, iron storage disorders, aging, and neurodegenerative diseases. Preferably, the other active ingredient is an antiviral.

Further aspects and advantages of the present invention will be described in the following examples, which should be regarded as illustrative and not limiting.

EXAMPLES

Example A—Chemistry

Abbreviations

Aq Aqueous
br s Broad singlet
$CDCl_3$ Deuterated chloroform
d Doublet
DAD Diode Array Detector
DCM Dichloromethane (methylene chloride)
dd Doublet of doublets
ddd Doublet of doublet of doublets
ddt Doublet of doublet of triplets
DIPEA N,N-Diisopropylethylamine
DMAP 4-Dimethylaminopyridine
DMF N,N-Dimethylformamide
DMSO Dimethyl sulfoxide
dq Doublet of quartets
dt Doublet of triplets
EtOAc Ethyl acetate
$Et_2O$ Diethyl ether
EtOH Ethanol
g Gram(s)
h Hour(s)
HCl Hydrochloric acid
HPLC High-pressure liquid chromatography
i-PrOH Isopropanol
LC/MS Liquid chromatography/mass spectrometry
LiGH Lithium hydroxide
m Multiplet
M Molar
MeCN Acetonitrile
MeOH Methyl alcohol
$MgSO_4$ Magnesiumsulfate
min Minute(s)
mmol Millimole
MHz MegaHertz
MS Mass spectrometry
N Normal
$NaHCO_3$ Sodium bicarbonate
$Na_2SO_4$ Sodium sulfate
$NH_4Cl$ Ammonium chloride
NMR Nuclear magnetic resonance
p para
PDA Photodiode Array
PG Protecting group
ppm Parts per million
q Quartet
quin Quintet
RP-HPLC Reverse-phase high-pressure liquid chromatography
$R_t$ Retention time
RT Room temperature
s Singlet
t Triplet
td Triplet of doublets
tdd Triplet of doublet of doublets
tert- Tertiary
THF Tetrahydrofuran
tt Triplet of triplets General Synthetic Schemes Compounds of the invention may be prepared using the synthetic transformations illustrated in Schemes I-V. Starting materials are commercially available or may be prepared by the procedures described herein, by literature procedures, or by procedures that would be well known to one skilled in the art of organic chemistry. Unless stated, all aqueous solutions are saturated.

Methods for preparing 2-[(benzoyl)amino]-4,6-dihydrobenzothiophene-3-carboxylic acid and 2-[(benzoyl)amino]-5,6-dihydrocyclopenta[b]thiophene-3-carboxylic acid compounds of the invention containing various substitutions on the bicyclic scaffold and on the benzamides are illustrated in Schemes I-II. In Scheme I, step a, the 2-aminothiophene-3-carboxylate scaffold 3 can be commercially available or synthesised from commercially available cyclic ketones 1 and cyanoacetate 2 in a 3-component reaction using sulfur and a suitable base. This reaction, called a Gewald reaction (as described in *Ber.*, 1966, 99, 94-100), can be carried out using for example one of the following procedures described in Preparation #1, Preparation #3 and Preparation #6, or by methods known to one skilled in the art (for example, *European Journal of Medicinal Chemistry*, 2016, 123, 31-47) to provide the 2-aminothiophene-3-carboxylate compounds 3. 2-Aminothiophene-3-carboxylate 3 may react with substituted benzoyl chloride as described in Scheme I, step b using conditions such as those described in Example #1, or by methods known to one skilled in the art (for instance, *J. Med. Chem.*, 2013, 56(24), 10118-10131) to give 2-(benzamido)thiophene-3-carboxylate derivatives 4. Acyl chlorides can be commercially available or synthesised as described for example in Preparation #2 and Example #11 or by methods known to one skilled in the art (for example, *J. Med. Chem.*, 2016, 59(13), 6201-6220). In Scheme I, step b, 2-aminothiophene-3-carboxylate 3 may also react with substituted benzoic acids in the presence of a coupling reagent, such as 2-chloro-1-methylpyridinium iodide (also called Mukaiyama's reagent), as described in Example #41, or by methods known to one skilled in the art (for example, *European Journal of Medicinal Chemistry*, 2014, 76, 110-117) to give 2-(benzamido)thiophene-3-carboxylate derivatives 4. In Scheme I, step c, the ester of 2-(benzamido)thiophene-3-carboxylate derivatives 4 may be hydrolysed to the 2-(benzamido)thiophene-3-carboxylic acids 5 using conditions such as those described in Example #1 and Example #8 or by methods known to one skilled in the art (for example, *J. Med. Chem.*, 2013, 56(24), 10118-10131).

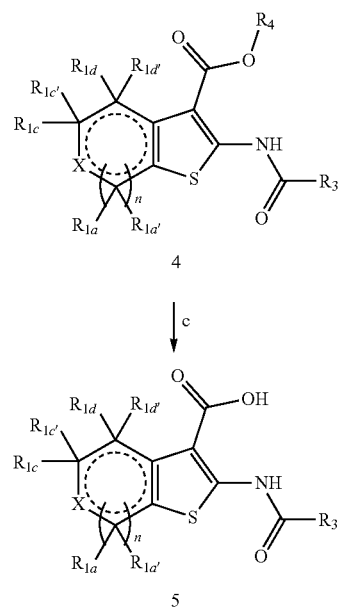

In Scheme II, an alternative method for preparing 2-aminothiophene-3-carboxylate derivatives 3 is reported. In Scheme II, step d, 2-cyano-2-(cyclopentylidene)acetate and 2-cyano-2-(cyclohexylidene)acetate compounds 6 can be synthesised from commercially available cyanoacetate 2 and cyclic ketones 1 using ammonium acetate, as described in Preparation #8 and Preparation #11 or by methods known to one skilled in the art (for example, *Synthetic Communications*, 2006, 36(22), 3305-3317). This reaction is generally known by those skilled in the art as a Knoevenagel condensation. In Scheme II, step e, 2-cyano-2-(cyclopentylidene)acetate and 2-cyano-2-(cyclohexylidene)acetate compounds 6 may react with sulfur and a base to give 2-aminothiophenes 3 as described in Preparation #8 and Preparation #11 or by methods known to one skilled in the art (for example, *J. Med. Chem.*, 2005, 48(26), 8270-8288).

Scheme I

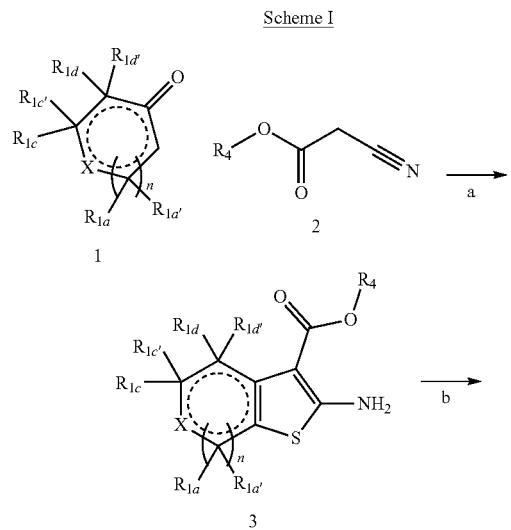

Scheme II

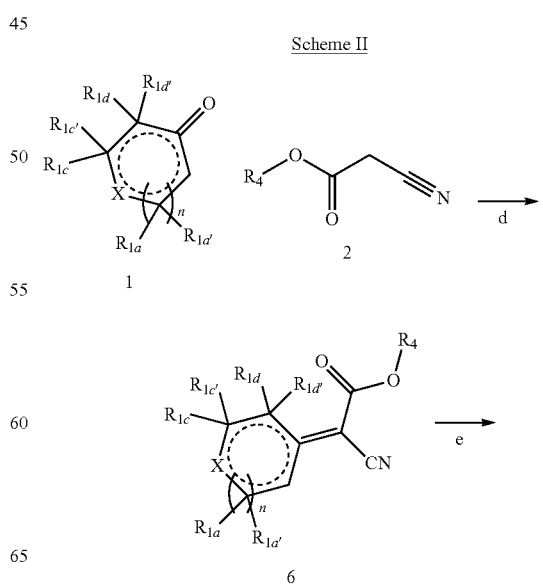

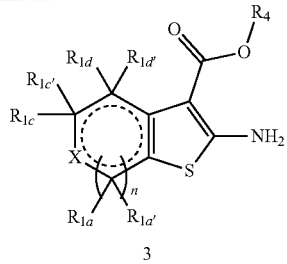

3

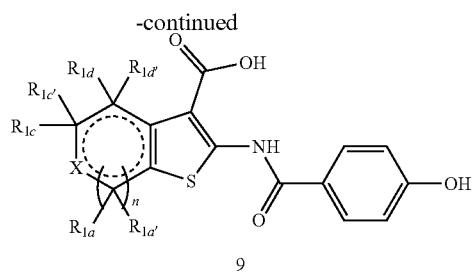

9

Compounds of general structure 4 as depicted in Scheme I may be modified later in the synthesis as described in Scheme III. 2-Aminothiophenes 3 may react with 0-protected benzoyl chloride as described in Scheme III, step b using, for example, similar conditions described in Scheme I, step b. A suitable protecting group may be, for instance, the acetoxy, as shown in Preparation #15. In Scheme III, step f, a suitable protecting group (PG) may be cleaved to give 2-(4-hydroxybenzamido)thiophene-3-carboxylate ester derivatives 8 using appropriate conditions such as those described in Preparation #15, for example, or by methods known to one skilled in the art (for example, *ACS Medicinal Chemistry Letters*, 2014, 5(1), 84-88). In Scheme III, step c, the ester of 2-(4-hydroxybenzamido)thiophene-3-carboxylate derivatives 8 may be hydrolysed to the 2-(4-hydroxybenzamido)thiophene-3-carboxylic acids 9 using conditions such as those described in Scheme I, step c.

Scheme IV, step g, shows a further modification of 2-(4-hydroxybenzamido)thiophene-3-carboxylate ester derivatives 8, which may react with an electrophile to give ethers of general structure 10. This transformation has been described as outlined for example in Example #77 or can be achieved by methods known to one skilled in the art (for example, *ACS Medicinal Chemistry Letters*, 2014, 5(11), 1230-1234). In Scheme IV, step c, the ester of 2-(benzamido)thiophene-3-carboxylate derivatives 10 may be hydrolysed to the 2-(benzamido)thiophene-3-carboxylic acids 11 using conditions such as those described in Scheme I, step c.

Scheme III

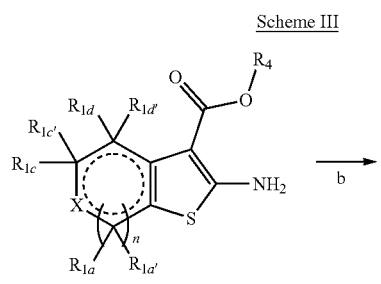

Scheme IV

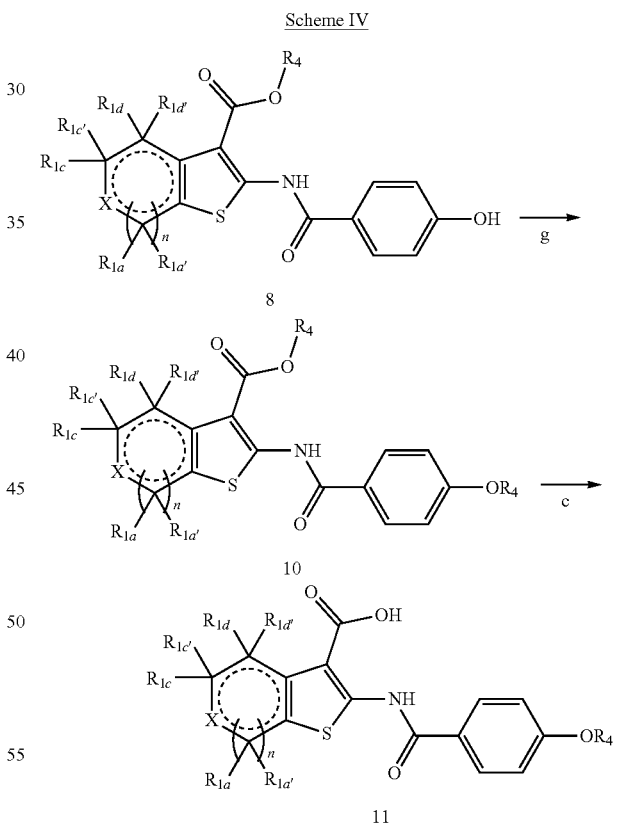

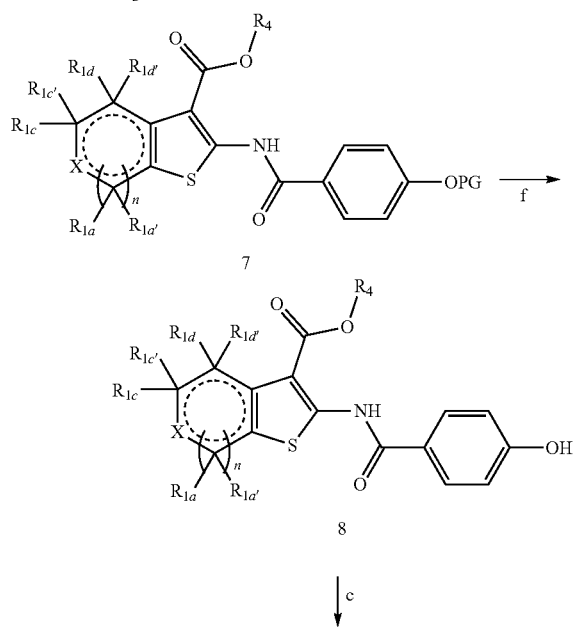

In Scheme V, a further derivatisation of the 2-aminothiophene-3-carboxylate scaffold 3 is reported. In Scheme V, step b, 2-aminothiophene-3-carboxylate 3 may react with a benzoyl chloride containing a suitable leaving group X for palladium catalysed reactions, such as a halide, to give 2-(benzamido)thiophene-3-carboxylate derivatives 12. Typical procedures have been described in Scheme I, step b and in Preparation #7. In Scheme V, step h, 2-(halobenzamido)thiophene-3-carboxylate derivatives 12 may react with amines to give 2-(aminobenzamido)thiophene-3-carboxylate derivatives 13 using a suitable palladium catalyst, as described for example in Example #20 or by methods known to one skilled in the art (for example, J. Med. Chem., 2014, 57(7), 3094-3116). In Scheme V, step c, the ester of 2-(aminobenzamido)thiophene-3-carboxylate derivatives 13 may be hydrolysed to the 2-(aminobenzamido)thiophene-3-carboxylic acids 14 using conditions such as those described in Scheme I, step c.

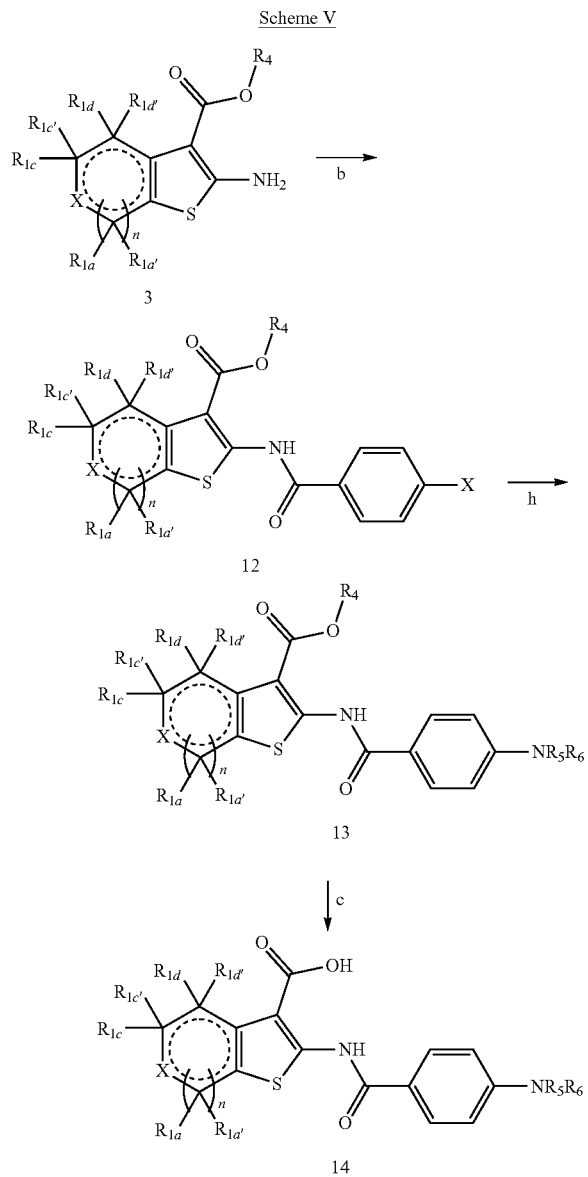

Scheme V

Analytical Methods

Analytical data is included within the procedures below, in the illustrations of the general procedures, or in the tables of examples. Unless otherwise stated, all $^1$H NMR data were collected on a Bruker Avance 400 MHz equipped with 5 mm QNP probe or Bruker Avance III 400 MHz, 5 mm BBFO plus probe instruments and chemical shifts are quoted in parts per million (ppm). LC/MS was performed on Acquity UPLC (binary pump/PDA detector) coupled to Waters ZQ Mass Spectrometer or Acquity i-Class (quaternary pump/PDA detector) coupled to Quattro Micro Mass Spectrometer or coupled to Waters DAD+Waters SQD2, single quadrapole UPLC-MS. LC/MS data is referenced to LC/MS conditions using the method number provided in Table 1.

TABLE 1

LC/MS analysis methods

| Method | Conditions |
|---|---|
| A | LC/MS analysis condition: Column: ACQUITY UPLC BEH C18 1.7 μm, 100 × 2.1 mm maintained at 40° C. Mobile phase: MeCN (0.1% formic acid) in water (0.1% formic acid), from 5% to 95% within 6 min; Flow rate: 0.4 ml/min; Wavelength: 200-500 nm DAD. ZQ Mass Spectrometer |
| B | LC/MS analysis condition: Column: Acquity UPLC BEH Shield RP18 1.7 μm, 100 × 2.1 mm plus guard cartridge, maintained at 40° C. Mobile phase: MeCN in water (with 10 mM ammonium bicarbonate), from 5% to 95% within 6 min; Flow rate: 0.5 ml/min; Wavelength: 210-400 nm DAD. Waters DAD + Waters SQD2, single quadrapole UPLC-MS |
| C | LC/MS analysis condition: Column: Acquity UPLC HSS C18 1.8 μm 100 × 2.1 mm plus guard cartridge, maintained at 40° C. Mobile phase: MeCN (0.1% formic acid) in water (0.1% formic acid), from 5% to 95% within 6 min; Flow rate: 0.5 ml/min; Wavelength: 210-400 nm DAD. Waters DAD + Waters SQD2, single quadrapole UPLC-MS |
| D | LC/MS analysis condition: Column: ACQUITY UPLC BEH C18 1.7 μm, 100 × 2.1 mm, maintained at 40° C. Mobile phase: MeCN (0.1% formic acid) in water (0.1% formic acid), from 5% to 95% within 6 min; Flow rate: 0.4 ml/min; Wavelength: 200-500 nm DAD. Quattro Micro Mass Spectrometer |
| E | LC/MS analysis condition: Column: Acquity UPLC HSS C18 1.8 μm, 100 × 2.1 mm plus guard cartridge, maintained at temp. Mobile phase: MeCN (0.1% formic acid) in water (0.1% formic acid), from 5% to 95% within 8 min; Flow rate: 0.4 ml/min; Wavelength: 210-400 nm DAD. Waters DAD + Waters SQD2, single quadrapole UPLC-MS |
| F | LC/MS analysis condition: Column: Acquity UPLC BEH Shield RP18 1.7 μm, 100 × 2.1 mm plus guard cartridge, maintained at temp. Mobile phase: MeCN in water (with 10 mM ammonium bicarbonate), from 5% to 95% within 8 min; Flow rate: 0.4 ml/min; Wavelength: 210-400 nm DAD. Waters DAD + Waters SQD2, single quadrapole UPLC-MS |

Purification Methods

For the general procedures, intermediate and final compounds may be purified by any technique or combination of techniques known to one skilled in the art. Some examples that are not limiting include flash chromatography with a solid phase (i.e. silica gel, alumina, etc.) and a solvent (or combination of solvents, i.e. heptane, EtOAc, DCM, MeOH, MeCN, water, etc.) that elutes the desired compounds; RP-HPLC purification performed on Agilent Technologies 1260 Infinity purification system and Agilent 6120 series Single Quadrupole Mass Spectrometer (see Table 2 for some non-limiting conditions); recrystallization from an appropriate solvent (i.e. MeOH, EtOH, i-PrOH, EtOAc, toluene, etc.) or combination of solvents (i.e. EtOAc/heptane, EtOAc/MeOH, etc.); precipitation from a combination of solvents (i.e. DMF/water, DMSO/DCM, EtOAc/heptane, etc.); trituration with an appropriate solvent (i.e. EtOAc, DCM, MeCN, MeOH, EtOH, i-PrOH, n-PrOH, etc.); extractions by dissolving a compound in a liquid and washing with an appropriately immiscible liquid (i.e. DCM/water, EtOAc/water, DCM/saturated NaHCO$_3$, EtOAc/saturated NaHCO$_3$, DCM/10% aqueous HCl, EtOAc/10% aqueous HCl, etc.); distillation (i.e. simple, fractional, Kugelrohr, etc.). Descriptions of these techniques can be found in the following references: Gordon, A. J. and Ford, R. A. "The Chemist's Companion", 1972; Palleros, D. R. "Experimental Organic Chemistry", 2000; Still, W. C., Kahn and M. Mitra, A. J. Org. Chem. 1978, 43(14), 2923-2925; Yan, B. "Analysis and Purification Methods in Combinatorial Chemistry" 2003; Harwood, L. M., Moody, C. J. and Percy, J. M. "Experimental Organic Chemistry: Standard and Microscale, 2$^{nd}$ Edition", 1999.

TABLE 2

RP-HPLC purification methods

| Method | Conditions |
|---|---|
| 1 | RP-HPLC purification condition: Column XSELECT CSH Prep C18 19 × 250 mm, 5 μm. Mobile phase: MeCN in water (0.1% HCOOH), Flow rate: 20 ml/min; Wavelength: 210-260 nm DAD. Sample injected in DMSO (+optional formic acid and water), 22 min non-linear gradient from 10% to 95% MeCN, centered around a specific focused gradient |
| 2 | RP-HPLC purification condition: Column Waters Sunfire C18 150 × 19 mm, 10 μm. Mobile phase: MeCN in water (0.1% NH$_4$CO$_3$), Flow rate: 20 ml/min; Wavelength: 210-400 nm DAD. Sample injected in DMSO, 25 min non-linear gradient from 5% to 80% MeCN, centered around a specific focused gradient |

PREPARATIONS AND EXAMPLES

All starting materials are commercially available from Sigma-Aldrich (including Fluka and Discovery CPR) or Acros unless otherwise noted after the chemical name. Reagent/reactant names given are as named on the commercial bottle or as generated by IUPAC conventions or ChemDraw 16.0. None of the specific conditions and reagents noted herein is to be construed as limiting the scope of the invention and are provided for illustrative purposes only.

Example #1. 2-Benzamido-6,6-dimethyl-5,7-dihydro-4H-benzothiophene-3-carboxylic acid (Compound #15)

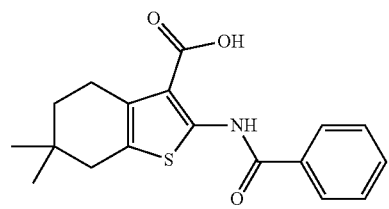 [SMILES: CC1(C)CCc2c(sc(NC(=O)c3ccccc3)c2C(=O)O)C1]

To a solution of methyl 2-amino-6,6-dimethyl-4,5,6,7-tetrahydrobenzo[b]thiophene-3-carboxylate (Preparation #1, 200 mg, 0.84 mmol) in DCM (5.0 ml) was added DIPEA (CAS: 7087-68-5, 220 μl, 1.25 mmol) and benzoyl chloride (CAS: 98-88-4, 120 μl, 1.00 mmol). The reaction mixture was stirred at RT overnight. The resulting mixture was diluted with DCM and water. The two phases were separated. The organic layer was passed through a phase separator and the solvent was removed under reduced pressure. The residue was dissolved in THF (4.0 ml) and MeOH (2.0 ml). To the solution was added LiGH aq. (CAS: 1310-66-3, 2.0M, 1.7 ml, 3.36 mmol). The reaction mixture was stirred at 50° C. for 2 hours. The mixture was allowed to cool to RT and acidified with 1N aqueous HCl solution. The reaction mixture was then extracted with EtOAc. The organic phase was washed with brine and dried over Na$_2$SO$_4$. The solvent was removed under reduced pressure. Purification by RP-HPLC (Table 2, Method 1) afforded 2-benzamido-6,6-dimethyl-5,7-dihydro-4H-benzothiophene-3-carboxylic acid as a pale yellow solid (71 mg, yield 26%). $^1$H NMR (DMSO-d$_6$, 400 MHz): δ=13.31 (br s, 1H), 12.48 (s, 1H), 7.92-7.90 (m, 2H), 7.70-7.60 (m, 3H), 2.76 (t, J=6.2 Hz, 2H), 2.44 (s, 2H), 1.50 (t, J=6.4 Hz, 2H), 0.97 (s, 6H). LC/MS (Table 1, Method A) R$_t$=5.53 min; MS/z: 330 [M+H]$^+$.

Example #2. 2-[(2-Fluoro-4-methoxybenzoyl)amino]-6,6-dimethyl-5,7-dihydro-4H-benzothiophene-3-carboxylic acid (Compound #16)

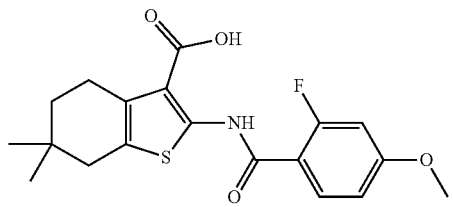

The title compound was synthesized according to the procedure described in Example #1 using methyl 2-amino-6,6-dimethyl-4,5,6,7-tetrahydrobenzo[b]thiophene-3-carboxylate (Preparation #1) and 2-fluoro-4-methoxybenzoyl chloride (CAS: 321-24-4) as starting materials (white solid, yield 44%). $^1$H NMR (DMSO-d$_6$, 400 MHz): δ=13.23 (br s. 1H), 12.36 (d, J=11.0 Hz, 1H), 8.00 (t, J=9.0 Hz, 1H), 7.09-6.98 (m, 2H), 3.88 (s, 3H), 2.75 (t, J=6.2 Hz, 2H), 2.42 (s, 2H), 1.49 (t, J=6.3 Hz, 2H), 0.97 (s, 6H). LC/MS (Table 1, Method A) R$_t$=5.61 min; MS I/z: 378 [M+H]$^+$.

Example #3. 2-[(2,4-Difluorobenzoyl)amino]-6,6-dimethyl-5,7-dihydro-4H-benzothiophene-3-carboxylic acid (Compound #17)

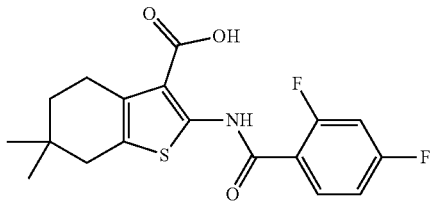 [SMILES: CC1(C)CCc2c(sc(NC(=O)c3ccc(F)cc3F)c2C(=O)O)C1]

The title compound was synthesized according to the procedure described in Example #1 using methyl 2-amino-6,6-dimethyl-4,5,6,7-tetrahydrobenzo[b]thiophene-3-carboxylate (Preparation #1) and 2,4-fluorobenzoyl chloride (CAS: 72482-64-5) as starting materials (pale yellow solid, yield 37%). $^1$H NMR (DMSO-d$_6$, 400 MHz): δ=13.29 (br s, 1H), 12.53 (s, 1H), 8.15-8.09 (m, 1H), 7.54 (dq, J=9.2, 2.4 Hz, 1H), 7.33 (dt, J=8.3, 2.4 Hz, 1H), 2.76 (t, J=6.3 Hz, 2H), 2.43 (s, 2H), 1.50 (t, J=6.4 Hz, 2H), 0.97 (s, 6H). LC/MS (Table 1, Method A) R$_t$=5.65 min; MS m/z: 366 [M+H]$^+$.

Example #4. 2-[(3,4-Dimethoxybenzoyl)amino]-6,6-dimethyl-5,7-dihydro-4H-benzothiophene-3-carboxylic acid (Compound #18)

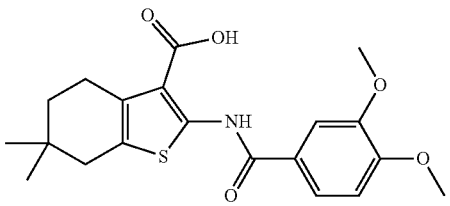

The title compound was synthesized according to the procedure described in Example #1 using methyl 2-amino-6,6-dimethyl-4,5,6,7-tetrahydrobenzo[b]thiophene-3-carboxylate (Preparation #1) and 3,4-dimethoxybenzoyl chloride (CAS: 3535-37-3) as starting materials (off-white solid, yield 56%). $^1$H NMR (DMSO-$d_6$, 400 MHz): δ=13.34 (br s, 1H), 12.36 (s, 1H), 7.49-7.45 (m, 2H), 7.18 (d, J=8.4 Hz, 1H), 3.86 (s, 3H), 3.85 (s, 3H), 2.75 (t, J=5.9 Hz, 2H), 2.42 (s, 2H), 1.50 (t, J=6.3 Hz, 2H), 0.98 (s, 6H). LC/MS (Table 1, Method A) $R_t$=5.31 min; MS m/z: 390 [M+H]$^+$.

Example #5. 2-[(4-Fluorobenzoyl)amino]-6,6-dimethyl-5,7-dihydro-4H-benzothiophene-3-carboxylic acid (Compound #19)

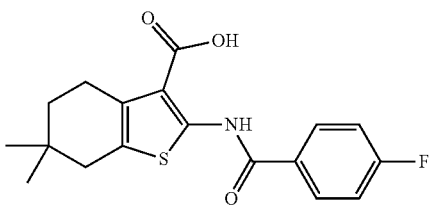 [SMILES: CC1(C)CCc2c(sc(NC(=O)c3ccc(F)cc3)c2C(=O)O)C1]

The title compound was synthesized according to the procedure described in Example #1 using methyl 2-amino-6,6-dimethyl-4,5,6,7-tetrahydrobenzo[b]thiophene-3-carboxylate (Preparation #1) and 4-fluorobenzoyl chloride (CAS: 403-43-0) as starting materials (white solid, yield 47%). $^1$H NMR (DMSO-$d_6$, 400 MHz): δ=13.34 (br s, 1H), 12.37 (s, 1H), 7.99-7.95 (m, 2H), 7.49-7.45 (m, 2H), 2.76 (t, J=6.3 Hz, 2H), 2.44 (s, 2H), 1.50 (t, J=6.4 Hz, 2H), 0.97 (s, 6H). LC/MS (Table 1, Method A) $R_t$=5.60 min; MS m/z: 348 [M+H]$^+$.

Example #6. 2-[(4-Methoxybenzoyl)amino]-6,6-dimethyl-5,7-dihydro-4H-benzothiophene-3-carboxylic acid (Compound #20)

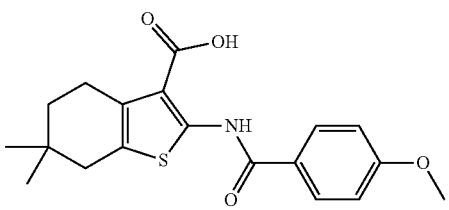

The title compound was synthesized according to the procedure described in Example #1 using methyl 2-amino-6,6-dimethyl-4,5,6,7-tetrahydrobenzo[b]thiophene-3-carboxylate (Preparation #1) and 4-methoxybenzoyl chloride (CAS: 100-07-2) as starting materials (white solid, yield 47%). $^1$H NMR (DMSO-$d_6$, 400 MHz): δ=13.28 (br s, 1H), 12.35 (s, 1H), 7.88-7.85 (m, 2H), 7.17-7.14 (m, 2H), 3.86 (s, 3H), 2.75 (t, J=6.2 Hz, 2H), 2.43 (s, 2H), 1.50 (t, J=6.4 Hz, 2H), 0.97 (s, 6H). LC/MS (Table 1, Method A) $R_t$=5.50 min; MS m/z: 360 [M+H]$^+$.

Example #7. 2-[(3-Methoxybenzoyl)amino]-6,6-dimethyl-5,7-dihydro-4H-benzothiophene-3-carboxylic acid (Compound #21)

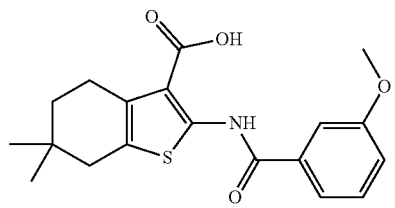 [SMILES: COc1cccc(C(=O)Nc2sc3c(c2C(=O)O)CCC(C)(C)C3)c1]

The title compound was synthesized according to the procedure described in Example #1 using methyl 2-amino-6,6-dimethyl-4,5,6,7-tetrahydrobenzo[b]thiophene-3-carboxylate (Preparation #1) and 3-methoxybenzoyl chloride (CAS: 1711-05-3) as starting materials (white solid, yield 52%). $^1$H NMR (DMSO-$d_6$, 400 MHz): δ=13.36 (br s, 1H), 12.38 (s, 1H), 7.54 (t, J=8.0 Hz, 1H), 7.47-7.42 (m, 2H), 7.27-7.24 (m, 1H), 3.85 (s, 3H), 2.76 (t, J=6.2 Hz, 2H), 2.44 (s, 2H), 1.50 (t, J=6.4 Hz, 2H), 0.97 (s, 6H). LC/MS (Table 1, Method A) $R_t$=5.58 min; MS m/z: 360 [M+H]$^+$.

Example #8. 6,6-Dimethyl-2-[(4-morpholinobenzoyl)amino]-5,7-dihydro-4H-benzothiophene-3-carboxylic acid (Compound #22)

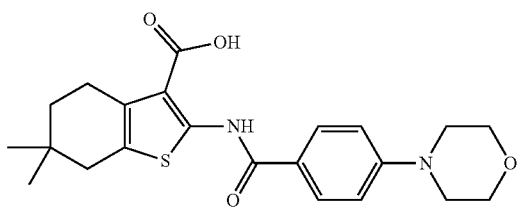 [SMILES: CC1(C)CCc2c(sc(NC(=O)c3ccc(N4CCOCC4)cc3)c2C(=O)O)C1]

To a solution of methyl 6,6-dimethyl-2-(4-morpholinobenzamido)-4,5,6,7-tetrahydrobenzo[b]thiophene-3-carboxylate (Preparation #2, 90 mg, 0.21 mmol) in THF (1.6 ml) and MeOH (1.6 ml) was added LiOH aq. (CAS: 1310-66-3, 1M, 1.0 ml, 1.05 mmol). The reaction mixture was stirred at 50° C. for 5 hours. The mixture was allowed to cool to RT. The reaction was partitioned between 1N aqueous HCl solution and DCM. The two phases were separated. The aqueous phase was extracted with DCM (×2). The combined organic layers were passed through a phase separator and the solvent was removed under reduced pressure. The residue was triturated with MeOH to give 6,6-dimethyl-2-[(4-morpholinobenzoyl)amino]-5,7-dihydro-4H-benzothiophene-3-carboxylic acid as a yellow solid (51 mg, yield 59%). $^1$H NMR (CDC$_3$, 400 MHz): δ=11.96 (s, 1H), 7.91 (d, J=8.9 Hz, 2H), 6.94 (d, J=9.0 Hz, 2H), 3.89-3.85 (m, 4H), 3.32-3.29 (m, 4H), 2.87 (t, J=6.3 Hz, 2H), 2.47 (s, 2H), 1.57 (t, J=6.4 Hz, 2H), 1.02 (s, 6H), one exchangeable proton not observed. LC/MS (Table 1, Method B) R$_t$=2.79 min; MS m/z: 415 [M+H]$^+$.

Example #9. 2-[[4-(Difluoromethoxy)benzoyl]amino]-6,6-dimethyl-5,7-dihydro-4H-benzothiophene-3-carboxylic acid (Compound #23)

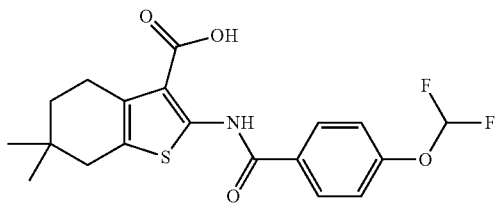 [SMILES: CC1(C)CCc2c(sc(NC(=O)c3ccc(OC(F)F)cc3)c2C(=O)O)C1]

The title compound was synthesized according to the procedure described in Example #1 using methyl 2-amino-6,6-dimethyl-4,5,6,7-tetrahydrobenzo[b]thiophene-3-carboxylate (Preparation #1) and 4-(difluoromethoxy)benzoyl chloride (CAS: 57320-63-5) as starting materials (off-white solid, yield 41%). $^1$H NMR (DMSO-d$_6$, 400 MHz): δ=13.36 (s, 1H), 12.50 (s, 1H), 7.98 (d, J=8.8 Hz, 2H), 7.61-7.24 (m, 3H), 2.78 (t, J=6.0 Hz, 2H), 2.46 (s, 2H), 1.52 (t, J=6.2 Hz, 2H), 0.98 (s, 6H). LC/MS (Table 1, Method C) R$_t$=3.87 min; MS m/z: 396 [M+H]$^+$.

Example #10. 6,6-Dimethyl-2-[[4-(trifluoromethoxy)benzoyl]amino]-5,7-dihydro-4H-benzothiophene-3-carboxylic acid (Compound #24)

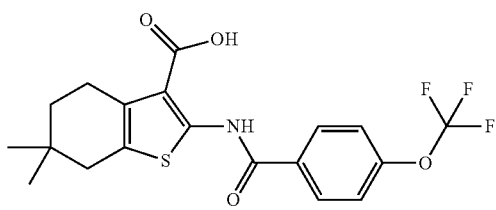 [SMILES: CC1(C)CCc2c(sc(NC(=O)c3ccc(OC(F)(F)F)cc3)c2C(=O)O)C1]

The title compound was synthesized according to the procedure described in Example #1 using methyl 2-amino-6,6-dimethyl-4,5,6,7-tetrahydrobenzo[b]thiophene-3-carboxylate (Preparation #1) and 4-(trifluoromethoxy)benzoyl chloride (CAS: 36823-88-8) as starting materials (pale yellow solid, yield 39%). $^1$H NMR (DMSO-d$_6$, 400 MHz): δ=13.38 (br s, 1H), 12.54 (s, 1H), 8.08 (d, J=8.8 Hz, 2H), 7.67 (d, J=8.2 Hz, 2H), 2.82 (t, J=5.9 Hz, 2H), 2.49 (s, 2H), 1.56 (t, J=6.4 Hz, 2H), 1.01 (s, 6H). LC/MS (Table 1, Method B) R$_t$=3.00 min; MS m/z: 414 [M+H]$^+$.

Example #11. 2-[(5-Methoxypyridine-2-carbonyl)amino]-6,6-dimethyl-5,7-dihydro-4H-benzothiophene-3-carboxylic acid (Compound #25)

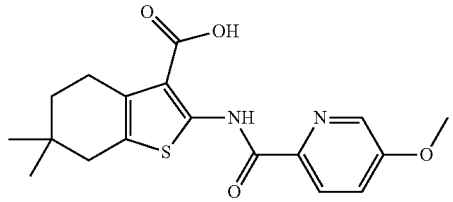

To a suspension of 5-methoxypicolinic acid (CAS: 29082-92-6, 166 mg, 1.09 mmol) in toluene (4.0 ml) and DMF (0.01 ml) was added oxalyl chloride (CAS: 79-37-8, 109 µl, 1.25 mmol). The reaction mixture was stirred at 50° C. for 3 hours. The reaction was allowed to cool to RT. The volatiles were removed in vacuo and the residue was dissolved in DCM (4 ml). Methyl 2-amino-6,6-dimethyl-4,5,6,7-tetrahydrobenzo[b]thiophene-3-carboxylate (Preparation #1, 200 mg, 0.84 mmol) and DIPEA (CAS: 7087-68-5, 190 µl, 1.09 mmol) were added to the reaction mixture. The reaction was stirred at RT overnight. The resulting mixture was diluted with DCM and the organic phase was washed with 0.1N aqueous HCl solution. The organic phase was passed through a phase separator and the solvent was removed under reduced pressure. The residue was dissolved in THF (6.0 ml) and methanol (2.0 ml) and LiGH aq. (CAS: 1310-66-3, 2M, 1.68 ml, 3.34 mmol) was added. The reaction mixture was stirred at 50° C. overnight. An additional aliquot of LiGH aq. (2M, 0.84 ml, 1.67 mmol) was added and the reaction mixture was heated at 60° C. for an additional 7 hours. The mixture was allowed to cool to RT and acidified with a 1N aqueous HCl solution. The precipitate was filtered and the solid collected was purified by RP-HPLC (Table 2, Method 1) to give 2-[(5-methoxypyridine-2-carbonyl)amino]-6,6-dimethyl-5,7-dihydro-4H-benzothiophene-3-carboxylic acid as a yellow solid (35 mg, yield 12%). $^1$H NMR (DMSO-d$_6$, 400 MHz): δ=13.11 (s, 1H), 12.91 (s, 1H), 8.43 (d, J=2.5 Hz, 1H), 8.14 (d, J=8.6 Hz, 1H), 7.63 (dd, J=2.9, 8.8 Hz, 1H), 3.95 (s, 3H), 2.77 (t, J=6.3 Hz, 2H), 2.43 (s, 2H), 1.50 (t, J=6.4 Hz, 2H), 0.98 (s, 6H). LC/MS (Table 1, Method A) R$_t$=5.32 min; MS m/z: 361 [M+H]$^+$.

Example #12. 2-Benzamido-5,5-dimethyl-6,7-dihydro-4H-benzothiophene-3-carboxylic acid (Compound #26)

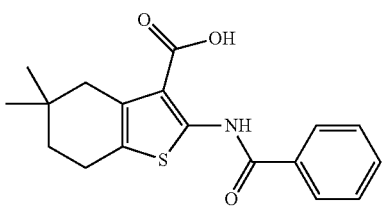 [SMILES: CC1(C)CCc2sc(NC(=O)c3ccccc3)c(C(=O)O)c2C1]

The title compound was synthesized according to the procedure described in Example #1 using methyl 2-amino-5,5-dimethyl-4,5,6,7-tetrahydrobenzo[b]thiophene-3-carboxylate (Preparation #3) and benzoyl chloride (CAS:

98-88-4) as starting materials (off-white solid, yield 45%). ¹H NMR (DMSO-d₆, 400 MHz): δ=13.33 (s, 1H), 12.51 (s, 1H), 7.94-7.89 (m, 2H), 7.71-7.65 (m, 1H), 7.65-7.59 (m, 2H), 2.67 (t, J=6.1 Hz, 2H), 2.58 (s, 2H), 1.54 (t, J=6.3 Hz, 2H), 0.97 (s, 6H). LC/MS (Table 1, Method A) $R_t$=5.46 min; MS m/z: 330 [M+H]⁺.

Example #13. 2-[(3,4-Dimethoxybenzoyl)amino]-5,5-dimethyl-6,7-dihydro-4H-benzothiophene-3-carboxylic acid (Compound #27)

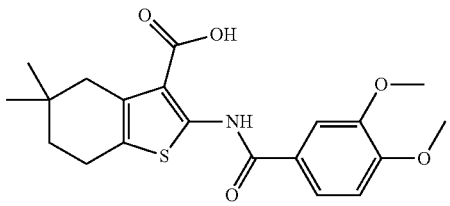

The title compound was synthesized according to the procedure described in Example #1 using methyl 2-amino-5,5-dimethyl-4,5,6,7-tetrahydrobenzo[b]thiophene-3-carboxylate (Preparation #3) and 3,4-dimethoxybenzoyl chloride (CAS: 3535-37-3) as starting materials (white solid, yield 46%). ¹H NMR (DMSO-d₆, 400 MHz): δ=13.36 (s, 1H), 12.39 (s, 1H), 7.50-7.46 (m, 2H), 7.18 (d, J=8.1 Hz, 1H), 3.86 (s, 3H), 3.85 (s, 3H), 2.65 (t, J=6.3 Hz, 2H), 2.57 (s, 2H), 1.54 (t, J=6.3 Hz, 2H), 0.97 (s, 6H). LC/MS (Table 1, Method A) $R_t$=5.25 min; MS I/z: 390 [M+H]⁺.

Example #14. 2-Benzamido-4,5,6,7-tetrahydro-4,7-methanobenzo[b]thiophene-3-carboxylic acid (Compound #28)

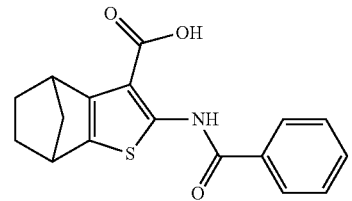 [SMILES: O=C(Nc1sc2c(c1C(=O)O)C1CCC2C1)c1ccccc1]

A solution of norcamphor (CAS: 497-38-1, 1000 mg, 9.08 mmol), ethyl cyanoacetate (CAS: 105-56-6, 1.1 ml, 9.99 mmol), morpholine (CAS: 110-91-8, 1.96 ml, 22.7 mmol) and sulfur (CAS: 7704-34-9, 320 mg, 9.99 mmol) in ethanol (14 ml) was stirred at 50° C. for 48 hours. The reaction mixture was allowed to cool to RT and the volatiles were removed under reduced pressure. The residue was partitioned between water and EtOAc and the two phases were separated. The aqueous phase was extracted with EtOAc. The combined organic phases were washed with brine and dried over Na₂SO₄. The solvent was removed under reduced pressure. Purification by flash chromatography on silica gel (eluting with 0-40% EtOAc in isohexane) afforded ethyl 2-amino-4,5,6,7-tetrahydro-4,7-methanobenzo[b]thiophene-3-carboxylate (150 mg, yield 7%). The title compound was then synthesized according to the procedure described in Example #1 using ethyl 2-amino-4,5,6,7-tetrahydro-4,7-methanobenzo[b]thiophene-3-carboxylate and benzoyl chloride (CAS: 98-88-4) as starting materials (white solid, yield 20%). ¹H NMR (DMSO-d₆, 400 MHz): δ=13.26 (s, 1H), 12.10 (s, 1H), 7.93-7.89 (m, 2H), 7.70-7.59 (m, 3H), 3.70 (s, 1H), 3.53 (s, 1H), 1.85-1.79 (m, 2H), 1.74 (d, J=8.5 Hz, 1H), 1.52 (d, J=8.5 Hz, 1H), 0.89-0.82 (m, 2H). LC/MS (Table 1, Method A) $R_t$=5.00 min; MS m/z: 314 [M+H]⁺.

Example #15. 2-Benzamidospiro[5,7-dihydro-4H-benzothiophene-6,1'-cyclopropane]-3-carboxylic acid (Compound #29)

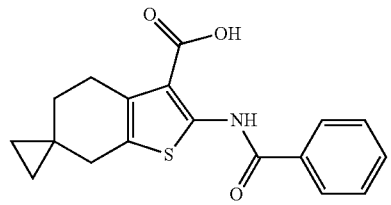 [SMILES: O=C(Nc1sc2c(c1C(=O)O)CCC1(CC1)C2)c1ccccc1]

The title compound was synthesized according to the procedure described in Example #1 using methyl 2-amino-4,7-dihydro-5H-spiro[benzo[b]thiophene-6,1'-cyclopropane]-3-carboxylate (Preparation #4) and benzoyl chloride (CAS: 98-88-4) as starting materials (white solid, yield 26%). ¹H NMR (DMSO-d₆, 400 MHz): δ=12.05 (s, 1H), 10.77 (s, 1H), 8.01-7.98 (m, 2H), 7.63-7.51 (m, 3H), 2.96 (t, J=6.2 Hz, 2H), 2.58 (s, 2H), 1.62 (t, J=6.2 Hz, 2H), 0.47-0.45 (m, 4H). LC/MS (Table 1, Method A) $R_t$=5.24 min; MS/z: 328 [M+H]⁺.

Example #16. 2-[(3,4-Dimethoxybenzoyl)amino]spiro[5,7-dihydro-4H-benzothiophene-6,1'-cyclopropane]-3-carboxylic acid (Compound #30)

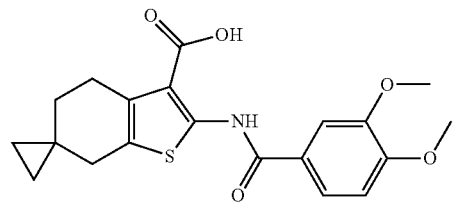 [SMILES: COc1ccc(C(=O)Nc2sc3c(c2C(=O)O)CCC2(CC2)C3)cc1OC]

The title compound was synthesize according to the procedure described in Example #1 using methyl 2-amino-4,7-dihydro-5H-spiro[benzo[b]thiophene-6,1'-cyclopropane]-3-carboxylate (Preparation #4) and 3,4-dimethoxybenzoyl chloride (CAS: 3535-37-3) as starting materials (white solid, yield 18%). ¹H NMR (DMSO-d₆, 400 MHz): δ=13.34 (s, 1H), 12.37 (s, 1H), 7.51-7.45 (m, 2H), 7.18 (d, J=8.5 Hz, 1H), 3.86 (s, 3H), 3.86 (s, 3H), 2.82 (t, J=5.6 Hz, 2H), 2.53 (s, 2H), 1.53 (t, J=6.0 Hz, 2H), 0.43-0.36 (m, 4H). LC/MS (Table 1, Method A) $R_t$=5.08 min; MS m/z: 388 [M+H]⁺.

Example #17. 2-[(4-Morpholinobenzoyl)amino]spiro[5,7-dihydro-4H-benzothiophene-6,1'-cyclopropane]-3-carboxylic acid (Compound #31)

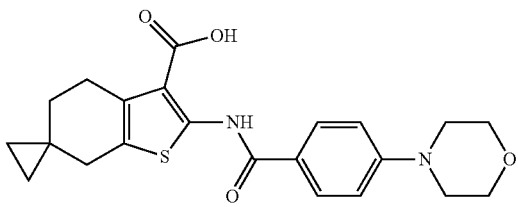 [SMILES: O=C(Nc1sc2c(c1C(=O)O)CCC1(CC1)C2)c1ccc(N2CCOCC2)cc1]

The title compound was synthesized according to the procedure described in Example #8 using methyl 2-(4-morpholinobenzamido)-4,7-dihydro-5H-spiro[benzo[b]thiophene-6,1'-cyclopropane]-3-carboxylate (Preparation #5) as a starting material (pale yellow solid, yield 34%). $^1$H NMR (CDCl$_3$, 400 MHz): δ=12.01 (s, 1H), 7.91 (d, J=9.0 Hz, 2H), 6.94 (d, J=9.0 Hz, 2H), 3.89-3.85 (m, 4H), 3.32-3.28 (m, 4H), 2.93 (t, J=6.4 Hz, 2H), 2.56 (s, 2H), 1.61 (t, J=6.3 Hz, 2H), 0.46-0.43 (m, 4H), one exchangeable proton not observed. LC/MS (Table 1, Method C) R$_t$=3.66 min: MS m/z: 413 [M+H]$^+$.

Example #18. 2-[(4-Fluorobenzoyl)amino]spiro[5,7-dihydro-4H-benzothiophene-6,1'-cyclopropane]-3-carboxylic acid (Compound #32)

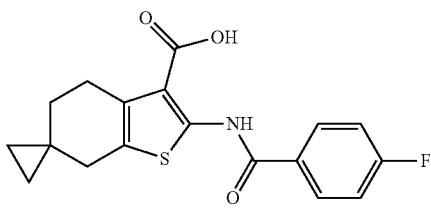 [SMILES: O=C(Nc1sc2c(c1C(=O)O)CCC1(CC1)C2)c1ccc(F)cc1]

The title compound was synthesized according to the procedure described in Example #1 using methyl 2-amino-4,7-dihydro-5H-spiro[benzo[b]thiophene-6,1'-cyclopropane]-3-carboxylate (Preparation #4) and 4-fluorobenzoyl chloride (CAS: 403-43-0) as starting materials (off-white solid, yield 21%). $^1$H NMR (DMSO-d$_6$, 400 MHz): δ=12.06 (s, 1H), 8.03-7.97 (m, 2H), 7.21 (t, J=8.6 Hz, 2H), 2.94 (t, J=6.1 Hz, 2H), 2.57 (s, 2H), 1.63 (t, J=6.0 Hz, 2H), 0.49-0.41 (m, 4H), one exchangeable proton not observed. LC/MS (Table 1, Method C) R$_t$=3.77 min; MS I/z: 346 [M+H]$^+$.

Example #19. 2-Benzamido-5,5,7,7-tetramethyl-4,6-dihydrobenzothiophene-3-carboxylic acid (Compound #33)

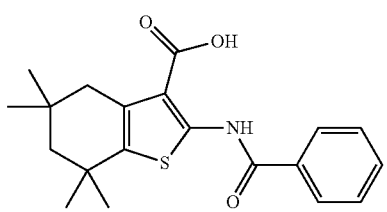 [SMILES: CC1(C)Cc2c(sc(NC(=O)c3ccccc3)c2C(=O)O)C(C)(C)C1]

The title compound was synthesized according to the procedure described in Example #1 using ethyl 2-amino-5,5,7,7-tetramethyl-4,5,6,7-tetrahydrobenzo[b]thiophene-3-carboxylate (Preparation #6) and benzoyl chloride (CAS: 98-88-4) as starting materials (off-white solid, yield 56%). $^1$H NMR (DMSO-d$_6$, 400 MHz): δ=13.37 (s, 1H), 12.44 (s, 1H), 7.93-7.89 (m, 2H), 7.72-7.61 (m, 3H), 2.60 (s, 2H), 1.57 (s, 2H), 1.33 (s, 6H), 1.00 (s, 6H). LC/MS (Table 1, Method A) R$_t$=5.88 min; MS m/z: 358 [M+H]$^+$.

Example #20. 2-[[4-(4-Hydroxy-1-piperidyl)benzoyl]amino]-5,5,7,7-tetramethyl-4,6-dihydrobenzothiophene-3-carboxylic acid (Compound #34)

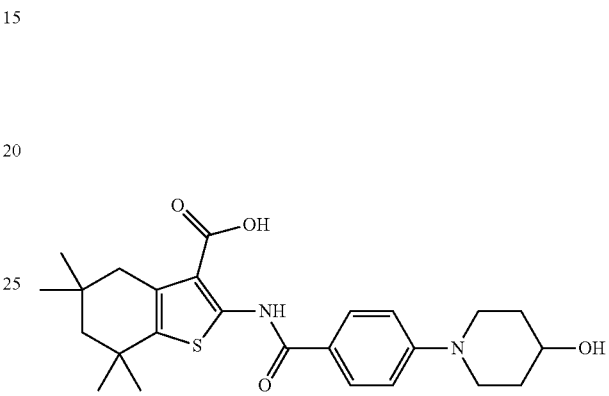

Ethyl 2-(4-bromobenzamido)-5,5,7,7-tetramethyl-4,5,6,7-tetrahydrobenzo[b]thiophene-3-carboxylate (Preparation #7, 100 mg, 0.22 mmol), piperidin-4-yl acetate hydrochloride (CAS: 81270-37-3, 63 mg, 0.32 mmol), RuPhos Pd G2 (CAS: 1375325-68-0, 33 mg, 0.04 mmol) and Cs$_2$CO$_3$ (CAS: 534-17-8, 175 mg, 0.54 mmol) were suspended in dioxane (3.0 ml). The reaction mixture was degassed with nitrogen for 5 minutes. The reaction was heated at 70° C. overnight and then allowed to cool to RT. The reaction was diluted with DCM. The organic phase was washed with water and passed through a phase separator. The solvent was removed under reduced pressure to give ethyl 2-(4-(4-acetoxypiperidin-1-yl)benzamido)-5,5,7,7-tetramethyl-4,5,6,7-tetrahydrobenzo[b]thiophene-3-carboxylate as a yellow oil (116 mg, yield quant.). Ethyl 2-(4-(4-acetoxypiperidin-1-yl)benzamido)-5,5,7,7-tetramethyl-4,5,6,7-tetrahydrobenzo[b]thiophene-3-carboxylate (116 mg, 0.22 mmol) was dissolved in THF (3.0 ml) and MeOH (3.0 ml). LiGH aq. (CAS: 1310-66-3, 1M, 60 mg, 1.43 mmol) was added. The reaction mixture was stirred at 35° C. overnight. The mixture was allowed to cool to RT. The volatiles were removed in vacuo and the residue was acidified with 1N aqueous HCl solution to pH-3. The precipitate was filtered and the solid was purified by RP-HPLC (Table 2, Method 2) to give 2-[[4-(4-hydroxy-1-piperidyl)benzoyl]amino]-5,5,7,7-tetramethyl-4,6-dihydrobenzothiophene-3-carboxylic acid as an off-white solid (8 mg, yield 8%). $^1$H NMR (DMSO-d$_6$, 400 MHz): δ=12.71 (s, 1H), 7.69 (d, J=8.6 Hz, 2H), 7.02 (d, J=8.9 Hz, 2H), 4.67 (s, 1H), 3.73-3.64 (m, 3H), 3.03 (t, J=11.0 Hz, 2H), 2.57 (s, 2H), 1.80-1.73 (m, 2H), 1.50 (s, 2H), 1.43-1.35 (m, 2H), 1.26 (s, 6H), 0.94 (s, 6H), one exchangeable proton not observed. LC/MS (Table 1, Method C) R$_t$=3.78 min; MS m/z: 457 [M+H]$^+$.

Example #21. 5,5,7,7-Tetramethyl-2-[[4-(tetrahydropyran-4-ylamino)benzoyl]amino]-4,6-dihydrobenzothiophene-3-carboxylic acid (Compound #35)

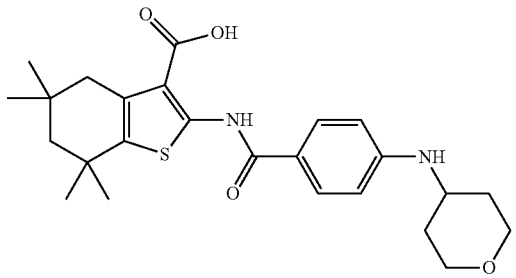 [SMILES: CC1(C)Cc2c(sc(NC(=O)c3ccc(NC4CCOCC4)cc3)c2C(=O)O)C(C)(C)C1]

The title compound was synthesized according to the procedure described in Example #20 using ethyl 2-(4-bromobenzamido)-5,5,7,7-tetramethyl-4,5,6,7-tetrahydrobenzo[b]thiophene-3-carboxylate (Preparation #7) and 4-aminotetrahydropyran (CAS: 38041-19-9) as starting materials (yellow solid, yield 29%). $^1$H NMR (DMSO-$d_6$, 400 MHz): δ=12.47 (s, 1H), 7.69 (d, J=8.8 Hz, 2H), 6.78 (d, J=8.6 Hz, 2H), 6.57 (d, J=7.5 Hz, 1H), 3.96-3.90 (m, 2H), 3.62 (br s, 1H), 3.49 (t, J=11.0 Hz, 2H, partially obscured by the water peak), 2.63 (s, 2H), 1.94 (d, J=12.2 Hz, 2H), 1.61 (s, 2H), 1.52-1.41 (m, 2H), 1.34 (s, 6H), 1.05 (s, 6H), one proton exchangeable not observed. LC/MS (Table 1, Method C) $R_t$=3.88 min; MS m/z: 457 [M+H]$^+$.

Example #22. 5,5,7,7-Tetramethyl-2-[(4-morpholinobenzoyl)amino]-4,6-dihydrobenzothiophene-3-carboxylic acid (Compound #36)

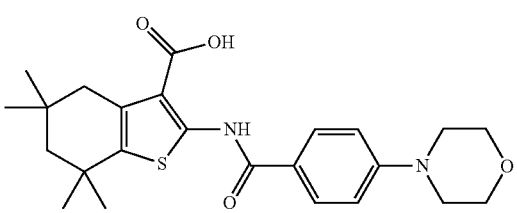 [SMILES: CC1(C)Cc2c(sc(NC(=O)c3ccc(N4CCOCC4)cc3)c2C(=O)O)C(C)(C)C1]

The title compound was synthesized according to the procedure described in Example #20 using ethyl 2-(4-bromobenzamido)-5,5,7,7-tetramethyl-4,5,6,7-tetrahydrobenzo[b]thiophene-3-carboxylate (Preparation #7) and morpholine (CAS: 110-91-8) as starting materials (white solid, yield 20%). $^1$H NMR (DMSO-$d_6$, 400 MHz): δ=12.76 (s, 1H), 7.82 (d, J=8.6 Hz, 2H), 7.14 (d, J=8.7 Hz, 2H), 3.80 (dd, J=4.1, 4.1 Hz, 4H), 3.35-3.33 (m, 4H, partially obscured by the water peak), 2.65 (s, 2H), 1.60 (s, 2H), 1.37 (s, 6H), 1.04 (s, 6H), one exchangeable proton not observed. LC/MS (Table 1, Method C) $R_t$=3.94 min; MS m/z: 443 [M+H]$^+$.

Example #23. 2-Benzamido-4,4-dimethyl-5,6-dihydrocyclopenta[b]thiophene-3-carboxylic acid (Compound #37)

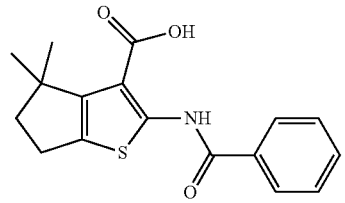 [SMILES: CC1(C)CCc2sc(NC(=O)c3ccccc3)c(C(=O)O)c21]

The title compound was synthesized according to the procedure described in Example #1 using ethyl 2-amino-4,4-dimethyl-5,6-dihydro-4H-cyclopenta[b]thiophene-3-carboxylate (Preparation #8) and benzoyl chloride (CAS: 98-88-4) as starting materials (white solid, yield 35%). $^1$H NMR (CDCl$_3$, 400 MHz): δ=12.20 (s, 1H), 8.02-7.98 (m, 2H), 7.60 (tt, J=1.5, 7.3 Hz, 1H), 7.55-7.49 (m, 2H), 2.85 (t, J=7.3 Hz, 2H), 2.29 (t, J=7.2 Hz, 2H), 1.42 (s, 6H), one exchangeable proton not observed. LC/MS (Table 1, Method C) $R_f$=3.74 min: MS m/z: 316 [M+H]$^+$.

Example #24. 2-[(3,4-Dimethoxybenzoyl)amino]-4,4-dimethyl-5,6-dihydrocyclopenta[b]thiophene-3-carboxylic acid (Compound #38)

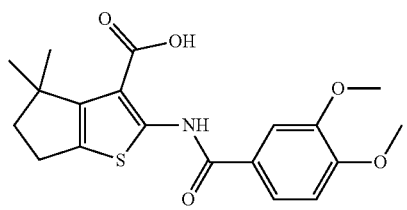

The title compound was synthesized according to the procedure described in Example #1 using ethyl 2-amino-4,4-dimethyl-5,6-dihydro-4H-cyclopenta[b]thiophene-3-carboxylate (Preparation #8) and 3,4-dimethoxybenzoyl chloride (CAS: 3535-37-3) as starting materials (white solid, yield 69%). $^1$H NMR (CDCl$_3$, 400 MHz): δ=12.16 (s, 1H), 7.61-7.55 (m, 2H), 6.95 (d, J=8.4 Hz, 1H), 3.98 (s, 3H), 3.96 (s, 3H), 2.88-2.83 (m, 2H), 2.31-2.26 (m, 2H), 1.42 (s, 6H), one exchangeable proton not observed. LC/MS (Table 1, Method C) $R_t$=3.66 min; MS I/z: 376 [M+H]$^+$.

Example #25. 2-[[4-(Difluoromethoxy)benzoyl]amino]-4,4-dimethyl-5,6-dihydrocyclopenta[b]thiophene-3-carboxylic acid (Compound #39)

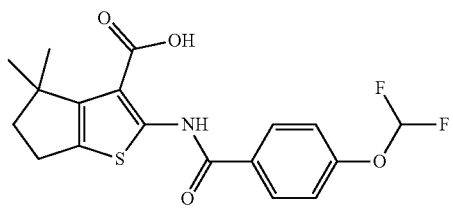 [SMILES: CC1(C)CCc2sc(NC(=O)c3ccc(OC(F)F)cc3)c(C(=O)O)c21]

The title compound was synthesized according to the procedure described in Example #1 using ethyl 2-amino-4,4-dimethyl-5,6-dihydro-4H-cyclopenta[b]thiophene-3-carboxylate (Preparation #8) and 4-(difluoromethoxy)benzoyl chloride (CAS: 57320-63-5) as starting materials (off-white solid, yield 35%). $^1$H NMR (DMSO-d$_6$, 400 MHz): δ=13.95 (s, 1H), 8.02-7.97 (m, 2H), 7.59-7.21 (m, 4H), 2.82-2.77 (m, 2H), 2.19 (t, J=7.1 Hz, 2H), 1.38 (s, 6H), one exchangeable proton not observed. LC/MS (Table 1, Method B) R$_t$=2.87 min; MS m/z: 382 [M+H]$^+$.

Example #26. 4,4-Dimethyl-2-[[4-(trifluoromethoxy)benzoyl]amino]-5,6-dihydrocyclopenta[b]thiophene-3-carboxylic acid (Compound #40)

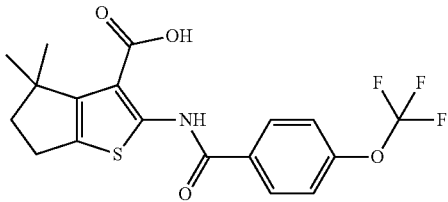 [SMILES: CC1(C)CCc2sc(NC(=O)c3ccc(OC(F)(F)F)cc3)c(C(=O)O)c21]

The title compound was synthesized according to the procedure described in Example #1 using ethyl 2-amino-4,4-dimethyl-5,6-dihydro-4H-cyclopenta[b]thiophene-3-carboxylate (Preparation #8) and 4-(trifluoromethoxy)benzoyl chloride (CAS: 36823-88-8) as starting materials (off-white solid, yield 29%). $^1$H NMR (DMSO-d$_6$, 400 MHz): δ=14.00 (s, 1H), 8.09-8.04 (m, 2H), 7.61-7.57 (m, 2H), 7.17 (s, 1H), 2.83-2.77 (m, 2H), 2.22-2.17 (m, 2H), 1.38 (s, 6H). LC/MS (Table 1, Method B) R$_t$=2.97 min; MS m/z: 400 [M+H]$^+$.

Example #27. 4,4-Dimethyl-2-[(4-morpholinobenzoyl)amino]-5,6-dihydrocyclopenta[b]thiophene-3-carboxylicacid (Compound #41)

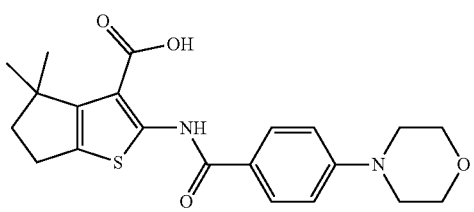 [SMILES: CC1(C)CCc2sc(NC(=O)c3ccc(N4CCOCC4)cc3)c(C(=O)O)c21]

The title compound was synthesized according to the procedure described in Example #20 using ethyl 2-(4-bromobenzamido)-4,4-dimethyl-5,6-dihydro-4H-cyclopenta[b]thiophene-3-carboxylate (Preparation #9) and morpholine (CAS: 110-91-8) as starting materials (off-white solid, yield 19%). $^1$H NMR (DMSO-d$_6$, 400 MHz): δ=13.45 (s, 1H), 12.38 (s, 1H), 7.82 (d, J=8.9 Hz, 2H), 7.17 (d, J=8.3 Hz, 2H), 3.83-3.79 (m, 4H), 3.37-3.33 (m, 4H, partially covered by the water peak), 2.84 (t, J=7.0 Hz, 2H), 2.25 (t, J=7.0 Hz, 2H), 1.40 (s, 6H). LC/MS (Table 1, Method B) R$_t$=2.81 min; MS m/z: 401 [M+H]$^+$.

Example #28. 2-Benzamido-4,4-dimethyl-6,7-dihydro-5H-benzothiophene-3-carboxylic acid (Compound #42)

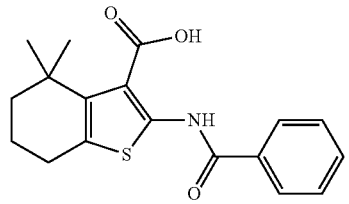 [SMILES: CC1(C)CCCc2sc(NC(=O)c3ccccc3)c(C(=O)O)c21]

To a stirred solution of 2,2-dimethylcyclohexanone (CAS: 1193-47-1, 0.33 ml, 2.38 mmol), methyl cyanoacetate (CAS: 105-34-0, 210 µl, 2.38 mmol) and sulfur (CAS: 7704-34-9, 76 mg, 2.38 mmol) in ethanol (3.5 ml) was added morpholine (CAS: 110-91-8, 210 µl, 2.38 mmol). The reaction mixture was heated at 50° C. for 48 hours and at 75° C. for a further 24 hours. The reaction mixture was allowed to cool to RT. The reaction was diluted with EtOAc and saturated aqueous NaHCO$_3$ solution. The aqueous phase was extracted with EtOAc (×3). The combined organic phases were washed with 0.5N aqueous HCl solution, passed through a phase separator and the solvent was removed under reduced pressure. Purification by flash chromatography on silica gel (eluting with 0-30% EtOAc in isohexane) afforded ethyl 2-benzamido-4,4-dimethyl-4,5,6,7-tetrahydrobenzo[b]thiophene-3-carboxylate as a yellow oil (40 mg, yield 9%). The title compound was then synthesized according to the procedure described in Example #1 using ethyl 2-amino-4,4-dimethyl-4,5,6,7-tetrahydrobenzo[b]thiophene-3-carboxylate and benzoyl chloride (CAS: 98-88-4) as starting materials (off-white solid, yield 4%). $^1$H NMR (DMSO-d$_6$, 400 MHz): δ=13.35 (s, 1H), 7.94-7.90 (m, 2H), 7.68-7.58 (m, 3H), 2.65 (t, J=6.2 Hz, 2H), 1.83-1.75 (m, 2H), 1.59-1.54 (m, 2H), 1.41 (s, 6H), one exchangeable proton not observed. LC/MS (Table 1, Method B) R$_t$=2.76 min; MS m/z: 330 [M+H]$^+$.

Example #29. 2-Benzamido-4,6,6-trimethyl-4,5-dihydrocyclopenta[b]thiophene-3-carboxylic acid (Compound #43)

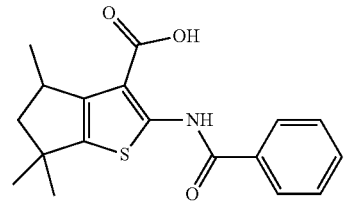 [SMILES: CC1CC(C)(C)c2sc(NC(=O)c3ccccc3)c(C(=O)O)c21]

The title compound was synthesized according to the procedure described in Example #1 using ethyl 2-amino-4,6,6-trimethyl-5,6-dihydro-4H-cyclopenta[b]thiophene-3-carboxylate (Preparation #10) and benzoyl chloride (CAS: 98-88-4) as starting materials (off-white solid, yield 44%). $^1$H NMR (DMSO-d$_6$, 400 MHz): δ=13.40 (br s, 1H), 12.32 (s, 1H), 7.97 (d, J=7.5 Hz, 2H), 7.77-7.66 (m, 3H), 3.38-3.30 (m, 1H, partially obscured by the water peak), 2.55-2.47 (m, 1H, partially obscured by the DMSO peak), 1.88 (dd, J=2.7,

Example #30. 2-Benzamido-4,6,6-trimethyl-5,7-dihydro-4H-benzothiophene-3-carboxylic acid (Compound #44)

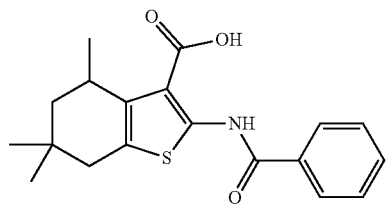 [SMILES: CC1CC(C)(C)Cc2sc(NC(=O)c3ccccc3)c(C(=O)O)c21]

The title compound was synthesized according to the procedure described in Example #1 using ethyl 2-amino-4,6,6-trimethyl-4,5,6,7-tetrahydrobenzo[b]thiophene-3-carboxylate (Preparation #11) and benzoyl chloride (CAS: 98-88-4) as starting materials (off-white solid, yield 3%). $^1$H NMR (DMSO-d$_6$, 400 MHz): δ=13.17 (br s, 2H), 7.92 (d, J=7.6 Hz, 2H), 7.69-7.56 (m, 3H), 3.16-3.10 (m, 1H), 2.50-2.35 (m, 3H), 1.75-1.71 (m, 1H), 1.20 (d, J=6.3 Hz, 3H), 1.06 (s, 3H), 0.88 (s, 3H). LC/MS (Table 1, Method B) R$_t$=2.86 min; MS m/z: 344 [M+H]$^+$.

Example #31. 2-[[4-(3-Methoxyazetidin-1-yl)benzoyl]amino]-5,5,7,7-tetramethyl-4,6-dihydrobenzothiophene-3-carboxylic acid (Compound #58)

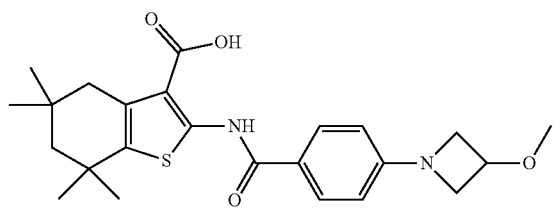

The title compound was synthesized according to the procedure described in Example #20 using ethyl 2-(4-bromobenzamido)-5,5,7,7-tetramethyl-4,5,6,7-tetrahydrobenzo[b]thiophene-3-carboxylate (Preparation #7) and 3-methoxyazetidine (CAS: 110925-17-2) as starting materials (white solid, yield 21%). $^1$H NMR (DMSO-d$_6$, 400 MHz): δ=12.65 (br s, 1H), 7.78 (d, J=8.6 Hz, 2H), 6.59 (d, J=8.6 Hz, 2H), 4.45-4.37 (m, 1H), 4.23-4.16 (m, 2H), 3.79 (dd, J=3.7, 8.7 Hz, 2H), 3.31 (s, 3H), 2.65 (s, 2H), 1.60 (s, 2H), 1.36 (s, 6H), 1.04 (s, 6H), one exchangeable proton not observed. LC/MS (Table 1, Method B) R$_t$=3.03 min; MS m/z: 443 [M+H]$^+$.

Example #32. 5,5,7,7-Tetramethyl-2-[[4-(oxetan-3-ylmethylamino)benzoyl]amino]-4,6-dihydrobenzothiophene-3-carboxylic acid (Compound #59)

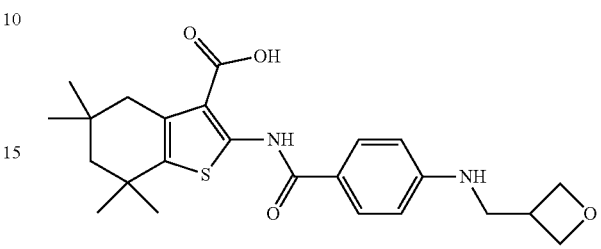

The title compound was synthesized according to the procedure described in Example #20 using ethyl 2-(4-bromobenzamido)-5,5,7,7-tetramethyl-4,5,6,7-tetrahydrobenzo[b]thiophene-3-carboxylate (Preparation #7) and 1-(3-aminoazetidin-1-yl)ethan-1-one (CAS: 6246-05-5) as starting materials (white solid, yield 6%). $^1$H NMR (DMSO-d$_6$, 400 MHz): δ=13.24 (br s, 1H), 12.33 (br s, 1H), 7.70 (d, J=8.6 Hz, 2H), 6.74 (dd, J=8.7, 8.7 Hz, 3H), 4.76-4.70 (m, 2H), 4.36 (dd, J=5.8, 5.8 Hz, 2H), 3.46 (dd, J=6.2, 6.2 Hz, 2H), 3.31-3.21 (m, 1H), 2.63 (s, 2H), 1.60 (s, 2H), 1.36 (s, 6H), 1.04 (s, 6H). LC/MS (Table 1, Method B) R$_t$=2.94 min: MS/z: 443 [M+H]$^+$.

Example #33. 2-[[4-(2-Methoxyethylamino)benzoyl]amino]-5,5,7,7-tetramethyl-4,6-dihydrobenzothiophene-3-carboxylic acid (Compound #60)

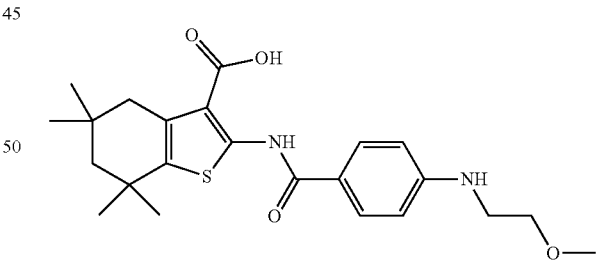

The title compound was synthesized according to the procedure described in Example #20 using ethyl 2-(4-bromobenzamido)-5,5,7,7-tetramethyl-4,5,6,7-tetrahydrobenzo[b]thiophene-3-carboxylate (Preparation #7) and 2-methoxyethylamine (CAS: 109-85-3) as starting materials (off-white solid, yield 23%). $^1$H NMR (DMSO-d$_6$, 400 MHz): δ=13.19 (br s, 1H), 12.28 (br s, 1H), 7.65 (d, J=8.8 Hz, 2H), 6.74 (d, J=8.9 Hz, 2H), 6.62 (dd, J=5.5, 5.5 Hz, 1H), 3.52 (dd, J=5.5, 5.5 Hz, 2H), 3.30 (s, 5H), 2.59 (s, 2H), 1.56 (s, 2H), 1.32 (s, 6H), 1.00 (s, 6H). LC/MS (Table 1, Method A) R$_t$=3.88 min; MS m/z: 431 [M+H]$^+$.

Example #34. 5,5,7,7-Tetramethyl-2-[[4-(tetrahydrofuran-3-ylamino)benzoyl]amino]-4,6-dihydrobenzothiophene-3-carboxylic acid (Compound #61)

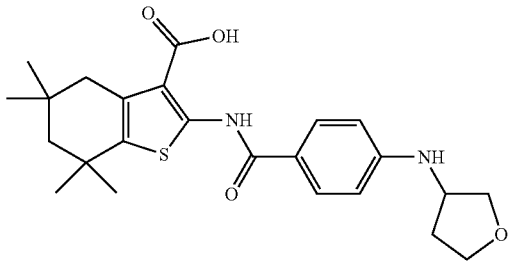 [SMILES: CC1(C)Cc2c(sc(NC(=O)c3ccc(NC4CCOC4)cc3)c2C(=O)O)C(C)(C)C1]

The title compound was synthesized according to the procedure described in Example #20 using ethyl 2-(4-bromobenzamido)-5,5,7,7-tetramethyl-4,5,6,7-tetrahydrobenzo[b]thiophene-3-carboxylate (Preparation #7) and 3-aminotetrahydrofuran (CAS: 88675-24-5) as starting materials (pale yellow solid, yield 42%). $^1$H NMR (DMSO-$d_6$, 400 MHz): δ=13.17 (br s, 1H), 12.24 (s, 1H), 7.67 (d, J=8.8 Hz, 2H), 6.81 (d, J=6.4 Hz, 1H), 6.73 (d, J=8.8 Hz, 2H), 4.13-4.06 (m, 1H), 3.94-3.72 (m, 3H), 3.57 (dd, J=3.5, 8.9 Hz, 1H), 2.59 (s, 2H), 2.23 (ddd, J=7.3, 12.6, 15.1 Hz, 1H), 1.85-1.76 (m, 1H), 1.56 (s, 2H), 1.32 (s, 6H), 1.00 (s, 6H). LC/MS (Table 1, Method B) $R_t$=2.89 min; MS m/z: 443 [M+H]$^+$.

Example #35. 4,4-Dimethyl-2-[[4-(tetrahydropyran-4-ylamino)benzoyl]amino]-5,6-dihydrocyclopenta[b]thiophene-3-carboxylic acid (Compound #62)

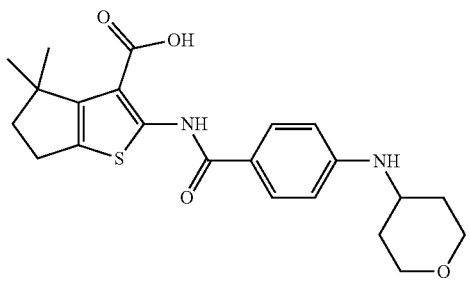 [SMILES: CC1(C)CCc2sc(NC(=O)c3ccc(NC4CCOCC4)cc3)c(C(=O)O)c21]

The title compound was synthesized according to the procedure described in Example #20 using ethyl 2-(4-bromobenzamido)-4,4-dimethyl-5,6-dihydro-4H-cyclopenta[b]thiophene-3-carboxylate (Preparation #9) and 4-aminotetrahydropyran (CAS: 38041-19-9) as starting materials (yellow solid, yield 45%). $^1$H NMR (DMSO-$d_6$, 400 MHz): δ=13.37 (br s, 1H), 12.26 (br s, 1H), 7.69 (d, J=8.3 Hz, 2H), 6.79 (d, J=8.1 Hz, 2H), 6.59 (d, J=7.6 Hz, 1H), 3.93 (d, J=11.4 Hz, 2H), 3.67-3.60 (m, 1H), 3.50 (dd, J=11.0, 11.0 Hz, 2H), 2.82 (dd, J=6.4, 6.4 Hz, 2H), 2.24 (dd, J=6.7, 6.7 Hz, 2H), 1.98-1.93 (m, 2H), 1.50-1.45 (m, 2H), 1.39 (s, 6H). LC/MS (Table 1, Method B) $R_t$=2.79 min; MS m/z: 415 [M+H]$^+$.

Example #36. 2-[[4-[(1-Acetyl-4-piperidyl)amino]benzoyl]amino]-5,5,7,7-tetramethyl-4,6-dihydrobenzothiophene-3-carboxylic acid (Compound #63)

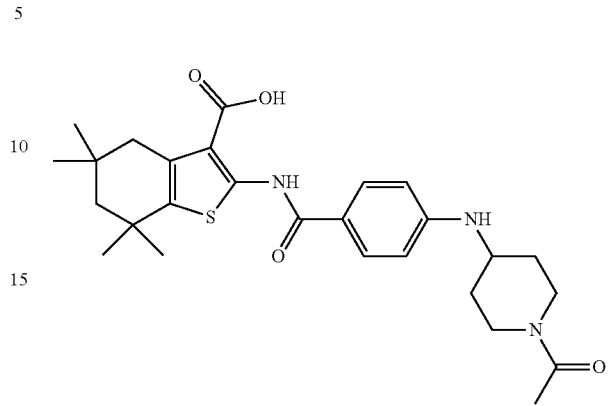

The title compound was synthesized according to the procedure described in Example #20 using ethyl 2-(4-bromobenzamido)-5,5,7,7-tetramethyl-4,5,6,7-tetrahydrobenzo[b]thiophene-3-carboxylate (Preparation #7) and 1-acetylpiperidin-4-amine (CAS: 160357-94-8) as starting materials (off-white solid, yield 6%). $^1$H NMR (DMSO-$d_6$, 400 MHz): δ=13.29 (br s, 1H), 12.47 (br s, 1H), 7.70 (d, J=8.6 Hz, 2H), 6.79 (d, J=8.6 Hz, 2H), 6.57 (d, J=7.8 Hz, 1H), 4.29 (d, J=12.6 Hz, 1H), 3.85 (d, J=13.1 Hz, 1H), 3.69-3.61 (m, 1H), 3.24 (dd, J=11.2, 11.2 Hz, 1H), 2.86 (dd, J=11.2, 11.2 Hz, 1H), 2.64 (s, 2H), 2.06 (s, 3H), 1.99 (dd, J=14.5, 19.8 Hz, 2H), 1.60 (s, 2H), 1.44-1.21 (m, 8H), 1.04 (s, 6H). LC/MS (Table 1, Method A) $R_t$=3.72 min; MS/z: 498 [M+H]$^+$.

Example #37. 2-[[4-(2-Methoxyethylamino)benzoyl]amino]-4,4-dimethyl-5,6-dihydrocyclopenta[b]thiophene-3-carboxylicacid (Compound #64)

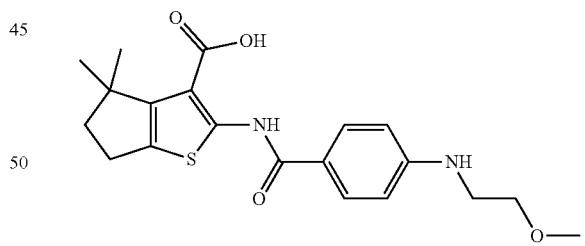

The title compound was synthesized according to the procedure described in Example #20 using ethyl 2-(4-bromobenzamido)-4,4-dimethyl-5,6-dihydro-4H-cyclopenta[b]thiophene-3-carboxylate (Preparation #9) and 2-methoxyethylamine (CAS: 109-85-3) as starting materials (off-white solid, yield 41%). $^1$H NMR (CDCl$_3$, 400 MHz): δ=12.08 (s, 1H), 7.85 (d, J=8.6 Hz, 2H), 6.67 (d, J=8.6 Hz, 2H), 3.65 (dd, J=5.1, 5.1 Hz, 2H), 3.42 (s, 3H), 3.38 (t, J=5.0 Hz, 2H), 2.82 (dd, J=7.1, 7.1 Hz, 2H), 2.26 (dd, J=7.1, 7.1 Hz, 2H), 1.40 (s, 6H), two exchangeable protons not observed. LC/MS (Table 1, Method B) $R_t$=2.77 min; MS m/z: 389 [M+H]$^+$.

Example #38. 5,5-Dimethyl-2-[(6-morpholinopyridine-3-carbonyl)amino]-6,7-dihydro-4H-benzothiophene-3-carboxylic acid (Compound #65)

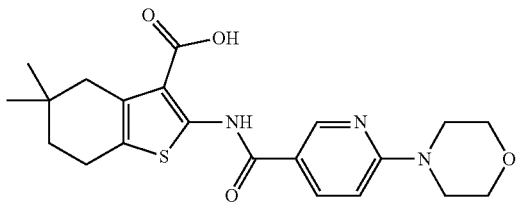 [SMILES: CC1(C)CCc2sc(NC(=O)c3ccc(N4CCOCC4)nc3)c(C(=O)O)c2C1]

The title compound was synthesized according to the procedure described in Example #11 using methyl 2-amino-5,5-dimethyl-4,5,6,7-tetrahydrobenzo[b]thiophene-3-carboxylate (Preparation #3) and 6-morpholinonicotinic acid (CAS: 120800-52-4) as starting materials (off-white solid, yield 13%). $^1$H NMR (DMSO-d$_6$, 400 MHz): δ=13.32 (br s, 1H), 12.27 (s, 1H), 8.70 (s, 1H), 8.00 (d, J=8.1 Hz, 1H), 7.04 (d, J=8.4 Hz, 1H), 3.73 (s, 4H), 3.68 (s, 4H), 2.69 (s, 2H), 2.61 (s, 2H), 1.60 (s, 2H), 1.01 (s, 6H). LC/MS (Table 1, Method B) R$_t$=2.73 min; MS/z: 416 [M+H]$^+$.

Example #39. 2-[[4-(4-Hydroxy-1-piperidyl)benzoyl]amino]-4,4-dimethyl-5,6-dihydrocyclopenta[b]thiophene-3-carboxylic acid (Compound #78)

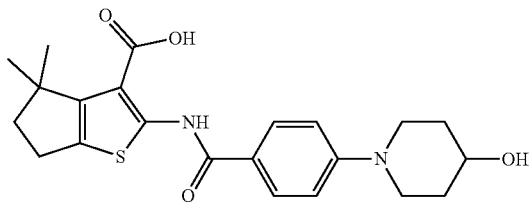 [SMILES: CC1(C)CCc2sc(NC(=O)c3ccc(N4CCC(O)CC4)cc3)c(C(=O)O)c21]

The title compound was synthesized according to the procedure described in Example #20 using ethyl 2-(4-bromobenzamido)-4,4-dimethyl-5,6-dihydro-4H-cyclopenta[b]thiophene-3-carboxylate (Preparation #9) and 4-acetoxy-piperidine hydrochloride (CAS: 94886-04-1) as starting materials (yellow solid, yield 20%). $^1$H NMR (DMSO-d$_6$, 400 MHz): δ=13.32 (br s, 1H), 12.37 (br s, 1H), 7.62 (d, J=8.7 Hz, 2H), 6.96 (d, J=8.4 Hz, 2H), 4.61 (s, 1H), 3.67-3.57 (m, 3H), 2.99-2.91 (m, 2H), 2.67 (t, J=7.0 Hz, 2H), 2.11-2.05 (m, 2H), 1.72-1.65 (m, 2H), 1.34-1.29 (m, 2H), 1.24 (s, 6H). LC/MS (Table 1, Method B) R$_t$=2.78 min, MS I/z: 415 [M+H]$^+$.

Example #40. 5,5,7,7-Tetramethyl-2-[[4-(4-methylpiperazin-1-yl)benzoyl]amino]-4,6-dihydrobenzothiophene-3-carboxylic acid (Compound #80)

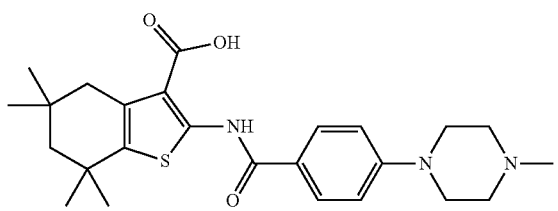

The title compound was synthesized according to the procedure described in Example #20 using ethyl 2-(4-bromobenzamido)-5,5,7,7-tetramethyl-4,5,6,7-tetrahydrobenzo[b]thiophene-3-carboxylate (Preparation #7) and 1-methylpiperizine (CAS: 109-01-3) as starting materials (white solid, yield 29%). $^1$H NMR (Pyr-d$_5$, 400 MHz): δ=13.21 (s, 1H), 8.24 (d, J=9.0 Hz, 2H), 6.91 (d, J=8.9 Hz, 2H), 3.26-3.21 (m, 4H), 3.02 (s, 2H), 2.38-2.33 (m, 4H), 2.17 (s, 3H), 1.52 (s, 2H), 1.37 (s, 6H), 1.05 (s, 6H), one exchangeable proton not observed. LC/MS (Table 1, Method B) R$_t$=2.95 min, MS m/z: 456 [M+H]$^+$.

Example #41. 5,5,7,7-Tetramethyl-2-(pyridine-2-carbonylamino)-4,6-dihydrobenzothiophene-3-carboxylic acid (Compound #90)

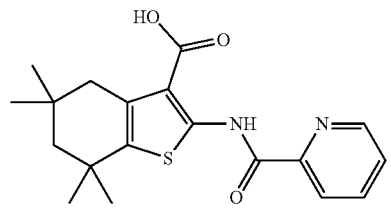 [SMILES: CC1(C)Cc2c(sc(NC(=O)c3ccccn3)c2C(=O)O)C(C)(C)C1]

To a stirred solution of ethyl 2-amino-5,5,7,7-tetramethyl-4,5,6,7-tetrahydrobenzo[b]thiophene-3-carboxylate (Preparation #6, 147 mg, 0.55 mmol) in DCM (4.0 ml) was added 2-picolinic acid (CAS: 98-98-6.81 mg, 0.66 mmol), 2-chloro-1-methylpyridinium iodide (CAS: 14338-32-0,281 mg, 1.10 mmol) and triethylamine (CAS: 121-44-8, 0.17 ml, 1.21 mmol). The reaction mixture was heated at 40° C. for 24 hours. The reaction was partitioned between DCM and saturated aqueous NaHCO$_3$ solution and the two phases were separated. The aqueous phase was further extracted with DCM (×2). The combined organic phases were passed through a phase separator and the solvent was removed under reduced pressure. Purification by flash chromatography on silica gel (eluting with 0-20% EtOAc in isohexane) afforded ethyl 5,5,7,7-tetramethyl-2-(picolinamido)-4,5,6,7-tetrahydrobenzo[b]thiophene-3-carboxylate as a yellow solid (121 mg, yield 59%). To a solution of ethyl 5,5,7,7-tetramethyl-2-(picolinamido)-4,5,6,7-tetrahydrobenzo[b]thiophene-3-carboxylate (121 mg, 0.31 mmol) in THF (2.5 ml) and MeOH (2.5 ml) was added LiGH aq. (CAS: 1310-66-3, 1M, 1.57 ml, 1.57 mmol). The reaction mixture was stirred at 50° C. for 20 hours and then at 40° C. for a further 72 hours. The reaction was allowed to cool to RT and acidified with 1N aqueous HCl solution. The reaction mixture was extracted with DCM (×2). The combined organic phases were dried over MgSO$_4$ and the solvent was removed under reduced pressure. The residue was purified by RP-HPLC (Table 2, Method 1) to give 5,5,7,7-tetramethyl-2-(pyridine-2-carbonylamino)-4,6-dihydrobenzothiophene-3-carboxylic acid as a yellow solid (35 mg, yield 31%). $^1$H NMR (DMSO-d$_6$, 400 MHz): δ=13.21 (br s, 2H), 8.81 (d, J=4.4 Hz, 1H), 8.23 (d, J=7.7 Hz, 1H), 8.17 (t, J=7.6 Hz, 1H), 7.79-7.73 (m, 1H), 2.66 (s, 2H), 1.62 (s, 2H), 1.38 (s, 6H), 1.05 (s, 6H). LC/MS (Table 1, Method B) R$_t$=2.91 min, MS m/z: 359 [M+H]$^+$.

Example #42. 2-[(5,6-Dimethoxypyridine-2-carbonyl)amino]-6,6-dimethyl-5,7-dihydro-4H-benzothiophene-3-carboxylic acid (Compound #94)

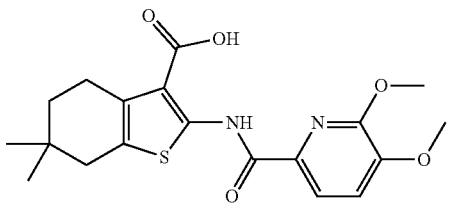

The title compound was synthesized according to the procedure described in Example #11 using methyl 2-amino-6,6-dimethyl-4,5,6,7-tetrahydrobenzo[b]thiophene-3-carboxylate (Preparation #1) and 5,6-dimethoxypicolinic acid (CAS: 324028-89-9) as starting materials (white solid, yield 21%). $^1$H NMR (DMSO-$d_6$, 400 MHz): δ=13.69 (br s, 1H), 8.30 (br s, 1H), 7.71 (d, J=8.0 Hz, 1H), 7.44 (d, J=8.1 Hz, 1H), 4.05 (s, 3H), 3.87 (s, 3H), 2.85-2.78 (m, 2H), 2.42 (s, 2H), 1.49 (t, J=6.1 Hz, 2H), 0.97 (s, 6H). LC/MS (Table 1, Method D) $R_t$=5.33 min. MS m/z: 391 [M+H]$^+$.

Example #43. 6,6-Dimethyl-2-(pyridine-2-carbonylamino)-5,7-dihydro-4H-benzothiophene-3-carboxylic acid (Compound #96)

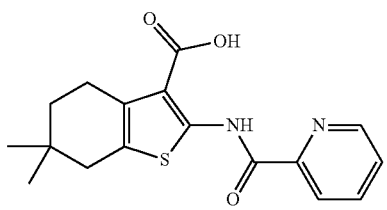

The title compound was synthesized according to the procedure described in Example #11 using methyl 2-amino-6,6-dimethyl-4,5,6,7-tetrahydrobenzo[b]thiophene-3-carboxylate (Preparation #1) and 2-picolinic acid (CAS: 98-98-6) as starting materials (yellow solid, yield 41%). $^1$H NMR (DMSO-$d_6$, 400 MHz): δ=13.05 (br s, 2H), 8.77-8.74 (m, 1H), 8.20-8.17 (m, 1H), 8.10 (ddd, J=7.7, 7.7, 1.7 Hz, 1H), 7.72 (ddd, J=1.2, 4.8, 7.5 Hz, 1H), 2.77 (t, J=6.2 Hz, 2H), 2.45 (s, 2H), 1.51 (t, J=6.4 Hz, 2H), 0.98 (s, 6H). LC/MS (Table 1, Method D) $R_t$=5.22 min, MS m/z: 331 [M+H]$^+$.

Example #44. 2-[[3-(Difluoromethoxy)benzoyl]amino]-4,4-dimethyl-5,6-dihydrocyclopenta[b]thiophene-3-carboxylic acid (Compound #98)

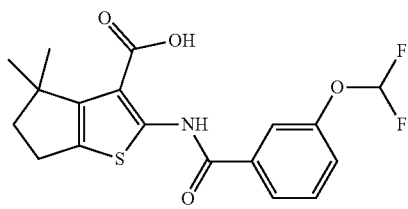 [SMILES: CC1(C)CCc2sc(NC(=O)c3cccc(OC(F)F)c3)c(C(=O)O)c21]

The title compound was synthesized according to the procedure described in Example #11 using ethyl 2-amino-4,4-dimethyl-5,6-dihydro-4H-cyclopenta[b]thiophene-3-carboxylate (Preparation #8) and 3-(difluoromethoxy)benzoic acid (CAS: 4837-19-8) as starting materials (off-white solid, yield 11%). $^1$H NMR (DMSO-$d_6$, 400 MHz): δ=13.23 (br s, 1H), 7.78 (d, J=7.7 Hz, 1H), 7.71-7.66 (m, 2H), 7.48 (dd, J=2.2, 8.2 Hz, 1H), 7.37 (t, J=73.6 Hz, 1H), 7.14 (br s, 1H), 2.81 (t, J=7.2 Hz, 2H), 2.20 (t, J=7.1 Hz, 2H), 1.37 (s, 6H). LC/MS (Table 1, Method C) $R_t$=3.78 min, MS m/z: 380 [M-H]$^-$.

Example #45. 6-Cyano-2-[(2-methylbenzoyl)amino]-6-phenyl-5,7-dihydro-4H-benzothiophene-3-carboxylic acid (Compound #105)

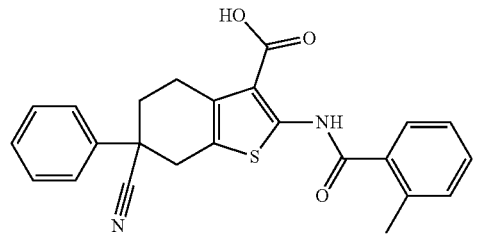 [SMILES: Cc1ccccc1C(=O)Nc1sc2c(c1C(=O)O)CCC(C#N)(c1ccccc1)C2]

The title compound was synthesized according to the procedure described in Example #1 using methyl 2-amino-6-cyano-6-phenyl-4,5,6,7-tetrahydrobenzo[b]thiophene-3-carboxylate (which was itself prepared according to Preparation #1 using 4-cyano-4-phenylcyclohexanone (CAS: 25115-74-6) as a starting material) and o-toluoyl chloride (CAS: 933-88-0) as starting materials (white solid, yield 22%). $^1$H NMR (DMSO-$d_6$, 400 MHz): δ=13.48 (br s, 1H), 11.92 (br s, 1H), 7.66-7.60 (m, 3H), 7.53-7.46 (m, 3H), 7.42-7.36 (m, 3H), 3.43-3.34 (m, 2H), 3.15-3.06 (m, 1H), 3.02-2.91 (m, 1H), 2.48 (s, 3H), 2.39-2.34 (m, 2H). LC/MS (Table 1, Method A) $R_t$=5.16 min, MS m/z: 417 [M+H]$^+$.

Example #46. 2-Benzamido-6,6-difluoro-5,7-dihydro-4H-benzothiophene-3-carboxylic acid (Compound #117)

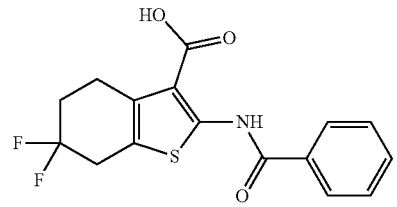 [SMILES: O=C(Nc1sc2c(c1C(=O)O)CCC(F)(F)C2)c1ccccc1]

The title compound was synthesized according to the procedure described in Example #1 using methyl 2-amino-6,6-difluoro-4,5,6,7-tetrahydrobenzo[b]thiophene-3-carboxylate (which was itself prepared according to Preparation #1 using 4,4-difluorocyclohexanone (CAS: 22515-18-0) as a starting material) and benzoyl chloride (CAS: 98-88-4) as starting materials (white solid, yield 19%). $^1$H NMR (DMSO-$d_6$, 400 MHz): δ=13.55 (br s, 1H), 12.44 (br s, 1H), 7.95-7.91 (m, 2H), 7.72-7.61 (m, 3H), 3.31-3.24 (m, 2H, partially obscured by the water peak), 3.01 (t, J=6.6 Hz, 2H), 2.30-2.17 (m 2H). LC/MS (Table 1, Method A) $R_t$=4.67 min. MS/z: 338 [M+H]$^+$.

Example #47. 5,5,7,7-Tetramethyl-2-[[4-(4-methylpiperazin-1-yl)benzoyl]amino]-4,6-dihydrobenzothiophene-3-carboxylic acid hydrochloride salt (Compound #131)

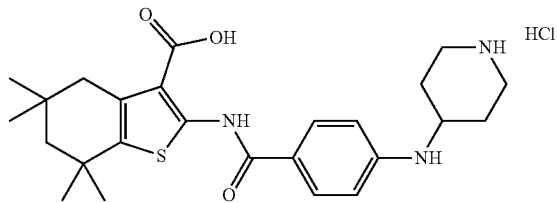 [SMILES: CC1(C)Cc2c(sc(NC(=O)c3ccc(NC4CCNCC4)cc3)c2C(=O)O)C(C)(C)C1 ; Cl]

Ethyl 2-(4-bromobenzamido)-5,5,7,7-tetramethyl-4,5,6,7-tetrahydrobenzo[b]thiophene-3-carboxylate (Preparation #7, 250 mg, 0.54 mmol), 4-amino-1-Boc-piperidine (CAS: 87120-72-7, 162 mg, 0.81 mmol), RuPhos Pd G2 (CAS: 1375325-68-0, 84 mg, 0.11 mmol) and $Cs_2CO_3$ (CAS: 534-17-8, 263 mg, 0.81 mmol) were suspended in dioxane (5.0 ml). The reaction mixture was degassed with nitrogen for 5 minutes. The reaction mixture was heated at 80° C. overnight and then allowed to cool to RT. The reaction was diluted with DCM. The mixture was filtered through a pad of Celite® and the solvent was removed under reduced pressure. Purification by flash chromatography on silica gel (eluting with 0-30% EtOAc in isohexane) afforded tert-butyl 4-((4-((3-(ethoxycarbonyl)-5,5,7,7-tetramethyl-4,5,6,7-tetrahydrobenzo[b]thiophen-2-yl)carbamoyl)phenyl)amino)piperidine-1-carboxylate as a white solid (193 mg, yield 61%), which was dissolved in THF (2.5 ml) and MeOH (2.5 ml). To the solution was added LiGH aq. (CAS: 1310-66-3, 1M, 69 mg, 1.65 mmol). The reaction mixture was stirred at 45° C. overnight.

The mixture was allowed to cool to RT. The reaction was diluted with DCM and 1N aqueous HCl solution. The two phases were separated and the aqueous phase was extracted with DCM (×2).

The combined organic phases were passed through a phase separator and the solvent was removed under reduced pressure. Trituration from MeOH afforded 2-(4-((1-(tert-butoxycarbonyl)piperidin-4-yl)amino)benzamido)-5,5,7,7-tetramethyl-4,5,6,7-tetrahydrobenzo[b]thiophene-3-carboxylic acid as a yellow solid (149 mg, yield 81%). The residue was dissolved in DCM (0.3 ml) and MeOH (0.9 ml) and then 4N HCl solution in dioxane (CAS: 7647-01-0, 0.9 ml) was added. The reaction mixture was stirred at RT for 1 hour. The solvents were removed under reduced pressure and the residue was purified by RP-HPLC (Table 2, Method 1). The residue (50 mg, 0.11 mmol) was dissolved in MeOH (0.5 ml) and DCM (0.2 ml) and then 4N HCl solution in dioxane (CAS: 7647-01-0, 0.9 ml) was added. The reaction mixture was stirred at RT for 90 minutes. The solvents were removed under reduced pressure and the compound was triturated with MeOH to give 5,5,7,7-tetramethyl-2-[[4-(4-methylpiperazin-1-yl)benzoyl]amino]-4,6-dihydrobenzothiophene-3-carboxylic acid hydrochloride salt as an off-white solid (50 mg, yield 18%). $^1$H NMR (DMSO-$d_6$, 400 MHz): δ=13.19 (br s, 1H), 12.24 (s, 1H), 8.74 (br s, 1H), 8.66 (br s, 1H), 7.69 (d, J=8.8 Hz, 2H), 6.79 (d, J=8.8 Hz, 2H), 6.73 (d, J=7.8 Hz, 1H), 3.73-3.67 (m, 1H), 3.31-3.26 (m, 2H, partially obscured bt the water peak), 3.05-3.04 (m, 2H), 2.60 (s, 2H), 2.10 (d, J=11.6 Hz, 2H), 1.67-1.56 (m, 4H), 1.33 (s, 6H), 1.02 (s, 6H). LC/MS (Table 1, Method C) $R_t$=3.07 min; MS m/z: 456 [M+H]$^+$.

Example #48. 5,5,7,7-Tetramethyl-2-[[4-(tetrahydropyran-4-ylmethylamino) benzoyl]amino]-4,6-dihydrobenzothiophene-3-carboxylic acid (Compound #132)

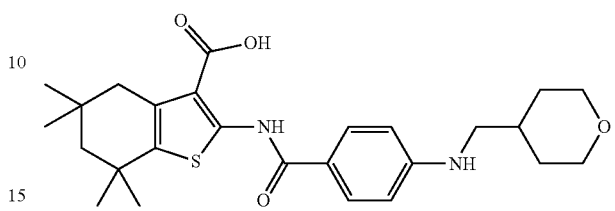

The title compound was synthesized according to the procedure described in Example #20 using ethyl 2-(4-bromobenzamido)-5,5,7,7-tetramethyl-4,5,6,7-tetrahydrobenzo[b]thiophene-3-carboxylate (Preparation #7) and tetrahydropyran-4-ylmethanamine (CAS: 130290-79-8) as starting materials (off-white solid, yield 10%). $^1$H NMR (DMSO-$d_6$, 400 MHz): δ=13.39 (br s, 1H), 12.65 (s, 1H), 7.69 (d, J=8.6 Hz, 2H), 6.74 (d, J=8.6 Hz, 2H), 6.68 (dd, J=4.9, 4.9 Hz, 1H), 3.91 (dd, J=2.5, 11.1 Hz, 2H), 3.34-3.28 (m, 2H, partially obscured by the water peak), 3.05 (dd, J=5.9, 5.9 Hz, 2H), 2.65 (s, 2H), 1.90-1.80 (m, 1H), 1.71 (d, J=12.6 Hz, 2H), 1.60 (s, 2H), 1.35 (s, 6H), 1.33-1.21 (m, 2H), 1.04 (s, 6H). LC/MS (Table 1, Method B) $R_t$=3.02 min; MS m/z: 471 [M+H]$^+$.

Example #49. 2-[[4-[(1-Acetylazetidin-3-yl)amino]benzoyl]amino]-5,5,7,7-tetramethyl-4,6-dihydrobenzothiophene-3-carboxylic acid (Compound #133)

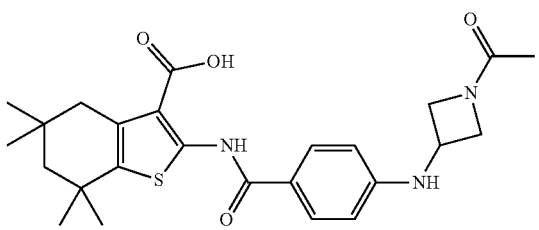 [SMILES: CC(=O)N1CC(Nc2ccc(C(=O)Nc3sc4c(c3C(=O)O)CC(C)(C)CC4(C)C)cc2)C1]

The title compound was synthesized according to the procedure described in Example #20 using ethyl 2-(4-bromobenzamido)-5,5,7,7-tetramethyl-4,5,6,7-tetrahydrobenzo[b]thiophene-3-carboxylate (Preparation #7) and 1-(3-aminoazetidin-1-yl)ethan-1-one (CAS: 1137870-15-5) as starting materials (white solid, yield 7%). $^1$H NMR (DMSO-$d_6$, 400 MHz): δ=13.36 (br s, 1H), 7.76 (d, J=8.6 Hz, 2H), 7.16 (d, J=5.6 Hz, 1H), 6.68 (d, J=8.6 Hz, 2H), 4.52 (dd, J=7.6, 7.6 Hz, 1H), 4.33-4.21 (m, 2H), 3.93 (dd, J=4.4, 8.5 Hz, 1H), 3.72 (dd, J=4.3, 9.1 Hz, 1H), 2.69 (s, 2H), 1.83 (s, 3H), 1.59 (s, 2H), 1.35 (s, 6H), 1.04 (s, 6H), one exchangeable proton not observed. LC/MS (Table 1, Method C) $R_t$=3.62 min: MS m/z: 470 [M+H]$^+$.

Example #50. 2-Benzamido-4,4-dimethyl-5,6-dihydrocyclopenta[b]thiophene-3-carboxylic acid (Compound #134)

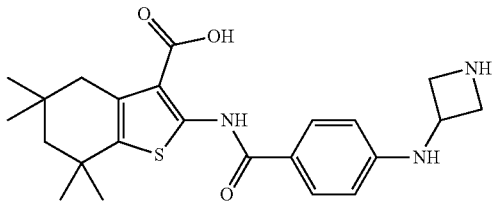 [SMILES: CC1(C)Cc2c(sc(NC(=O)c3ccc(NC4CNC4)cc3)c2C(=O)O)C(C)(C)C1]

The title compound was synthesized according to the procedure described in Example #20 using ethyl 2-(4-bromobenzamido)-5,5,7,7-tetramethyl-4,5,6,7-tetrahydrobenzo[b]thiophene-3-carboxylate (Preparation #7) and 1-(3-aminoazetidin-1-yl)ethan-1-one (CAS: 1137870-15-5) as starting materials (white solid, yield 8%). $^1$H NMR (DMSO-$d_6$, 400 MHz): δ=14.57 (br s, 1H), 7.84 (d, J=8.3 Hz, 2H), 7.42 (d, J=6.6 Hz, 1H), 6.76 (d, J=8.3 Hz, 2H), 4.59 (dd, J=6.2, 6.2 Hz, 1H), 4.37 (dd, J=8.5, 8.5 Hz, 2H), 4.01-3.92 (m, 2H), 2.76 (s, 2H), 1.58 (s, 2H), 1.34 (s, 6H), 1.02 (s, 6H), two exchangeable protons not observed. LC/MS (Table 1, Method C) $R_t$=3.03 min; MS m/z: 428 [M+H]$^+$.

Example #51. 5,5,7,7-Tetramethyl-2-[[4-[methyl(tetrahydropyran-4-yl)amino]benzoyl]amino]-4,6-dihydrobenzothiophene-3-carboxylic acid (Compound #135)

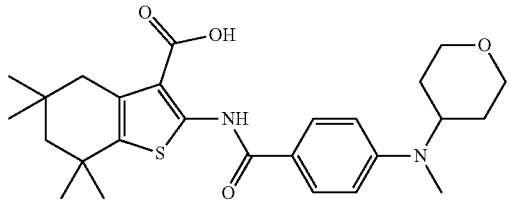 [SMILES: CN(c1ccc(C(=O)Nc2sc3c(c2C(=O)O)CC(C)(C)CC3(C)C)cc1)C1CCOCC1]

The title compound was synthesized according to the procedure described in Example #20 using ethyl 2-(4-bromobenzamido)-5,5,7,7-tetramethyl-4,5,6,7-tetrahydrobenzo[b]thiophene-3-carboxylate (Preparation #7) and N-methyl-4-aminotetrahydropyran (CAS: 220641-87-2) as starting materials (off-white solid, yield 16%). $^1$H NMR (DMSO-$d_6$, 400 MHz): δ=13.17 (br s, 1H), 12.31 (s, 1H), 7.74 (d, J=9.0 Hz, 2H), 6.98 (d, J=9.2 Hz, 2H), 4.08 (ddd, J=3.9, 7.7, 15.4 Hz, 1H), 3.95 (dd, J=4.1, 11.0 Hz, 2H), 3.50 (dd, J=10.2, 11.5 Hz, 2H), 2.86 (s, 3H), 2.59 (s, 2H), 1.87-1.74 (m, 2H), 1.63-1.55 (m, 4H), 1.32 (s, 6H), 1.01 (s, 6H). LC/MS (Table 1, Method B) $R_t$=3.08 min; MS m/z: 471 [M+H]$^+$.

Example #52. 4,6,6-Trimethyl-2-[[4-(tetrahydropyran-4-ylamino)benzoyl]amino]-5,7-dihydro-4H-benzothiophene-3-carboxylic acid (Compound #136)

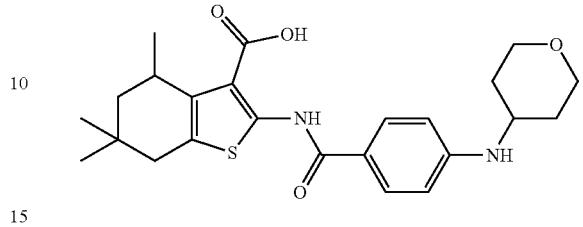

The title compound was synthesized according to the procedure described in Example #20 using ethyl 2-(4-bromobenzamido)-4,6,6-trimethyl-4,5,6,7-tetrahydrobenzo[b]thiophene-3-carboxylate (Preparation #12) and 4-aminotetrahydropyran (CAS: 38041-19-9) as starting materials (off-white solid, yield 40%). $^1$H NMR (DMSO-$d_6$, 400 MHz): δ=7.69 (d, J=8.6 Hz, 2H), 6.78 (d, J=8.6 Hz, 2H), 6.53 (d, J=7.3 Hz, 1H), 3.93 (dd, J=3.4, 7.5 Hz, 2H), 3.65-3.60 (m, 1H), 3.49 (dd, J=10.7, 10.7 Hz, 2H, partially obscured by the water peak), 3.19-3.11 (m, 1H), 2.37 (d, J=15.7 Hz, 1H), 1.93 (d, J=12.1 Hz, 2H), 1.81-1.73 (m, 1H), 1.52-1.40 (m, 2H), 1.25 (d, J=6.6 Hz, 4H), 1.22-1.14 (m, 1H), 1.10 (s, 3H), 0.92 (s, 3H), two exchangeable protons not observed. LC/MS (Table 1, Method B) $R_t$=2.93 min; MS m/z: 443 [M+H]$^+$.

Example #53. 5,5,7,7-Tetramethyl-2-[[4-(4-piperidylamino)benzoyl]amino]-4,6-dihydrobenzothiophene-3-carboxylic acid (Compound #137)

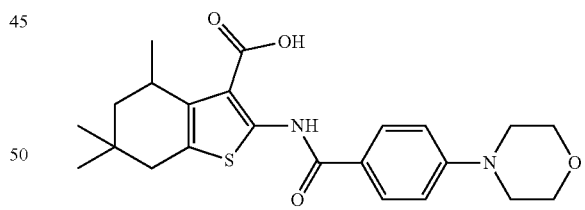

The title compound was synthesized according to the procedure described in Example #20 using ethyl 2-(4-bromobenzamido)-4,6,6-trimethyl-4,5,6,7-tetrahydrobenzo[b]thiophene-3-carboxylate (Preparation #12) and morpholine (CAS: 110-91-8) as starting materials (pale yellow solid, yield 46%). $^1$H NMR (DMSO-$d_6$, 400 MHz): δ=13.39 (s, 1H), 12.14 (s, 1H), 7.81 (d, J=8.6 Hz, 2H), 7.15 (d, J=8.6 Hz, 2H), 3.84-3.76 (m, 4H), 3.37-3.32 (m, 4H, partially obscured by the water peak), 3.18-3.10 (m, 1H), 2.52-2.49 (m, 1H, partially obscured by the DMSO peak), 2.39 (d, J=15.7 Hz, 1H), 1.82-1.76 (m, 1H), 1.26-1.21 (m, 4H), 1.11 (s, 3H), 0.92 (s, 3H). LC/MS (Table 1, Method B) $R_t$=2.85 min; MS m/z: 429 [M+H]$^+$.

Example #54. 2-[(4-Bromobenzoyl)amino]-5,5,7,7-tetramethyl-4,6-dihydrobenzothiophene-3-carboxylic acid (Compound #138)

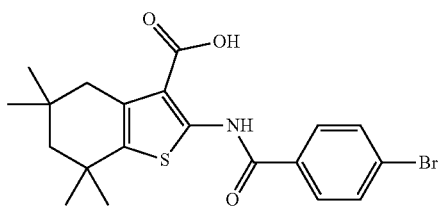 [SMILES: CC1(C)Cc2c(sc(NC(=O)c3ccc(Br)cc3)c2C(=O)O)C(C)(C)C1]

The title compound was synthesized according to the procedure described in Example #8 using ethyl 2-(4-bromobenzamido)-5,5,7,7-tetramethyl-4,5,6,7-tetrahydrobenzo[b]thiophene-3-carboxylate (Preparation #7) as the starting material (white solid, yield 47%). $^1$H NMR (DMSO-d$_6$, 400 MHz): δ=13.35 (br s, 1H), 12.43 (br s, 1H), 7.85 (d, J=2.8 Hz, 4H), 2.60 (s, 2H), 1.57 (s, 2H), 1.33 (s, 6H), 1.01 (s, 6H). LC/MS (Table 1, Method B) R$_t$=3.06 min; MS/z: 436 [M+H]$^+$.

Example #55. 5,5,7,7-Tetramethyl-2-[[4-(oxetan-3-ylamino)benzoyl]amino]-4,6-dihydrobenzothiophene-3-carboxylic acid (Compound #139)

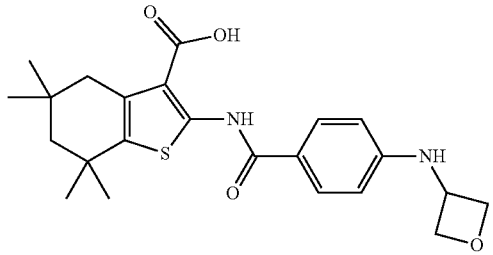 [SMILES: CC1(C)Cc2c(sc(NC(=O)c3ccc(NC4COC4)cc3)c2C(=O)O)C(C)(C)C1]

The title compound was synthesized according to the procedure described in Example #20 using ethyl 2-(4-bromobenzamido)-5,5,7,7-tetramethyl-4,5,6,7-tetrahydrobenzo[b]thiophene-3-carboxylate (Preparation #7) and 3-aminooxetane (CAS: 21635-88-1) as starting materials (white solid, yield 32%). $^1$H NMR (DMSO-d$_6$, 400 MHz): δ=12.43 (br s, 1H), 7.72 (d, J=8.6 Hz, 2H), 7.32 (d, J=5.8 Hz, 1H), 6.67 (d, J=8.6 Hz, 2H), 4.92 (dd, J=6.4, 6.4 Hz, 2H), 4.69 (dd, J=6.3, 12.6 Hz, 1H), 4.49 (dd, J=6.1, 6.1 Hz, 2H), 2.64 (s, 2H), 1.60 (s, 2H), 1.35 (s, 6H), 1.04 (s, 6H), one exchangeable proton not observed. LC/MS (Table 1, Method B) R$_t$=2.98 min; MS m/z: 429 [M+H]$^+$.

Example #56. 2-[[4-(3-Methoxypropylamino)benzoyl]amino]-5,5,7,7-tetramethyl-4,6-dihydrobenzothiophene-3-carboxylic acid (Compound #140)

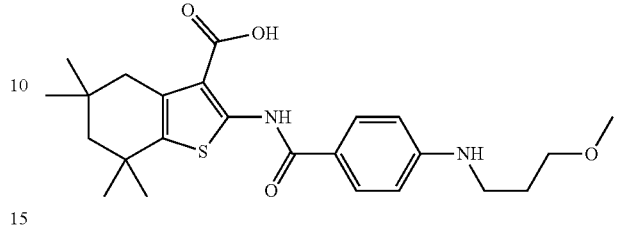

The title compound was synthesized according to the procedure described in Example #20 using ethyl 2-(4-bromobenzamido)-5,5,7,7-tetramethyl-4,5,6,7-tetrahydrobenzo[b]thiophene-3-carboxylate (Preparation #7) and 3-methoxypropylamine (CAS: 5332-73-0) as starting materials (off-white solid, yield 15%). $^1$H NMR (DMSO-d$_6$, 400 MHz): δ=13.34 (br s, 1H), 7.71 (d, J=8.6 Hz, 2H), 7.35 (br s, 1H), 6.70 (d, J=8.6 Hz, 2H), 6.54 (br s, 1H), 3.44 (m, 2H, partially obscured by water peak), 3.30 (s, 3H), 3.23-3.14 (m, 2H), 2.68 (s, 2H), 1.87-1.78 (m, 2H), 1.59 (s, 2H), 1.35 (s, 6H), 1.04 (s, 6H). LC/MS (Table 1, Method B) R$_t$=3.06 min; MS/z: 445 [M+H]$^+$.

Example #57. 5,5,7,7-Tetramethyl-2-[[4-(tetrahydropyran-3-ylmethylamino) benzoyl]amino]-4,6-dihydrobenzothiophene-3-carboxylic acid (Compound #141)

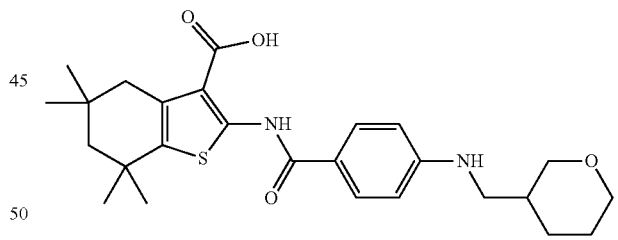

The title compound was synthesized according to the procedure described in Example #20 using ethyl 2-(4-bromobenzamido)-5,5,7,7-tetramethyl-4,5,6,7-tetrahydrobenzo[b]thiophene-3-carboxylate (Preparation #7) and tetrahydropyran-3-ylmethanamine (CAS: 7179-99-9) as starting materials (white solid, yield 20%). $^1$H NMR (DMSO-d$_6$, 400 MHz): δ=13.30 (br s, 1H), 12.37 (br s, 1H), 7.69 (d, J=8.8 Hz, 2H), 6.74 (d, J=8.8 Hz, 2H), 6.67 (dd, J=5.3, 5.3 Hz, 1H), 3.90 (d, J=10.1 Hz, 1H), 3.81-3.74 (m, 1H), 3.37 (m, 2H, partially obscured by water peak), 3.25-3.16 (m, 1H), 3.03 (q, J=6.0 Hz, 2H), 2.63 (s, 2H), 1.89 (dd, J=11.5, 11.5 Hz, 2H), 1.60 (s, 3H), 1.57-1.48 (m, 1H), 1.35 (s, 6H), 1.04 (s, 6H). LC/MS (Table 1, Method C) R$_t$=3.96 min; MS/z: 471 [M+H]$^+$.

Example #58. 5,5,7,7-Tetramethyl-2-[[4-(tetrahydro-pyran-3-ylamino) benzoyl]amino]-4,6-dihydrobenzothiophene-3-carboxylic acid (Compound #142)

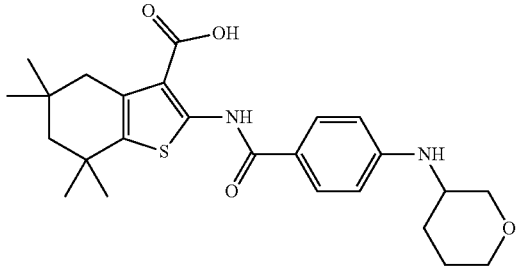 [SMILES: CC1(C)Cc2c(sc(NC(=O)c3ccc(NC4CCCOC4)cc3)c2C(=O)O)C(C)(C)C1]

The title compound was synthesized according to the procedure described in Example #20 using ethyl 2-(4-bromobenzamido)-5,5,7,7-tetramethyl-4,5,6,7-tetrahydrobenzo[b]thiophene-3-carboxylate (Preparation #7) and tetrahydro-2H-pyran-3-amine hydrochloride (CAS: 120811-32-7) as starting materials (off-white solid, yield 18%). $^1$H NMR (DMSO-d$_6$, 400 MHz): δ=13.30 (br s, 1H), 12.37 (br s, 1H), 7.69 (d, J=8.8 Hz, 2H), 6.74 (d, J=8.8 Hz, 2H), 6.67 (dd, J=5.3, 5.3 Hz, 1H), 3.90 (d, J=10.1 Hz, 1H), 3.81-3.74 (m 1H), 3.59-3.41 (m 2H, partially obscured by water peak), 3.25-3.16 (m, 1H), 2.63 (s, 2H), 2.06-1.99 (m, 1H), 1.79-1.49 (m, 5H), 1.35 (s, 6H), 1.04 (s, 6H). LC/MS (Table 1, Method B) R$_t$=3.06 min; MS m/z: 457 [M+H]$^+$.

Example #59. 5,5,7,7-Tetramethyl-2-[[4-(2-oxa-6-azaspiro[3.3]heptan-6-yl) benzoyl]amino]-4,6-dihydrobenzothiophene-3-carboxylic acid (Compound #143)

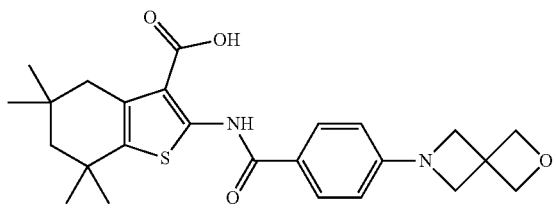 [SMILES: CC1(C)Cc2c(sc(NC(=O)c3ccc(N4CC5(COC5)C4)cc3)c2C(=O)O)C(C)(C)C1]

The title compound was synthesized according to the procedure described in Example #20 using ethyl 2-(4-bromobenzamido)-5,5,7,7-tetramethyl-4,5,6,7-tetrahydrobenzo[b]thiophene-3-carboxylate (Preparation #7) and 2-oxa-6-azaspiro[3.3]heptane (CAS: 174-78-7) as starting materials (yellow solid, yield 41%). $^1$H NMR (DMSO-d$_6$, 400 MHz): δ=13.26 (br s, 1H), 12.31 (s, 1H), 7.76 (d, J=8.6 Hz, 2H), 6.59 (d, J=8.6 Hz, 2H), 4.78 (s, 4H), 4.17 (s, 4H), 2.63 (s, 2H), 1.60 (s, 2H), 1.35 (s, 6H), 1.04 (s, 6H). LC/MS (Table 1, Method C) R$_t$=3.91 min; MS m/z: 455 [M+H]$^+$.

Example #60. 5,5,7,7-Tetramethyl-2-[[4-(2-oxa-7-azaspiro[3.5]nonan-7-yl)benzoyl]amino]-4,6-dihydrobenzothiophene-3-carboxylic acid (Compound #144)

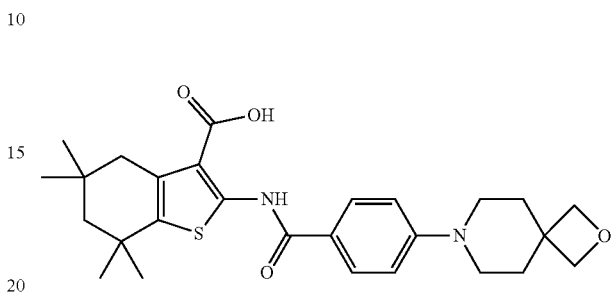

The title compound was synthesized according to the procedure described in Example #20 using ethyl 2-(4-bromobenzamido)-5,5,7,7-tetramethyl-4,5,6,7-tetrahydrobenzo[b]thiophene-3-carboxylate (Preparation #7) and 2-oxa-7-azaspiro[3.5]nonane (CAS: 241820-91-7) as starting materials (off-white solid, yield 53%). $^1$H NMR (DMSO-d$_6$, 400 MHz): δ=13.27 (br s, 1H), 12.35 (s, 1H), 7.77 (d, J=8.8 Hz, 2H), 7.14 (d, J=8.8 Hz, 2H), 4.40 (s, 4H), 3.36 (m, 4H, partially obscured by water peak), 2.63 (s, 2H), 1.90 (dd, J=5.3, 5.3 Hz, 4H), 1.60 (s, 2H), 1.36 (s, 6H), 1.04 (s, 6H). LC/MS (Table 1, Method B) R$_t$=3.07 min; MS m/z: 483 [M+H]$^+$.

Example #61. 2-1-[[4-(2-Methoxyethylamino)benzoyl]amino]-4,6,6-trimethyl-5,7-dihydro-4H-benzothiophene-3-carboxylic acid (Compound #145)

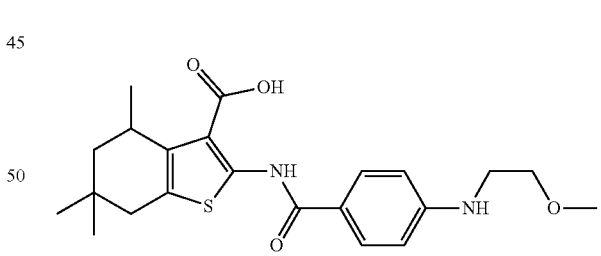

The title compound was synthesized according to the procedure described in Example #20 using ethyl 2-(4-bromobenzamido)-4,6,6-trimethyl-4,5,6,7-tetrahydrobenzo[b]thiophene-3-carboxylate (Preparation #12) and 2-methoxyethylamine (CAS 109-85-3) as starting materials (white solid, yield 47%). $^1$H NMR (DMSO-d$_6$, 400 MHz): δ=13.34 (br s, 1H), 12.10 (s, 1H), 7.69 (d, J=8.6 Hz, 2H), 6.77 (d, J=8.6 Hz, 2H), 6.66 (dd, J=5.4, 5.4 Hz, 1H), 3.55 (dd, J=5.6, 5.6 Hz, 2H), 3.41-3.35 (m, 5H, partially obscured by the water peak), 3.15 (m, 1H), 2.50 (d, J=16.7 Hz, 1H), 2.38 (d, J=15.4 Hz, 1H), 1.78 (dd, J=6.9, 13.0 Hz, 1H), 1.28-1.21 (m, 4H), 1.10 (s, 3H), 0.92 (s, 3H). LC/MS (Table 1, Method C) R$_t$=3.80 min; MS m/z: 417 [M+H]$^+$.

Example #62. 2-[[4-(3-Methoxyazetidin-1-yl)benzoyl]amino]-4,4-dimethyl-5,6-dihydrocyclopenta[b]thiophene-3-carboxylicacid (Compound #146)

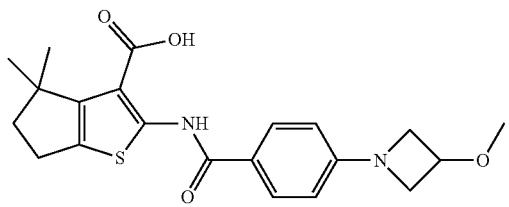

The title compound was synthesized according to the procedure described in Example #20 using ethyl 2-(4-bromobenzamido)-4,4-dimethyl-5,6-dihydro-4H-cyclopenta[b]thiophene-3-carboxylate (Preparation #9) and 3-methoxyazetidine hydrochloride (CAS: 148644-09-1) as starting materials (off-white solid, yield 63%). $^1$H NMR (DMSO-$d_6$, 400 MHz): δ=13.42 (br s, 1H), 12.34 (br s, 1H), 7.78 (d, J=8.6 Hz, 2H), 6.60 (d, J=8.6 Hz, 2H), 4.45-4.38 (m, 1H), 4.25-4.18 (m, 2H), 3.81 (dd, J=3.8, 8.6 Hz, 2H), 3.31 (s, 3H), 2.83 (dd, J=7.1, 7.1 Hz, 2H), 2.24 (dd, J=7.1, 7.1 Hz, 2H), 1.39 (s, 6H). LC/MS (Table 1, Method B) $R_t$=2.94 min; MS n/z: 401 [M+H]$^+$.

Example #63. 2-[[4-(3-Methoxyazetidin-1-yl)benzoyl]amino]-6,6-dimethyl-5,7-dihydro-4H-benzothiophene-3-carboxylic acid (Compound #147)

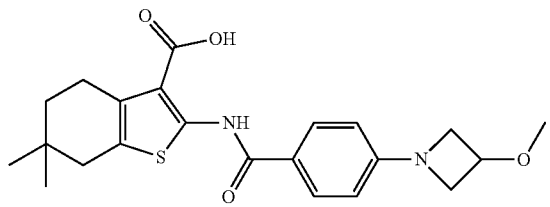

The title compound was synthesized according to the procedure described in Example #20 using methyl 2-(4-bromobenzamido)-6,6-dimethyl-4,5,6,7-tetrahydrobenzo[b]thiophene-3-carboxylate (Preparation #13) and 3-methoxyazetidine hydrochloride (CAS: 148644-09-1) as starting materials (off-white solid, yield 73%). $^1$H NMR (DMSO-$d_6$, 400 MHz): δ=7.78 (d, J=8.6 Hz, 2H), 6.60 (d, J=8.6 Hz, 2H), 4.24-4.17 (m, 2H), 3.80 (dd, J=3.8, 8.6 Hz, 2H), 3.31 (s, 4H), 2.81 (s, 2H), 2.46 (s, 2H), 1.54 (dd, J=6.2, 6.2 Hz, 2H), 1.02 (s, 6H), two exchangeable protons not observed. LC/MS (Table 1, Method B) $R_t$=2.97 min; MS m/z: 415 [M+H]$^+$.

Example #64. 2-[[4-(3,3-Difluoroazetidin-1-yl)benzoyl]amino]-5,5,7,7-tetramethyl-4,6-dihydrobenzothiophene-3-carboxylic acid (Compound #148)

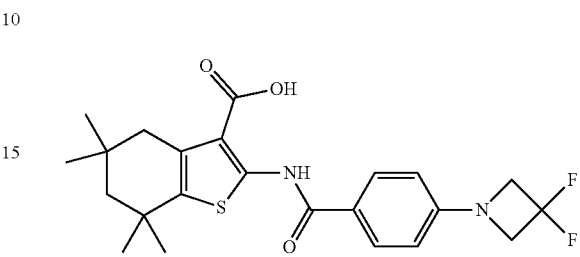

The title compound was synthesized according to the procedure described in Example #20 using ethyl 2-(4-bromobenzamido)-5,5,7,7-tetramethyl-4,5,6,7-tetrahydrobenzo[b]thiophene-3-carboxylate (Preparation #7) and 3,3-difluoroazetidine hydrochloride (CAS: 288315-03-7) as starting materials (off-white solid, yield 39%). $^1$H NMR (DMSO-$d_6$, 400 MHz): δ=7.83 (d, J=8.6 Hz, 2H), 6.76 (d, J=8.6 Hz, 2H), 4.47 (dd, J=12.3, 12.3 Hz, 4H), 2.63 (s, 2H), 1.60 (s, 2H), 1.36 (s, 6H), 1.05 (s, 6H), two exchangeable protons not observed. LC/MS (Table 1, Method C) $R_t$=4.01 min; MS m/z: 449 [M+H]$^+$.

Example #65. 2-[[4-(Cyclohexylamino)benzoyl]amino]-5,5,7,7-tetramethyl-4,6-dihydrobenzothiophene-3-carboxylic acid (Compound #149)

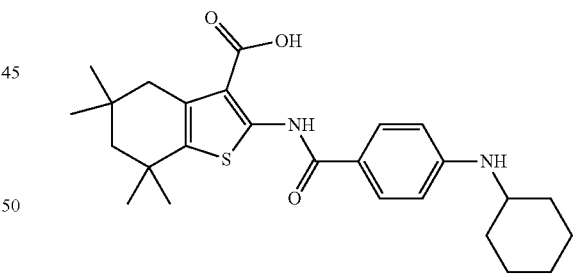

The title compound was synthesized according to the procedure described in Example #20 using ethyl 2-(4-bromobenzamido)-5,5,7,7-tetramethyl-4,5,6,7-tetrahydrobenzo[b]thiophene-3-carboxylate (Preparation #7) and cyclohexylamine (CAS: 108-91-8) as starting materials (pale yellow solid, yield 11%). $^1$H NMR (DMSO-$d_6$, 400 MHz): δ=13.16 (br s, 1H), 12.22 (s, 1H), 7.67 (d, J=8.8 Hz, 2H), 6.74 (d, J=8.6 Hz, 2H), 6.50-6.49 (m, 1H), 3.39-3.32 (m, 1H, partially obscured by the water peak), 2.62 (s, 2H), 2.05-1.94 (m, 2H), 1.82-1.73 (m, 2H), 1.58 (s, 2H), 1.46-1.38 (m, 2H), 1.35 (s, 6H), 1.30-1.19 (m, 4H), 1.04 (s, 6H). LC/MS (Table 1, Method B) $R_t$=3.27 min: MS m/z: 455 [M+H]$^+$.

Example #66. 2-[[4-[2-Methoxyethyl(methyl)amino]benzoyl]amino]-5,5,7,7-tetramethyl-4,6-dihydrobenzothiophene-3-carboxylic acid (Compound #150)

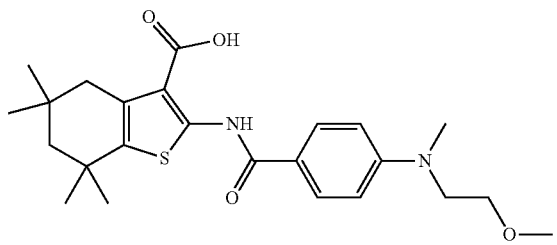

The title compound was synthesized according to the procedure described in Example #20 using ethyl 2-(4-bromobenzamido)-5,5,7,7-tetramethyl-4,5,6,7-tetrahydrobenzo[b]thiophene-3-carboxylate (Preparation #7) and (2-methoxyethyl)methylamine (CAS: 38256-93-8) as starting materials (off-white solid, yield 44%). $^1$H NMR (DMSO-d$_6$, 400 MHz): δ=13.19 (br s, 1H), 12.24 (s, 1H), 7.71 (d, J=8.8 Hz, 2H), 6.85 (d, J=8.8 Hz, 2H), 3.61 (dd, J=5.3, 5.3 Hz, 2H), 3.51 (dd, J=5.3, 5.3 Hz, 2H), 3.27 (s, 3H), 3.02 (s, 3H), 2.58 (s, 2H), 1.55 (s, 2H), 1.31 (s, 6H), 0.99 (s, 6H). LC/MS (Table 1, Method B) R$_t$=3.11 min; MS m/z: 445 [M+H]$^+$.

Example #67. 5,5,7,7-Tetramethyl-2-[[4-[methyl(tetrahydropyran-4-ylmethyl) amino]benzoyl]amino]-4,6-dihydrobenzothiophene-3-carboxylicacid (Compound #152)

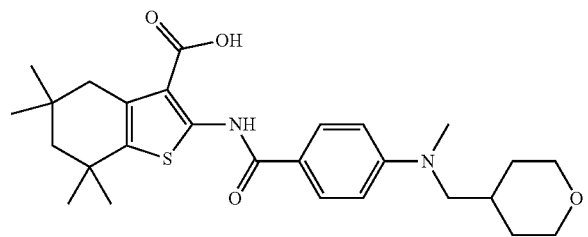 [SMILES: CN(CC1CCOCC1)c1ccc(C(=O)Nc2sc3c(c2C(=O)O)CC(C)(C)CC3(C)C)cc1]

The title compound was synthesized according to the procedure described in Example #20 using ethyl 2-(4-bromobenzamido)-5,5,7,7-tetramethyl-4,5,6,7-tetrahydrobenzo[b]thiophene-3-carboxylate (Preparation #7) and methyl-(tetrahydropyran-4-ylmethyl)amine (CAS: 439081-52-4) as starting materials (off-white solid, yield 3%). $^1$H NMR (DMSO-d$_6$, 400 MHz): δ=13.20 (br s, 1H), 12.28 (s, 1H), 7.76 (d, J=8.8 Hz, 2H), 6.89 (d, J=8.8 Hz, 2H), 3.91-3.86 (m, 2H), 3.38 (m, 2H, partially obscured by water peak), 3.34-3.24 (m, 2H), 3.09 (s, 3H), 2.63 (s, 2H), 2.06-1.97 (m, 1H), 1.62-1.53 (m, 4H), 1.35 (s, 8H), 1.05 (s, 6H). LC/MS (Table 1, Method B) R$_t$=3.15 min: MS m/z: 485 [M+H]$^+$.

Example #68. 2-[[4-(3-Methoxyazetidin-1-yl)benzoyl]amino]-4,6,6-trimethyl-5,7-dihydro-4H-benzothiophene-3-carboxylic acid (Compound #153)

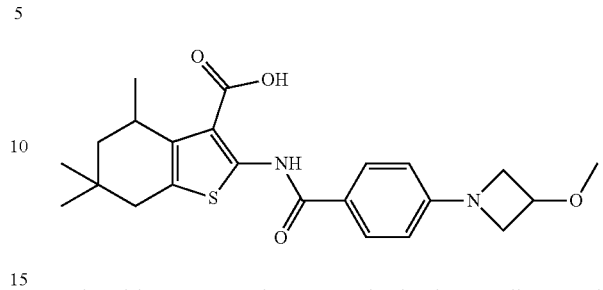

The title compound was synthesized according to the procedure described in Example #20 using ethyl 2-(4-bromobenzamido)-4,6,6-trimethyl-4,5,6,7-tetrahydrobenzo[b]thiophene-3-carboxylate (Preparation #12) and 3-methoxyazetidine hydrochloride (CAS: 148644-09-1) as starting materials (pale yellow solid, yield 38%). $^1$H NMR (DMSO-d$_6$, 400 MHz): δ=13.09 (br s, 1H), 7.79 (d, J=8.6 Hz, 2H), 7.25-7.25 (m, 1H), 6.57 (d, J=8.8 Hz, 2H), 4.44-4.37 (m, 1H), 4.19 (dd, J=7.3, 7.3 Hz, 2H), 3.79 (dd, J=3.8, 8.6 Hz, 2H), 3.31 (s, 3H), 3.23-3.13 (m, 1H), 2.50 (d, J=16.4 Hz, 1H), 2.37 (d, J=15.4 Hz, 1H), 1.80-1.72 (m, 1H), 1.25 (d, J=6.8 Hz, 4H), 1.10 (s, 3H), 0.92 (s, 3H). LC/MS (Table 1, Method B) R$_t$=3.04 min; MS m/z: 429 [M+H]$^+$.

Example #69. 2-[(4-Bromobenzoyl)amino]-5,5-dimethyl-6,7-dihydro-4H-benzothiophene-3-carboxylic acid (Compound #154)

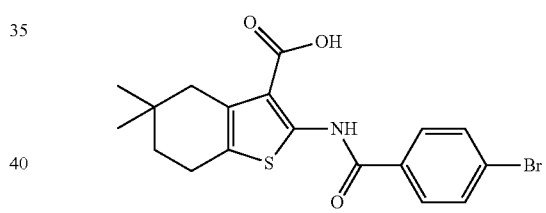

The title compound was synthesized according to the procedure described in Example #8 using methyl 2-(4-bromobenzamido)-5,5-dimethyl-4,5,6,7-tetrahydrobenzo[b]thiophene-3-carboxylate (Preparation #14) as the starting material (off-white solid, yield 37%). $^1$H NMR (DMSO-d$_6$, 400 MHz): δ=13.36 (br s, 1H), 12.42 (br s, 1H), 7.85 (s, 4H), 2.67 (dd, J=6.1, 6.1 Hz, 2H), 2.58 (s, 2H), 1.55 (dd, J=6.3, 6.3 Hz, 2H), 0.98 (s, 6H). LC/MS (Table 1, Method B) R$_t$=3.07 min; MS m/z: 408 [M+H]$^+$.

Example #70. 2-[[4-(4-Methoxy-1-piperidyl)benzoyl]amino]-5,5,7,7-tetramethyl-4,6-dihydrobenzothiophene-3-carboxylic acid (Compound #155)

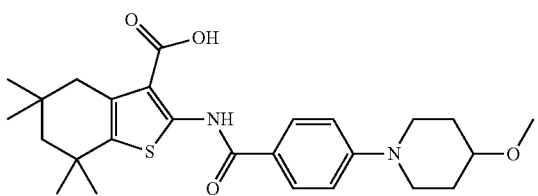

The title compound was synthesized according to the procedure described in Example #20 using ethyl 2-(4-bromobenzamido)-5,5,7,7-tetramethyl-4,5,6,7-tetrahydrobenzo[b]thiophene-3-carboxylate (Preparation #7) and 4-methoxypiperidine (CAS: 4045-24-3) as starting materials (pale yellow solid, yield 68%). $^1$H NMR (DMSO-d$_6$, 400 MHz): δ=13.27 (br s, 1H), 12.32 (br s, 1H), 7.77 (d, J=9.1 Hz, 2H), 7.13 (d, J=8.8 Hz, 2H), 3.78-3.69 (m, 2H), 3.51-3.44 (m, 1H), 3.33 (s, 3H), 3.20-3.12 (m, 2H), 2.63 (s, 2H), 2.05-1.92 (m, 2H), 1.60 (s, 2H), 1.59-1.48 (m, 2H), 1.36 (s, 6H), 1.04 (s, 6H). LC/MS (Table 1, Method B) R$_t$=3.12 min; MS/z: 471 [M+H]$^+$.

Example #71. 2-[[4-(3-Ethoxyazetidin-1-yl)benzoyl]amino]-5,5,7,7-tetramethyl-4,6-dihydrobenzothiophene-3-carboxylic acid (Compound #156)

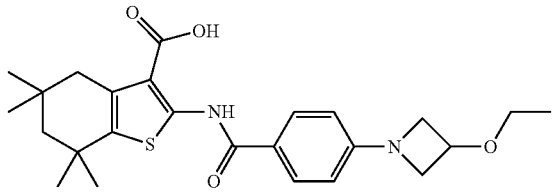 [SMILES: CCOC1CN(c2ccc(C(=O)Nc3sc4c(c3C(=O)O)CC(C)(C)CC4(C)C)cc2)C1]

The title compound was synthesized according to the procedure described in Example #20 using ethyl 2-(4-bromobenzamido)-5,5,7,7-tetramethyl-4,5,6,7-tetrahydrobenzo[b]thiophene-3-carboxylate (Preparation #7) and 3-ethoxyazetidine hydrochloride (CAS: 88536-21-4) as starting materials (white solid, yield 53%). $^1$H NMR (DMSO-d$_6$, 400 MHz): δ=13.27 (br s, 1H), 12.31 (s, 1H), 7.77 (d, J=8.6 Hz, 2H), 6.59 (d, J=8.6 Hz, 2H), 4.53-4.45 (m, 1H), 4.25-4.19 (m, 2H), 3.79 (dd, J=3.9, 8.5 Hz, 2H), 3.51 (q, J=6.9 Hz, 2H), 2.63 (s, 2H), 1.60 (s, 2H), 1.36 (s, 6H), 1.20 (dd, J=6.9, 6.9 Hz, 3H), 1.04 (s, 6H). LC/MS (Table 1, Method B) R$_t$=3.15 min; MS I/z: 457 [M+H]$^+$.

Example #72. 4,6,6-Trimethyl-2-[[4-(tetrahydropyran-4-ylmethylamino)benzoyl]amino]-5,7-dihydro-4H-benzothiophene-3-carboxylic acid (Compound #157)

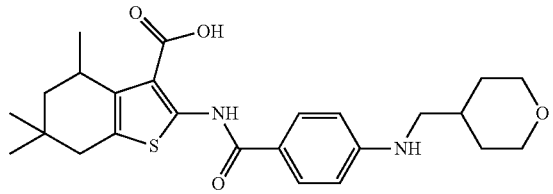 [SMILES: CC1CC(C)(C)Cc2sc(NC(=O)c3ccc(NCC4CCOCC4)cc3)c(C(=O)O)c21]

The title compound was synthesized according to the procedure described in Example #20 using ethyl 2-(4-bromobenzamido)-4,6,6-trimethyl-4,5,6,7-tetrahydrobenzo[b]thiophene-3-carboxylate (Preparation #12) and tetrahydropyran-4-ylmethanamine (CAS: 130290-79-8) as starting materials (pale yellow solid, yield 20%). $^1$H NMR (DMSO-d$_6$, 400 MHz): δ=12.22 (s, 1H), 7.68 (d, J=8.6 Hz, 2H), 6.75 (d, J=8.6 Hz, 2H), 6.72-6.69 (m, 1H), 3.95-3.87 (m, 2H), 3.32 (t, J=11.7 Hz, 2H, partially obscured by the water peak), 3.18-3.13 (m, 1H), 3.05 (dd, J=5.8, 5.8 Hz, 2H), 2.50 (d, J=16.9 Hz, 1H), 2.38 (d, J=15.8 Hz, 1H), 1.89-1.70 (m 4H), 1.31-1.21 (m 6H), 1.10 (s, 3H), 0.92 (s, 3H), one exchangeable proton not observed. LC/MS (Table 1, Method B) R$_t$=3.15 min; MS m/z: 457 [M+H]$^+$.

Example #73. 2-[(4-Bromobenzoyl)amino]-4,4-dimethyl-5,6-dihydro cyclopenta[b]thiophene-3-carboxylic acid (Compound #158)

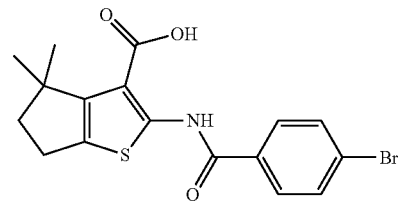 [SMILES: CC1(C)CCc2sc(NC(=O)c3ccc(Br)cc3)c(C(=O)O)c21]

The title compound was synthesized according to the procedure described in Example #8 using ethyl 2-(4-bromobenzamido)-4,4-dimethyl-5,6-dihydro-4H-cyclopenta[b]thiophene-3-carboxylate (Preparation #9) as the starting material (off-white solid, yield 35%). $^1$H NMR (DMSO-d$_6$, 400 MHz): δ=13.08 (s, 1H), 7.89 (s, 4H), 2.85 (dd, J=6.9, 6.9 Hz, 2H), 2.24 (dd, J=7.1, 7.1 Hz, 2H), 1.40 (s, 6H), one exchangeable proton not observed. LC/MS (Table 1, Method B) Rt=3.01 min; MS m/z: 394 [M+H]$^+$.

Example #74. 5,5-Dimethyl-2-[(4-morpholinobenzoyl)amino]-6,7-dihydro-4H-benzothiophene-3-carboxylic acid (Compound #159)

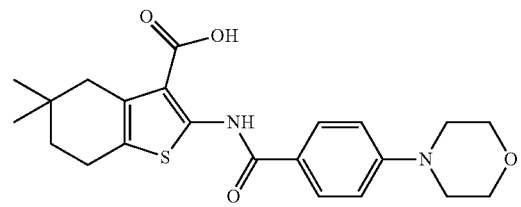

The title compound was synthesized according to the procedure described in Example #20 using methyl 2-(4-bromobenzamido)-5,5-dimethyl-4,5,6,7-tetrahydrobenzo[b]thiophene-3-carboxylate (Preparation #14) and morpholine (CAS: 110-91-8) as starting materials (yellow solid, yield 50%). $^1$H NMR (DMSO-d$_6$, 400 MHz): δ=13.28 (br s, 1H), 12.37 (s, 1H), 7.81 (d, J=9.0 Hz, 2H), 7.15 (d, J=9.0 Hz, 2H), 3.82-3.78 (m, 4H), 3.40-3.33 (m, 4H, partially obscured by the water peak), 2.69 (t, J=5.3 Hz, 2H), 2.61 (s, 2H), 1.58 (t, J=6.1 Hz, 2H), 1.02 (s, 6H). LC/MS (Table 1, Method B) R$_t$=2.95 min; MS m/z: 415 [M+H]$^+$.

Example #75. 5,5-Dimethyl-2-[[4-[methyl(tetrahydropyran-4-yl)amino]benzoyl]amino]-6,7-dihydro-4H-benzothiophene-3-carboxylic acid (Compound #160)

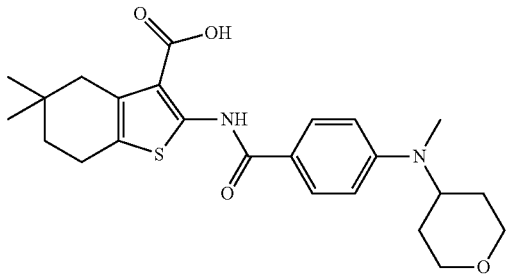 [SMILES: CN(c1ccc(C(=O)Nc2sc3c(c2C(=O)O)CC(C)(C)CC3)cc1)C1CCOCC1]

The title compound was synthesized according to the procedure described in Example #20 using methyl 2-(4-bromobenzamido)-5,5-dimethyl-4,5,6,7-tetrahydrobenzo[b]thiophene-3-carboxylate (Preparation #14) and N-methyltetrahydropyran-4-amine (CAS: 220641-87-2) as starting materials (off-white solid, yield 31%). $^1$H NMR (DMSO-$d_6$, 400 MHz): δ=13.24 (br s, 1H), 12.30 (s, 1H), 7.78 (d, J=8.8 Hz, 2H), 7.03 (d, J=8.9 Hz, 2H), 4.16-4.09 (m, 1H), 3.99 (dd, J=3.6, 10.9 Hz, 2H), 3.55 (t, J=11.4 Hz, 2H), 2.91 (s, 3H), 2.69 (t, J=5.7 Hz, 2H), 2.61 (s, 2H), 1.85 (dq, J=4.2, 11.8 Hz, 2H), 1.65 (d, J=13.1 Hz, 2H), 1.58 (t, J=5.9 Hz, 2H), 1.02 (s, 6H). LC/MS (Table 1, Method B) $R_t$=3.00 min; MS m/z: 443 [M+H]$^+$.

Example #76. 5,5-Dimethyl-2-[[4-(tetrahydropyran-4-ylamino)benzoyl]amino]-6,7-dihydro-4H-benzothiophene-3-carboxylic acid (Compound #161)

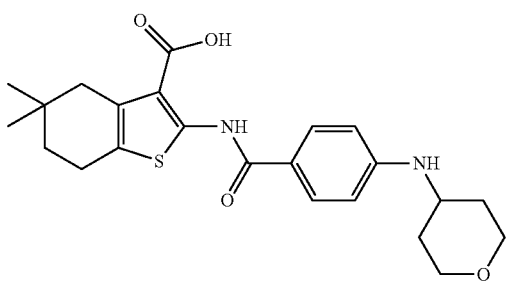 [SMILES: CC1(C)CCc2sc(NC(=O)c3ccc(NC4CCOCC4)cc3)c(C(=O)O)c2C1]

The title compound was synthesized according to the procedure described in Example #20 using methyl 2-(4-bromobenzamido)-5,5-dimethyl-4,5,6,7-tetrahydrobenzo[b]thiophene-3-carboxylate (Preparation #14) and 4-aminotetrahydropyran (CAS: 38041-19-9) as starting materials (pale yellow solid, yield 25%). $^1$H NMR (DMSO-$d_6$, 400 MHz): δ=13.19 (br s, 1H), 12.26 (s, 1H), 7.69 (d, J=8.7 Hz, 2H), 6.79 (d, J=8.9 Hz, 2H), 6.58 (d, J=7.5 Hz, 1H), 3.94 (d, J=11.0 Hz, 2H), 3.67-3.58 (m, 1H), 3.49 (t, J=10.8 Hz, 2H), 2.68 (t, J=5.8 Hz, 2H), 2.60 (s, 2H), 1.95 (d, J=12.7 Hz, 2H), 1.58 (t, J=6.1 Hz, 2H), 1.52-1.41 (m, 2H), 1.02 (s, 6H). LC/MS (Table 1, Method B) $R_t$=2.94 min; MS m/z: 429 [M+H]$^+$.

Example #77. 5,5,7,7-Tetramethyl-2-[[4-(tetrahydropyran-4-ylmethoxy)benzoyl]amino]-4,6-dihydrobenzothiophene-3-carboxylic acid (Compound #162)

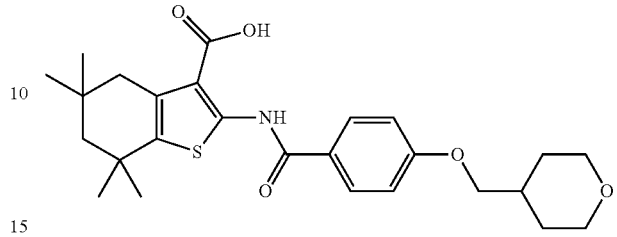

To a stirred solution of ethyl 2-(4-hydroxybenzamido)-5,5,7,7-tetramethyl-4,5,6,7-tetrahydrobenzo[b]thiophene-3-carboxylate (Preparation #15, 200 mg, 0.50 mmol) in THF (3.0 ml) at 0° C. was added 4-(hydroxymethyl)tetrahydropyran (CAS: 14774-37-9, 58 mg, 0.50 mmol) and triphenylphosphine (CAS: 603-35-0, 157 mg, 0.60 mmol). This was followed by the addition of diisopropyl azodicarboxylate (CAS: 2446-83-5, 120 µl, 0.60 mmol). The reaction mixture was stirred at 0° C. for 15 minutes and allowed to warm to RT overnight. The reaction was partitioned between EtOAc and saturated aqueous NaHCO$_3$ solution. The two phases were separated. The aqueous phase was extracted with DCM and the combined organic phases were passed through a phase separator. The solvents were removed under reduced pressure. The residue was triturated with EtOAc and the solid was dried in vacuo to give ethyl 5,5,7,7-tetramethyl-2-(4-((tetrahydro-2H-pyran-4-yl)methoxy)benzamido)-4,5,6,7-tetrahydrobenzo[b]thiophene-3-carboxylate as a white solid (183 mg, yield 73%). The title compound was then synthesized according to the procedure described in Example #8 using ethyl 5,5,7,7-tetramethyl-2-(4-((tetrahydro-2H-pyran-4-yl)methoxy)benzamido)-4,5,6,7-tetrahydrobenzo[b]thiophene-3-carboxylate as starting material (white solid, yield 73%). $^1$H NMR (Pyr-$d_5$, 400 MHz): δ=13.25 (s, 1H), 8.28 (d, J=8.9 Hz, 2H), 7.01 (d, J=8.8 Hz, 2H), 3.96 (dd, J=3.0, 11.2 Hz, 2H), 3.74 (d, J=6.4 Hz, 2H), 3.32 (t, J=11.4 Hz, 2H), 3.02 (s, 2H), 1.92 (br s, 1H), 1.60 (d, J=12.1 Hz, 2H), 1.52 (s, 2H), 1.44-1.33 (m, 8H), 1.04 (s, 6H), one exchangeable proton not observed. LC/MS (Table 1, Method C) $R_t$=4.11 min; MS m/z: 472 [M+H]$^+$.

Example #78. 2-[[4-(3-Methoxyazetidin-1-yl)benzoyl]amino]-5,5-dimethyl-6,7-dihydro-4H-benzothiophene-3-carboxylic acid (Compound #163)

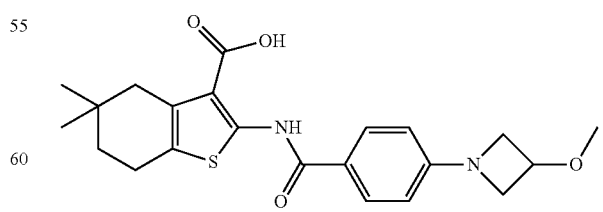

The title compound was synthesized according to the procedure described in Example #20 using methyl 2-(4-bromobenzamido)-5,5-dimethyl-4,5,6,7-tetrahydrobenzo[b]thiophene-3-carboxylate (Preparation #14) and 3-methoxyazetidine hydrochloride (CAS: 148644-09-1) as starting materials (off-white solid, yield 59%). ¹H NMR (DMSO-d₆, 400 MHz): δ=13.25 (br s, 1H), 12.32 (s, 1H), 7.77 (d, J=8.4 Hz, 2H), 6.60 (d, J=8.7 Hz, 2H), 4.44-4.39 (m, 1H), 4.21 (t, J=7.3 Hz, 2H), 3.81 (dd, J=3.8, 8.7 Hz, 2H), 3.32 (s, 3H), 2.68 (t, J=5.5 Hz, 2H), 2.60 (s, 2H), 1.58 (t, J=6.1 Hz, 2H), 1.02 (s, 6H). LC/MS (Table 1, Method B) $R_t$=2.96 min; MS I/z: 415 [M+H]⁺.

Example #79. 5,5-Dimethyl-2-[[4-(tetrahydropyran-4-ylmethylamino)benzoyl]amino]-6,7-dihydro-4H-benzothiophene-3-carboxylic acid (Compound #164)

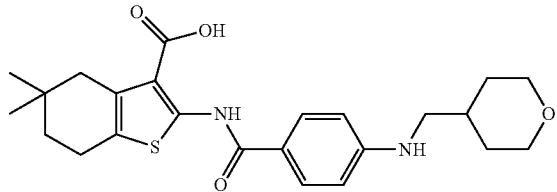 [SMILES: CC1(C)CCc2sc(NC(=O)c3ccc(NCC4CCOCC4)cc3)c(C(=O)O)c2C1]

The title compound was synthesized according to the procedure described in Example #20 using methyl 2-(4-bromobenzamido)-5,5-dimethyl-4,5,6,7-tetrahydrobenzo[b]thiophene-3-carboxylate (Preparation #14) and tetrahydropyran-4-ylmethanamine (CAS: 130290-79-8) as starting materials (pale yellow solid, yield 39%). ¹H NMR (DMSO-d₆, 400 MHz): δ=13.19 (br s, 1H), 12.25 (s, 1H), 7.69 (d, J=8.0 Hz, 2H), 6.78-6.71 (m, 3H), 3.91 (dd, J=2.9, 11.2 Hz, 2H), 3.35-3.28 (m, 2H, partially obscured by the water peak), 3.06 (t, J=5.8 Hz, 2H), 2.68 (t, J=5.4 Hz, 2H), 2.60 (s, 2H), 1.86 (br s, 1H), 1.73 (d, J=12.8 Hz, 2H), 1.57 (t, J=5.9 Hz, 2H), 1.27 (ddt, J=3.9, 12.0, 12.1 Hz, 2H), 1.01 (s, 6H). LC/MS (Table 1, Method B) $R_t$=2.89 min; MS/z: 443 [M+H]⁺.

Example #80. 2-[[4-[(3-Methoxycyclobutyl)-methyl-amino]benzoyl]amino]-5,5,7,7-tetramethyl-4,6-dihydrobenzothiophene-3-carboxylic acid (Compound #165)

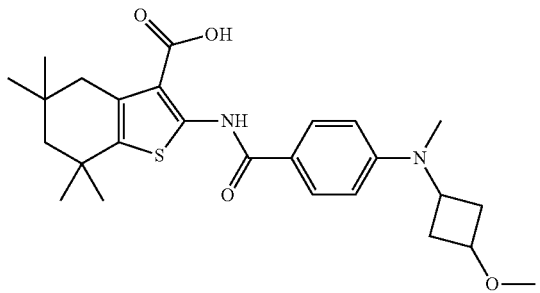

The title compound was synthesized according to the procedure described in Example #20 using ethyl 2-(4-bromobenzamido)-5,5,7,7-tetramethyl-4,5,6,7-tetrahydrobenzo[b]thiophene-3-carboxylate (Preparation #7) and 3-methoxy-N-methylcyclobutan-1-amine (CAS: 1520446-07-4) as starting materials (off-white solid, yield 25%, isolated as a mixture of isomers with ratio 2:1). ¹H NMR (DMSO-d₆, 400 MHz): δ=13.25 (br s, 1H), 12.31 (s, 1H), 7.77 (d, J=8.4 Hz, 2H), 6.96-6.89 (m, 2H), 4.51-4.43 (m, 0.3H, minor isomer), 4.01-3.87 (m, 1H), 3.69 (tt, J=6.9, 6.7 Hz, 0.7H, major isomer), 3.24 (s, 1H), 3.22 (s, 2H), 2.99 (s, 1H), 2.97 (s, 2H), 2.78-2.70 (m, 1H), 2.64 (s, 2H), 2.42-2.35 (m, 2H), 2.03-1.94 (m, 1H), 1.61 (s, 2H), 1.37 (s, 6H), 1.04 (s, 6H). LC/MS (Table 1, Method B) $R_t$=3.16 min; MS m/z: 471 [M+H]⁺.

Example #81. 5,5,7,7-Tetramethyl-2-[[4-(tetrahydropyran-2-ylmethylamino)benzoyl]amino]-4,6-dihydrobenzothiophene-3-carboxylic acid (Compound #166)

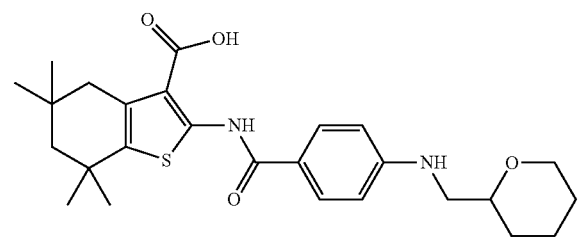 [SMILES: CC1(C)Cc2c(sc(NC(=O)c3ccc(NCC4CCCCO4)cc3)c2C(=O)O)C(C)(C)C1]

The title compound was synthesized according to the procedure described in Example #20 using ethyl 2-(4-bromobenzamido)-5,5,7,7-tetramethyl-4,5,6,7-tetrahydrobenzo[b]thiophene-3-carboxylate (Preparation #7) and tetrahydropyran-2-ylmethylamine (CAS: 6628-83-7) as starting materials (white solid, yield 55%). ¹H NMR (DMSO-d₆, 400 MHz): δ=13.10 (br s, 1H), 12.24 (s, 1H), 7.68 (d, J=8.6 Hz, 2H), 6.78 (d, J=8.7 Hz, 2H), 6.66 (t, J=5.5 Hz, 1H), 3.94 (d, J=11.8 Hz, 1H), 3.53-3.45 (m, 1H), 3.25-3.11 (m, 3H), 2.63 (s, 2H), 1.83 (s, 1H), 1.71 (d, J=12.6 Hz, 1H), 1.60 (s, 2H), 1.56-1.46 (m, 3H), 1.37-1.24 (m, 7H), 1.04 (s, 6H). LC/MS (Table 1, Method B) Rt=3.16 min; MS m/z: 471 [M+H]⁺.

Example #82. 5,5,7,7-Tetramethyl-2-[[4-(oxetan-3-ylmethoxy)benzoyl]amino]-4,6-dihydrobenzothiophene-3-carboxylic acid (Compound #167)

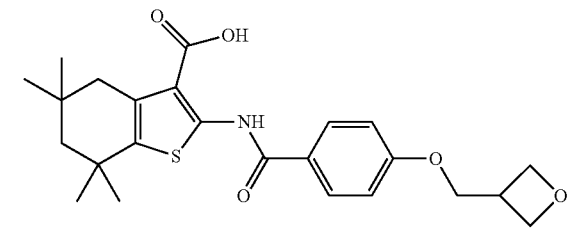 [SMILES: CC1(C)Cc2c(sc(NC(=O)c3ccc(OCC4COC4)cc3)c2C(=O)O)C(C)(C)C1]

The title compound was synthesize according to the procedure described in Example #77 using ethyl 2-(4-hydroxybenzamido)-5,5,7,7-tetramethyl-4,5,6,7-tetrahydrobenzo[b]thiophene-3-carboxylate (Preparation #15) and oxetane-3-methanol (CAS: 6246-06-6) as starting materials (off-white solid, yield 57%). ¹H NMR (DMSO-d₆, 400 MHz): δ=13.35 (br s, 1H), 12.42 (s, 1H), 7.91 (d, J=8.7 Hz, 2H), 7.24 (d, J=8.7 Hz, 2H), 4.78 (t, J=7.0 Hz, 2H), 4.49 (t, J=6.0 Hz, 2H), 4.37 (d, J=6.8 Hz, 2H), 3.52-3.44 (m, 1H), 2.65 (s, 2H), 1.62 (s, 2H), 1.38 (s, 6H), 1.06 (s, 6H). LC/MS (Table 1, Method B) $R_t$=3.09 min: MS m/z: 444 [M+H]⁺.

Example #83. 2-[[4-(2-Methoxyethoxy)benzoyl]amino]-5,5,7,7-tetramethyl-4,6-dihydrobenzothiophene-3-carboxylic acid (Compound #168)

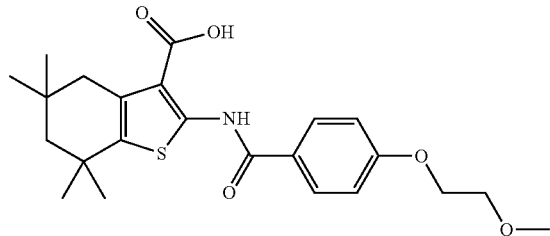

The title compound was synthesized according to the procedure described in Example #77 using ethyl 2-(4-hydroxybenzamido)-5,5,7,7-tetramethyl-4,5,6,7-tetrahydrobenzo[b]thiophene-3-carboxylate (Preparation #15) and 2-methoxyethanol (CAS: 109-86-4) as starting materials (white solid, yield 58%). $^1$H NMR (CDCl$_3$, 400 MHz): δ=12.10 (s, 1H), 7.94 (d, J=7.1 Hz, 2H), 7.01 (d, J=7.2 Hz, 2H), 4.18 (s, 2H), 3.78 (s, 2H), 3.47 (s, 3H), 2.68 (s, 2H), 1.60 (s, 2H), 1.39 (s, 6H), 1.05 (s, 6H), one exchangeable proton not observed. LC/MS (Table 1, Method B) R$_t$=3.15 min; MS m/z: 432 [M+H]$^+$.

Example #84. 2-[[4-[3-(Methoxymethyl)azetidin-1-yl]benzoyl]amino]-5,5,7,7-tetramethyl-4,6-dihydrobenzothiophene-3-carboxylic acid (Compound #169)

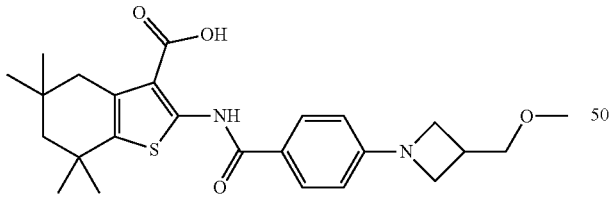

The title compound was synthesized according to the procedure described in Example #20 using ethyl 2-(4-bromobenzamido)-5,5,7,7-tetramethyl-4,5,6,7-tetrahydrobenzo[b]thiophene-3-carboxylate (Preparation #7) and 3-(methoxymethyl)azetidine hydrochloride (CAS: 942400-33-1) as starting materials (white solid, yield 59%). $^1$H NMR (DMSO-d$_6$, 400 MHz): δ=13.45 (s, 1H), 12.53 (s, 1H), 7.95 (d, J=8.7 Hz, 2H), 6.76 (d, J=8.8 Hz, 2H), 4.24 (t, J=7.9 Hz, 2H), 3.92 (dd, J=5.6, 7.6 Hz, 2H), 3.78 (d, J=6.1 Hz, 2H), 3.53 (s, 3H), 3.26-3.18 (m, 1H), 2.82 (s, 2H), 1.79 (s, 2H), 1.55 (s, 6H), 1.23 (s, 6H). LC/MS (Table 1, Method B) R$_t$=3.14 min; MS/z: 457 [M+H]$^+$.

Example #85. 5,5,7,7-Tetramethyl-2-[(4-tetrahydropyran-4-yloxybenzoyl)amino]-4,6-dihydrobenzothiophene-3-carboxylic acid (Compound #170)

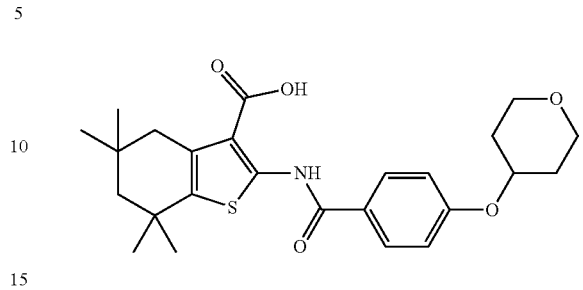

The title compound was synthesized according to the procedure described in Example #77 using ethyl 2-(4-hydroxybenzamido)-5,5,7,7-tetramethyl-4,5,6,7-tetrahydrobenzo[b]thiophene-3-carboxylate (Preparation #15) and tetrahydropyran-4-ol (CAS: 2081-44-9) as starting materials (off-white solid, yield 37%). $^1$H NMR (DMSO-d$_6$, 400 MHz): δ=13.00 (s, 1H), 7.86 (d, J=8.8 Hz, 2H), 7.20 (d, J=8.7 Hz, 2H), 4.77-4.69 (m, 1H), 3.87 (td, J=4.4, 11.4 Hz, 2H), 3.52 (ddd, J=2.4, 9.5, 11.7 Hz, 2H), 2.62 (s, 2H), 2.06-2.00 (m, 2H), 1.63 (tdd, J=4.6, 13.1, 13.1 Hz, 4H), 1.33 (s, 6H), 1.01 (s, 6H), one exchangeable proton not observed. LC/MS (Table 1, Method B) R$_t$=3.14 min; MS m/z: 458 [M+H]$^+$.

Example #86. 5,5,7,7-Tetramethyl-2-[(4-tetrahydropyran-4-yloxybenzoyl)amino]-4,6-dihydrobenzothiophene-3-carboxylic acid (Compound #171)

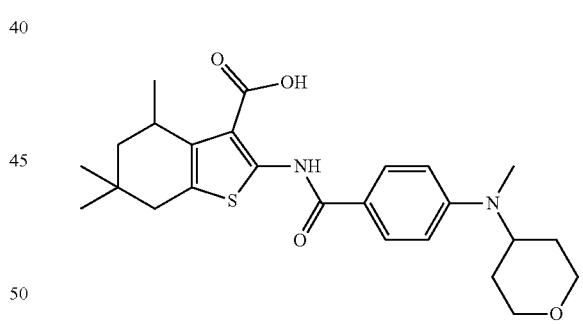

The title compound was synthesized according to the procedure described in Example #20 using ethyl 2-(4-bromobenzamido)-4,6,6-trimethyl-4,5,6,7-tetrahydrobenzo[b]thiophene-3-carboxylate (Preparation #12) and N-methyltetrahydropyran-4-amine (CAS: 220641-87-2) as starting materials (pale yellow solid, yield 22%). $^1$H NMR (DMSO-d$_6$, 400 MHz): δ=12.40 (s, 1H), 7.78 (d, J=8.6 Hz, 2H), 7.02 (d, J=8.9 Hz, 2H), 4.14-4.08 (m, 1H), 3.99 (dd, J=3.3, 10.9 Hz, 2H), 3.54 (t, J=11.7 Hz, 2H), 3.19-3.13 (m, 1H), 2.90 (s, 3H), 2.50 (d, J=15.1 Hz, 1H), 2.38 (d, J=15.6 Hz, 1H), 1.90-1.74 (m, 3H), 1.64 (d, J=11.5 Hz, 2H), 1.29-1.22 (m, 4H), 1.10 (s, 3H), 0.93 (s, 3H), one exchangeable proton not observed. LC/MS (Table 1, Method C) R$_t$=3.96 min; MS I/z: 457 [M+H]$^+$.

Example #87. 2-[[4-(2-Methoxyethylamino)benzoyl]amino]-5,5-dimethyl-6,7-dihydro-4H-benzothiophene-3-carboxylic acid (Compound #173)

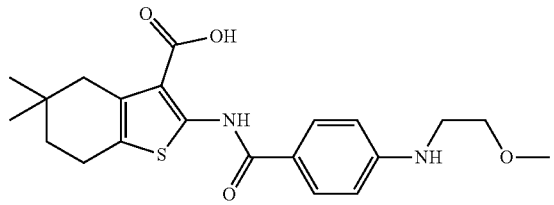

The title compound was synthesized according to the procedure described in Example #20 using methyl 2-(4-bromobenzamido)-5,5-dimethyl-4,5,6,7-tetrahydrobenzo[b]thiophene-3-carboxylate (Preparation #14) and 2-methoxyethanamine (CAS: 109-85-3) as starting materials (white solid, yield 29%). $^1$H NMR (DMSO-$d_6$, 400 MHz): δ=13.19 (br s, 1H), 12.23 (s, 1H), 7.69 (d, J=8.8 Hz, 2H), 6.78 (d, J=8.7 Hz, 2H), 6.67 (t, J=5.3 Hz, 1H), 3.56 (t, J=5.4 Hz, 2H), 3.38 (s, 3H), 3.36-3.30 (m, 2H, partially obscured by the water peak), 2.68 (t, J=5.6 Hz, 2H), 2.60 (s, 2H), 1.57 (t, J=6.1 Hz, 2H), 1.01 (s, 6H). LC/MS (Table 1, Method C) $R_t$=3.73 min; MS m/z: 403 [M+H]$^+$.

Example #88. 5,5,7,7-Tetramethyl-2-[(4-tetrahydropyran-4-ylbenzoyl)amino]-4,6-dihydrobenzothiophene-3-carboxylic acid (Compound #174)

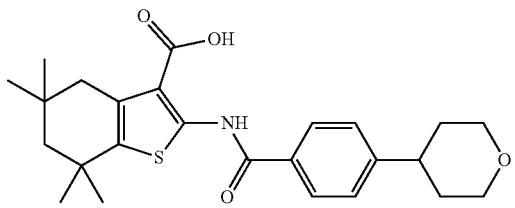 [SMILES: CC1(C)Cc2c(sc(NC(=O)c3ccc(C4CCOCC4)cc3)c2C(=O)O)C(C)(C)C1]

A reaction vessel was charged with ethyl 2-(4-bromobenzamido)-5,5,7,7-tetramethyl-4,5,6,7-tetrahydrobenzo[b]thiophene-3-carboxylate (Preparation #7, 247 mg, 0.53 mmol), tetrahydropyran-4-enyl pinacol borane (CAS: 287944-16-5, 167 mg, 0.80 mmol), tetrakis(triphenylphosphine)palladium(0) (CAS: 14221-01-3, 123 mg, 0.11 mmol), Cs$_2$CO$_3$ (CAS: 534-17-8, 260 mg, 0.80 mmol) and solvated in 1,4-dioxane (4.0 ml) and water (1.0 ml). The reaction was degassed with nitrogen for 5 minutes and set to stir at RT. The mixture was next heated at 90° C. for 16 hours. The reaction was allowed to cool to RT and partitioned between EtOAc and brine. The two phases were separated. The organic phase was dried over MgSO$_4$ and the solvent was removed under reduced pressure. Purification by flash chromatography on silica gel (eluting with 0-40% EtOAc in isohexane) afforded ethyl 2-(4-(3,6-dihydro-2H-pyran-4-yl)benzamido)-5,5,7,7-tetramethyl-4,5,6,7-tetrahydrobenzo[b]thiophene-3-carboxylate as a yellow solid (207 mg, yield 85%). The residue was dissolved in EtOAc (5.0 ml) and methanol (1.0 ml) and the solution was degassed with nitrogen for 5 minutes before palladium on carbon (5.0%, 450 mg) was added. The reaction was evacuated and filled with hydrogen. The mixture was then stirred at RT under atmospheric hydrogen for 16 hours. The reaction was evacuated and filled with nitrogen. The mixture was filtered through a pad of Celite®, which was washed with EtOAc/MeOH (1:1). The solvents were removed under reduced pressure to give ethyl 5,5,7,7-tetramethyl-2-(4-(tetrahydro-2H-pyran-4-yl)benzamido)-4,5,6,7-tetrahydrobenzo[b]thiophene-3-carboxylate as a white solid (135 mg, yield 65%). The title compound was then synthesized according to the procedure described in Example #8 using ethyl 5,5,7,7-tetramethyl-2-(4-(tetrahydro-2H-pyran-4-yl)benzamido)-4,5,6,7-tetrahydrobenzo[b]thiophene-3-carboxylate as starting material (white solid, yield 33%). $^1$H NMR (DMSO-$d_6$, 400 MHz): δ=13.36 (br s, 1H), 12.42 (s, 1H), 7.89 (d, J=8.1 Hz, 2H), 7.56 (d, J=7.9 Hz, 2H), 4.02 (d, J=10.2 Hz, 2H), 3.55-3.45 (m, 2H), 2.97-2.88 (m, 1H), 2.64 (s, 2H), 1.81-1.72 (m, 4H), 1.62 (s, 2H), 1.37 (s, 6H), 1.05 (s, 6H). LC/MS (Table 1, Method C) $R_t$=4.09 min; MS m/z: 442 [M+H]$^+$.

Example #89. 5,5,7,7-Tetramethyl-2-[(1-methylpyrazole-4-carbonyl)amino]-4,6-dihydrobenzothiophene-3-carboxylic acid (Compound #176)

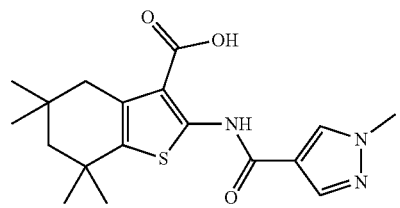

The title compound was synthesized according to the procedure described in Example #11 using ethyl 2-amino-5,5,7,7-tetramethyl-4,5,6,7-tetrahydrobenzo [b]thiophene-3-carboxylate (Preparation #6) and 1-methyl-1H-pyrazole-4-carboxylic acid (CAS: 5952-92-1) as starting materials (white solid, yield 23%). $^1$H NMR (DMSO-$d_6$, 400 MHz): δ=13.51 (br s, 1H), 12.30 (br s, 1H), 8.36 (s, 1H), 7.87 (s, 1H), 3.94 (s, 3H), 2.61 (s, 2H), 1.56 (s, 2H), 1.31 (s, 6H), 1.00 (s, 6H). LC/MS (Table 1, Method B) $R_t$=2.77 min; MS m/z: 362 [M+H]$^+$.

Example #90. 5,5,7,7-Tetramethyl-2-[(6-morpholinopyridine-3-carbonyl)amino]-4,6-dihydrobenzothiophene-3-carboxylic acid (Compound #201)

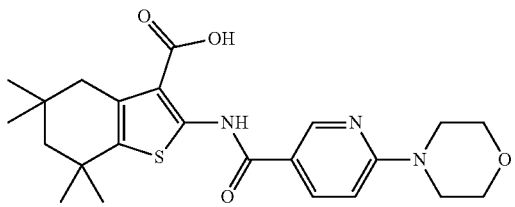 [SMILES: CC1(C)Cc2c(sc(NC(=O)c3ccc(N4CCOCC4)nc3)c2C(=O)O)C(C)(C)C1]

The title compound was synthesized according to the procedure described in Example #11 using ethyl 2-amino-5,5,7,7-tetramethyl-4,5,6,7-tetrahydrobenzo [b]thiophene-3-carboxylate (Preparation #6) and 6-morpholinopyridine-3-carboxylic acid (CAS: 120800-52-4) as starting materials (white solid, yield 47%). $^1$H NMR (DMSO-$d_6$, 400 MHz): δ=13.37 (br s, 1H), 12.44 (s, 1H), 8.71 (d, J=2.7 Hz, 1H), 8.00 (dd, J=2.5, 9.1 Hz, 1H), 7.05 (d, J=8.9 Hz, 1H), 3.77-3.67 (m, 8H), 2.65 (s, 2H), 1.62 (s, 2H), 1.37 (s, 6H), 1.06 (s, 6H). LC/MS (Table 1, Method C) $R_t$=3.87 min; MS m/z: 444 [M+H]$^+$.

Example #91. 5,5-Dimethyl-2-[(1-methylpyrazole-4-carbonyl)amino]-6,7-dihydro-4H-benzothiophene-3-carboxylic acid (Compound #202)

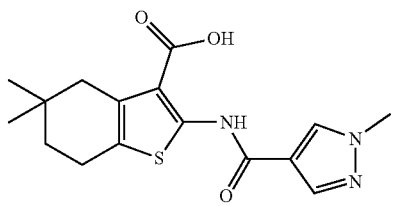

The title compound was synthesized according to the procedure described in Example #11 using methyl 2-amino-5,5-dimethyl-4,5,6,7-tetrahydrobenzo[b]thiophene-3-carboxylate (Preparation #3) and 1-methyl-1H-pyrazole-4-carboxylic acid (CAS: 5952-92-1) as starting materials (off-white solid, yield 8%). $^1$H NMR (DMSO-d$_6$, 400 MHz): δ=13.12 (br s, 1H), 12.01 (s, 1H), 8.36 (s, 1H), 7.86 (s, 1H), 3.94 (s, 3H), 2.64 (t, J=6.7 Hz, 2H), 2.57 (s, 2H), 1.53 (t, J=6.3 Hz, 2H), 0.97 (s, 6H). LC/MS (Table 1, Method B) $R_t$=2.61 min; MS m/z: 334 [M+H]$^+$.

Example #92. 6,6-Dimethyl-2-[(3-morpholinobenzoyl)amino]-5,7-dihydro-4H-benzothiophene-3-carboxylic acid (Compound #203)

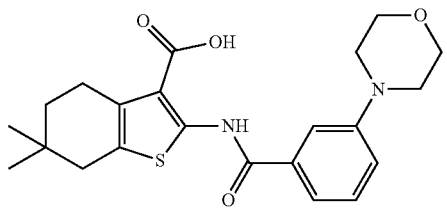 [SMILES: CC1(C)CCc2c(sc(NC(=O)c3cccc(N4CCOCC4)c3)c2C(=O)O)C1]

The title compound was synthesized according to the procedure described in Example #11 using methyl 2-amino-6,6-dimethyl-4,5,6,7-tetrahydrobenzo[b]thiophene-3-carboxylate (Preparation #1) and 3-morpholinobenzoic acid (CAS: 215309-00-5) as starting materials (white solid, yield 14%). $^1$H NMR (DMSO-d$_6$, 400 MHz): δ=13.36 (br s, 1H), 12.39 (s, 1H), 7.47 (t, J=8.0 Hz, 1H), 7.43 (t, J=1.8 Hz, 1H), 7.32 (d, J=7.8 Hz, 1H), 7.28 (dd, J=2.3, 8.4 Hz, 1H), 3.79-3.76 (m, 4H), 3.24-3.19 (m, 4H), 2.78 (t, J=6.1 Hz, 2H), 2.45 (s, 2H), 1.51 (t, J=6.4 Hz, 2H), 0.98 (s, 6H). LC/MS (Table 1, Method C) $R_t$=3.82 min; MS m/z: 415 [M+H]$^+$.

Example #93. 6,6-Dimethyl-2-[(6-morpholinopyridine-3-carbonyl)amino]-5,7-dihydro-4H-benzothiophene-3-carboxylic acid (Compound #204)

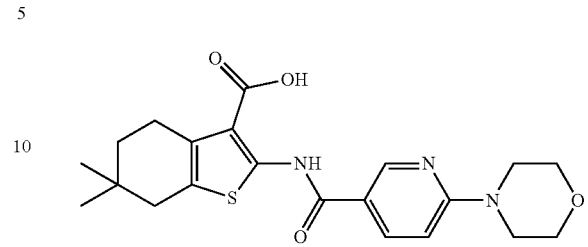

The title compound was synthesized according to the procedure described in Example #11 using methyl 2-amino-6,6-dimethyl-4,5,6,7-tetrahydrobenzo[b]thiophene-3-carboxylate (Preparation #1) and 6-morpholinopyridine-3-carboxylic acid (CAS: 120800-52-4) as starting materials (white solid, yield 20%). $^1$H NMR (DMSO-d$_6$, 400 MHz): δ=14.38 (br s, 1H), 8.71 (s, 1H), 8.01 (d, J=9.0 Hz, 1H), 6.94 (d, J=7.7 Hz, 1H), 3.73 (br s, 4H), 3.62 (br s, 4H), 2.87 (br s, 2H), 2.44 (s, 2H), 1.52 (s, 2H), 1.01 (s, 6H), one exchangeable proton not observed. LC/MS (Table 1, Method C) $R_t$=3.69 min; MS m/z: 416 [M+H]$^+$.

Example #94. 5,5,7,7-Tetramethyl-2-(pyrimidine-4-carbonylamino)-4,6-dihydrobenzothiophene-3-carboxylic acid (Compound #205)

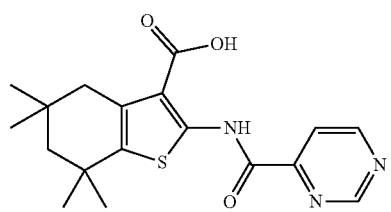 [SMILES: CC1(C)Cc2c(sc(NC(=O)c3ccncn3)c2C(=O)O)C(C)(C)C1]

The title compound was synthesized according to the procedure described in Example #11 using ethyl 2-amino-5,5,7,7-tetramethyl-4,5,6,7-tetrahydrobenzo [b]thiophene-3-carboxylate (Preparation #6) and pyrimidine-4-carboxylic acid (CAS: 31462-59-6) as starting materials (off-white solid, yield 29%). $^1$H NMR (DMSO-d$_6$, 400 MHz): δ=13.59 (br s, 1H), 9.44 (d, J=1.4 Hz, 1H), 9.17 (d, J=5.0 Hz, 1H), 8.16 (dd, J=1.4, 5.0 Hz, 1H), 2.64 (s, 2H), 1.58 (s, 2H), 1.34 (s, 6H), 1.01 (s, 6H), one exchangeable proton not observed. LC/MS (Table 1, Method C) $R_t$=3.76 min; MS m/z: 360 [M+H]$^+$.

Example #95. 5,5-Dimethyl-2-(pyrimidine-4-carbonylamino)-6,7-dihydro-4H-benzothiophene-3-carboxylic acid (Compound #206)

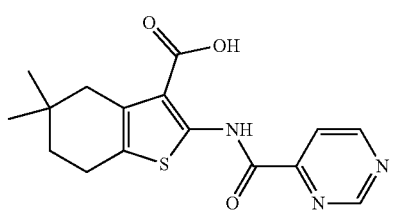 [SMILES: CC1(C)CCc2sc(NC(=O)c3ccncn3)c(C(=O)O)c2C1]

The title compound was synthesized according to the procedure described in Example #11 using methyl 2-amino-5,5-dimethyl-4,5,6,7-tetrahydrobenzo[b]thiophene-3-carboxylate (Preparation #3) and pyrimidine-4-carboxylic acid (CAS: 31462-59-6) as starting materials (yellow solid, yield 8%). $^1$H NMR (DMSO-d$_6$, 400 MHz): δ=14.04 (br s, 1H), 9.33 (s, 1H), 9.06 (d, J=5.1 Hz, 1H), 8.07 (dd, J=1.1, 5.0 Hz, 1H), 7.23 (br s, 1H), 2.60 (t, J=5.8 Hz, 2H), 2.55 (s, 2H), 1.45 (t, J=6.3 Hz, 2H), 0.90 (s, 6H). LC/MS (Table 1, Method C) R$_t$=3.55 min: MS m/z: 332 [M+H]$^+$.

Example #96. 6,6-Dimethyl-2-[(2-morpholinopyrimidine-5-carbonyl)amino]-5,7-dihydro-4H-benzothiophene-3-carboxylic acid (Compound #208)

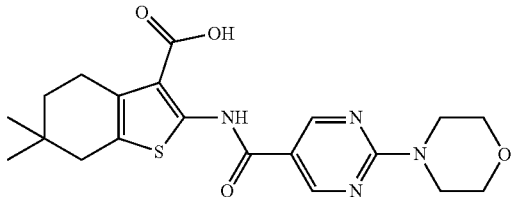 [SMILES: CC1(C)CCc2c(sc(NC(=O)c3cnc(N4CCOCC4)nc3)c2C(=O)O)C1]

The title compound was synthesized according to the procedure described in Example #11 using methyl 2-amino-6,6-dimethyl-4,5,6,7-tetrahydrobenzo[b]thiophene-3-carboxylate (Preparation #1) and 2-morpholinopyrimidine-5-carboxylic acid (CAS: 253315-05-8) as starting materials (white solid, yield 18%). $^1$H NMR (DMSO-d$_6$, 400 MHz): δ=13.50 (br s, 1H), 8.81 (s, 2H), 3.86-3.80 (m, 4H), 3.71-3.65 (m, 4H), 2.81 (t, J=5.8 Hz, 2H), 2.41 (s, 2H), 1.49 (t, J=6.3 Hz, 2H), 0.98 (s, 6H), one exchangeable proton not observed. LC/MS (Table 1, Method C) R$_t$=3.75 min; MS m/z: 417 [M+H]$^+$.

Example #97. 5,5-Dimethyl-2-[(2-morpholinopyrimidine-5-carbonyl)amino]-6,7-dihydro-4H-benzothiophene-3-carboxylic acid (Compound #209)

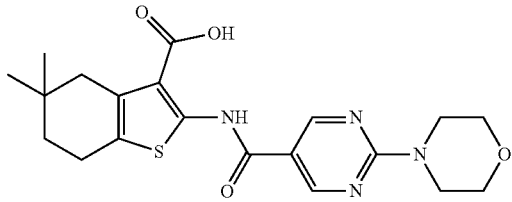 [SMILES: CC1(C)CCc2sc(NC(=O)c3cnc(N4CCOCC4)nc3)c(C(=O)O)c2C1]

The title compound was synthesized according to the procedure described in Example #11 using methyl 2-amino-5,5-dimethyl-4,5,6,7-tetrahydrobenzo[b]thiophene-3-carboxylate (Preparation #3) and 2-morpholinopyrimidine-5-carboxylic acid (CAS: 253315-05-8) as starting materials (white solid, yield 13%). $^1$H NMR (DMSO-d$_6$, 400 MHz): δ=13.29 (s, 1H), 12.24 (s, 1H), 8.81 (s, 2H), 3.88-3.84 (m, 4H), 3.72-3.67 (m, 4H), 2.66 (t, J=6.0 Hz, 2H), 2.57 (s, 2H), 1.55 (t, J=6.2 Hz, 2H), 0.97 (s, 6H). LC/MS (Table 1, Method B) R$_t$=2.82 min; MS I/z: 417 [M+H]$^+$.

Example #98. 6,6-Dimethyl-2-[(1-methylpyrazole-4-carbonyl)amino]-5,7-dihydro-4H-benzothiophene-3-carboxylic acid (Compound #212)

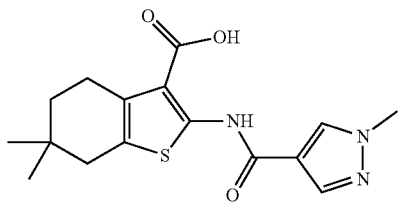

The title compound was synthesized according to the procedure described in Example #11 using methyl 2-amino-6,6-dimethyl-4,5,6,7-tetrahydrobenzo[b]thiophene-3-carboxylate (Preparation #1) and 1-methyl-1H-pyrazole-4-carboxylic acid (CAS: 5952-92-1) as starting materials (off-white solid, yield 41%). $^1$H NMR (DMSO-d$_6$, 400 MHz): δ=13.18 (br s, 1H), 11.88 (s, 1H), 8.36 (s, 1H), 7.86 (s, 1H), 3.94 (s, 3H), 2.75 (t, J=6.3 Hz, 2H), 2.42 (s, 2H), 1.50 (t, J=6.4 Hz, 2H), 0.98 (s, 6H). LC/MS (Table 1, Method C) R$_t$=3.43 min; MS m/z: 334 [M+H]$^+$.

Example #99. 5,5-Dimethyl-2-[(6-morpholinopyridine-2-carbonyl)amino]-6,7-dihydro-4H-benzothiophene-3-carboxylic acid (Compound #213)

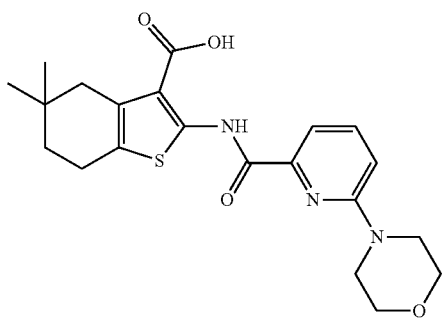 [SMILES: CC1(C)CCc2sc(NC(=O)c3cccc(N4CCOCC4)n3)c(C(=O)O)c2C1]

The title compound was synthesized according to the procedure described in Example #11 using methyl 2-amino-5,5-dimethyl-4,5,6,7-tetrahydrobenzo[b]thiophene-3-carboxylate (Preparation #3) and 6-morpholinopyridine-2-carboxylic acid (CAS 554405-17-3) as starting materials (pale yellow solid, yield 40%). $^1$H NMR (DMSO-d$_6$, 400 MHz): δ=13.20 (br s, 1H), 7.79 (dd, J=7.2, 8.6 Hz, 1H), 7.45 (d, J=7.2 Hz, 1H), 7.14 (d, J=8.6 Hz, 1H), 3.74-3.72 (m, 4H), 3.62-3.60 (m, 4H), 2.65 (t, J=6.3 Hz, 2H), 2.58 (s, 2H), 1.53 (t, J=6.3 Hz, 2H), 0.96 (s, 6H), one exchangeable proton not observed. LC/MS (Table 1, Method D) R$_t$=5.52 min; MS I/z: 416 [M+H]$^+$.

Example #100. 6,6-Dimethyl-2-[(6-morpholinopyridine-2-carbonyl)amino]-5,7-dihydro-4H-benzothiophene-3-carboxylic acid (Compound #219)

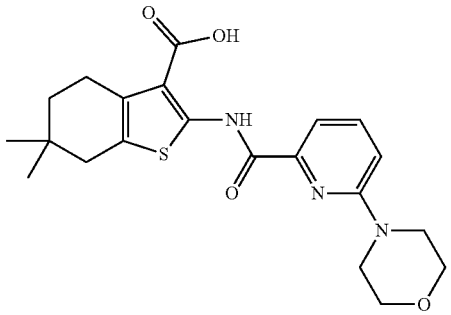 [SMILES: CC1(C)CCc2c(sc(NC(=O)c3cccc(N4CCOCC4)n3)c2C(=O)O)C1]

The title compound was synthesized according to the procedure described in Example #11 using methyl 2-amino-6,6-dimethyl-4,5,6,7-tetrahydrobenzo[b]thiophene-3-carboxylate (Preparation #1) and 6-morpholinopyridine-2-carboxylic acid (CAS 554405-17-3) as starting materials (yellow solid, yield 97%). $^1$H NMR (DMSO-$d_6$, 400 MHz): δ=13.37 (br s, 1H), 7.79 (dd, J=7.2, 8.6 Hz, 1H), 7.44 (d, J=7.2 Hz, 1H), 7.12 (d, J=8.6 Hz, 1H), 3.74-3.71 (m, 4H), 3.63-3.60 (m, 4H), 2.78 (t, J=6.3 Hz, 2H), 2.42 (s, 2H), 1.48 (t, J=6.3 Hz, 2H), 0.96 (s, 6H), one exchangeable proton not observed. LC/MS (Table 1, Method A) $R_t$=5.68 min; MS m/z: 416 [M+H]$^+$.

Example #101. 5,5-Dimethyl-2-(pyrimidine-5-carbonylamino)-6,7-dihydro-4H-benzothiophene-3-carboxylic acid (Compound #220)

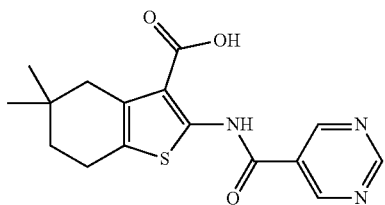 [SMILES: CC1(C)CCc2sc(NC(=O)c3cncnc3)c(C(=O)O)c2C1]

The title compound was synthesized according to the procedure described in Example #11 using methyl 2-amino-5,5-dimethyl-4,5,6,7-tetrahydrobenzo[b]thiophene-3-carboxylate (Preparation #3) and pyrimidine-5-carboxylic acid (CAS: 4595-61-3) as starting materials (yellow solid, yield 70%). $^1$H NMR (DMSO-$d_6$, 400 MHz): δ=13.42 (br s, 1H), 12.32 (s, 1H), 9.42 (s, 1H), 9.22 (s, 2H), 2.67 (t, J=6.4 Hz, 2H), 2.57 (s, 2H), 1.54 (t, J=6.4 Hz, 2H), 0.97 (s, 6H). LC/MS (Table 1, Method D) $R_t$=4.59 min; MS m/z: 332 [M+H]$^+$.

Example #102. 5,5-Dimethyl-2-[(2-morpholinopyridine-4-carbonyl)amino]-6,7-dihydro-4H-benzothiophene-3-carboxylic acid (Compound #221)

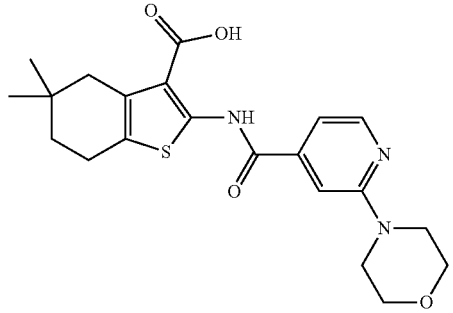 [SMILES: CC1(C)CCc2sc(NC(=O)c3ccnc(N4CCOCC4)c3)c(C(=O)O)c2C1]

The title compound was synthesized according to the procedure described in Example #11 using methyl 2-amino-5,5-dimethyl-4,5,6,7-tetrahydrobenzo[b]thiophene-3-carboxylate (Preparation #3) and 2-morpholinopyridine-4-carboxylic acid (CAS: 295349-64-3) as starting materials (yellow solid, yield 16%). $^1$H NMR (DMSO-$d_6$, 400 MHz): δ=13.52 (br s, 1H), 12.61 (s, 1H), 8.41 (d, J=5.1 Hz, 1H), 7.26 (s, 1H), 7.07 (d, J=5.1 Hz, 1H), 3.81-3.74 (m, 4H), 3.62-3.55 (m, 4H), 2.72 (s, 2H), 2.62 (s, 2H), 1.59 (t, J=6.1 Hz, 2H), 1.01 (s, 6H). LC/MS (Table 1, Method C) $R_t$=3.67 min; MS m/z: 416 [M+H]$^+$.

Example #103. 6,6-Dimethyl-2-[(2-morpholinopyridine-4-carbonyl)amino]-5,7-dihydro-4H-benzothiophene-3-carboxylic acid (Compound #222)

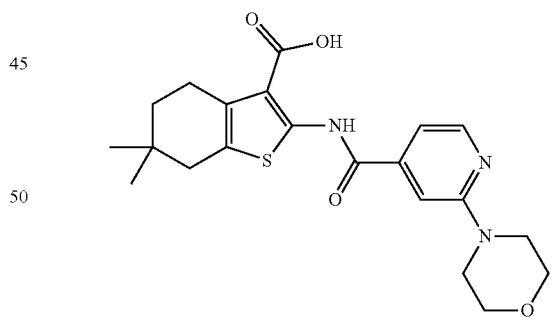

The title compound was synthesized according to the procedure described in Example #11 using methyl 2-amino-6,6-dimethyl-4,5,6,7-tetrahydrobenzo[b]thiophene-3-carboxylate (Preparation #1) and 2-morpholinopyridine-4-carboxylic acid (CAS: 295349-64-3) as starting materials (yellow solid, yield 5%). $^1$H NMR (CDCl$_3$, 400 MHz): δ=12.29 (br s, 1H), 8.35 (d, J=5.1 Hz, 1H), 7.22 (s, 1H), 7.06 (d, J=5.1 Hz, 1H), 3.85-3.82 (m, 4H), 3.62-3.59 (m, 4H), 2.86 (t, J=6.4 Hz, 2H), 2.47 (s, 2H), 1.57 (t, J=6.4 Hz, 2H), 1.02 (s, 6H), one exchangeable proton not observed. LC/MS (Table 1, Method D) $R_t$=5.16 min; MS m/z: 416 [M+H]$^+$.

Example #104. 5,5-Dimethyl-2-(1H-pyrazole-3-carbonylamino)-6,7-dihydro-4H-benzothiophene-3-carboxylic acid (Compound #225)

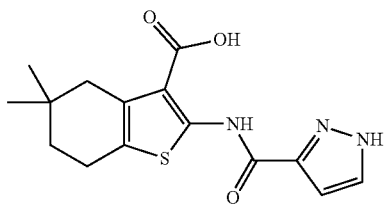 [SMILES: CC1(C)CCc2sc(NC(=O)c3cc[nH]n3)c(C(=O)O)c2C1]

To a stirred solution of methyl 2-amino-5,5-dimethyl-4,5,6,7-tetrahydrobenzo[b]thiophene-3-carboxylate (Preparation #3, 200 mg, 0.84 mmol) in DCM (4.0 ml) was added 1H-pyrazole-3-carboxylic acid (CAS: 1621-91-6, 141 mg, 1.25 mmol), 2-chloro-1-methylpyridinium iodide (CAS: 14338-32-0, 256 mg, 1.00 mmol), DMAP (CAS: 1122-58-3, 51 mg, 0.42 mmol) and triethylamine (CAS: 121-44-8, 0.35 ml, 2.51 mmol). The reaction mixture was heated at 40° C. for 72 hours. The reaction was allowed to cool to RT. The mixture was partitioned between EtOAc and brine. The two phases were separated and the organic phase was dried over MgSO$_4$. The solvent was removed under reduced pressure. Purification by flash chromatography on silica gel (eluting with 0-50% EtOAc in isohexane) afforded methyl 5,5-dimethyl-2-(1H-pyrazole-3-carboxamido)-4,5,6,7-tetrahydrobenzo[b]thiophene-3-carboxylate as a yellow oil (140 mg, yield 50%). The title compound was then synthesized according to the procedure described in Example #8 using methyl 5,5-dimethyl-2-(1H-pyrazole-3-carboxamido)-4,5,6,7-tetrahydrobenzo[b]thiophene-3-carboxylate as starting material (white solid, yield 26%). $^1$H NMR (DMSO-d$_6$, 400 MHz): δ=13.67 (br s, 1H), 13.23 (br s, 1H), 7.99 (s, 1H), 7.46 (br s, 1H), 6.84 (s, 1H), 2.71-2.63 (m, 4H), 1.56 (t, J=5.9 Hz, 2H), 0.99 (s, 6H). LC/MS (Table 1, Method C) R$_t$=3.44 min; MS m/z: 320 [M+H]$^+$.

Example #105. 2-[[1-(2-Methoxyethyl)pyrazole-3-carbonyl]amino]-5,5-dimethyl-6,7-dihydro-4H-benzothiophene-3-carboxylic acid (Compound #226)

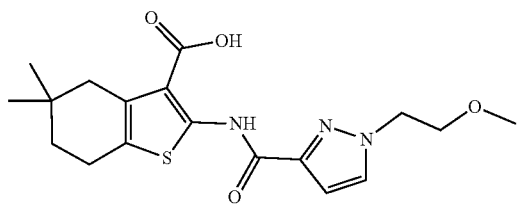

The title compound was synthesized according to the procedure described in Example #104 using methyl 2-amino-5,5-dimethyl-4,5,6,7-tetrahydrobenzo[b]thiophene-3-carboxylate (Preparation #3) and 1-(2-methoxyethyl)$_1$H-pyrazole-3-carboxylic acid (CAS: 936249-32-0) as starting materials (off-white solid, yield 49%). $^1$H NMR (DMSO-d$_6$, 400 MHz): δ=12.95 (s, 1H), 7.96 (d, J=2.1 Hz, 1H), 6.83 (d, J=2.2 Hz, 1H), 4.43 (t, J=5.0 Hz, 2H), 3.80 (t, J=5.1 Hz, 2H), 3.29 (s, 3H), 2.73-2.60 (m, 4H), 1.56 (t, J=6.0 Hz, 2H), 1.01 (s, 6H), one exchangeable proton not observed. LC/MS (Table 1, Method C) R$_t$=3.58 min; MS m/z: 378 [M+H]$^+$.

Example #106. 5,5-Dimethyl-2-[(6-morpholino-pyridazine-3-carbonyl)amino]-6,7-dihydro-4H-benzothiophene-3-carboxylic acid (Compound #227)

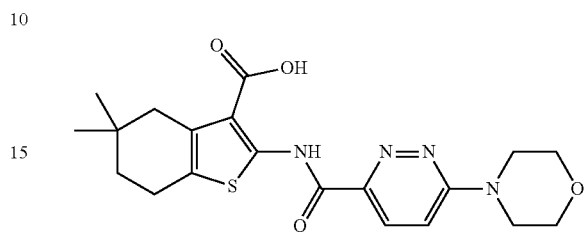

The title compound was synthesized according to the procedure described in Example #104 using methyl 2-amino-5,5-dimethyl-4,5,6,7-tetrahydrobenzo[b]thiophene-3-carboxylate (Preparation #3) and 6-morpholin-4-ylpyridazine-3-carboxylic acid (CAS: 914637-36-8) as starting materials (off-white solid, yield 24%). $^1$H NMR (DMSO-d$_6$, 400 MHz): δ=13.24 (br s, 1H), 12.98 (s, 1H), 8.04 (d, J=9.3 Hz, 1H), 7.48 (d, J=9.9 Hz, 1H), 3.81 (s, 8H), 2.74-2.68 (m, 2H), 2.63 (s, 2H), 1.59 (t, J=6.1 Hz, 2H), 1.02 (s, 6H). LC/MS (Table 1, Method B) R$_t$=2.77 min; MS m/z: 417 [M+H]$^+$.

Example #107. 5,5-Dimethyl-2-[[1-(tetrahydropyran-4-ylmethyl)pyrazole-3-carbonyl]amino]-6,7-dihydro-4H-benzothiophene-3-carboxylic acid (Compound #228)

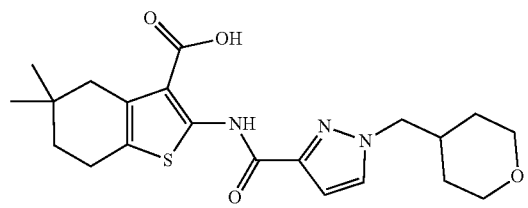 [SMILES: CC1(C)CCc2sc(NC(=O)c3ccn(CC4CCOCC4)n3)c(C(=O)O)c2C1]

To a solution of ethyl 1H-pyrazole-3-carboxylate (CAS: 5932-27-4, 260 mg, 1.86 mmol) in acetonitrile (5.0 ml) was added Cs$_2$CO$_3$ (CAS: 534-17-8, 604 mg, 1.86 mmol) and 4-(bromomethyl)tetrahydro-2H-pyran (CAS: 125552-89-8, 365 mg, 2.04 mmol). The reaction mixture was stirred at RT overnight. The reaction was partitioned between DCM and water. The two phases were separated and the organic phase was passed through a phase separator. The solvent was removed under reduced pressure. Purification by flash chromatography on silica gel (eluting with 0-60% EtOAc in DCM) afforded ethyl 1-((tetrahydro-2H-pyran-4-yl)methyl)-1H-pyrazole-3-carboxylate (220 mg, yield 50%). A solution of ethyl 1-((tetrahydro-2H-pyran-4-yl)methyl)-1H-pyrazole-3-carboxylate (220 mg, 0.93 mmol) in MeOH (3.0 ml) was treated with 2N NaOH aqueous solution (CAS: 1310-73-2, 1.2 ml, 2.40 mmol). The reaction mixture was stirred at RT for 20 hours. The reaction was acidified to pH~3 with a 2M HCl aqueous solution and the solvents were removed under reduced pressure. The residue was triturated with EtOAc to give 1-((tetrahydro-2H-pyran-4-yl)methyl)-

1H-pyrazole-3-carboxylic acid (194 mg, yield quant.). The title compound was then synthesized according to the procedure described in Example #104 using methyl 2-amino-5,5-dimethyl-4,5,6,7-tetrahydrobenzo[b]thiophene-3-carboxylate (Preparation #3) and 1-((tetrahydro-2H-pyran-4-yl)methyl)-1H-pyrazole-3-carboxylic acid as starting materials (white solid, yield 6%). $^1$H NMR (DMSO-d$_6$, 400 MHz): δ=13.23 (br s, 1H), 12.52 (s, 1H), 7.95 (d, J=2.3 Hz, 1H), 6.82 (d, J=2.3 Hz, 1H), 4.15 (d, J=7.2 Hz, 2H), 3.84 (dd, J=2.6, 11.6 Hz, 2H), 3.27 (dt, J=1.7, 11.6 Hz, 2H), 2.65 (t, J=6.1 Hz, 2H), 2.57 (s, 2H), 2.18-2.07 (m, 1H), 1.55 (t, J=6.4 Hz, 2H), 1.44 (d, J=13.0 Hz, 2H), 1.34-1.21 (m, 2H), 0.98 (s, 6H). LC/MS (Table 1, Method B) R$_t$=2.8 min; MS m/z: 418 [M+H]$^+$.

Example #108. 6,6-Dimethyl-2-[(5-morpholinopyridine-2-carbonyl)amino]-5,7-dihydro-4H-benzothiophene-3-carboxylic acid (Compound #229)

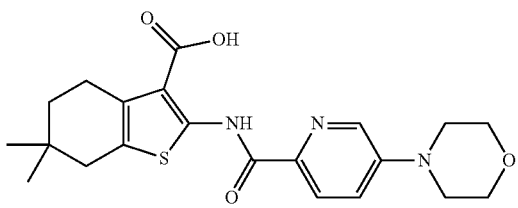

To a stirred solution of methyl 2-amino-6,6-dimethyl-4,5,6,7-tetrahydrobenzo[b]thiophene-3-carboxylate (Preparation #1, 300 mg, 1.25 mmol) in DMF (10.0 ml) was added 5-bromopyridine-2-carboxylic acid (CAS: 30766-11-1, 380 mg, 1.88 mmol), 2-chloro-1-methylpyridinium iodide (CAS: 14338-32-0, 512 mg, 2.01 mmol), DMAP (CAS: 1122-58-3, 46 mg, 0.38 mmol) and triethylamine (CAS: 121-44-8, 0.52 ml, 3.76 mmol). The reaction mixture was heated at 40° C. for 24 hours. The reaction was allowed to cool to RT. The mixture was partitioned between DCM and 1N aqueous HCl solution. The two phases were separated and the aqueous phase was extracted with DCM. The combined organic phases were washed with saturated aqueous NaHCO$_3$ solution and passed through a phase separator. The solvent was removed under reduced pressure. Purification by flash chromatography on silica gel (eluting with 0-100% EtOAc in isohexane) afforded methyl 2-(5-bromopicolinamido)-6,6-dimethyl-4,5,6,7-tetrahydrobenzo[b]thiophene-3-carboxylate as a pale yellow solid (517 mg, yield 97%). The title compound was then synthesized according to the procedure described in Example #20 using methyl 2-(5-bromopicolinamido)-6,6-dimethyl-4,5,6,7-tetrahydrobenzo[b]thiophene-3-carboxylate and morpholine (CAS: 110-91-8) as starting materials (off-white solid, yield 10%). $^1$H NMR (DMSO-d$_6$, 400 MHz): δ=13.03 (br s, 1H), 12.86 (s, 1H), 8.43 (d, J=2.7 Hz, 1H), 7.99 (d, J=8.8 Hz, 1H), 7.49 (dd, J=2.8, 8.9 Hz, 1H), 3.80-3.76 (m, 4H), 3.40 (t, J=4.7 Hz, 4H), 2.78 (t, J=5.9 Hz, 2H), 2.44 (s, 2H), 1.51 (t, J=6.1 Hz, 2H), 0.98 (s, 6H). LC/MS (Table 1, Method E) R$_t$=5.5 min; MS m/z: 416 [M+H]$^+$.

Example #109. 6,6-Dimethyl-2-[(5-morpholinopyrazine-2-carbonyl)amino]-5,7-dihydro-4H-benzothiophene-3-carboxylic acid (Compound #230)

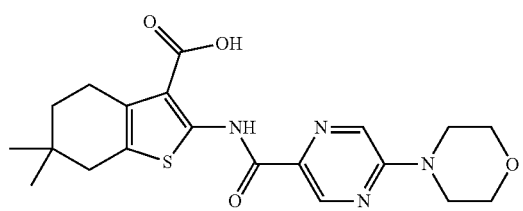 [SMILES: CC1(C)CCc2c(sc(NC(=O)c3cnc(N4CCOCC4)cn3)c2C(=O)O)C1]

The title compound was then synthesized according to the procedure described in Example #108 using methyl 2-amino-6,6-dimethyl-4,5,6,7-tetrahydrobenzo[b]thiophene-3-carboxylate (Preparation #1), 5-bromo-2-pyrazinecarboxylic acid (CAS: 876161-05-6) and morpholine (CAS: 110-91-8) as starting materials (pale yellow solid, yield 23%). $^1$H NMR (DMSO-d$_6$, 400 MHz): δ=13.12 (br s, 1H), 12.71 (s, 1H), 8.81 (s, 1H), 8.45 (s, 1H), 3.79 (s, 8H), 2.81 (t, J=5.5 Hz, 2H), 2.48 (s, 2H), 1.54 (t, J=6.1 Hz, 2H), 1.03 (s, 6H). LC/MS (Table 1, Method F) R$_t$=3.36 min; MS m/z: 417 [M+H]$^+$.

Preparation #1. Methyl 2-amino-6,6-dimethyl-4,5,6,7-tetrahydrobenzo[b]thiophene-3-carboxylate

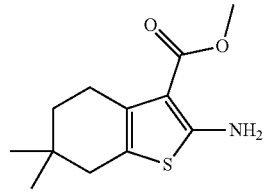 [SMILES: COC(=O)c1c(N)sc2c1CCC(C)(C)C2]

A reaction vessel was charged 4,4-dimethylcyclohexanone (CAS: 4255-62-3, 5.00 g, 39.6 mmol), methyl cyanoacetate (CAS: 105-34-0, 3.8 ml, 43.6 mmol), diethylamine (CAS: 109-89-7, 2.0 ml, 19.8 mmol) and sulfur (CAS: 7704-34-9, 1.52 g, 47.5 mmol). The reaction was solvated in methanol (25 ml) and set to stir at RT. The reaction mixture was stirred at room temperature for 60 hours. The volatiles were removed under reduced pressure and the residue was purified by flash chromatography on silica gel (eluting with 0-20% EtOAc in isohexane) which afforded methyl 2-amino-6,6-dimethyl-4,5,6,7-tetrahydrobenzo[b]thiophene-3-carboxylate as a pale yellow solid (7.22 g, yield 76%). $^1$H NMR (CDCl$_3$, 400 MHz): δ=5.92 (s, 2H), 3.79 (s, 3H), 2.69 (t, J=6.4 Hz, 2H), 2.27 (s, 2H), 1.48 (t, J=6.4 Hz, 2H), 0.98 (s, 6H).

Preparation #2. Methyl 6,6-dimethyl-2-(4-morpholinobenzamido)-4,5,6,7-tetrahydrobenzo[b]thiophene-3-carboxylate

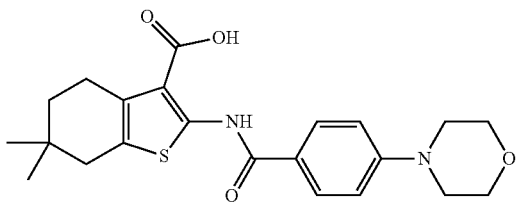

To a stirred suspension of 4-morpholinobenzoic acid (CAS: 7470-38-4, 104 mg, 0.50 mmol) in DCM (5 ml) at RT was added catalytic DMF (3 µl, 0.033 mmol) and oxalyl chloride (CAS: 79-37-8, 52 µl, 0.60 mmol). The reaction mixture was stirred at RT for 90 minutes. A solution of methyl 2-amino-6,6-dimethyl-4,5,6,7-tetrahydrobenzo[b]thiophene-3-carboxylate (Preparation #1, 80 mg, 0.33 mmol) and DIPEA (CAS: 7087-68-5, 170 µl, 1.00 mmol) in DCM (5 ml) was added to the reaction. The reaction was stirred at RT overnight. The reaction was next partitioned between DCM and a saturated aqueous NaHCO$_3$ solution and the two phases were separated. The aqueous phase was extracted with DCM (×2). The combined organic phases were passed through a phase separator and the solvent was removed under reduced pressure. Purification by flash chromatography on silica gel (eluting with 0-50% DCM in iso-hexane) gave methyl 6,6-dimethyl-2-(4-morpholinobenzamido)-4,5,6,7-tetrahydrobenzo[b]thiophene-3-carboxylate (90 mg, yield 63%). $^1$H NMR (CDCl$_3$, 400 MHz): δ=12.16 (s, 1H), 7.93 (d, J=9.1 Hz, 2H), 6.94 (d, J=8.8 Hz, 2H), 3.91 (s, 3H), 3.87 (t, J=4.8 Hz, 4H), 3.30 (t, J=4.7 Hz, 4H), 3.06 (d, J=9.5 Hz, 2H), 2.79 (t, J=6.3 Hz, 2H), 2.45 (s, 2H), 1.01 (s, 6H).

Preparation #3. Methyl 2-amino-5,5-dimethyl-4,5,6,7-tetrahydrobenzo[b]thiophene-3-carboxylate

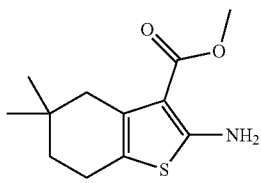 [SMILES: COC(=O)c1c(N)sc2c1CC(C)(C)CC2]

A reaction vessel was charged with 3,3-dimethylcyclohexanone (CAS: 2979-19-3, 1.00 ml, 7.20 mmol), methyl cyanoacetate (CAS: 105-34-0, 0.70 ml, 7.92 mmol), diethylamine (CAS: 109-89-7, 370 µl, 3.60 mmol) and sulfur (CAS: 7704-34-9, 277 mg, 8.64 mmol). The reaction was solvated in methanol (10 ml) and set to stir at RT. The reaction was stirred at RT for 48 hours. The reaction was partitioned between EtOAc and a saturated aqueous NaHCO$_3$ solution and the two phases were separated. The aqueous phase was extracted with EtOAc (×3). The combined organic phases were passed through a phase separator and the solvent was removed under reduced pressure. The residue was purified by flash chromatography on silica gel (eluting with 0-20% EtOAc in iso-hexane) which afforded methyl 2-amino-5,5-dimethyl-4,5,6,7-tetrahydrobenzo[b]thiophene-3-carboxylate as a yellow solid (588 mg, yield 34%). $^1$H NMR (CDCl$_3$, 400 MHz): δ=5.91 (s, 2H), 3.79 (s, 3H), 2.53-2.47 (m, 4H), 1.55-1.50 (m, 2H, partially covered by the water peak), 0.98 (s, 6H).

Preparation #4. Methyl 2-amino-4,7-dihydro-5H-spiro[benzo[b]thiophene-6,1'-cyclopropane]-3-carboxylate

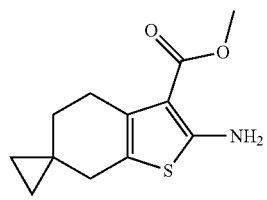 [SMILES: COC(=O)c1c(N)sc2c1CCC1(CC1)C2]

The title compound was synthesized according to the procedure described in Preparation #3 using spiro[2.5]octan-6-one (CAS: 15811-21-9) as a starting material (220 mg, yield 29%). $^1$H NMR (CDCl$_3$, 400 MHz): δ=6.00 (s, 2H), 3.79 (s, 3H), 2.42 (t, J=6.7 Hz, 2H), 2.37 (t, J=1.8 Hz, 2H), 1.69 (t, J=6.6 Hz, 2H), 0.42-0.36 (m 4H).

Preparation #5. Methyl 2-(4-morpholinobenzamido)-4,7-dihydro-5H-spiro[benzo[b]thiophene-6,1'-cyclopropane]-3-carboxylate

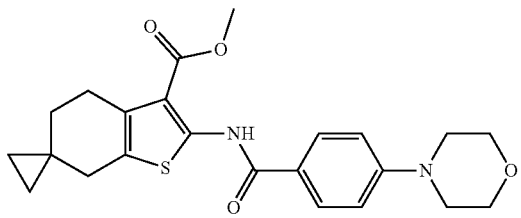 [SMILES: COC(=O)c1c(NC(=O)c2ccc(N3CCOCC3)cc2)sc2c1CCC1(CC1)C2]

The title compound was synthesized according to the procedure described in Preparation #2 using methyl 2-amino-4,7-dihydro-5H-spiro[benzo[b]thiophene-6,1'-cyclopropane]-3-carboxylate (Preparation #4) and 4-(4-morpholinyl)benzoic acid as starting materials (yield 61%). $^1$H NMR (CDCl$_3$, 400 MHz): δ=12.17 (s, 1H), 7.94 (d, J=8.8 Hz, 2H), 6.95 (d, J=9.0 Hz, 2H), 3.91 (s, 3H), 3.88-3.85 (m, 4H), 3.33-3.28 (m, 4H), 3.21-3.17 (m, 2H), 2.90-2.85 (m, 2H), 2.54 (s, 2H), 0.44 (s, 4H).

Preparation #6. Ethyl 2-amino-5,5,7,7-tetramethyl-4,5,6,7-tetrahydrobenzo[b]thiophene-3-carboxylate

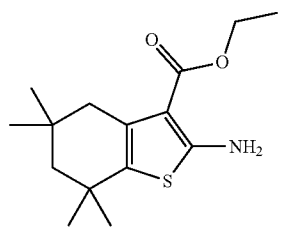 [SMILES: CCOC(=O)c1c(N)sc2c1CC(C)(C)CC2(C)C]

A reaction vessel was charged with 3,3,5,5-tetramethylcyclohexanone (CAS: 14376-79-5, 0.56 ml, 3.20 mmol), ethyl cyanoacetate (CAS: 105-56-6, 370 µl, 3.52 mmol), morpholine (CAS: 110-91-8, 310 µl, 3.52 mmol) and sulfur (CAS: 7704-34-9, 121 mg, 3.78 mmol). The reaction was solvated in ethanol (20 ml) and set to stir at RT. The reaction was next heated at 60° C. for 6 hours. The reaction was allowed to cool to RT and partitioned between EtOAc and a 1N aqueous HCl solution. The two phases were separated and the organic phase was washed with saturated aqueous NaHCO$_3$ solution. The organic phase was dried over MgSO$_4$ and the solvent was removed under reduced pressure. Purification by flash chromatography on silica gel (eluting with 20% EtOAc in isohexane) afforded ethyl 2-amino-5,5,7,7-tetramethyl-4,5,6,7-tetrahydrobenzo[b]thiophene-3-carboxylate (340 mg, yield 38%). $^1$H NMR (CDCl$_3$, 400 MHz): δ=5.93 (s, 2H), 4.27 (q, J=7.2 Hz, 2H), 2.51 (s, 2H), 1.53 (s, 2H), 1.35 (t, J=7.2 Hz, 3H), 1.24 (s, 6H), 1.02 (s, 6H).

Preparation #7. Ethyl 2-(4-bromobenzamido)-5,5,7,7-tetramethyl-4,5,6,7-tetrahydrobenzo[b]thiophene-3-carboxylate

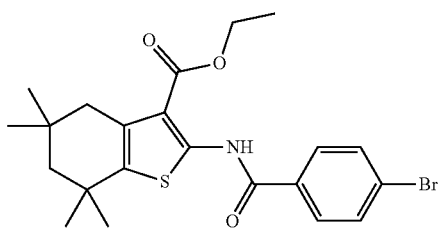 [SMILES: CCOC(=O)c1c(NC(=O)c2ccc(Br)cc2)sc2c1CC(C)(C)CC2(C)C]

To a stirred reaction of ethyl 2-amino-5,5,7,7-tetramethyl-4,5,6,7-tetrahydrobenzo[b]thiophene-3-carboxylate (Preparation #6, 600 mg, 2.13 mmol) in DCM (30 ml) at RT was added DIPEA (CAS: 7087-68-5, 0.74 ml, 4.26 mmol), followed by 4-bromobenzoyl chloride (CAS: 586-75-4, 934 mg, 4.26 mmol). The reaction mixture was stirred at RT overnight. The reaction was partitioned between DCM and a saturated aqueous NaHCO$_3$ solution. The two phases were separated. The aqueous phase was extracted with DCM (×2). The combined organic phases were passed through a phase separator and the solvent was removed under reduced pressure. Purification by flash chromatography on silica gel (eluting with 0-20% EtOAc in iso-hexane) gave ethyl 2-(4-bromobenzamido)-5,5,7,7-tetramethyl-4,5,6,7-tetrahydrobenzo[b]thiophene-3-carboxylate as a white solid (298 mg, yield 31%). $^1$H NMR (CDCl$_3$, 400 MHz): δ=12.40 (s, 1H), 7.90-7.86 (m, 2H), 7.67-7.64 (m, 2H), 4.39 (q, J=7.1 Hz, 2H), 2.60 (s, 2H), 1.58 (s, 2H), 1.42 (t, J=7.1 Hz, 3H), 1.37 (s, 6H), 1.04 (s, 6H).

Preparation #8. Ethyl 2-amino-4,4-dimethyl-5,6-dihydro-4H-cyclopenta[b]thiophene-3-carboxylate

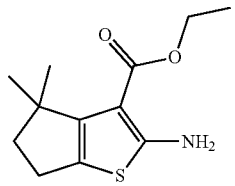 [SMILES: CCOC(=O)c1c(N)sc2c1C(C)(C)CC2]

Step A. Ethyl 2-cyano-2-(2,2-dimethylcyclopentylidene)acetate

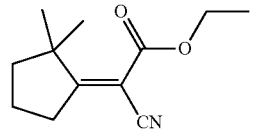

To a stirred reaction of 2,2-dimethylcyclopentanone (CAS: 4541-32-6, 0.56 ml, 4.46 mmol) in toluene (10 ml) at RT was added ethyl cyanoacetate (CAS: 105-56-6, 0.47 ml, 4.46 mmol), ammonium acetate (CAS: 631-61-8, 241 mg, 3.12 mmol) and acetic acid (0.3 ml). The reaction mixture was heated at reflux overnight. The reaction was allowed to cool to RT. The mixture was partitioned between EtOAc and brine. The two phases were separated. The organic phase was passed through a phase separator and the solvent was removed under reduced pressure. Purification by flash chromatography on silica gel (eluting with 20% EtOAc in isohexane) afforded ethyl 2-cyano-2-(2,2-dimethylcyclopentylidene)acetate as a colourless oil (703 mg, yield 76%). $^1$H NMR (CDCl$_3$, 400 MHz): δ=4.26 (q, J=7.1 Hz, 2H), 3.10 (t, J=7.0 Hz, 2H), 1.79-1.65 (m, 4H), 1.41 (s, 6H), 1.35 (t, J=7.1 Hz, 3H).

Step B. Ethyl 2-amino-4,4-dimethyl-5,6-dihydro-4H-cyclopenta[b]thiophene-3-carboxylate

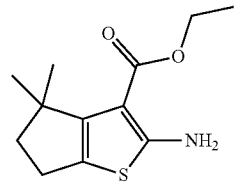 [SMILES: CCOC(=O)c1c(N)sc2c1C(C)(C)CC2]

To a stirred reaction of ethyl 2-cyano-2-(2,2-dimethylcyclopentylidene)acetate (Preparation #8, Step A, 200 mg, 0.97 mmol) and sulfur (CAS: 7704-34-9, 34 mg, 1.06 mmol) in ethanol (10 ml) was added diethylamine (CAS: 109-89-7, 50 µl, 0.48 mmol). The reaction mixture was heated at 50° C. for 150 minutes. The reaction was allowed to cool to RT. The mixture was diluted with EtOAc and filtered. The solvent was removed under reduced pressure and the residue was purified by flash chromatography on silica gel (eluting with 20% EtOAc in isohexane) to give ethyl 2-amino-4,4-dimethyl-5,6-dihydro-4H-cyclopenta[b]thiophene-3-carboxylate as a yellow solid (227 mg, yield 98%). $^1$H NMR (CDCl$_3$, 400 MHz): δ=5.98 (s, 2H), 4.31 (q, J=7.2 Hz, 2H), 2.68-2.64 (m, 2H), 2.19-2.14 (m, 2H), 1.38 (t, J=7.2 Hz, 3H), 1.32 (s, 6H).

Preparation #9. Ethyl 2-(4-bromobenzamido)-4,4-dimethyl-5,6-dihydro-4H-cyclopenta[b]thiophene-3-carboxylate

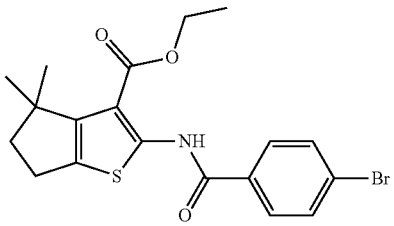 [SMILES: CCOC(=O)c1c(NC(=O)c2ccc(Br)cc2)sc2c1C(C)(C)CC2]

The title compound was synthesized according to the procedure described in Preparation #7 using ethyl 2-amino-4,4-dimethyl-5,6-dihydro-4H-cyclopenta[b]thiophene-3-carboxylate (Preparation #8, Step B) and 4-bromobenzoyl chloride (CAS: 586-75-4) as starting materials (yield 85%). $^1$H NMR (CDCl$_3$, 400 MHz): δ=12.44 (s, 1H), 7.88 (d, J=8.5 Hz, 2H), 7.66 (d, J=8.7 Hz, 2H), 4.44 (q, J=7.1 Hz, 2H), 2.83 (t, J=7.0 Hz, 2H), 2.26 (t, J=7.0 Hz, 2H), 1.46 (t, J=7.2 Hz, 3H), 1.36 (s, 6H).

Preparation #10. Ethyl 2-amino-4,6,6-trimethyl-5,6-dihydro-4H-cyclopenta[b]thiophene-3-carboxylate

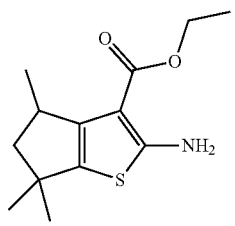 [SMILES: CCOC(=O)c1c(N)sc2c1C(C)CC2(C)C]

The title compound was synthesized according to the procedure described in Preparation #6 using 2,4,4-trimethylcyclopentan-1-one (CAS: 4694-12-6) as a starting material (yellow solid, yield 21%). $^1$H NMR (CDCl$_3$, 400 MHz): δ=5.90 (s, 2H), 4.32-4.20 (m, 2H), 3.29-3.20 (m, 1H), 2.41 (dd, J=8.8, 12.8 Hz, 1H), 1.78 (dd, J=2.6, 12.7 Hz, 1H), 1.33 (t, J=7.1 Hz, 3H), 1.29 (s, 3H), 1.26 (d, J=7.0 Hz, 3H), 1.22 (s, 3H).

Preparation #11. Ethyl 2-amino-4,6,6-trimethyl-4,5,6,7-tetrahydrobenzo[b]thiophene-3-carboxylate

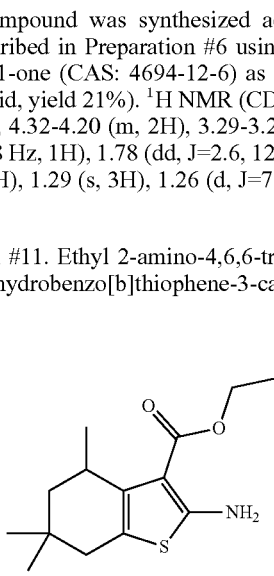

The title compound was synthesized according to the procedure described in Preparation #8 using 2,4,4-trimethylcyclohexan-1-one (CAS: 2230-70-8) as a starting material (yellow oil, yield 65%). $^1$H NMR (CDCl$_3$, 400 MHz): δ=5.82 (s, 2H), 4.36-4.20 (m, 2H), 3.03 (q, J=6.5 Hz, 1H), 2.36 (dd, J=1.6, 15.5 Hz, 1H), 2.16 (d, J=15.5 Hz, 1H), 1.74-1.66 (m, 1H), 1.55-1.51 (m, 1H), 1.35 (t, J=7.2 Hz, 3H), 1.16 (d, J=7.0 Hz, 3H), 1.05 (s, 3H), 0.94 (s, 3H).

Preparation #12. Ethyl 2-(4-bromobenzamido)-4,6,6-trimethyl-4,5,6,7-tetrahydrobenzo[b]thiophene-3-carboxylate

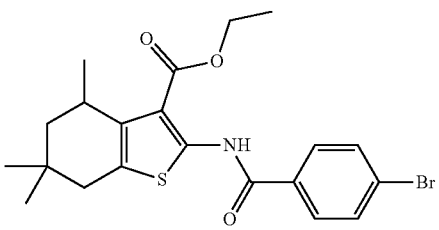 [SMILES: CCOC(=O)c1c(NC(=O)c2ccc(Br)cc2)sc2c1C(C)CC(C)(C)C2]

The title compound was synthesized according to the procedure described in Preparation #7 using ethyl 2-amino-4,6,6-trimethyl-4,5,6,7-tetrahydrobenzo[b]thiophene-3-carboxylate (Preparation #11) and 4-bromobenzoyl chloride (CAS: 586-75-4) as starting materials (pale yellow solid, yield 64%). $^1$H NMR (CDCl$_3$, 400 MHz): δ=12.21 (s, 1H), 7.87 (d, J=8.5 Hz, 2H), 7.65 (d, J=8.7 Hz, 2H), 4.48-4.31 (m, 2H), 3.18-3.11 (m, 1H), 2.52 (d, J=15.8 Hz, 1H), 2.38 (d, J=16.3 Hz, 1H), 1.80-1.75 (m, 1H), 1.42 (t, J=7.4 Hz, 3H), 1.31-1.18 (m, 4H), 1.10 (s, 3H), 0.92 (s, 3H).

Preparation #13. Methyl 2-(4-bromobenzamido)-6,6-dimethyl-4,5,6,7-tetrahydrobenzo[b]thiophene-3-carboxylate

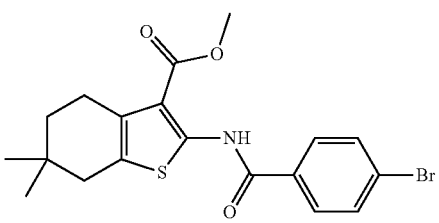 [SMILES: COC(=O)c1c(NC(=O)c2ccc(Br)cc2)sc2c1CCC(C)(C)C2]

The title compound was synthesized according to the procedure described in Preparation #7 using methyl 2-amino-6,6-dimethyl-4,5,6,7-tetrahydrobenzo[b]thiophene-3-carboxylate (Preparation #1) and 4-bromobenzoyl chloride (CAS: 586-75-4) as starting materials (yield 100%). $^1$H NMR (CDCl$_3$, 400 MHz): δ=12.30 (s, 1H), 7.88 (d, J=8.2 Hz, 2H), 7.66 (d, J=8.4 Hz, 2H), 3.92 (s, 3H), 2.79 (t, J=6.3 Hz, 2H), 2.46 (s, 2H), 1.58-1.55 (m, 2H, partially obscured by the water peak), 1.01 (s, 6H).

Preparation #14. Methyl 2-(4-bromobenzamido)-5,5-dimethyl-4,5,6,7-tetrahydrobenzo[b]thiophene-3-carboxylate

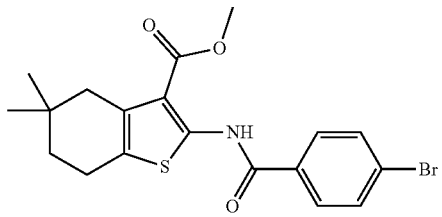 [SMILES: COC(=O)c1c(NC(=O)c2ccc(Br)cc2)sc2c1CC(C)(C)CC2]

The title compound was synthesized according to the procedure described in Preparation #7 using methyl 2-amino-5,5-dimethyl-4,5,6,7-tetrahydrobenzo[b]thiophene-3-carboxylate (Preparation #3) and 4-bromobenzoyl chloride (CAS: 586-75-4) as starting materials (yield 99%). $^1$H NMR (CDCl$_3$, 400 MHz): δ=12.32 (s, 1H), 7.88 (d, J=8.2 Hz, 2H), 7.66 (d, J=8.2 Hz, 2H), 3.92 (s, 3H), 2.70 (t, J=6.2 Hz, 2H), 2.57 (s, 2H), 1.59 (t, J=6.3 Hz, 2H), 1.01 (s, 6H).

Preparation #15. Ethyl 2-(4-hydroxybenzamido)-5,5,7,7-tetramethyl-4,5,6,7-tetrahydrobenzo[b]thiophene-3-carboxylate

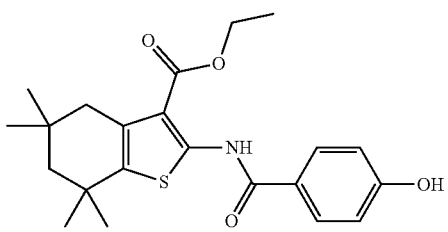 [SMILES: CCOC(=O)c1c(NC(=O)c2ccc(O)cc2)sc2c1CC(C)(C)CC2(C)C]

To a stirred reaction of ethyl 2-amino-5,5,7,7-tetramethyl-4,5,6,7-tetrahydrobenzo[b]thiophene-3-carboxylate (Preparation #6, 1.00 g, 3.55 mmol) in DCM (50 ml) was added DIPEA (CAS: 7087-68-5, 3.1 ml, 17.8 mmol), followed by 4-(acetoxy)benzoyl chloride (CAS: 27914-73-4, 1.41 g, 7.11 mmol). The reaction was stirred at RT overnight. The reaction was next partitioned between DCM and saturated aqueous NaHCO$_3$ solution. The two phases were separated. The aqueous phase was extracted with DCM (×3). The combined organic phases were passed through a phase separator and the solvent was removed under reduced pressure. The residue was triturated with MeOH (×2). The solid was collected and dried in vacuo to give ethyl 2-(4-acetoxybenzamido)-5,5,7,7-tetramethyl-4,5,6,7-tetrahydrobenzo[b]thiophene-3-carboxylate as an off-white solid (1.22 g, yield 77%). Ethyl 2-(4-acetoxybenzamido)-5,5,7,7-tetramethyl-4,5,6,7-tetrahydrobenzo[b]thiophene-3-carboxylate (900 mg) was dissolved in DCM (30 ml) and then a methanolic ammonia solution (CAS: 67-56-1, 2.0M, 7.2 ml, 14.4 mmol) was added. The reaction mixture was stirred at RT for 20 hours. Another aliquot of methanolic ammonia solution (CAS: 7664-41-7, 7.0M, 1 ml) was added and the reaction mixture was stirred at RT for a further 72 hours. The organic solvents were removed under reduced pressure and the residue was triturated with MeOH (×2) to give ethyl 2-(4-hydroxybenzamido)-5,5,7,7-tetramethyl-4,5,6,7-tetrahydrobenzo[b]thiophene-3-carboxylate as a white solid (766 mg, yield 94%). $^1$H NMR (CDCl$_3$, 400 MHz): δ=12.26 (s, 1H), 7.94 (d, J=8.6 Hz, 2H), 6.95 (d, J=8.8 Hz, 2H), 4.39 (q, J=7.1 Hz, 2H), 2.60 (s, 2H), 1.57 (s, 2H), 1.42 (t, J=7.1 Hz, 3H), 1.37 (s, 6H), 1.04 (s, 6H), one exchangeable proton not observed.

Example B—Biology

Example B0—Antiviral Effect

Example B1—A Influenza

The antiviral effect of the compounds of the invention has been tested on A549 cell lines infected with H1N1 (influenza A/New Caledonia/20/99). IC50 are reported in the following Table 1. The results show that the compounds of the present invention present an antiviral effect.

TABLE 1

| Compound | IC50 (µM) | Compound | IC50 (µM) | Compound | IC50 (µM) |
| --- | --- | --- | --- | --- | --- |
| #58 | 0.0009 | #59 | 0.01 | #60 | 0.01 |
| #35 | 0.0168 | #61 | 0.0279 | #33 | 0.0346 |
| #36 | 0.0401 | #27 | 0.04 | #18 | 0.05 |
| #62 | 0.05 | #16 | 0.0438 | #21 | 0.0558 |
| #15 | 0.06 | #30 | 0.07 | #20 | 0.074 |
| #63 | 0.08 | #23 | 0.08 | #26 | 0.0849 |
| #29 | 0.09 | #44 | 0.09 | #64 | 0.09 |
| #25 | 0.09 | #31 | 0.1 | #41 | 0.1049 |
| #19 | 0.11 | #34 | 0.1131 | #22 | 0.12 |
| #40 | 0.23 | #32 | 0.16 | #24 | 0.16 |
| #17 | 0.26 | #42 | 0.1924 | #37 | 0.1957 |
| #39 | 0.2766 | #43 | 0.28 | #78 | 0.29 |
| #38 | 0.3387 | #80 | 0.31 | #90 | 0.6 |
| #94 | 0.66 | #96 | 0.8 | #98 | 0.8 |
| #105 | 1.077 | #28 | 1.27 | #117 | 1.9003 |
| #131 | 0.35 | #132 | 0.0017 | #133 | 0.75 |
| #134 | 0.56 | #135 | 0.0061 | #136 | 0.012 |
| #137 | 0.035 | #138 | 0.0088 | #139 | 0.011 |
| #140 | 0.0034 | #141 | 0.0033 | #142 | 0.0064 |
| #143 | 0.16 | #144 | 0.035 | #145 | 0.032 |
| #146 | 0.083 | #147 | 0.0111 | #148 | 0.0026 |
| #149 | 0.0071 | #150 | 0.0039 | #152 | 0.0005 |
| #153 | 0.014 | #154 | 0.03 | #155 | 0.01 |
| #156 | 0.002 | #157 | 0.005 | #158 | 0.32 |
| #159 | 0.018 | #160 | 0.006 | #161 | 0.015 |
| #162 | 0.039 | #163 | 0.018 | #164 | 0.016 |
| #165 | 0.0117 | #166 | 0.0067 | #167 | 0.1084 |
| #168 | 0.0232 | #169 | 0.0155 | #170 | 0.035 |
| #171 | 0.0063 | #65 | 0.2 | #173 | 0.024 |
| #174 | 0.039 | #202 | 0.9 | #176 | 0.46 |
| #201 | 0.15 | #205 | 0.74 | #203 | 0.13 |
| #204 | 0.26 | #209 | 0.82 | #208 | 0.74 |
| #219 | 0.51 | #212 | 0.9 | #213 | 0.61 |
| #222 | 0.051 | #221 | 0.38 | #227 | 1.39 |
| #225 | 0.11 | #226 | 0.82 | #230 | 0.42 |
| #228 | 0.9 | #229 | 0.37 | | |

Materials and Methods

Human A549 cells (80,000 cells/well in a 96 well plate) were treated with a range of concentration of test molecules and immediately infected by H1N1 A/New Caledonia/20/99 virus (clinical isolate) at MOI of 0.1 in DMEM/1% Penicillin/streptomycin supplemented with 0.25 g/ml TPCK trypsin (Sigma) and incubated at 37° C. in 5% CO$_2$. 48 h post-infection, supernatants (25 µl) were collected and transferred into a 96-well black flat-bottom plate, mixed with 25 µl PBS with Ca++/Mg++(Thermo Fisher) and 50 µl of 2'-(4-Methylumbelliferyl)-α-D-N-acetylneuraminic acid sodium salt hydrate stock-solution (20 µM, MUNANA, Sigma). Plates were incubated 1 h at 37° C. and reaction is stopped by adding 100 µl of Stop Solution (glycine 0.1 M pH10.7/25% ethanol). The amount of fluorescent product released by MUNANA hydrolysis (4-MU) was measured in a Tecan spectrophotometer with excitation and emission wavelengths of 365 and 450 nm respectively.

Example B1-B West Nile Virus, Dengue and Zika

Compound #18 was tested on other viruses. The results is shown in Table 4. The NEET protein modulators are capable of inhibiting other viruses such as West Nile Virus, Dengue and Zika with a high efficiency.

TABLE 2

| Virus | IC50 (µM) |
|---|---|
| West Nile Virus | 2.5 |
| Dengue | 5 |
| Zika | 3 |

Materials & Methods
Assays were performed with the following strains/serotypes:
DENV serotype 2 strain New Guinea C
ZIKV strain MR766
WNV stain New-York 99
$1\times10^5$ Huh7 cells were infected with DENV, ZIKV, or WNV at a MOI of 0,1 pfu per cell in presence of the test compound. Two hours post-infection the inoculum was removed and cells washed twice with PBS 1x. Fresh medium containing the test compound was added. Supernatants were harvested 48 h post infection, filtered through a 0.45 µm pore membrane and directly used for plaque assays.
Plaque Assays
VeroE6 cells were infected with serial dilutions of virus supernatants. Two hours post-infection inoculum was replaced by serum-free MEM medium (Gibco, Life Technologies) containing 1.5% carboxymethyl cellulose (Sigma-Aldrich). At different days post infection (day 3 for WNV, day 4 for ZIKV, day 7 for DENV) cells were fixed by addition of formaldehyde to a final concentration of 5%. Cells were stained with crystal violet solution (1% crystal violet, 10% ethanol in H2O) for 30 min at room temperature and extensively rinsed with H2O. Infectious titers were calculated considering the corresponding dilution factor.

Example B2—Antitumoral Effect

Results
The cytotoxicity was tested for compounds of the invention on five different cell-lines, namely LXFL 1121, MAXF 401, MMXF L-636, PRXF PC-3M and UXF 1138 which are respectively lung large cell carcinoma, breast adeno carcinoma, multiple myeloma, prostate adeno carcinoma and uterine sarcoma.
The IC50 are provided in the following table 3.

TABLE 3

| Absolute IC50 (µM) | Compound | | | | | |
|---|---|---|---|---|---|---|
| Cell Line | #22 | #35 | #58 | #60 | #36 | #37 |
| LXFL 1121 | 0,546 | 1,071 | 1,77 | 2,117 | 2,329 | 24,739 |
| MAXF 401 | 0,539 | 1,215 | 1,032 | 1,127 | 2,043 | 11,294 |
| MMXF L-363 | 1,311 | 2,081 | 1,122 | 1,014 | 1,72 | 13,895 |
| PRXF PC-3M | 0,705 | 0,702 | 0,888 | 1,017 | 1,114 | 9,666 |
| UXF 1138 | 0,332 | 0,743 | 0,819 | 0,851 | 0,988 | 9,421 |

Therefore, the compounds have a cytotoxicity against tumor cells and can be used for treating cancer.
Materials and Methods
Compound Handling
A working stock solution of the test compounds was prepared in DMSO at a concentration of 33 mM or 8.25 mM, and small aliquots were stored at −20° C. On each day of an experiment, a frozen aliquot of the working stock solution was thawed and stored at room temperature prior to and during treatment.
All liquid handling steps were performed using the Tecan Freedom EVO 200 platform. First, serial 2-fold dilutions of the 33 mM DMSO working stock solution were done in DMSO. The DMSO dilutions were then diluted 1:22 into cell culture medium in an intermediate dilution plate. Finally, 10 µl taken from the intermediate dilution plate were transferred to 140 µl/well of the final assay plate. Thus, the DMSO serial dilutions were diluted 1:330 with cell culture medium, and the DMSO concentration in the assay was 0.3% v/v.
Tumor Cell Lines
The cell lines used in this study were derived from solid tumors as well as from hematological malignancies.
Cell lines were routinely passaged once or twice weekly and maintained in culture for up to 20 passages. Most cell lines were grown at 37° C. in a humidified atmosphere with 5% $CO_2$ in RPMI 1640 medium (25 mM HEPES, with L-glutamine, #FG1385, Biochrom, Berlin, Germany) supplemented with 10% (v/v) fetal calf serum (Sigma, Taufkirchen, Germany) and 0.05 mg/mL gentamicin (Life Technologies, Karlsruhe, Germany).
Propidium Ioded-Based Monolayer Assay
A modified propidium iodide (PI) based monolayer assay was used to assess the anti-cancer activity of the compounds. Briefly, cells were harvested from exponential phase cultures, counted and plated in 96 well flat-bottom microtiter plates at a cell density of 4,000 to 40,000 cells/well dependent on the cell line's growth rate. The individual seeding density for each cell line ensure exponential growth conditions over the whole or at least the bigger part of the treatment period. After a 24 h recovery period, to allow the cells to resume exponential growth, 10 µl of culture medium (6 control wells/cell line/plate) or of culture medium with test compounds were added. Compounds were applied at ten concentrations in 2-fold increments in duplicates up to 25 µM or 100 µM and treatment continued for four days. After four days of treatment, cells were next washed with 200 µl PBS to remove dead cells and debris, then 200 µl of a solution containing 7 µg/ml propidium iodide (PI) and 0.1% (v/v) Triton X-100 was added. After an incubation period of 1-2 hours at room temperature, fluorescence (FU) was measured using the Enspire Multimode Plate Reader (excitation $\lambda$=530 nm, emission k=620 nm) to quantify the amount of attached viable cells.
Data Evaluation
An assay was considered fully evaluable if the following quality control criteria were fulfilled:
Z'-factor calculated within the assay plate $\geq 0.5$
control/background ratio >3.0
coefficient of variation in the growth control wells $\leq 30\%$
Drug effects were expressed in terms of the percentage of the fluorescence signal, obtained by comparison of the mean signal in the treated wells with the mean signal of the untreated controls (expressed by the test-versus-control value, T/C-value [%]):

$$\frac{T}{C}[\%] = \frac{\text{mean fluorescence signal}_{treatedgroup}}{\text{meanfluorescence signal}_{controlgroup}} \cdot 100$$

IC values reported reflect the concentration of the test compound that achieves T/C=50%. Calculation was done by 4 parameter non-linear curve fit.

Example B3—Modulators of NEET Proteins

The modulator effect on the NEET proteins encoded by human CISD1, CISD2, and CISD3 genes by the compounds of the invention has been tested and is reported below. Particularly, the biochemical function of the NEET proteins is measured by the stability of Fe—S cluster binding of the purified NEET proteins.

The Fe—S cluster binding capacity of NEET proteins is known to be coordinated by four amino-acids in a stretch of 16 (three Cysteine and one Histidine). As the lability of the Fe—S cluster of NEET proteins is sensitive to the environment, cluster stability measurements are one of the measures of interactions of NEET proteins with small molecules and compounds. NEET protein/2Fe-2S cluster stability can be assessed by monitoring the decay in absorbance of its characteristic 458-nm peak (characteristic of the oxidized 2Fe-2S cluster) over time. Each NEET protein (mitoNEET, NAF-1 and Miner 2) was tested for its Fe—S binding in the absence or presence of a compound according to the invention (see table 4 below). The rate of cluster release (time in minutes to achieve 50% loss of bound Fe—S cluster) was compared for each NEET protein in the presence of one of the compounds of the invention (in a 1:3 protein:compound molar ratio) relative to each protein alone.

At pH 6, all the three NEET proteins (mitoNEET, NAF-1 and Miner 2) have a characteristic rate of loss of the bound Fe—S cluster that can be measured by the decrease of absorbance at wavelength 458 nm over time, using a spectrophotometer. Thus, Bis-Tris buffer (100 mM Bis-Tris pH6, 100 mM Nacl) was used at pH 6 to dilute either DMSO (Blank sample: Bis-Tris Buffer pH 6, 66 µM DMSO), DMSO and one of the three NEET proteins (Control sample: Bis-Tris Buffer pH 6, 66 µM DMSO, 20 µM purified NEET protein) or DMSO, one of the three NEET proteins and a compound of the invention (Test sample: Bis-Tris Buffer pH 6, 66 µM DMSO, 20 µM purified NEET protein, 60 µM compound of the invention).

A reaction mix containing DMSO diluted in the Bis-Tris Buffer with or without a compound of the invention was prepared. The purified NEET protein was the last component added to the reaction mix which was then aliquoted into 4 replicates in 96 wells plates. The absorbance at wavelength 458 nm was taken at 5 minutes intervals at 37° C. with a spectrofluorimeter. The assay run time for CISD2 gene product (NAF-1) was 500 minutes and 180 minutes for both the CISD1 gene product (mitoNEET) and the CISD3 gene product (Miner2).

In addition to time monitoring, residual bound Fe—S cluster to NEET protein was measured at the final point of the spectrometry assay for each Test sample and compared to the Control sample data (in parenthesis table 4). This residual binding is measured by the differential percentage between the absorbance 458 nm at time zero and the absorbance 458 nm at the end of the experiment (i.e. respectively 500 or 180 minutes as described here above), showing the percentage of NEET protein still able to bind a Fe—S cluster.

TABLE 4

| Compound | Time (in minutes) to achieve 50% loss of bound cluster (Absorbance 458 nm), (Vehicle Control sample data in parenthesis) | | | Residual cluster bound at end of experiment (Percentage Absorbance 458 nm at time zero) (Vehicle Control sample data in parenthesis) | | |
|---|---|---|---|---|---|---|
| | CISD1 Gene Product (mitoNEET) | CISD2 Gene Product (NAF-1) | CISD3 Gene Product (Miner2) | CISD1 Gene Product (mitoNEET) | CISD2 Gene Product (NAF-1) | CISD3 Gene Product (DMSO 11%) |
| #147 | 75 (80) | 85 (310) | 60 (60) | 11% (16%) | 5% (3%) | 10% (11%) |
| #132 | 90 (80) | 210 (310) | 50% loss not achieved during 180 minutes (60) | 19% (16%) | 19% (3%) | 50% (11%) |
| #20 | 65 (80) | 300 (310) | 35 (60) | 0% (16%) | 4% (3%) | 9% (11%) |
| #18 | 50% loss not achieved during 180 minutes (80) | 425 (310) | 50% loss not achieved during 180 minutes (60) | 62% (16%) | 42% (3%) | 70% (11%) |
| #136 | 75 (80) | 325 (310) | 45 (60) | 2% (16%) | 5% (3%) | 10% (11%) |
| #35 | 85 (80) | 220 (310) | 50 (60) | 26% (16%) | 13% (3%) | 20% (11%) |
| #60 | 100 (80) | 120 (310) | 90 (60) | 35% (16%) | 12% (3%) | 38% (11%) |
| #135 | 100 (80) | 160 (310) | 80 | 24% (16%) | 16% (3%) | 20% (11%) |
| #138 | 50% loss not achieved during 180 minutes (80) | 435 (210) | 50% loss not achieved during 180 minutes (60) | 53% (16%) | 30% (3%) | 66% (11%) |
| #58 | 100 (80) | 280 (310) | 125 (60) | 36% (16%) | 39% (3%) | 44% (11%) |
| #36 | 98 (80) | 210 (210) | 80 (60) | 36 % (16%) | 30% (3%) | 39% (11%) |
| #37 | 85 (80) | 280 (210) | 75 (60) | 23% (16%) | 3% (3%) | 37% (11%) |

Analysis of the absorbance enables the time for which 50% loss of bound Fe—S cluster is reached (i.e. a 50% absorbance decrease at 458 nm) for each Test sample and each Control sample (in parenthesis table 4) to be determined. The data are then compared to determine whether the compound of the invention stabilizes or destabilizes the NEET protein/Fe—S cluster binding.

Destabilisers enhance the release of bound Fe—S cluster (i.e. decrease the time needed to reach 50% Fe—S cluster bound loss by more than 25% for the Test sample compared to the Control sample). As illustrated by table 4, at the concentrations tested, destabilisers of CISD2 Gene Product (NAF-1) are compounds #147, #132, #35, #60, and #135. Destabilisers of CISD3 Gene Product (Miner2) are compounds #20 and #136.

Stabilisers of Fe—S cluster binding by the NEET proteins slow the release of bound Fe—S (i.e. increase the time needed to reach 50% Fe—S cluster bound loss by more than 25% for the Test sample compared to the Control sample). As illustrated by table 4, at the concentrations tested, stabilisers of CISD1 Gene Product (mitoNEET) are compounds #18, #60, #135, #138, and #58. Stabilisers of CISD2 Gene Product (NAF-1) is the compound #138. Stabilisers of CISD3 Gene Product (Miner2) are the compounds #132, #18, #60, #135, #138, #58, #36, and #37.

As reported by table 4 (second part: "Residual cluster bound at end of experiment"), stabilizers may prevent the Fe—S cluster release by the NEET protein, the residual cluster bound at the end of the spectrometry experiment being in a range of 30% to 78% meaning that 30% to 78 % of the Fe—S cluster remains bound to the total protein in the assay at the end of the experiment.

Example B4—Compounds Inhibit NFkB Activation in Response to TNFa Stimulation Compounds of the present invention have been tested for their capacity to inhibit NFκB. The results are shown in the following table.

TABLE 5

| Compounds | NFκB EC50 (µM) |
|---|---|
| # 15 | 0.15 |
| # 33 | 0.40 |
| # 36 | 0.2 |
| # 132 | 0.04 |
| # 164 | 0.09 |
| # 16 | 0.15 |
| # 62 | 0.38 |

Materials and Methods

Construction of a NFκB Reporter Cell Line

The NFκB reporter construct was made by cloning 5 NFκB responsive elements upstream of a NanoLuciferase reporter gene flanked by AAVS1 genomic sequences.

NFκB Responsive element fused with NanoLuciferase and SV40 late Poly(A) signal was amplified from pNL3.2-NFκB-Nluc (Promega) using NFKB-NLUC-F and NFKB-NLUC-R primers and inserted by Infusion (TaKaRa) in AAVS1 SA-2A-puro-pA donor plasmid (Hockemeyer et al, Nat Biotechnol. 2009, 27, 851-7) digested by SalI. pCRISPR AAVS1-T2 expressing a guide RNA (gRNA) to target human AAVS1 (T2 target sequence) was constructed by inserting AAVS1-T2A hybridized primers in pLentiCRISPR v2-blast (Sanjana et al, Nat Methods. 2014, 11, 783-4) digested by BsmbI.

```
Oligonucleotide sequences
NFKB-NLUC-F:
                                        (SEQ ID NO: 1)
ggctctatggGTCGACGGCCTAACTGGCCGGTACC NFKB-NLUC-R:
                                        (SEQ ID NO: 2)
agcttagtactGTCGACGATCAGCGGAAGAGCGCCCA AAVS1-T2A-1
                                        (SEQ ID NO: 3)
CACCGGGGGCCACTAGGGACAGGAT AAVS1-T2A-2
                                        (SEQ ID NO: 4)
AAACATCCTGTCCCTAGTGGCCCCC
```

A549 cells were transfected by the plasmids and puromycine selected for 5 days (1 µg mL-1). Then clones were obtained by limiting dilution and selected to maximize TNF dependent NFκB-NanoLuciferase induction.

NFκB Reporter Assay

The reporter cells were seeded on a 96-well plate for overnight with DMEM including 10% FBS. Test compounds were added at varying concentrations. The cells then were treated with 4 ng/ml TNFα (Peprotech, ref E251) in DMEM+10% FBS. NanoGlo luciferase assay (Promega) was carried out 6 hours later. Luminescence was measured using a Spark 20M spectrofluorimeter (Tecan). Values were normalized to the luminescence measured in untreated cells.

The invention claimed is:

1. A compound of formula (I):

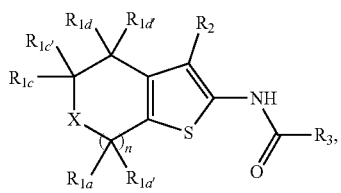

wherein:

X represents:
—$CR_{1b}R_{1b'}$;
n is 0, 1, or 2;
$R_{1a}$, $R_{1a'}$, $R_{1b}$, $R_{1b'}$, $R_{1c}$, $R_{1c'}$, $R_{1d}$, and $R_{1d'}$ represent independently:
a hydrogen,
a halogen,
a $(C_1-C_6)$alkyl, optionally substituted by at least one halogen,
a $(C_1-C_6)$alkyloxy,
a cyano, or
an aryl optionally substituted by at least one radical selected from the group consisting of:
a halogen,
a $(C_1-C_6)$alkyl optionally substituted by at least one halogen,
a hydroxy, and
a $(C_1-C_6)$alkyloxy; or
$R_{1a}$ and $R_{1a'}$, $R_{1b}$ and $R_{1b'}$, $R_{1c}$ and $R_{1c'}$, or $R_{1d}$ and $R_{1d'}$ form together a cycloalkyl; or
$R_{1a}$ or $R_{1a'}$ and $R_{1d}$ or $R_{1d'}$ form together a bridged carbocyclyl;
and wherein at least two of $R_{1a}$, $R_{1a'}$, $R_{1b}$, $R_{1b'}$, $R_{1c}$, $R_{1c'}$, $R_{1d}$, and $R_{1d'}$ are not a hydrogen;
$R_2$ represents —COOH;

$R_3$ represents:
a 5-10 membered ring, saturated or unsaturated, selected from the group consisting of:
an aryl optionally fused to a dioxole,
a heteroaryl selected from the group consisting of a pyridinyl, a pyridazinyl, a pyrimidinyl, a pyrazinyl, an imidazolyl, and a pyrazolyl,
a cycloalkyl,
a heterocycloalkyl, and
a 5-10 membered bridged carbocyclyl or heterocyclyl, said 5-10 membered ring is optionally substituted by at least one radical selected from the group consisting of:
a halogen,
a $(C_1-C_6)$alkyl optionally substituted by at least one halogen, or a $(C_1-C_6)$alkyloxy,
a —NH—$(C_1-C_6)$alkyl or a —N—$((C_1-C_6)$alkyl$)_2$, optionally substituted by a heterocycloalkyl or a $(C_1-C_6)$alkyloxy,
a —NH-heterocycloalkyl, a —NH-cycloalkyl, a —N$((C_1-C_6)$alkyl$)$-heterocycloalkyl or a —N$((C_1-C_6)$alkyl$)$-cycloalkyl, optionally substituted by a $(C_1-C_6)$alkyloxy or a —CO—$R_4$ with $R_4$ being a hydrogen or a $(C_1-C_6)$alkyl,
a hydroxy,
a $(C_1-C_6)$alkyloxy optionally substituted by at least one radical selected from the group consisting of a halogen, a hydroxy, a $(C_1-C_6)$alkyloxy, a —$NR_5R_6$ with $R_5$ and $R_6$ are independently a hydrogen or a $(C_1-C_6)$alkyl, a —$NHCOR_7$, a —$NHCO_2R_7$, with $R_7$ being a $(C_1-C_6)$alkyl, a —$CO_2R_4$ with $R_4$ being a hydrogen or a $(C_1-C_6)$alkyl, and a heterocycle,
a —$NHCOR_7$ or —$NHCO_2R_7$ with $R_7$ being a $(C_1-C_6)$alkyl, and
a heterocycloalkyl, a heterocycloalkyloxy or a spiroheterocycloalkyl, optionally substituted by a $(C_1-C_6)$alkyloxy, a hydroxy, a halogen or a $(C_1-C_6)$alkyl optionally substituted by a $(C_1-C_6)$alkyloxy; and the stereoisomers, and the pharmaceutical salts thereof; and with the proviso that the compound of formula (I) is not 2-[(4-Chlorobenzoylamino]-6,6-dimethyl-5,7-dihydro-4H-benzothiophene-3-carboxylic acid.

2. The compound according to claim 1, wherein $R_{1a}$, $R_{1a'}$, $R_{1b}$, $R_{1b'}$, $R_{1c}$, $R_{1c'}$, $R_{1d}$, and $R_{1d'}$ represent independently a hydrogen, a $(C_1-C_6)$alkyl, optionally substituted by at least one halogen, or a halogen; or $R_{1a}$ or $R_{1a'}$ and $R_{1d}$ or $R_{1d'}$ form together a bridged carbocyclyl; or $R_{1a}$ and $R_{1a'}$, $R_{1b}$ and $R_{1b'}$, $R_{1c}$ and $R_{1c'}$, or $R_{1d}$ and $R_{1d'}$ forms together a cyclopropyl.

3. The compound according to claim 1, wherein $R_{1a}=R_{1a'}$, $R_{1b}=R_{1b'}$, $R_{1c}=R_{1c'}$, and $R_{1d}=R_{1d'}$.

4. The compound according to claim 1, wherein two of $R_{1a}$, $R_{1a'}$, $R_{1b}$, $R_{1b'}$, $R_{1c}$, $R_{1c'}$, $R_{1d}$, and $R_{1d'}$ represent a methyl and the others are a hydrogen.

5. The compound according to claim 1, wherein at least three of $R_{1a}$, $R_{1a'}$, $R_{1b}$, $R_{1b'}$, $R_{1c}$, $R_{1c'}$, $R_{1d}$, and $R_{1d'}$ represent a methyl and the others are a hydrogen.

6. The compound according to claim 1, wherein $R_{1b}$ and $R_{1b'}$ form together a cycloalkyl, and $R_{1a}$, $R_{1a'}$, $R_{1c}$, $R_{1c'}$, $R_{1d}$, and $R_{1d'}$ are a hydrogen.

7. The compound according to claim 1, wherein $R_3$ is a phenyl, a pyridinyl, a pyridazinyl, a pyrimidinyl, a pyrazinyl, an imidazolyl, or a pyrazolyl, optionally substituted by at least one radical selected from the group consisting of:
a halogen,
a $(C_1-C_6)$alkyl optionally substituted by at least one halogen, or a $(C_1-C_6)$alkyloxy,
a —NH—$(C_1-C_6)$alkyl or a —N—$((C_1-C_6)$alkyl$)_2$, optionally substituted by a heterocycloalkyl or a $(C_1-C_6)$alkyloxy,
a —NH-heterocycloalkyl, a —NH-cycloalkyl, a —N$((C_1-C_6)$alkyl$)$-heterocycloalkyl or a —N$((C_1-C_6)$alkyl$)$-cycloalkyl, optionally substituted by a $(C_1-C_6)$alkyloxy or a —CO—$R_4$ with $R_4$ being a hydrogen or a $(C_1-C_6)$alkyl,
a hydroxy,
a $(C_1-C_6)$alkyloxy optionally substituted by at least one radical selected from the group consisting of a halogen, a hydroxy, a $(C_1-C_6)$alkyloxy, a —$NR_5R_6$ with $R_5$ and $R_6$ are independently a hydrogen or a $(C_1-C_6)$alkyl, a —$NHCOR_7$, a —$NHCO_2R_7$, with $R_7$ being a $(C_1-C_6)$alkyl, a —$CO_2R_4$ with $R_4$ being a hydrogen or a $(C_1-C_6)$alkyl, and a heterocycle,
a —$NHCOR_7$ or —$NHCO_2R_7$ with $R_7$ being a $(C_1-C_6)$alkyl, and
a heterocycloalkyl, a heterocycloalkyloxy or a spiroheterocycloalkyl, optionally substituted by a $(C_1-C_6)$alkyloxy, a hydroxy, a halogen or a $(C_1-C_6)$alkyl optionally substituted by a $(C_1-C_6)$alkyloxy.

8. The compound according to claim 1, wherein $R_3$ represents a phenyl optionally substituted by at least one radical selected from the group consisting of:
a halogen;
a $(C_1-C_6)$alkyl optionally substituted by at least one halogen,
a —NH—$(C_1-C_6)$alkyl, or a —N—$((C_1-C_6)$alkyl$)_2$, optionally substituted by a $(C_1-C_6)$alkyloxy, or a heterocycloalkyl selected from the group consisting of a tetrahydropyranyl, a tetrahydrofuranyl, an oxetanyl, a piperidinyl, and an azetidinyl, said heterocycloalkyl being optionally substituted by a $(C_1-C_6)$alkyloxy or a —CO—$R_4$ with $R_4$ being a hydrogen or a $(C_1-C_6)$alkyl,
a —NH-heterocycloalkyl, a —NH-cycloalkyl, a —N$((C_1-C_6)$alkyl$)$-heterocycloalkyl, or a —N$((C_1-C_6)$alkyl$)$-cycloalkyl, a —NH-tetrahydropyranyl, a —N$(CH_3)$-tetrahydropyranyl, a —NH-tetrahydrofuranyl, a NH-piperidinyl, a —NH-azetidinyl, a —NH-oxetanyl, a-NH-cyclohexyl, or a —N$(CH_3)$-cyclobutyl, said —NH-heterocycloalkyl, —NH-cycloalkyl, —N$((C_1-C_6)$alkyl$)$-heterocycloalkyl, or —N$((C_1-C_6)$alkyl$)$-cycloalkyl being optionally substituted by a $(C_1-C_6)$alkyloxy or a —CO—$R_4$ with $R_4$ being a hydrogen or a $(C_1-C_6)$alkyl,
a $(C_1-C_6)$alkyloxy optionally substituted by at least one radical selected from the group consisting of a halogen, a $(C_1-C_6)$alkyloxy, and a heterocycle, and
a heterocycloalkyl or a spiroheterocycloalkyl, said heterocycloalkyl and spiroheterocycloalkyl are optionally substituted by a $(C_1-C_6)$alkyloxy, a hydroxy, a halogen or a $(C_1-C_6)$alkyl optionally substituted by a $(C_1-C_6)$ alkyloxy, and
a heterocycloalkyloxy.

9. The compound according to claim 1, wherein $R_3$ represents a pyridinyl, a pyridazinyl, a pyrimidinyl, a pyrazolyl, an imidazolyl, or a pyrazinyl, optionally substituted by at least one radical selected from the group consisting of:
a $(C_1-C_6)$alkyl optionally substituted by at least one halogen,
a $(C_1-C_6)$alkyloxy optionally substituted by at least one halogen,
a heterocycloalkyl, and
a heterocycloalkyloxy.

10. The compound according to claim 1, wherein said compound is selected from the group consisting of:

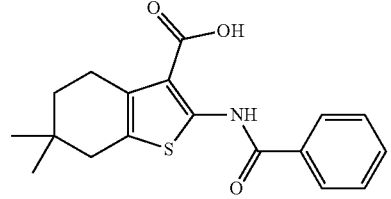

Compound #15

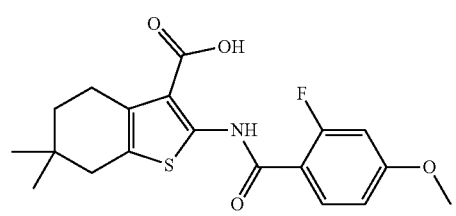

Compound #16

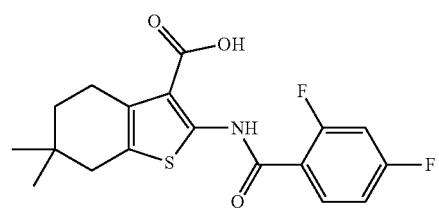

Compound #17

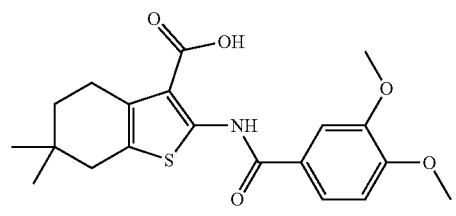

Compound #18

-continued
Compound #19
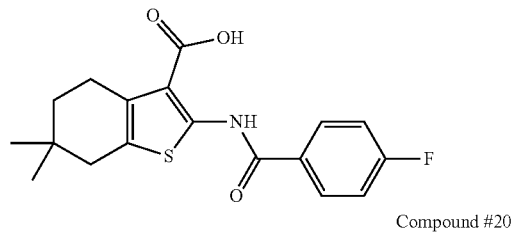
Compound #20
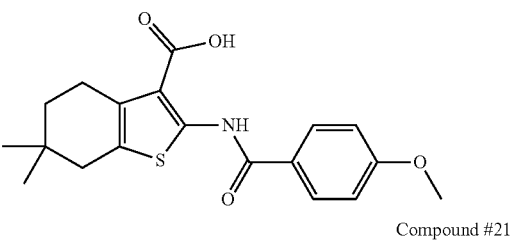
Compound #21
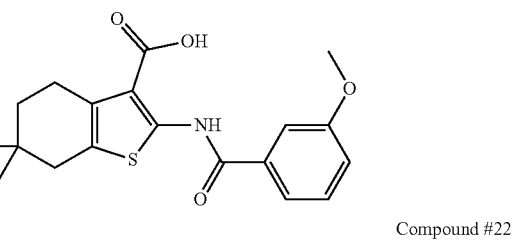
Compound #22
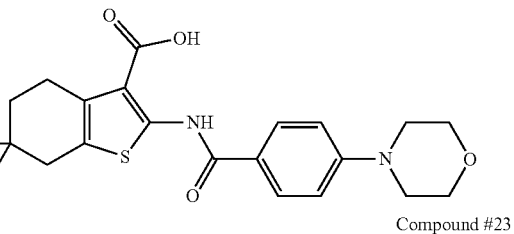
Compound #23
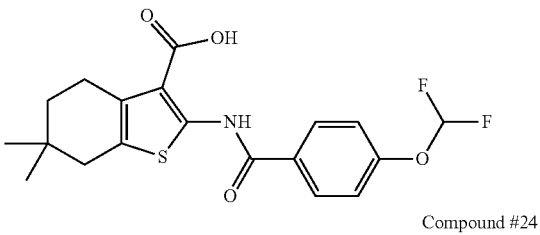
Compound #24
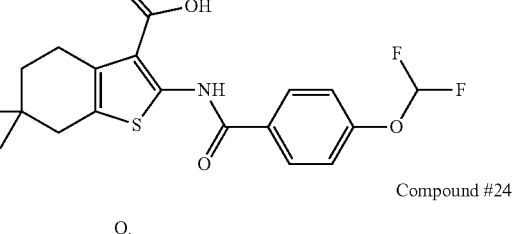
Compound #25
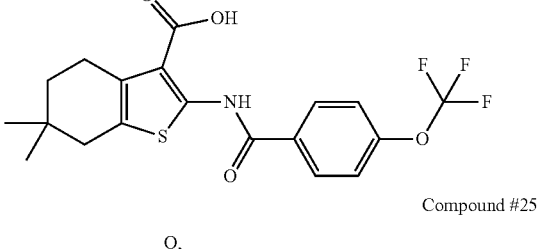
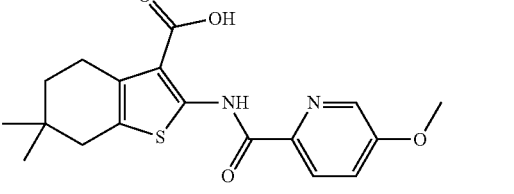
-continued
Compound #26
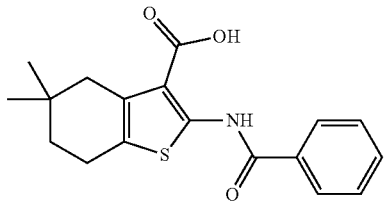
Compound #27
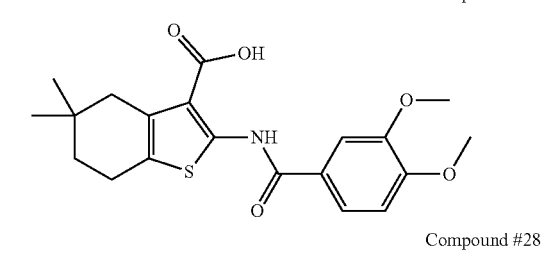
Compound #28
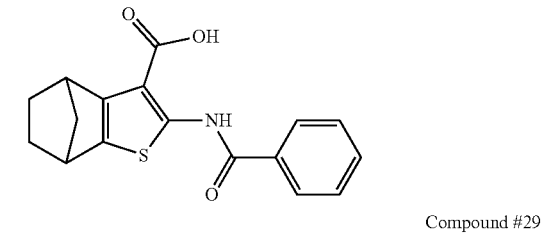
Compound #29
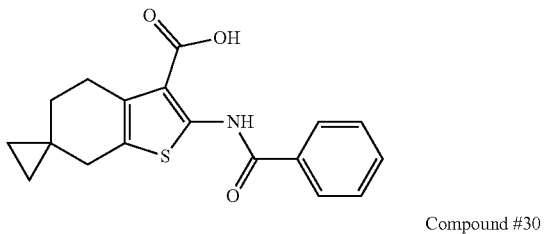
Compound #30
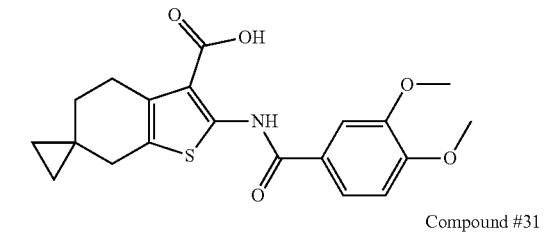
Compound #31
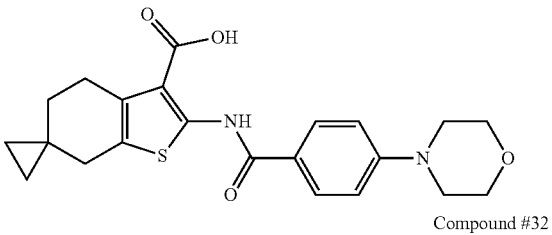
Compound #32
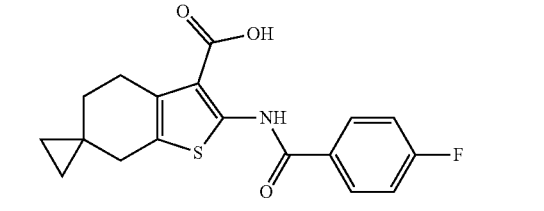

Compound #33
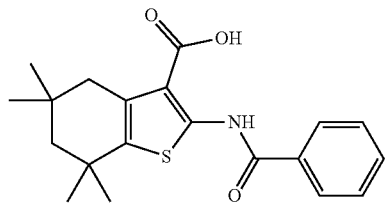
Compound #34
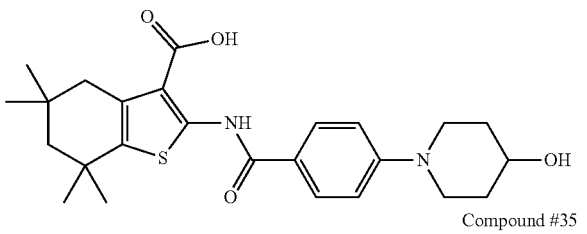
Compound #35
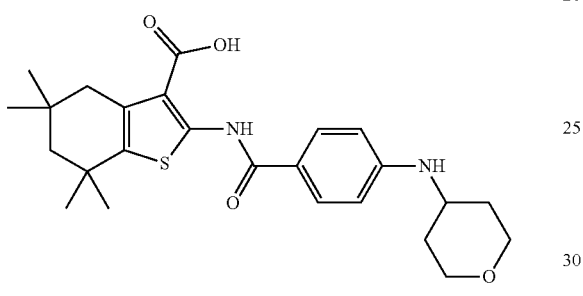
Compound #36
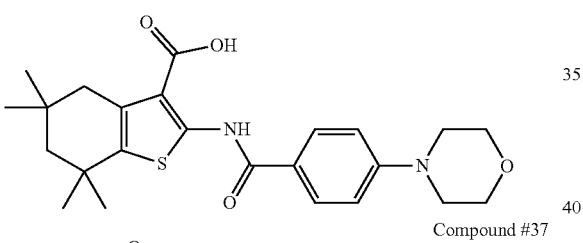
Compound #37
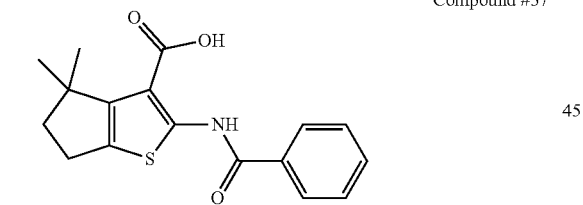
Compound #38
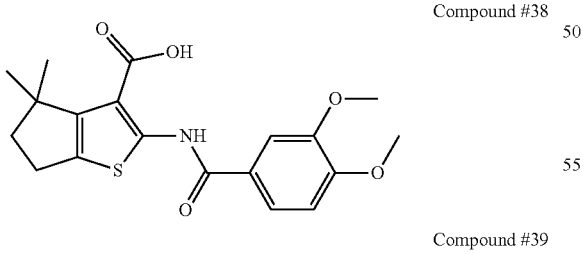
Compound #39
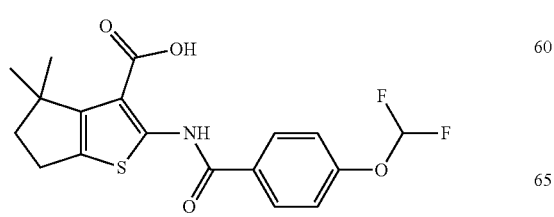
Compound #40
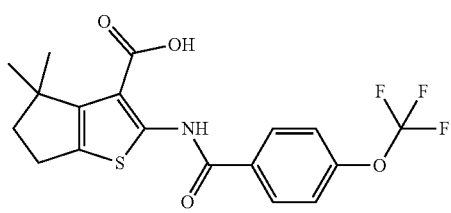
Compound #41
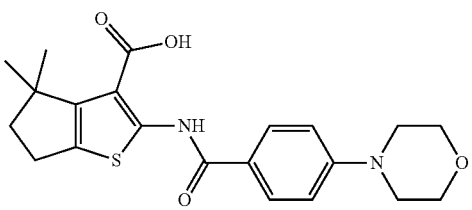
Compound #42
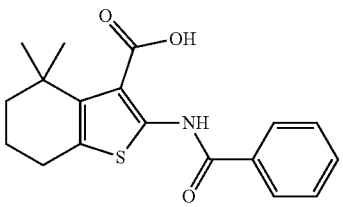
Compound #43
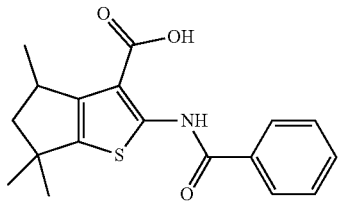
Compound #44
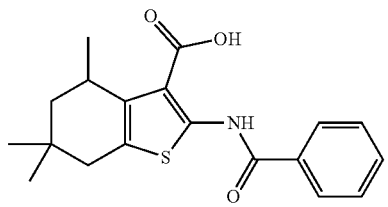
Compound #58
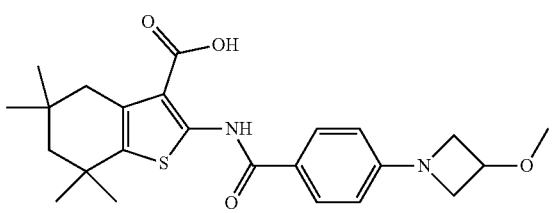

Compound #59
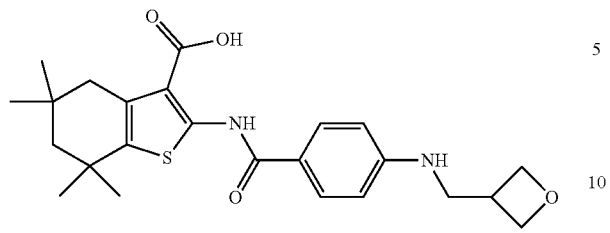
Compound #60
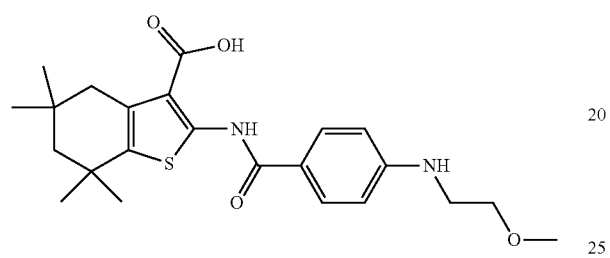
Compound #61
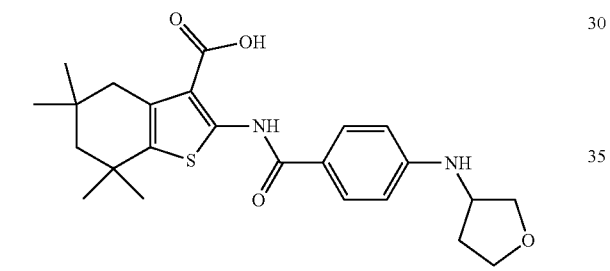
Compound #62
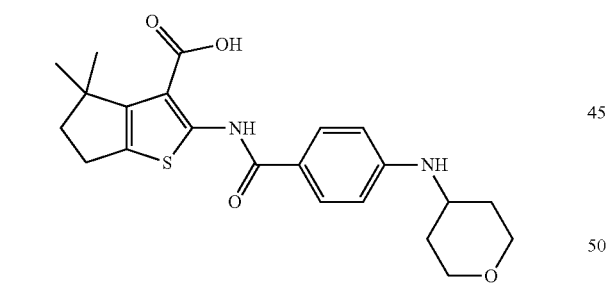
Compound #63
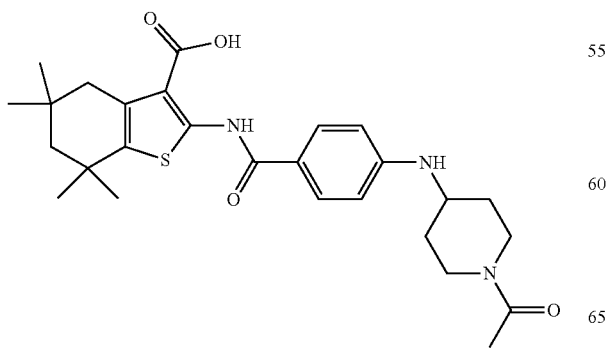
Compound #64
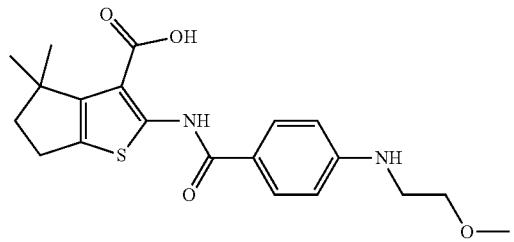
Compound #65
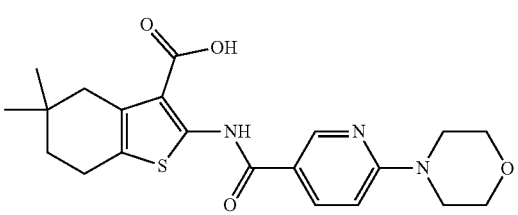
Compound #78
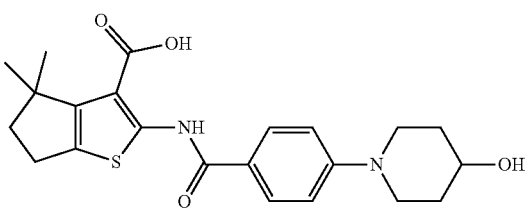
Compound #80
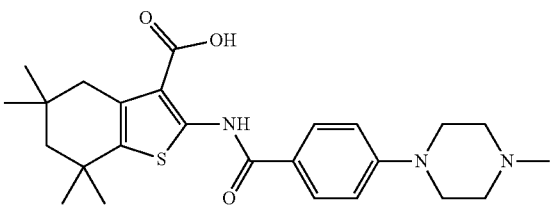
Compound #90
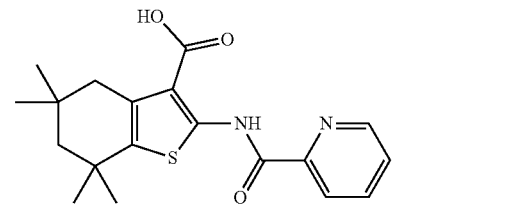
Compound #94
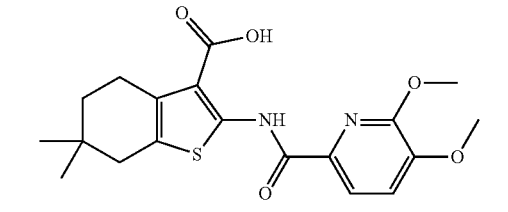

-continued
Compound #96
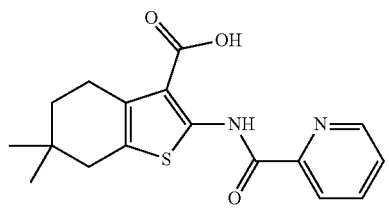
Compound #98
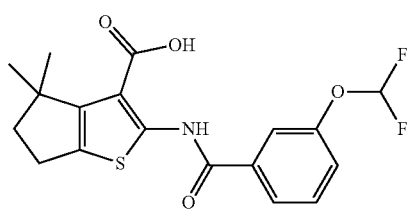
Compound #105
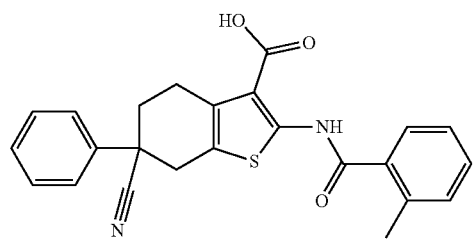
Compound #117
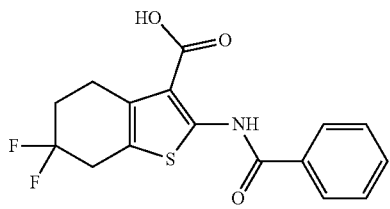
Compound #131
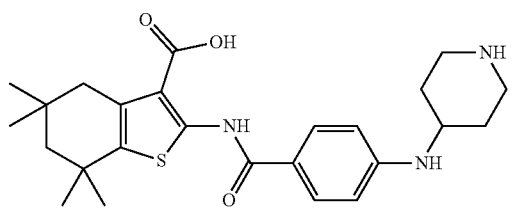
Compound #132
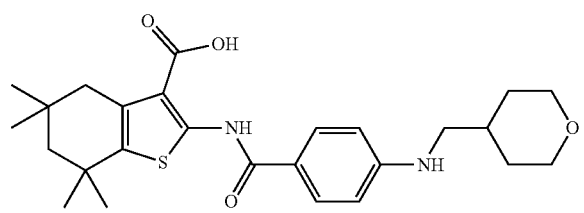
-continued
Compound #133
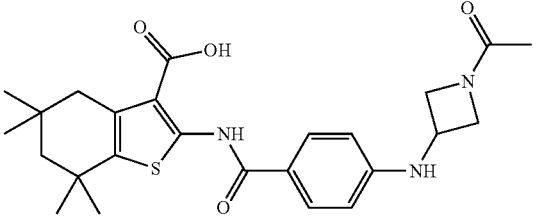
Compound #134
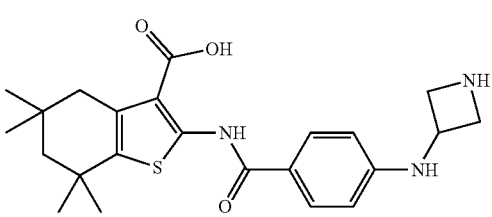
Compound #135
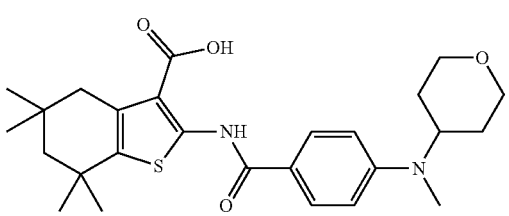
Compound #136
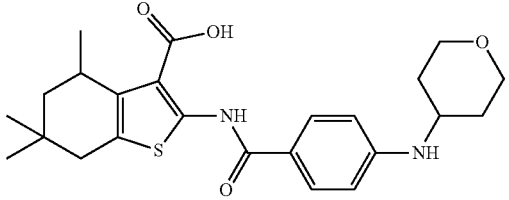
Compound #137
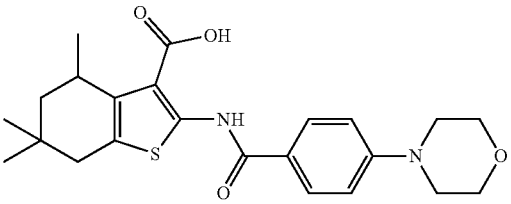
Compound #138
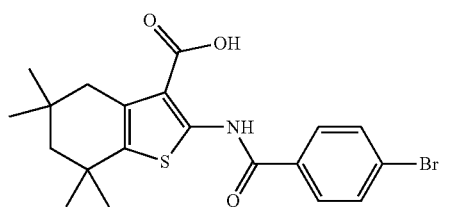

Compound #139
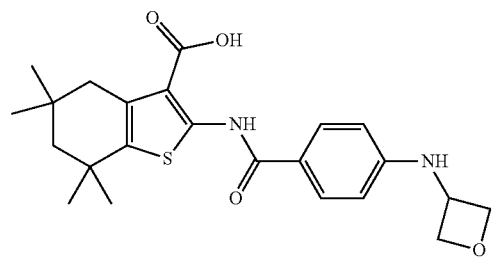
Compound #140
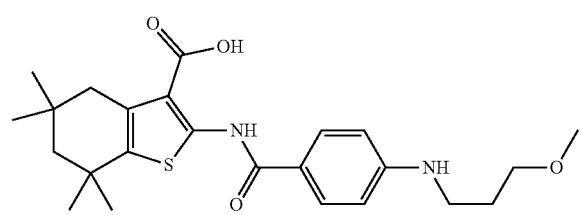
Compound #141
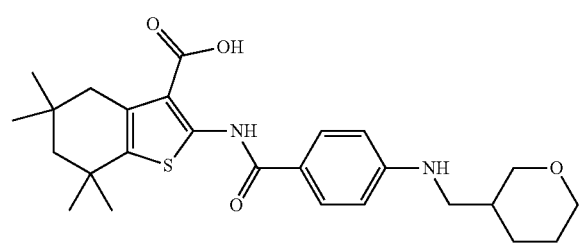
Compound #142
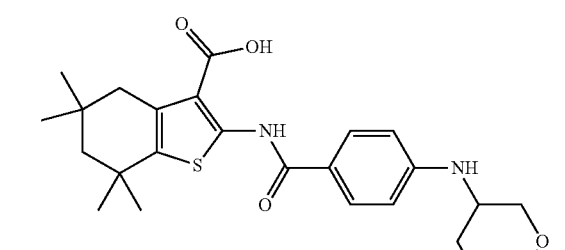
Compound #143
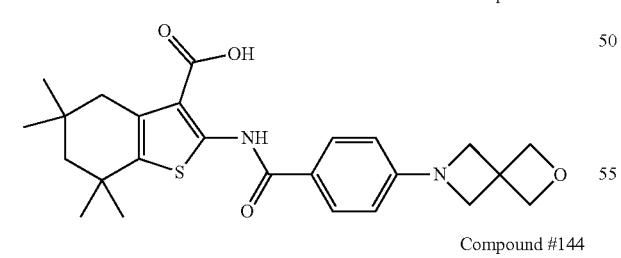
Compound #144
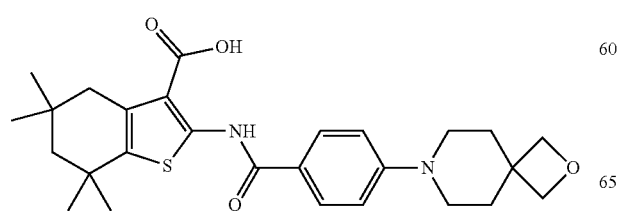
Compound #145
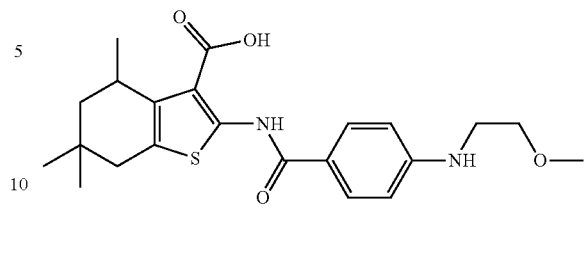
Compound #146
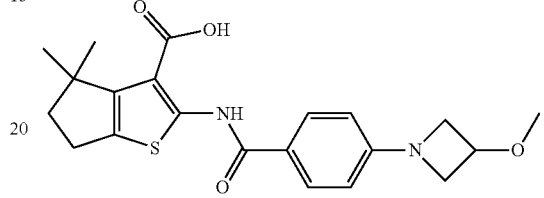
Compound #147
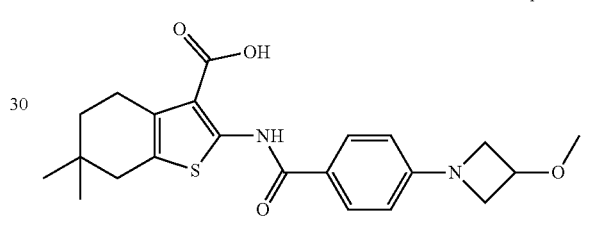
Compound #148
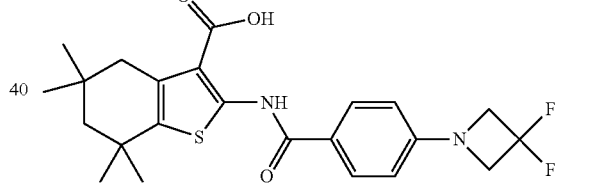
Compound #149
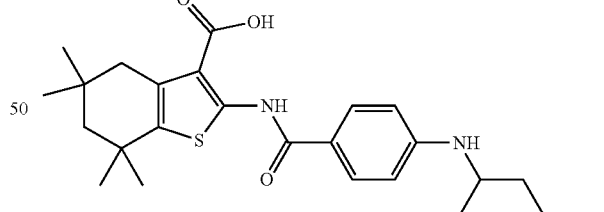
Compound #150
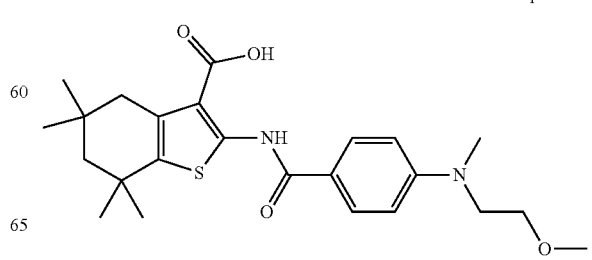

Compound #152
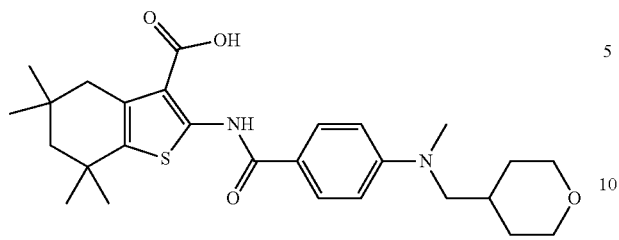
Compound #158
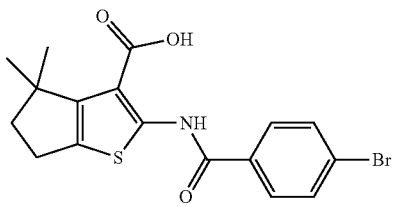
Compound #153
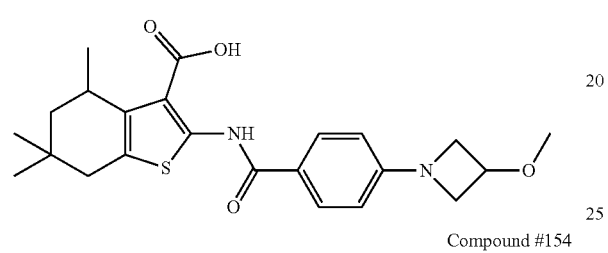
Compound #159
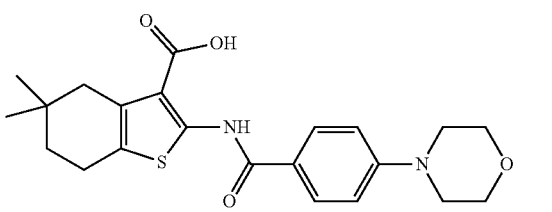
Compound #154
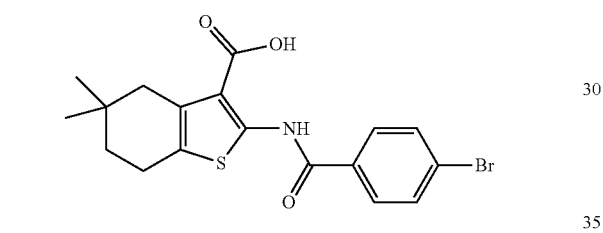
Compound #160
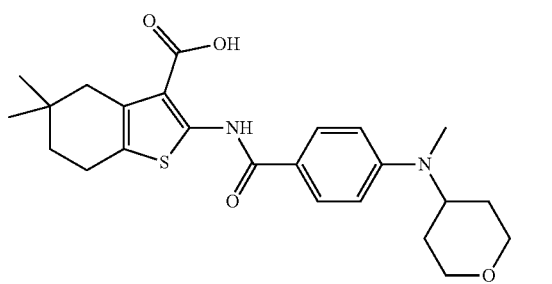
Compound #155
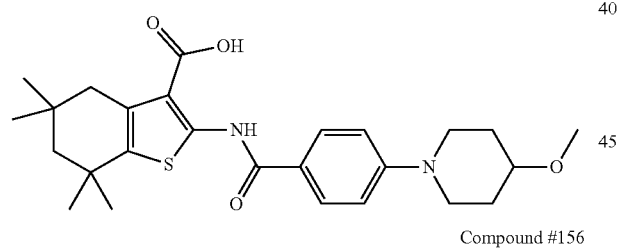
Compound #161
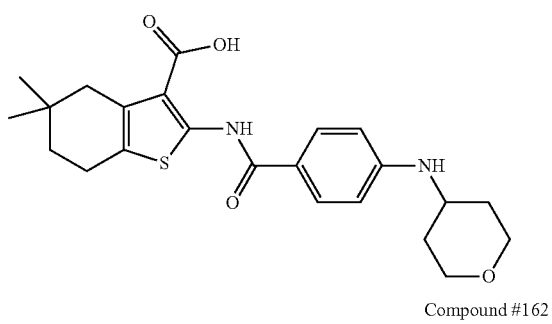
Compound #156
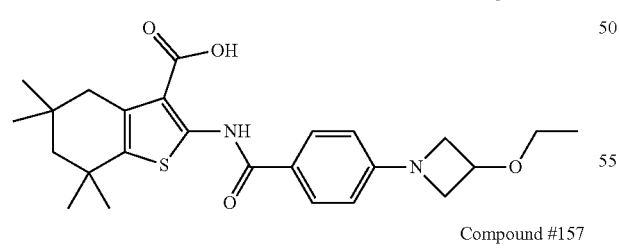
Compound #162
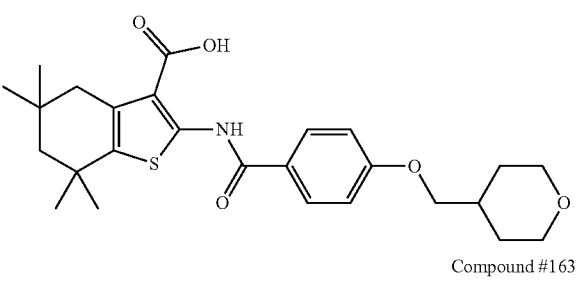
Compound #157
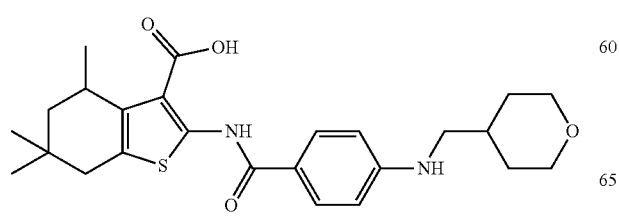
Compound #163
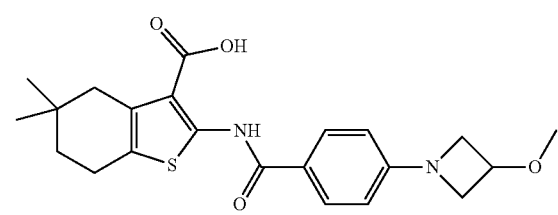

Compound #164
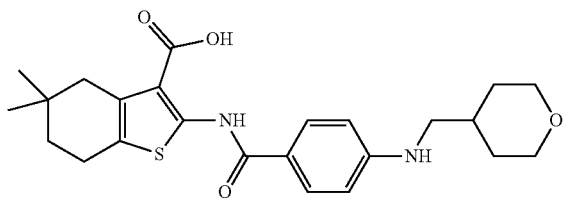
Compound #165
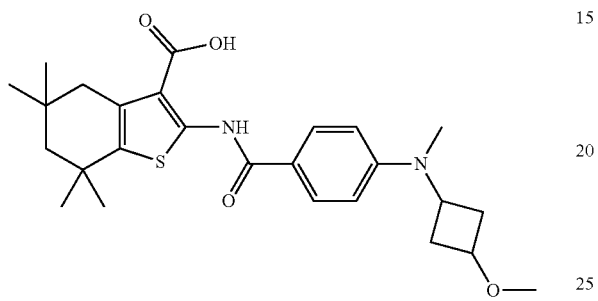
Compound #166
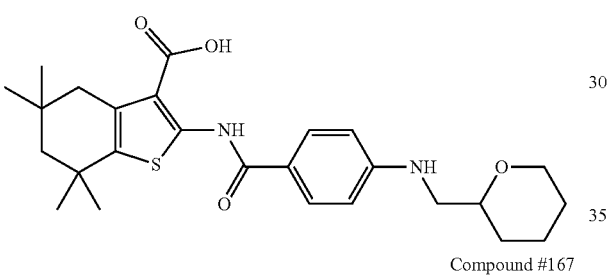
Compound #167
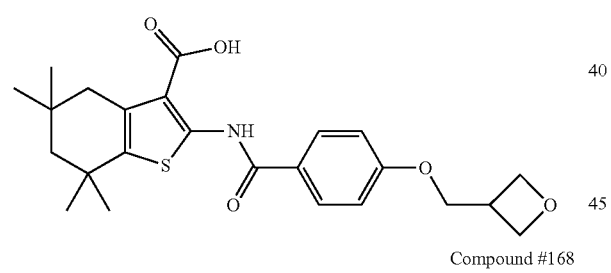
Compound #168
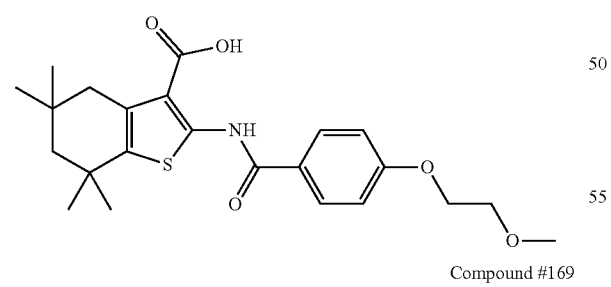
Compound #169
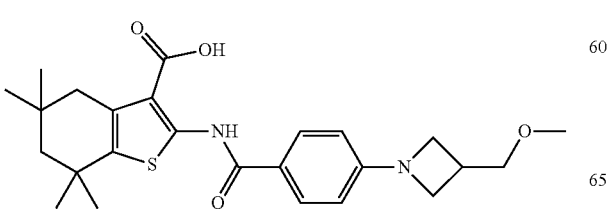
Compound #170
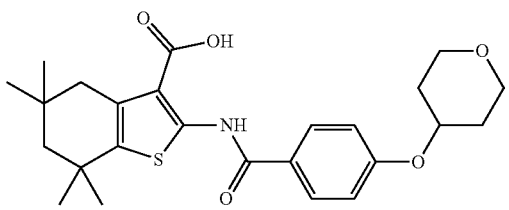
Compound #171
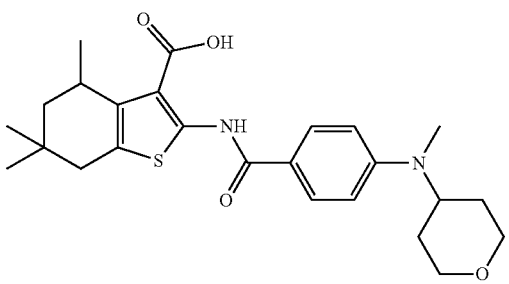
Compound #173
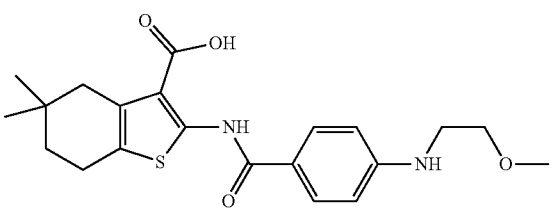
Compound #174
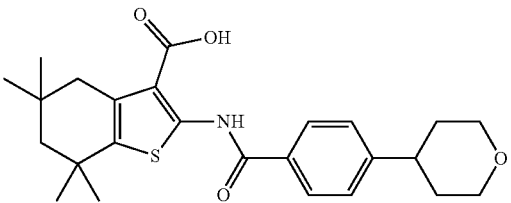
Compound #176
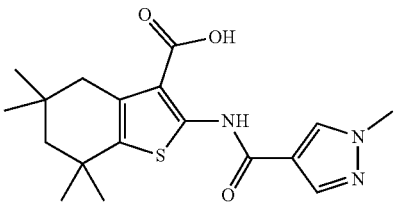
Compound #201
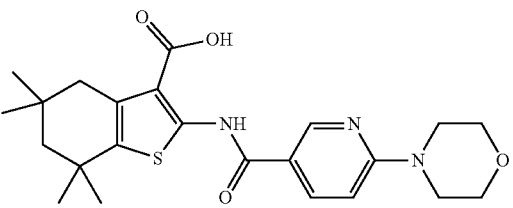

Compound #202
Compound #203
Compound #204
Compound #205
Compound #206
Compound #208
Compound #209
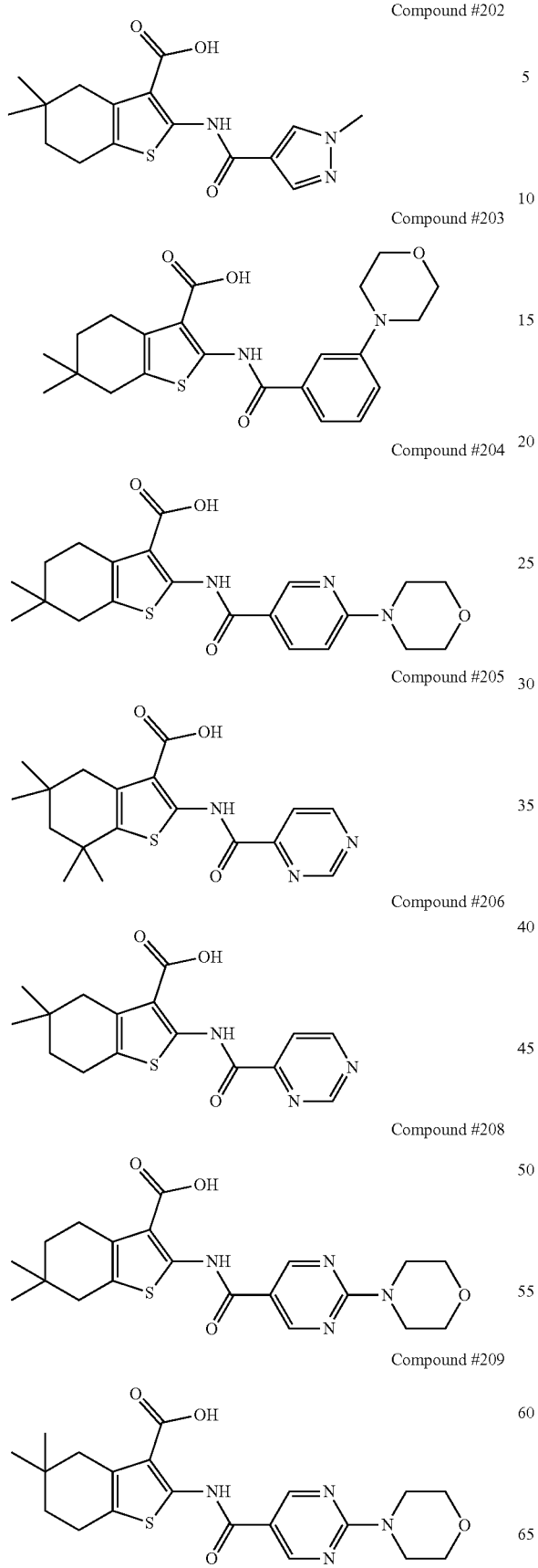
Compound #212
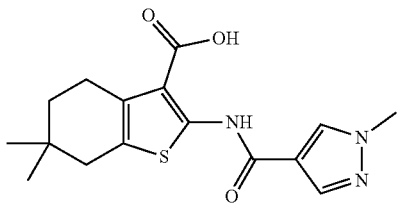
Compound #213
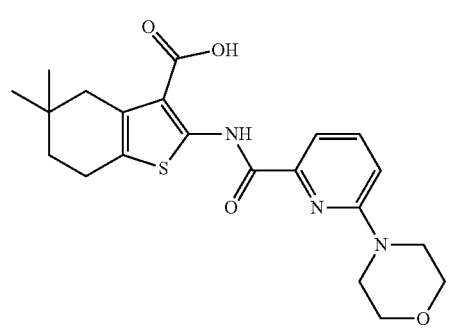
Compound #219
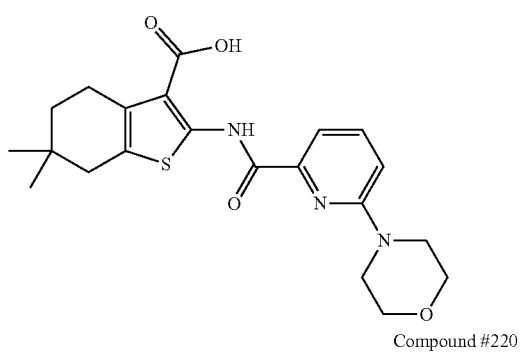
Compound #220
Compound #221
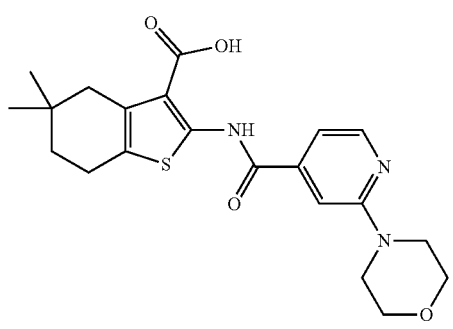

Compound #224
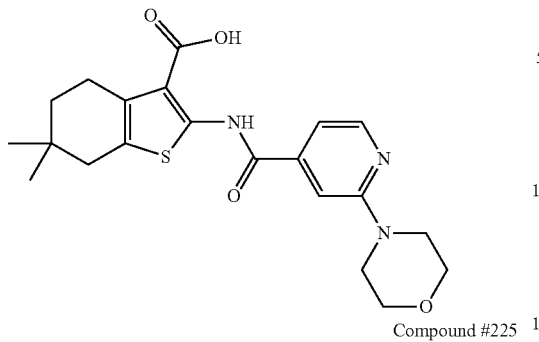
Compound #225
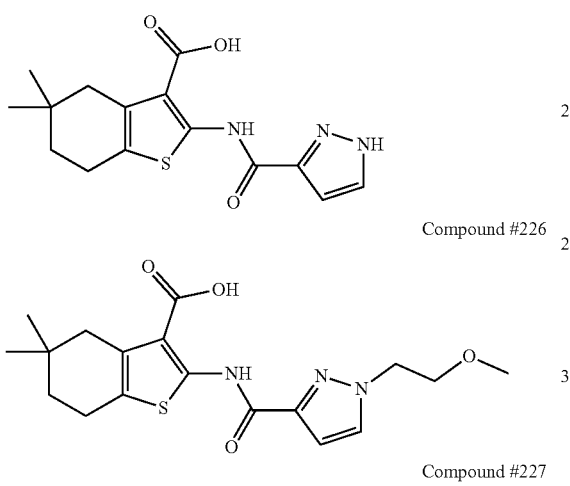
Compound #226
Compound #227
Compound #228
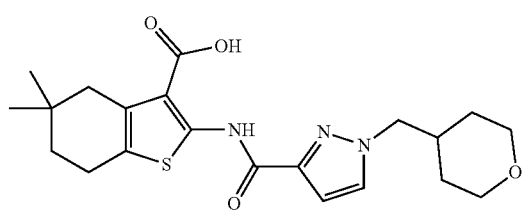
Compound #229
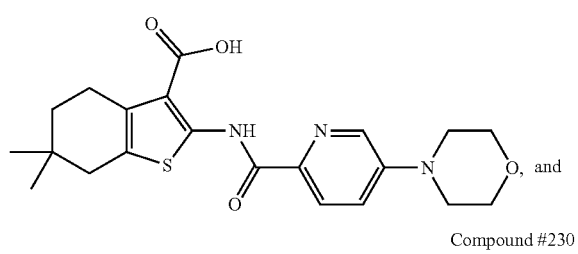
, and
Compound #230
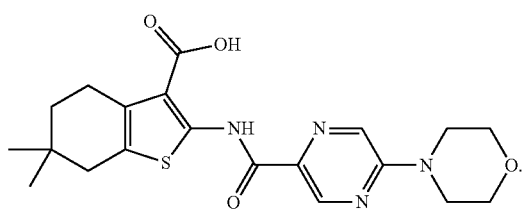
.
11. A pharmaceutical composition comprising a compound as defined in claim 1 and an acceptable pharmaceutical excipient.
12. A pharmaceutical composition comprising a compound as defined in claim 10 and an acceptable pharmaceutical excipient.
* * * * *

UNITED STATES PATENT AND TRADEMARK OFFICE
CERTIFICATE OF CORRECTION

PATENT NO. : 11,492,347 B2
APPLICATION NO. : 16/967746
DATED : November 8, 2022
INVENTOR(S) : Eric Meldrum et al.

It is certified that error appears in the above-identified patent and that said Letters Patent is hereby corrected as shown below:

In the Specification

Column 4,
Line 22, "and $R_{1d'}$ and" should read --and $R_{1d}$ and--.

Column 5,
Line 12, "$R_{1a'}$ forms" should read --$R_{1d'}$ forms--.
Line 15, "$R_{1d}=R_{1a}$" should read --$R_{1d}=R_{1d'}$--.

Column 11,
Lines 51-52, "$R_{1d'}$ and $R_{1a}$" should read --$R_{1d}$ and $R_{1d'}$--.
Line 54, "$R_{1d'}$ or $R_{1d}$" should read --$R_{1d}$ or $R_{1d'}$--.

Column 13,
Lines 23-24, "$R_{1d'}$ and $R_{1d}$" should read --$R_{1d}$ and $R_{1d'}$--.
Line 26, "$R_{1d'}$ or $R_{1d}$" should read --$R_{1d}$ or $R_{1d'}$--.

Column 14,
Line 23, "$R_{1d}$ represent" should read --$R_{1d'}$ represent--.
Line 31, "Rib-represent" should read --$R_{1b'}$ represent--.
Line 32, "$R_{1d}$ represent" should read --$R_{1d'}$ represent--.

Column 54,
Line 24, "LiGH" should read --LiOH--.

Signed and Sealed this
Tenth Day of September, 2024

Katherine Kelly Vidal
*Director of the United States Patent and Trademark Office*